United States Patent
Lee et al.

(10) Patent No.: US 11,858,906 B2
(45) Date of Patent: Jan. 2, 2024

(54) AMINE COMPOUND AND HIGH-EFFICIENCY ORGANIC LIGHT-EMITTING DIODE INCLUDING SAME

(71) Applicant: SFC CO., LTD., Cheongju-si (KR)

(72) Inventors: Tae Gyun Lee, Cheongju-si (KR); Sang-woo Park, Cheongju-si (KR); Seung-Soo Lee, Cheongju-si (KR); Jun-young Moon, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 539 days.

(21) Appl. No.: 17/196,395

(22) Filed: Mar. 9, 2021

(65) Prior Publication Data

US 2021/0284619 A1    Sep. 16, 2021

(30) Foreign Application Priority Data

Mar. 10, 2020  (KR) .................. 10-2020-0029765
Mar. 9, 2021   (KR) .................. 10-2021-0030861

(51) Int. Cl.
| | | |
|---|---|---|
| *C07D 307/93* | (2006.01) | |
| *H10K 85/60* | (2023.01) | |
| *H10K 50/15* | (2023.01) | |
| *H10K 50/16* | (2023.01) | |
| *H10K 50/18* | (2023.01) | |
| *H10K 50/17* | (2023.01) | |

(52) U.S. Cl.
CPC ......... *C07D 307/93* (2013.01); *H10K 85/615* (2023.02); *H10K 85/636* (2023.02); *H10K 85/655* (2023.02); *H10K 85/6574* (2023.02); *H10K 50/15* (2023.02); *H10K 50/16* (2023.02); *H10K 50/171* (2023.02); *H10K 50/18* (2023.02)

(58) Field of Classification Search
CPC .. C07D 307/93; H10K 85/636; H10K 85/655; H10K 85/6574; H10K 85/615; H10K 50/16; H10K 50/18; H10K 50/171; H10K 50/15
USPC .......................................... 257/40
See application file for complete search history.

(56) References Cited

U.S. PATENT DOCUMENTS

| | | | |
|---|---|---|---|
| 10,693,084 B2 * | 6/2020 | Park ................. | C07D 495/04 |
| 11,696,491 B2 * | 7/2023 | Ahn .................. | H10K 50/13 |
| | | | 252/301.16 |

FOREIGN PATENT DOCUMENTS

| | | |
|---|---|---|
| KR | 101074193 B1 | 10/2011 |
| KR | 101455156 B1 | 10/2014 |

* cited by examiner

*Primary Examiner* — Tu-Tu V Ho
(74) *Attorney, Agent, or Firm* — STIP Law Group, LLC

(57) ABSTRACT

Disclosed herein are a novel amine compound and an organic light-emitting diode of high efficiency including the same and, more particularly, to an amine compound with a specific structure which exhibits high efficiency as a material for a hole transport layer in an organic light-emitting diode, and an organic light-emitting diode including same. Here, Chemical Formulas A and B are as described in the specification.

18 Claims, 1 Drawing Sheet

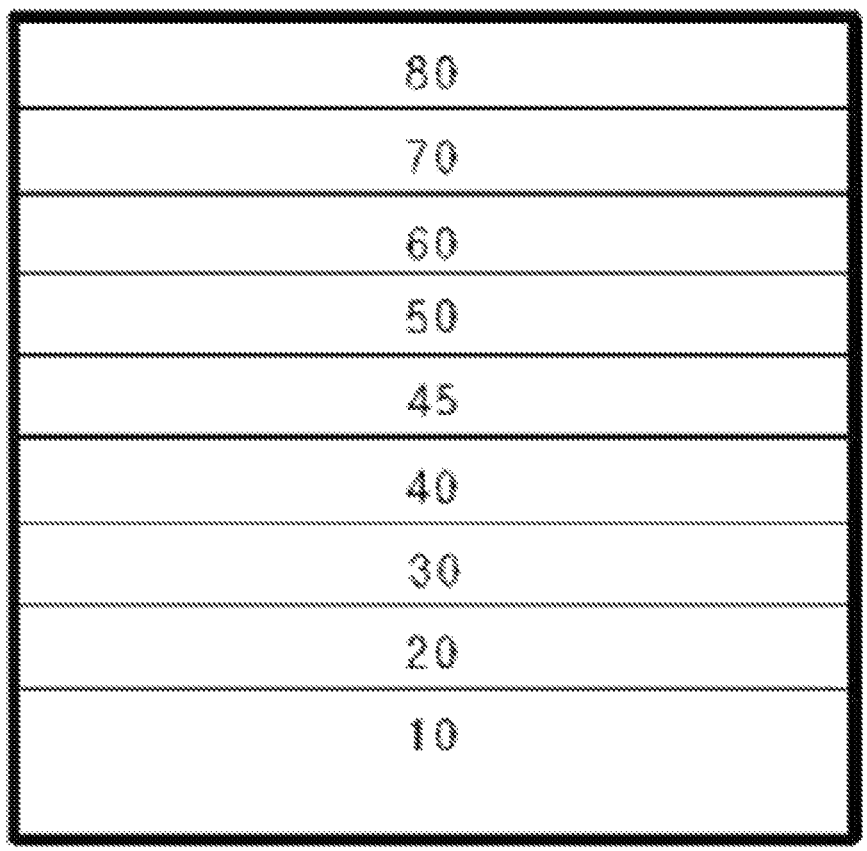

AMINE COMPOUND AND HIGH-EFFICIENCY ORGANIC LIGHT-EMITTING DIODE INCLUDING SAME

CROSS-REFERENCE TO RELATED APPLICATIONS

This application claims the priority of the Korean Patent Applications NO 10-2020-0029765 filed on Mar. 10, 2020 and NO 10-2021-0030861 filed on Mar. 9, 2021, in the Korean Intellectual Property Office, the disclosure of which is incorporated herein by reference.

BACKGROUND OF THE INVENTION

1. Field of the Invention

The present disclosure relates to an amine compound and a high efficiency organic light-emitting diode including the same and, more particularly, to an amine compound with a specific structure which exhibits high efficiency as a material for a hole transport layer in an organic light-emitting diode, and an organic light-emitting diode including same.

2. Description of the Prior Art

Organic light-emitting diodes (OLEDs), based on self-luminescence, are used to create digital displays with the advantage of having a wide viewing angle, being able to be made thinner and lighter than liquid crystal displays, and exhibiting a fast response time. Accordingly, OLEDs find applications in the full color display field or the illumination field.

In general, the term "organic light-emitting phenomenon" refers to a phenomenon in which electrical energy is converted to light energy by means of an organic material. An organic light-emitting diode using the organic light-emitting phenomenon has a structure usually including an anode, a cathode, and an organic material layer interposed therebetween.

In this regard, the organic material layer may have, for the most part, a multilayer structure consisting of different materials, for example, a hole injection layer, a hole transport layer, a light-emitting layer, an electron transport layer, and an electron injection layer in order to enhance the efficiency and stability of the organic light-emitting diode. In the organic light-emitting diode having such a structure, application of a voltage between the two electrodes injects a hole from the anode and an electron from the cathode to the organic layer. In the luminescent zone, the hole and the electron recombine to produce an exciton. When the exciton returns to the ground state from the excited state, the molecule of the organic layer emits light. Such an organic light-emitting diode is known to have characteristics such as self-luminescence, high luminance, high efficiency, low driving voltage, a wide viewing angle, high contrast, and high-speed response.

Materials used as organic layers in OLEDs may be divided according to functions into luminescent materials and charge transport materials, for example, a hole injection material, a hole transport material, an electron transport material, and an electron injection material and, as needed, further into an electron-blocking material or a hole-blocking material.

With regard to related arts pertaining to hole transport layers, reference may be made to Korean Patent No. 10-1074193 (issued Oct. 14, 2011), which describes an organic light-emitting diode using a carbazole structure fused with at least one benzene ring in a hole transport layer, and Korean Patent No. 10-1455156 (issued Oct. 27, 2014), which describes an organic light-emitting diode in which the HOMO energy level of an auxiliary light-emitting layer is set between those of a hole transport layer and a light-emitting layer.

In spite of enormous effort for fabricating organic light-emitting diodes in the related arts including the documents, there is still a continuing need to develop compounds having further improved emission efficiency for organic light-emitting diodes, and an organic light-emitting diode employing the same.

RELATED ART DOCUMENT

Korean Patent Number 10-1074193 (issued Oct. 14, 2011)
Korean Patent Number 10-1455156 (issued Oct. 27, 2014)

SUMMARY OF THE INVENTION

An aspect of the present disclosure is to provide a compound, which exhibits a high efficiency as a material for a hole transport layer in an organic light-emitting diode.

Another aspect of the present disclosure is to provide an organic light-emitting diode (OLED) comprising the compound.

According to an aspect thereof, the present disclosure provides an amine compound represented by the following Chemical Formula A or Chemical Formula B:

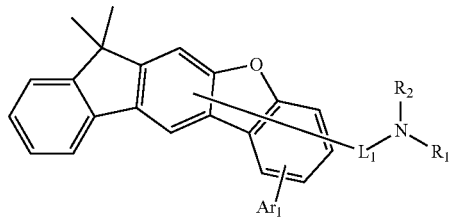

[Chemical Formula A]

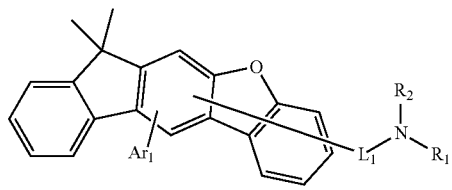

[Chemical Formula B]

wherein, the substituent $Ar_1$ is one selected from a substituted or unsubstituted alkyl of 1 to 30 carbon atoms, a substituted or unsubstituted haloalkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, and a substituted or unsubstituted arylsilyl of 5 to 30 carbon atoms, the linker $L_1$ is one selected from a single bond, a substituted or unsubstituted arylene of 6 to 30 carbon atoms, and a substituted or unsubstituted heteroarylene of 1 to 30 carbon atoms, the substituents $R_1$ and $R_2$, which may be same or different, are each independently one selected from a substituted or unsubstituted alkyl of 1 to 30 carbon atoms, a substituted or unsubstituted haloalkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, a nitro, and a halogen, $R_1$ and $R_2$ may be connected to each other to form a ring, and each of the carbon atoms on the aromatic rings of the indenodibenzofuran fused ring moiety

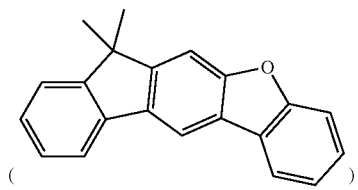 [SMILES: CC1(C)c2ccccc2-c2cc3c(cc21)oc1ccccc13]

in Chemical Formulas A and B may be bound with a hydrogen or deuterium, except for the carbon atoms bound with $Ar_1$ or $L_1$, wherein the term "substituted" in the expression "substituted or unsubstituted" means having at least one substituent selected from the group consisting of a deuterium atom, a cyano, a halogen, a hydroxy, a nitro, an alkyl of 1 to 24 carbon atoms, a cycloalkyl of 3 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, an alkylaryl of 7 to 24 carbon atoms, a heteroaryl of 2 to 24 carbon atoms, a heteroarylalkyl of 2 to 24 carbon atoms, an alkoxy of 1 to 24 carbon atoms, an alkylamino of 1 to 24 carbon atoms, a diarylamino of 12 to carbon atoms, a diheteroarylamino of 2 to 24 carbon atoms, an aryl(heteroaryl)amino of 7 to 24 carbon atoms, an alkylsilyl of 1 to 24 carbon atoms, an arylsilyl of 6 to 24 carbon atoms, an aryloxy of 6 to 24 carbon atoms, and an arylthionyl of 6 to 24 carbon atoms.

BRIEF DESCRIPTION OF THE DRAWINGS

The above and other aspects, features and advantages of the present disclosure will be more apparent from the following detailed description taken in conjunction with the accompanying drawings, in which:

FIG. 1 is a schematic diagram of an organic light-emitting diode according to some embodiments of the present disclosure

DETAILED DESCRIPTION OF THE EXEMPLARY EMBODIMENTS

Below, a detailed description will be given of the present disclosure. In each drawing of the present disclosure, sizes or scales of components may be enlarged or reduced from their actual sizes or scales for better illustration, and known components may not be depicted therein to clearly show features of the present disclosure. Therefore, the present disclosure is not limited to the drawings. When describing the principle of the embodiments of the present disclosure in detail, details of well-known functions and features may be omitted to avoid unnecessarily obscuring the presented embodiments.

In drawings, for convenience of description, sizes of components may be exaggerated for clarity. For example, since sizes and thicknesses of components in drawings are arbitrarily shown for convenience of description, the sizes and thicknesses are not limited thereto. Furthermore, throughout the description, the terms "on" and "over" are used to refer to the relative positioning, and mean not only that one component or layer is directly disposed on another component or layer but also that one component or layer is indirectly disposed on another component or layer with a further component or layer being interposed therebetween. Also, spatially relative terms, such as "below", "beneath", "lower", and "between", may be used herein for ease of description to refer to the relative positioning.

Throughout the specification, when a portion may "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

The amine compound according to the present invention may be represented by the following [Chemical Formula A] or [Chemical Formula B]:

[Chemical Formula A]

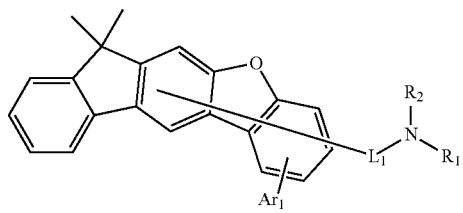

[Chemical Formula B]

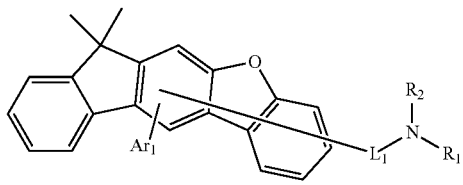

wherein, the substituent $Ar_1$ is one selected from a substituted or unsubstituted alkyl of 1 to 30 carbon atoms, a substituted or unsubstituted haloalkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, and a substituted or unsubstituted arylsilyl of 5 to 30 carbon atoms, the linker $L_1$ is one selected from a single bond, a substituted or unsubstituted arylene of 6 to 30 carbon atoms, and a substituted or unsubstituted heteroarylene of 1 to 30 carbon atoms, the substituents $R_1$ and $R_2$, which may be same or different, are each independently one selected from a substituted or unsubstituted alkyl of 1 to 30 carbon atoms, a substituted or unsubstituted haloalkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, a nitro, and a halogen, $R_1$ and $R_2$ may be connected to each other to form a ring, and each of the carbon atoms on the aromatic rings of the indenodibenzofuran fused ring moiety

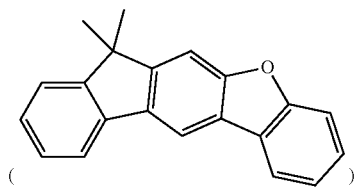 [SMILES: CC1(C)c2ccccc2-c2cc3c(cc21)oc1ccccc13]

in Chemical Formulas A and B may be bound with a hydrogen or deuterium, except for the carbon atoms bound with $Ar_1$ or $L_1$, wherein the term "substituted" in the expression "substituted or unsubstituted" means having at least one substituent selected from the group consisting of a deuterium, a cyano, a halogen, a hydroxy, a nitro, an alkyl of 1 to 24 carbon atoms, a cycloalkyl of 3 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, an alkylaryl of 7 to 24 carbon atoms, a heteroaryl of 2 to 24 carbon atoms, a heteroarylalkyl of 2 to 24 carbon atoms, an alkoxy of 1 to 24 carbon atoms, an alkylamino of 1 to 24 carbon atoms, a diarylamino of 12 to 24 carbon atoms, a diheteroarylamino of 2 to 24 carbon atoms, an aryl(heteroaryl)amino of 7 to 24 carbon atoms, an alkylsilyl of 1 to 24 carbon atoms, an arylsilyl of 6 to 24 carbon atoms, an aryloxy of 6 to 24 carbon atoms, and an arylthionyl of 6 to 24 carbon atoms.

The expression indicating the number of carbon atoms, such as "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical derived from an aromatic hydrocarbon by removing one hydrogen that is bonded to the aromatic hydrocarbon. The aromatic system may include a fused ring that is formed by adjacent substituents on the aryl radical.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl. At least one hydrogen atom of the aryl may be substituted by a deuterium atom, a halogen atom, a hydroxy, a nitro, a cyano, a silyl, an amino (—$NH_2$, —NH(R), —N(R') (R") wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The term "heteroaryl substituent" used in the compound of the present disclosure refers to a hetero aromatic radical of 2 to 50 carbon atoms, preferably 2 to 24 carbon atoms, bearing 1 to 3 heteroatoms selected from among N, O, P, Si, S, Ge, Se, and Te. In the aromatic radical, two or more rings may be fused. One or more hydrogen atoms on the heteroaryl may be substituted by the same substituents as on the aryl.

In addition, the term "heteroaromatic ring", as used herein, refers to an aromatic hydrocarbon ring bearing at least one heteroatom as aromatic ring member. In the heteroaromatic ring, one to three carbon atoms of the aromatic hydrocarbon may be substituted by at least one selected particularly from N, O, P, Si, S, Ge, Se, and Te.

As used herein, the term "alkyl" refers to an alkane missing one hydrogen atom and includes linear or branched structures. Examples of the alkyl substituent useful in the present disclosure include methyl, ethyl, propyl, isopropyl, isobutyl, sec-butyl, tert-butyl, pentyl, isoamyl, and hexyl. At least one hydrogen atom of the alkyl may be substituted by the same substituent as in the aryl.

The term "cyclo" as used in substituents of the present disclosure refers to a structure responsible for a mono- or polycyclic ring of saturated hydrocarbons in an alkyl. Concrete examples of cycloalkyl radicals include cyclopropyl, cyclobutyl, cyclopentyl, cyclohexyl, methylcyclopentyl, methylcyclohexyl, ethylcyclopentyl, ethylcyclohexyl, adamantyl, dicyclopentadienyl, decahydronaphthyl, norbornyl, bornyl, and isobornyl. One or more hydrogen atoms on the cycloalkyl may be substituted by the same substituents as on the aryl.

The term "alkoxy" as used in the compounds of the present disclosure refers to an alkyl or cycloalkyl singularly bonded to oxygen. Concrete examples of the alkoxy include methoxy, ethoxy, propoxy, isobutoxy, sec-butoxy, pentyloxy, iso-amyloxy, hexyloxy, cyclobutyloxy, cyclopentyloxy, adamantyloxy, dicyclopentyloxy, bornyloxy, and isobornyloxy. One or more hydrogen atoms on the alkoxy may be substituted by the same substituents as on the aryl.

Concrete examples of the arylalkyl used in the compounds of the present disclosure include phenylmethyl (benzyl), phenylethyl, phenylpropyl, naphthylmethyl, and naphthylethyl. One or more hydrogen atoms on the arylalkyl may be substituted by the same substituents as on the aryl.

Concrete examples of the silyl radicals used in the compounds of the present disclosure include trimethylsilyl, triethylsilyl, triphenylsilyl, trimethoxysilyl, dimethoxyphenylsilyl, diphenylmethylsilyl, diphenylvinlysilyl, methylcyclobutylsilyl, and dimethyl furylsilyl. One or more hydrogen atoms on the silyl may be substituted by the same substituents as on the aryl.

As used herein, the term "alkenyl" refers to an unsaturated hydrocarbon group that contains a carbon-carbon double bond between two carbon atoms and the term "alkynyl" refers to an unsaturated hydrocarbon group that contains a carbon-carbon triple bond between two carbon atoms.

As used herein, the term "alkylene" refers to an organic aliphatic radical regarded as derived from a linear or branched saturated hydrocarbon alkane by removal of two hydrogen atoms from different carbon atoms. Concrete examples of the alkylene include methylene, ethylene, propylene, isopropylene, isobutylene, sec-butylene, tert-butylene, pentylene, iso-amylene, hexylene, and so on. One or more hydrogen atoms on the alkylene may be substituted by the same substituents as on the aryl.

Furthermore, as used herein, the term "diarylamino" refers to an amine radical having two identical or different aryl groups bonded to the nitrogen atom thereof, the term "diheteroarylamino" refers to an amine radical having two identical or different heteroaryl groups bonded to the nitrogen atom thereof, and the term "aryl(heteroaryl)amino" refers to an amine radical having an aryl group and a heteroaryl group both bonded to the nitrogen atom thereof.

As more particular examples accounting for the term "substituted" in the expression "substituted or unsubstituted" used for compounds of Chemical Formulas A and B, the compounds may be substituted by at least one substituents selected from the group consisting of a deuterium atom, a cyano, a halogen, a hydroxy, a nitro, an alkyl of 1 to 12 carbon atoms, a halogenated alkyl of 1 to carbon atoms, an alkenyl of 2 to 12 carbon atoms, an alkynyl of 2 to 12 carbon atoms, a cycloalkyl of 3 to 12 carbon atoms, a heteroalkyl of 1 to 12 carbon atoms, an aryl of 6 to 18 carbon atoms, an arylalkyl of 7 to 20 carbon atoms, an alkylaryl of 7 to 20 carbon atoms, a heteroaryl of 2 to 18 carbon atoms, a heteroarylalkyl of 2 to 18 carbon atoms, an alkoxy of 1 to 12 carbon atoms, an alkylamino of 1 to 12 carbon atoms, a diarylamino of 12 to 18 carbon atoms, a diheteroarylamino of 2 to 18 carbon atoms, an aryl(heteroaryl)amino of 7 to 18 carbon atoms, an alkylsilyl of 1 to 12 carbon atoms, an arylsilyl of 6 to 18 carbon atoms, an aryloxy of 6 to 18 carbon atoms, an arylthionyl of 6 to 18 carbon atoms.

The amine compound of the present invention, represented by Chemical Formula A or B, is characterized by the structure in which the 9,9-dimethyl fluorene moiety represented by diagram A,

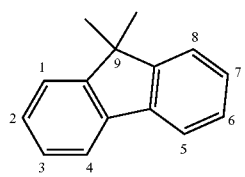

[diagram A: 9,9-dimethyl fluorene]

is bonded at position 7 (or 2) with the oxygen atom and in the benzofuran ring moiety

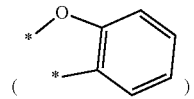 [SMILES: *Oc1ccccc1*]

and at position 6 (or 3) with an aromatic carbon atom near the carbon atom bonded to the oxygen atom in the benzofuran ring moiety

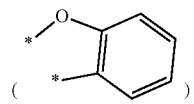 [SMILES: *Oc1ccccc1*]

to form an indenodibenzofuran fused ring structure

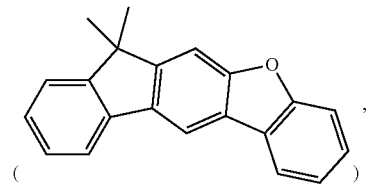 [SMILES: CC1(C)c2ccccc2-c2cc3c(cc21)oc1ccccc13]

which is the polycondensed ring system of "6-membered aromatic ring/5-membered ring having two methyl groups bound thereto/6-membered aromatic ring/5-membered ring bearing an oxygen atom/6-membered aromatic ring", wherein the amine radical

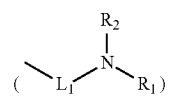

is connected to the terminal aromatic ring having the substituent $Ar_1$ thereon or to the middle 6-membered ring in the indenodibenzofuran ring structure of Chemical Formula A, or the amine radical

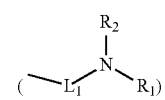

is connected to the middle 6-membered ring having the substituent $Ar_1$ thereon or to the terminal 6-membered aromatic ring in the indenodibenzofuran ring structure of Chemical Formula B, wherein the substituent $Ar_1$ is selected from a substituted or unsubstituted alkyl of 1 to 30 carbon atoms, a substituted or unsubstituted haloalkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, and a substituted or unsubstituted arylsilyl of 5 to 30 carbon atoms.

Compared to a structure in which the indenodibenzofuran framework has only the amine radical bonded thereto, the structural feature in which the substituent $Ar_1$ such as an aryl, a heteroaryl, an alkyl, etc. is further added to the middle aromatic ring or to the terminal aromatic ring of the indenodibenzofuran framework is made more planar and thus exhibits a higher deposition yield, whereby the organic light-emitting diode of the present disclosure can achieve high emission efficiency, compared to conventional organic light-emitting diodes.

According to an embodiment, the amine radical

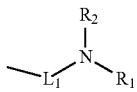

in Chemical Formulas A and B may be connected to the aromatic ring which has the substituent $Ar_1$ bonded thereto. According to an embodiment, the amine radical

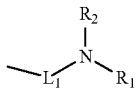

in Chemical Formulas A and B may be connected to the aromatic ring which does not have the substituent $Ar_1$ bonded thereto.

In an embodiment, the substituent $Ar_1$ in Chemical Formulas A and B may be one selected from a substituted or unsubstituted an aryl of 6 to 18 carbon atoms and a substituted or unsubstituted a heteroaryl of 2 to 18 carbon atoms, and the aryl of 6 to 18 carbon atoms for $Ar_1$ may be exemplified by phenyl, biphenyl, terphenyl, naphthalenyl, phenanthrenyl, and anthracenyl.

In addition, the substituent $Ar_1$ may be represented by the following Structural Formula A:

[Structural Formula A]

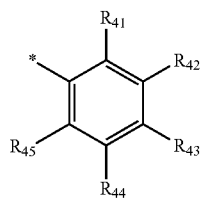

wherein "-*" denotes a bonding site at which the substituent $Ar_1$ is bonded to a carbon atom within the terminal aromatic ring or middle aromatic ring of the dibenzofuran moiety in Chemical Formulas A and B and, $R_{41}$ to $R_{45}$, which may be the same or different, are each independently selected from a hydrogen, a deuterium, a cyano, a halogen, a hydroxy, a nitro, an alkyl of 1 to 24 carbon atoms, a cycloalkyl of 3 to 24 carbon atoms, a halogenated alkyl of 1 to 24 carbon atoms, an alkenyl of 2 to 24 carbon atoms, an alkynyl of 2 to carbon atoms, a heteroalkyl of 1 to 24 carbon atoms, an aryl of 6 to 24 carbon atoms, an arylalkyl of 7 to 24 carbon atoms, an alkylaryl of 7 to 24 carbon atoms, a heteroaryl of 2 to 50 carbon atoms, a heteroarylalkyl of 2 to 24 carbon atoms, an alkoxy of 1 to carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

According to an embodiment, at least one of the substituents $R_1$ and $R_2$ in Chemical Formulas A and B may be any one selected from a substituted or unsubstituted an aryl of 6 to 18 carbon atoms and a substituted or unsubstituted a heteroaryl of 2 to 18 carbon atoms.

In this regard, the substituents $R_1$ and $R_2$, which may be same or different, may be each independently a substituted or unsubstituted an aryl of 6 to 18 carbon atoms or a substituted or unsubstituted a heteroaryl of 2 to 18 carbon atoms. When the substituents $R_1$ and $R_2$, which may be same or different, are each independently an aryl of 6 to 18 carbon atoms, each of them may be selected from phenyl, biphenyl, and terphenyl.

According to an embodiment, at least one of the substituents $Ar_1$, $R_1$, and $R_2$ in Chemical Formulas A and B may be a deuterium-substituted of 6 to 18 carbon atoms. In this regard, at least one of the substituents $Ar_1$, $R_1$, and $R_2$ may be a deuterium-substituted phenyl.

In an embodiment, the substituent $Ar_1$ may be bonded to the terminal benzene ring of the dibenzofuran moiety

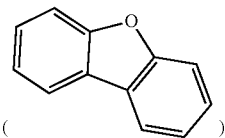 [SMILES: c1ccc2c(c1)oc1ccccc12]

at position 1, 2, 3, or 4 in Chemical Formula A, and the substituent $Ar_1$ may be bonded to middle aromatic ring of the dibenzofuran moiety

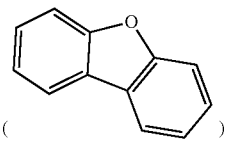 [SMILES: c1ccc2c(c1)oc1ccccc12]

at the carbon adjacent to the aromatic carbon atom bonded to the oxygen atom or at the carbon atom opposite thereto in Chemical Formula B.

In an embodiment, the linker $L_1$ in Chemical Formula A or B may be selected from a single bond and a substituted or unsubstituted arylene of 6 to 18 carbon atoms or may be selected from a single bond, phenylene, naphthalenylene, and biphenylene.

In addition, concrete examples of the amine compound represented by Chemical Formula A or B include the following [Compound 1] to [Compound 72]:
[Compound 1]
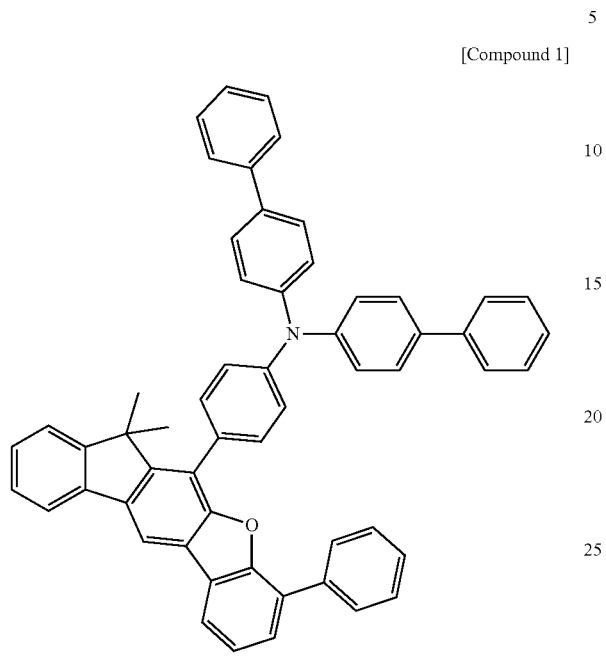
[Compound 2]
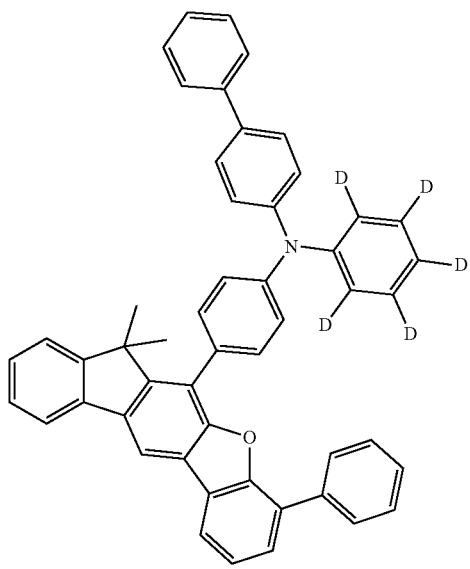
[Compound 3]
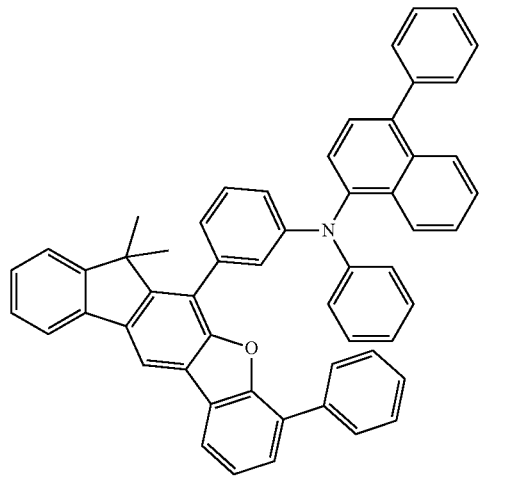
[Compound 4]
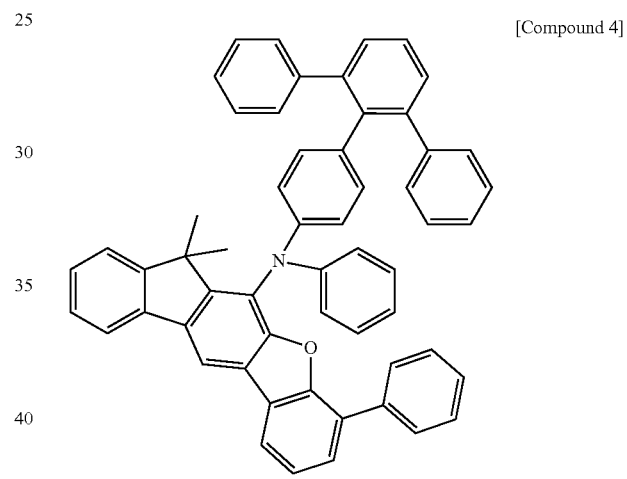
[Compound 5]
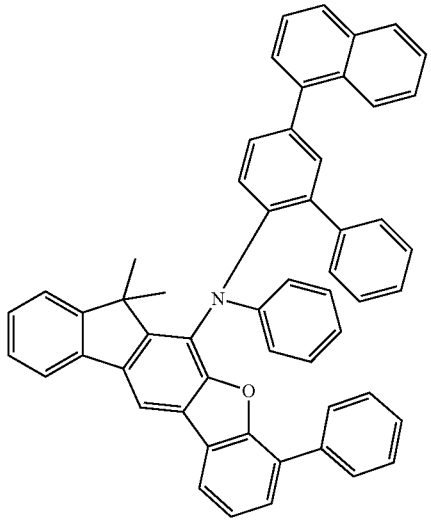

-continued
[Compound 6]
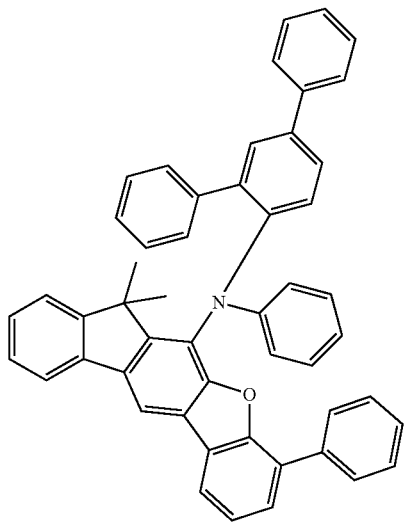
[Compound 7]
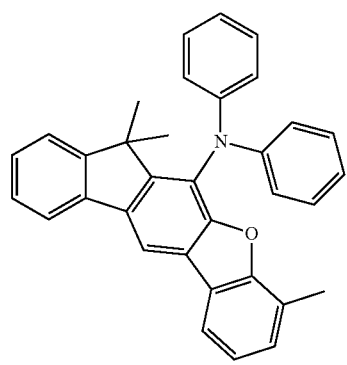
[Compound 8]
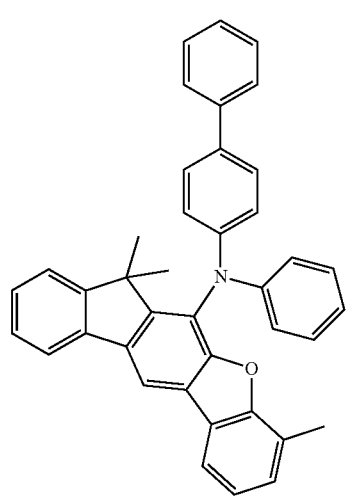
[Compound 9]
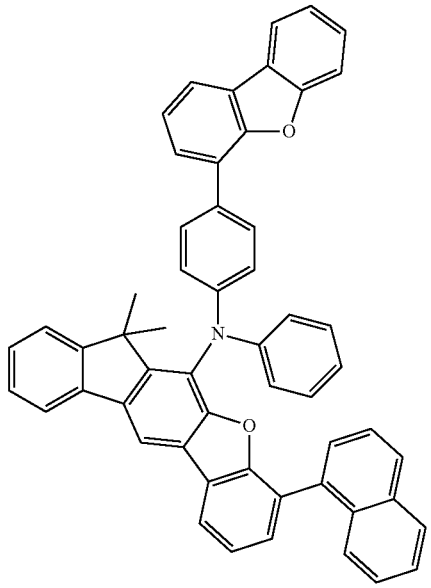
[Compound 10]
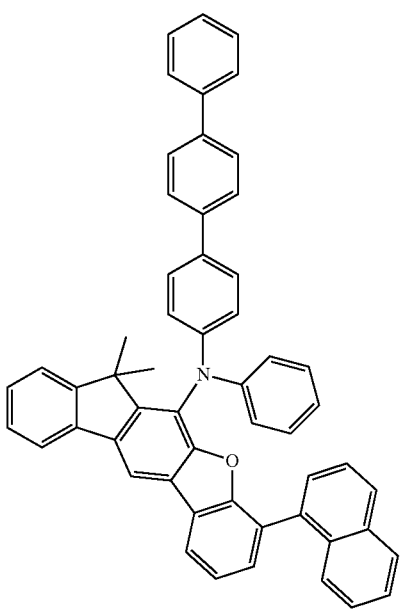

[Compound 11]
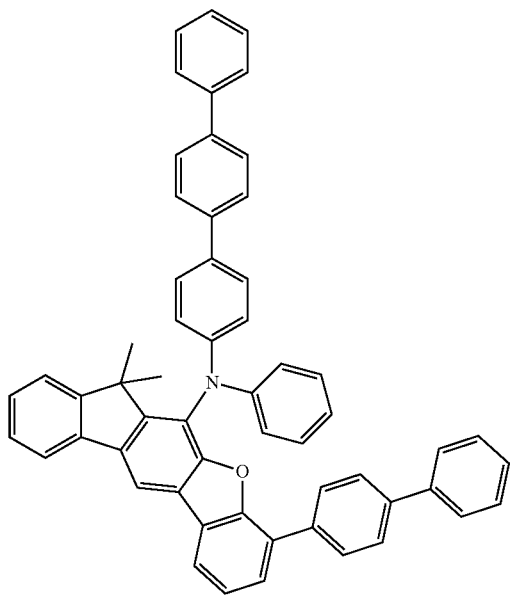
[Compound 12]
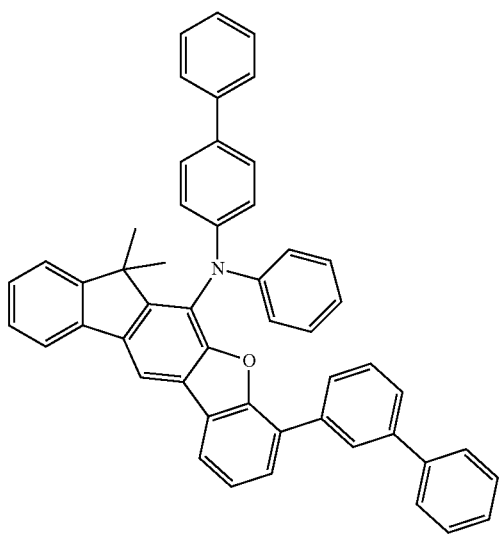
[Compound 13]
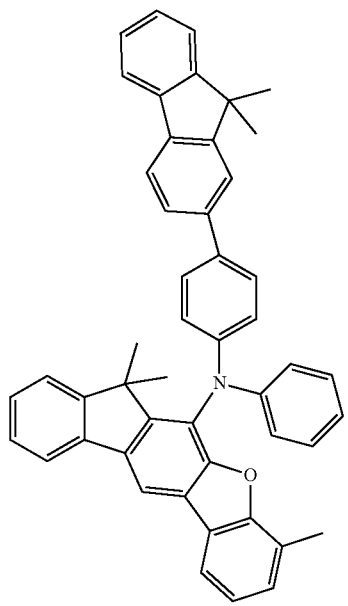
[Compound 14]
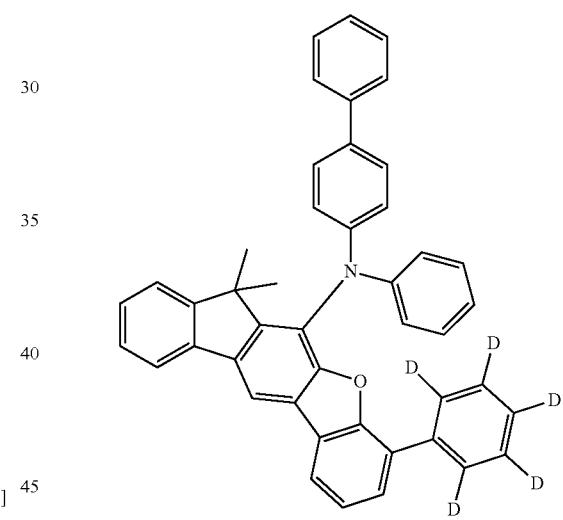
[Compound 15]
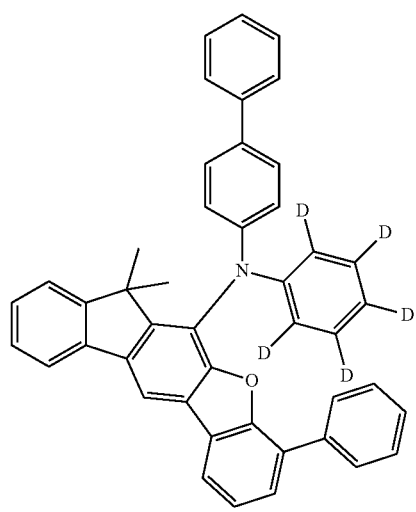

[Compound 16]
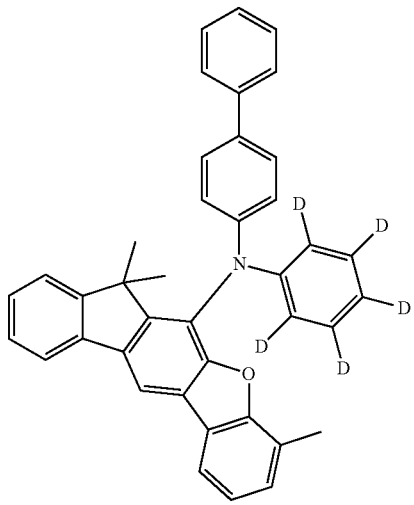
[Compound 17]
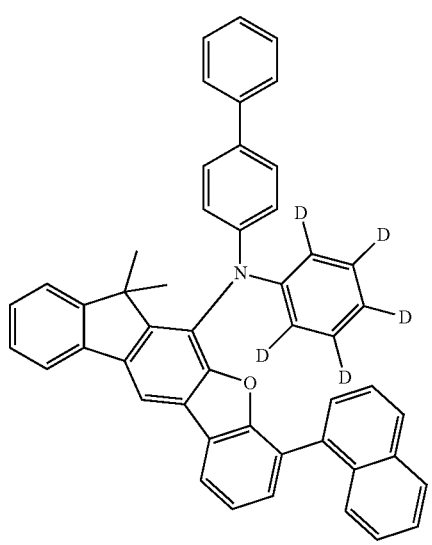
[Compound 18]
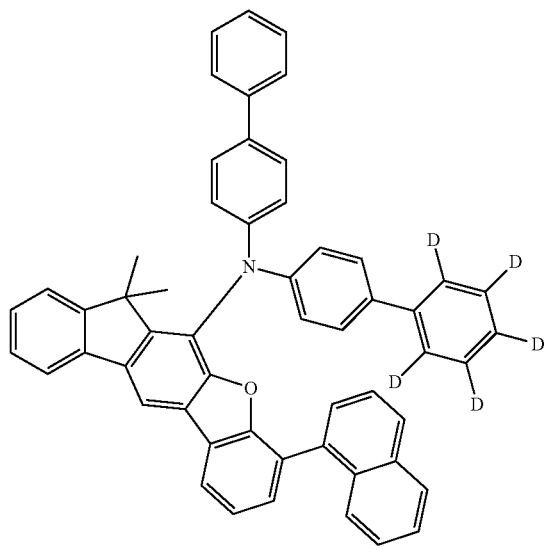
[Compound 19]
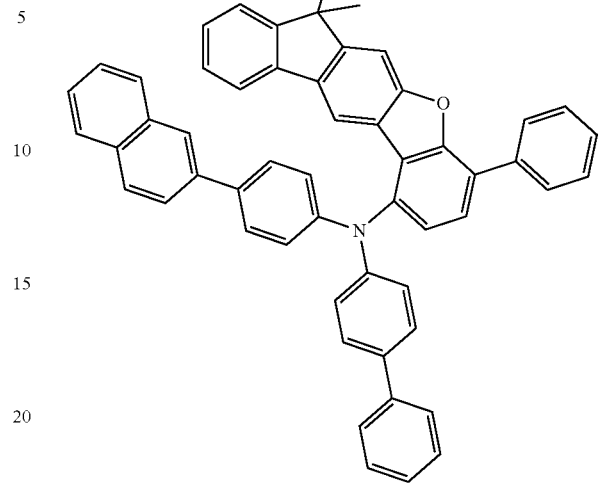
[Compound 20]
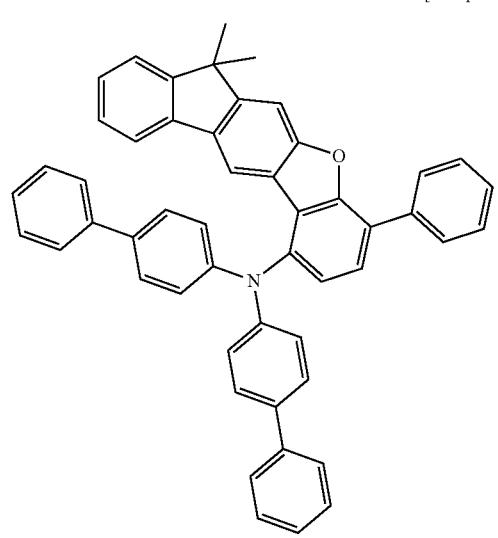
[Compound 21]
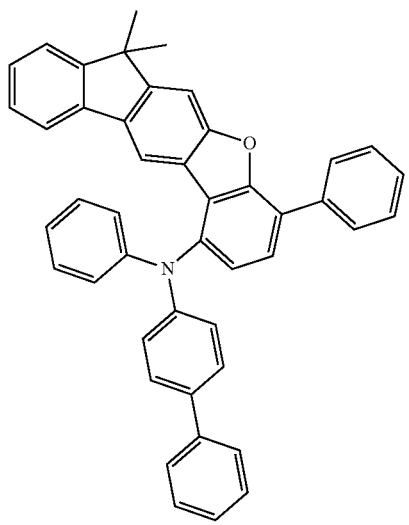

[Compound 22]
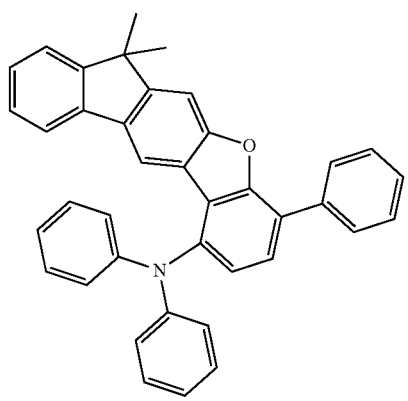
[Compound 23]
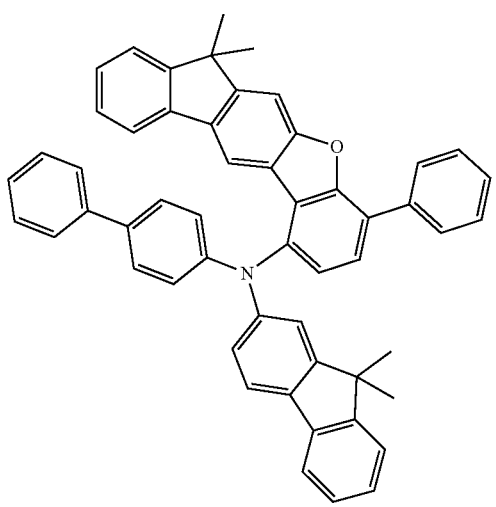
[Compound 24]
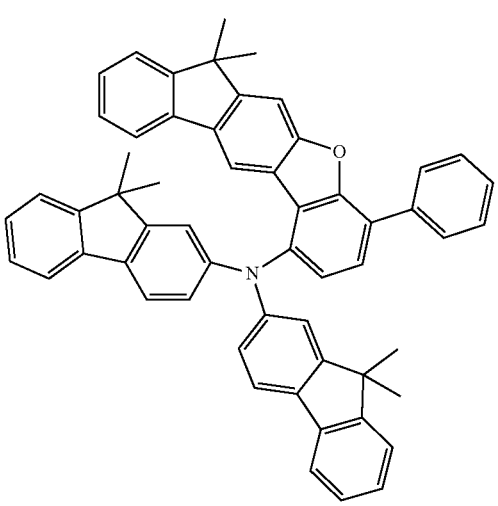
[Compound 25]
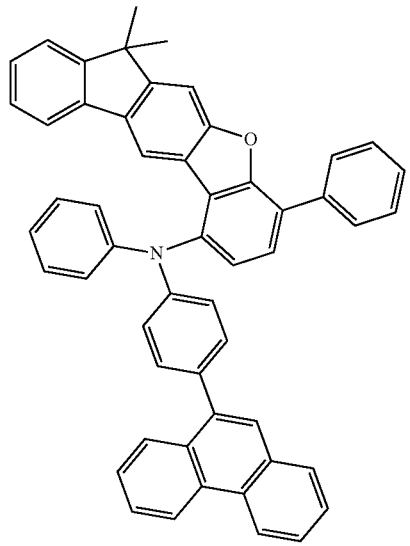
[Compound 26]
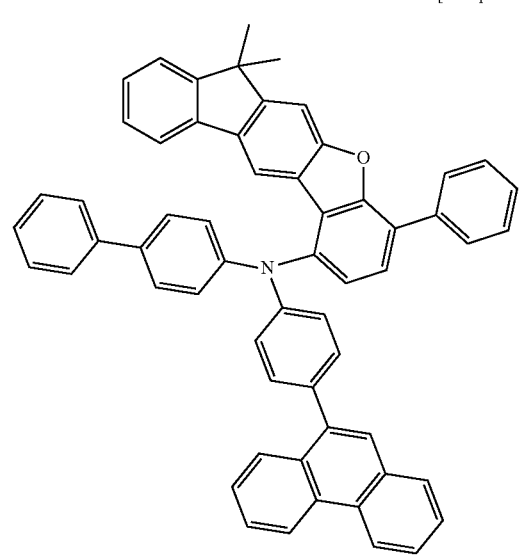
[Compound 27]
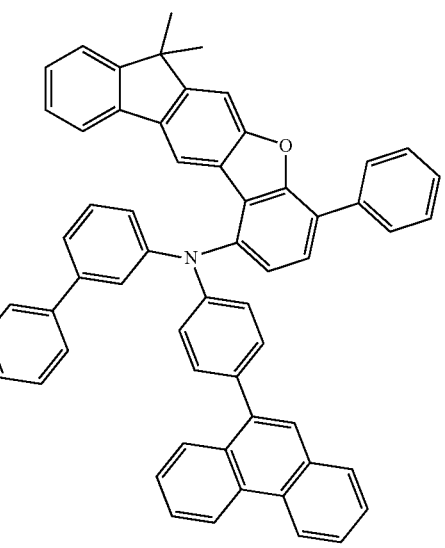

[Compound 28]
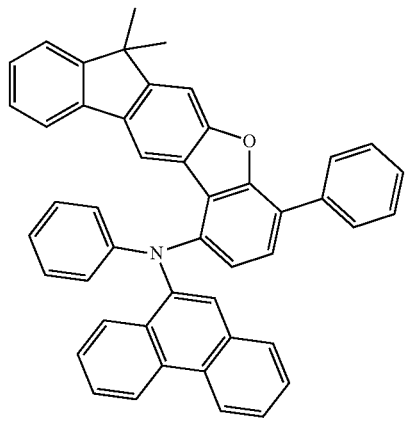
[Compound 29]
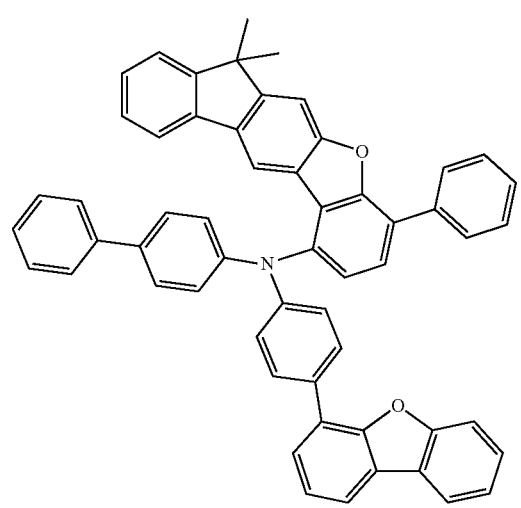
[Compound 30]
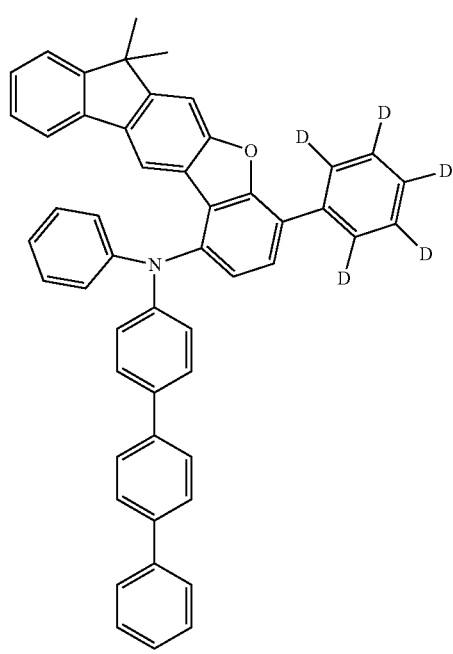
[Compound 31]
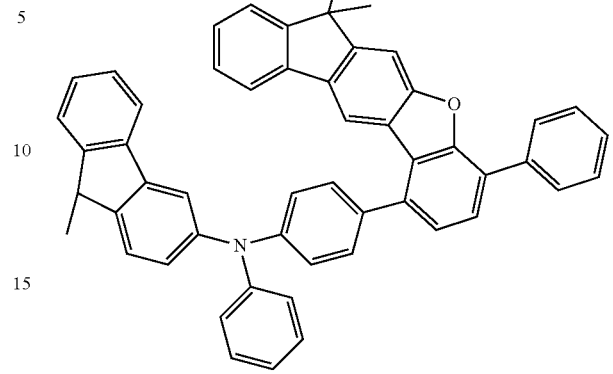
[Compound 32]
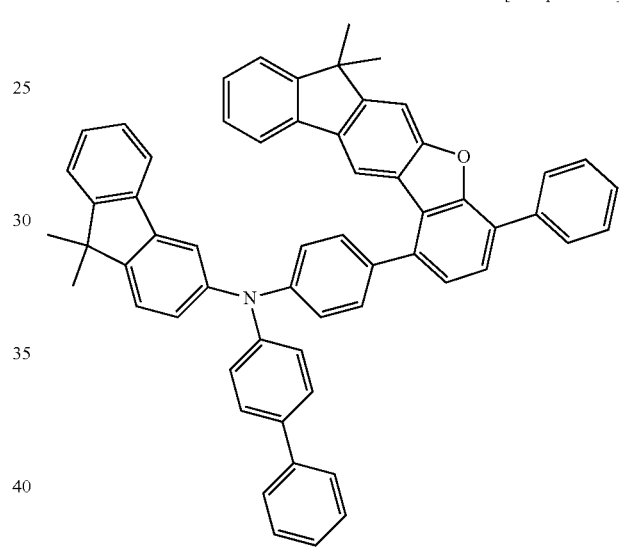
[Compound 33]
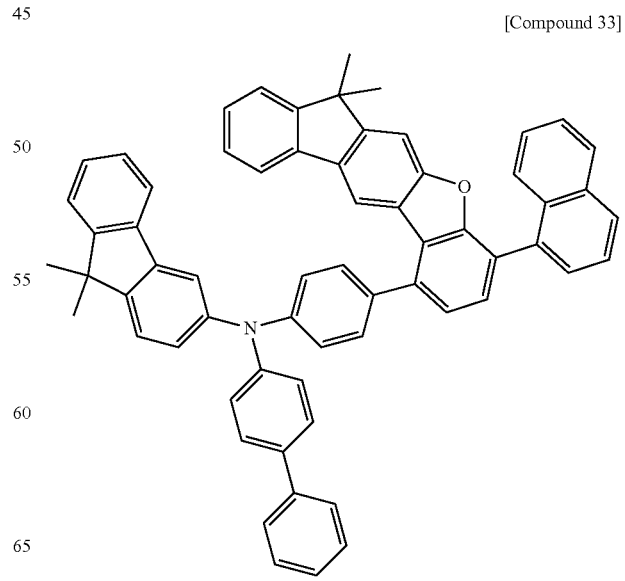

[Compound 34]
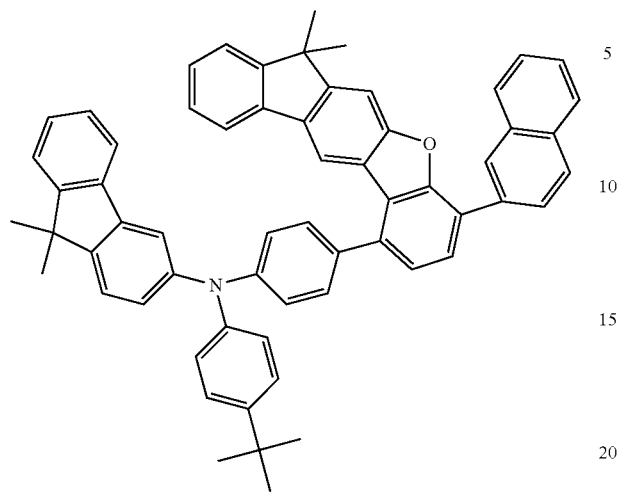
[Compound 35]
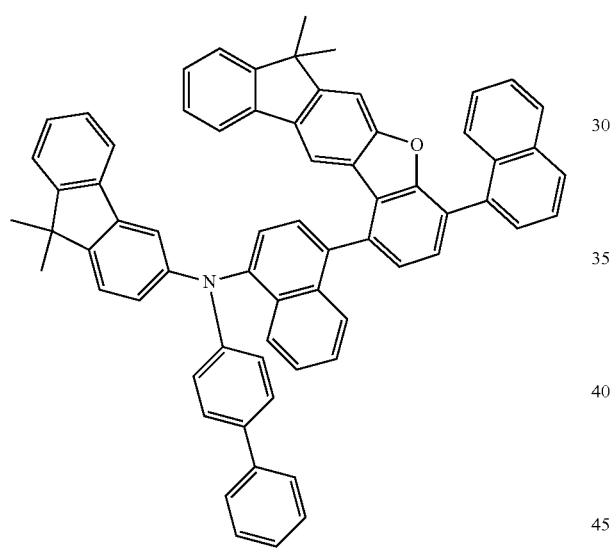
[Compound 36]
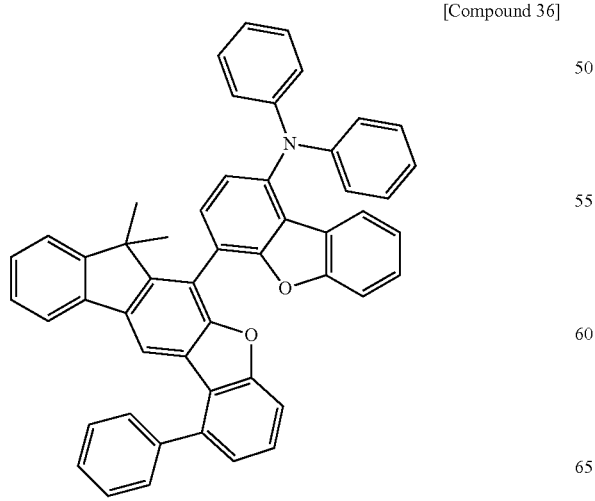
[Compound 37]
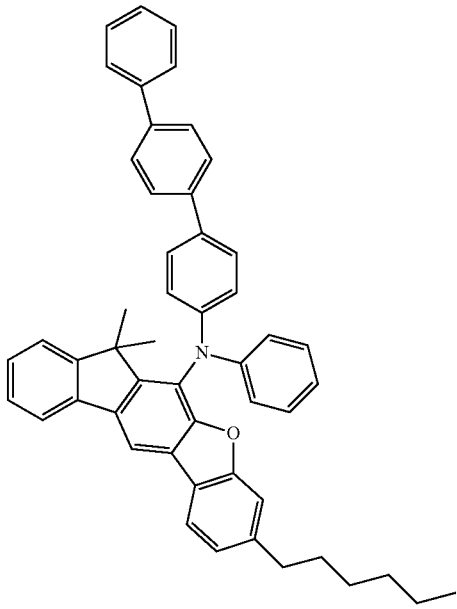
[Compound 38]
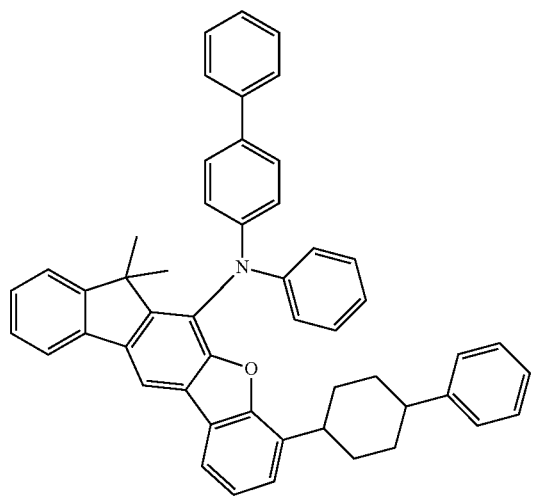

[Compound 39]
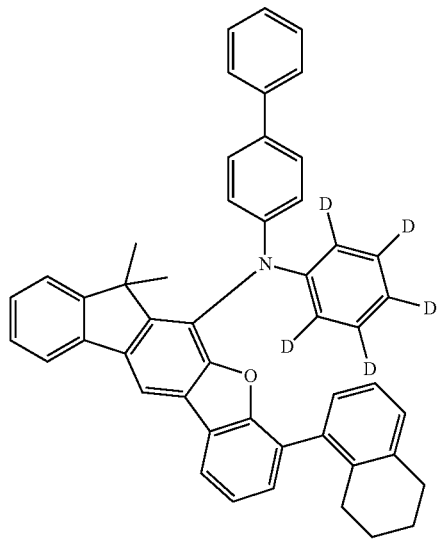
[Compound 40]
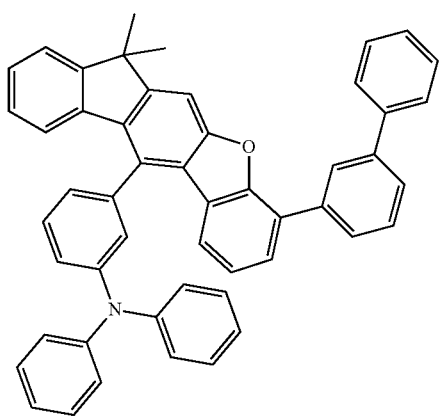
[Compound 41]
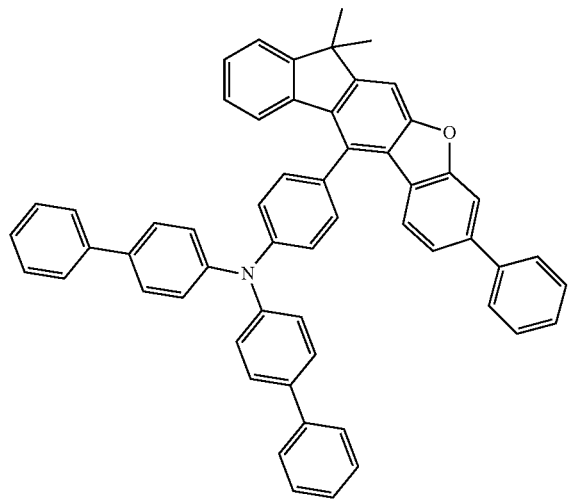
[Compound 42]
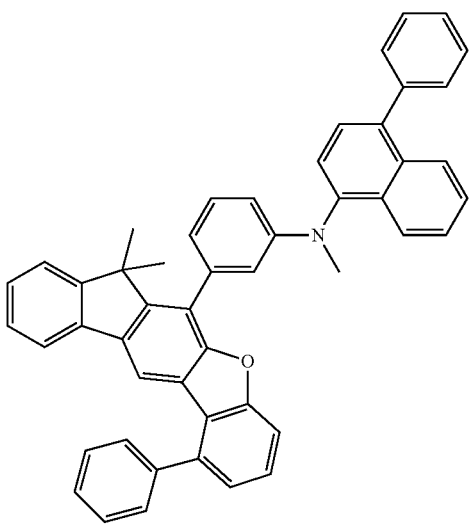
[Compound 43]
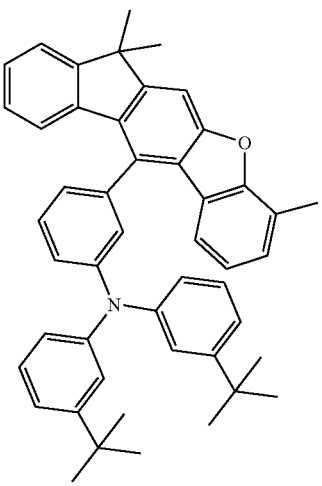
[Compound 44]
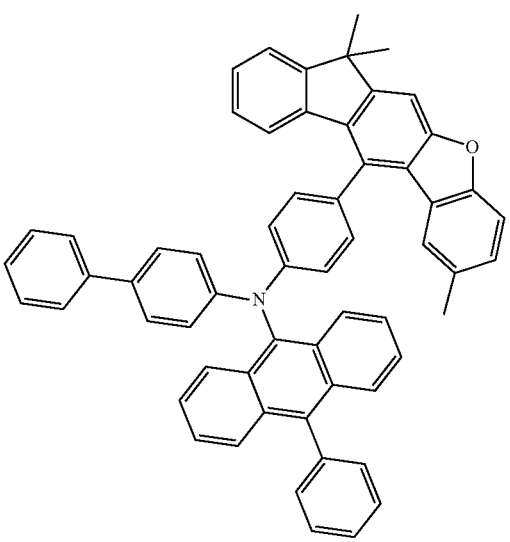

[Compound 45]
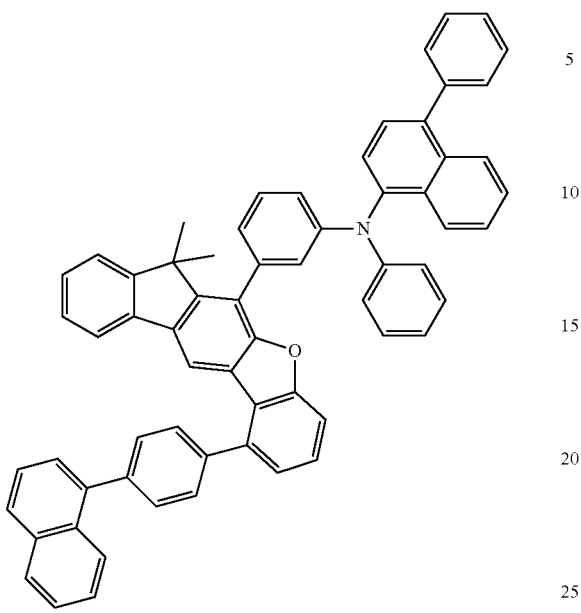
[Compound 46]
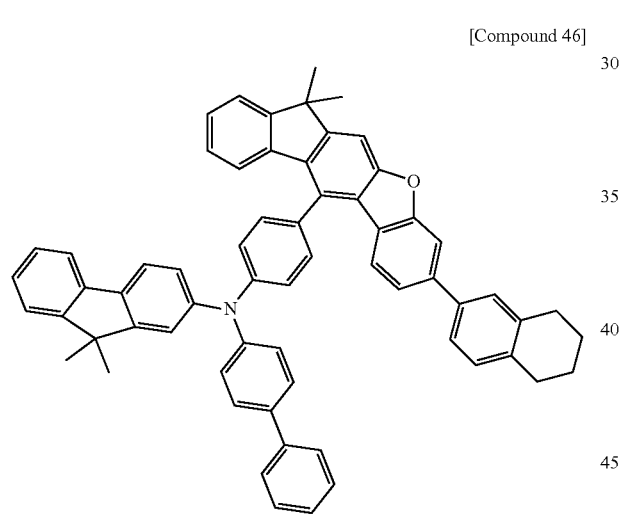
[Compound 47]
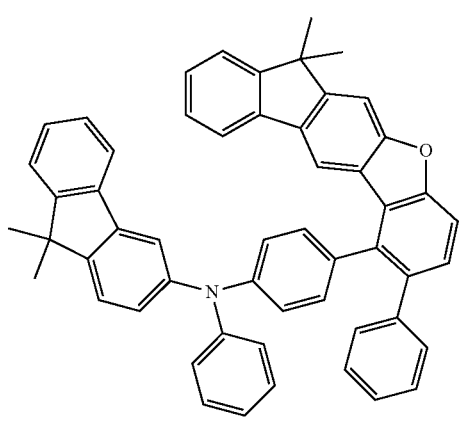
[Compound 48]
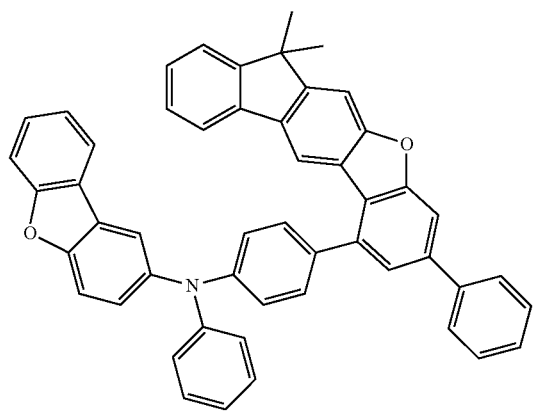
[Compound 49]
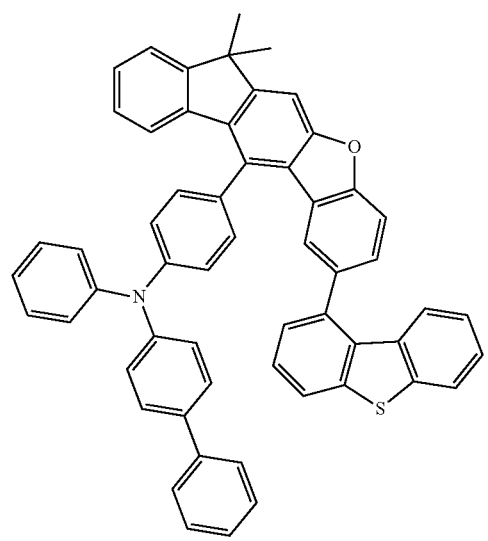
[Compound 50]
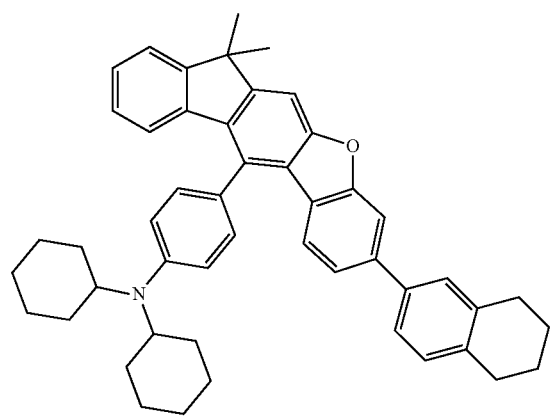

[Compound 51]
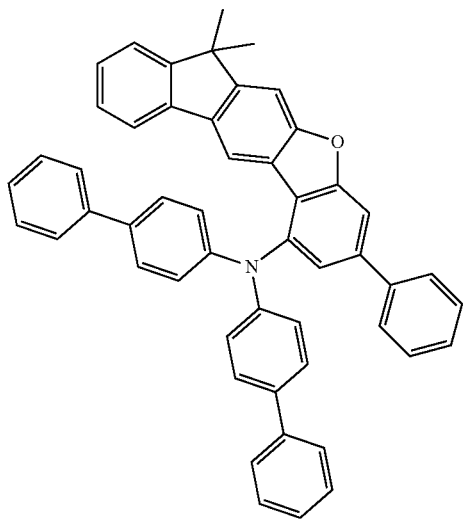
[Compound 52]
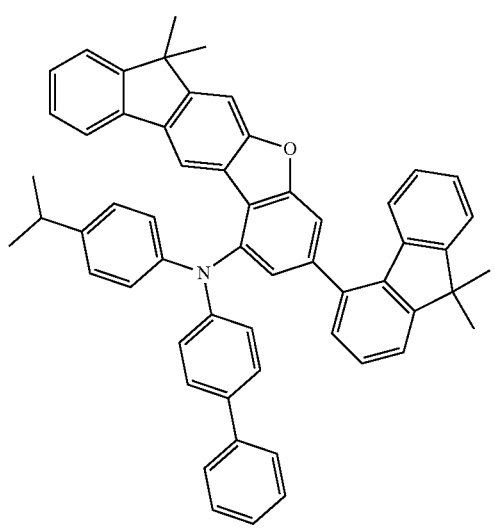
[Compound 53]
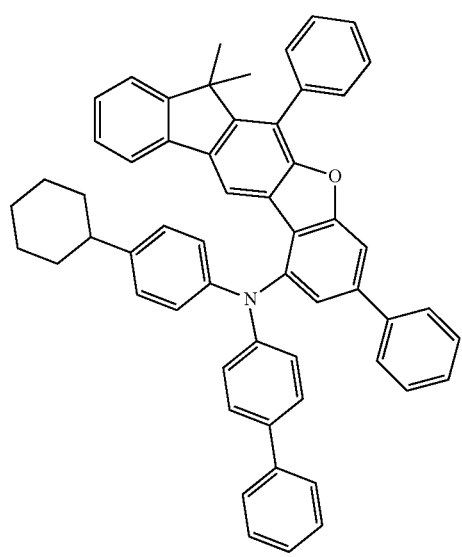
[Compound 54]
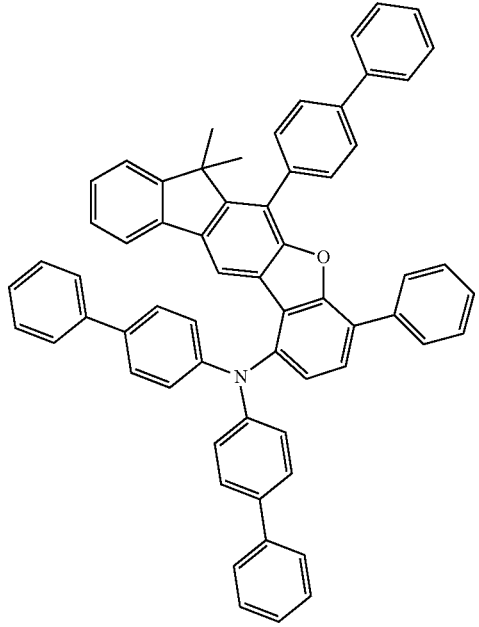
[Compound 55]
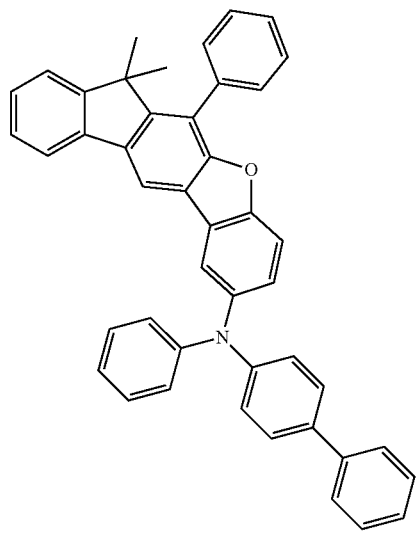
[Compound 56]
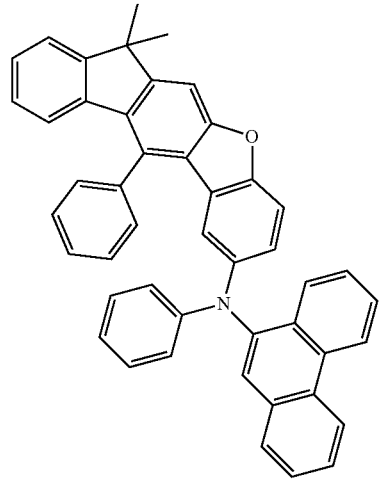

[Compound 57]
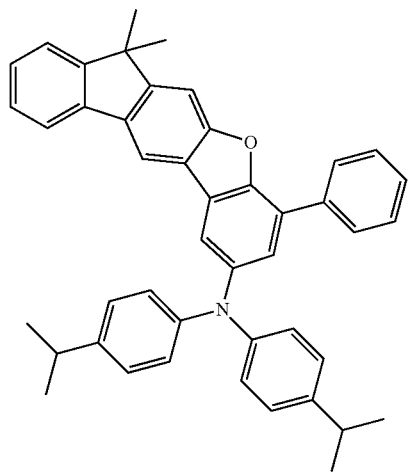
[Compound 58]
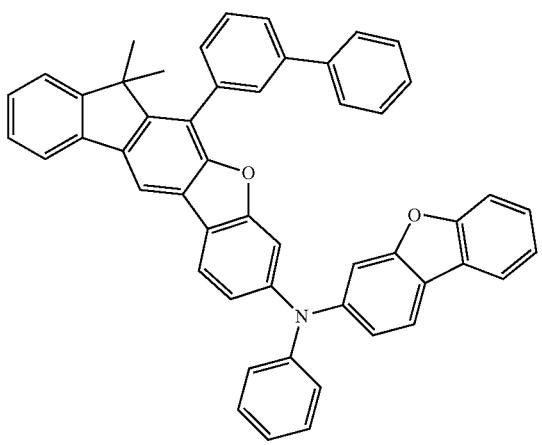
[Compound 59]
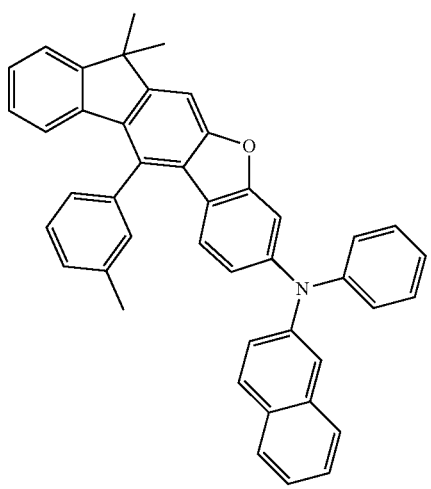
[Compound 60]
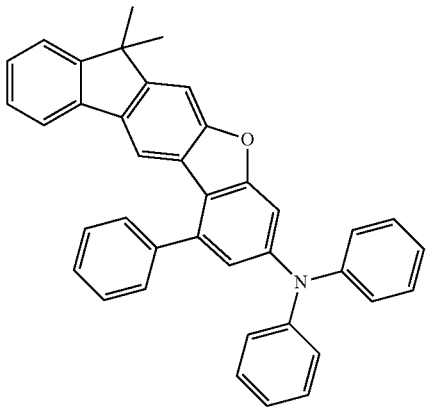
[Compound 61]
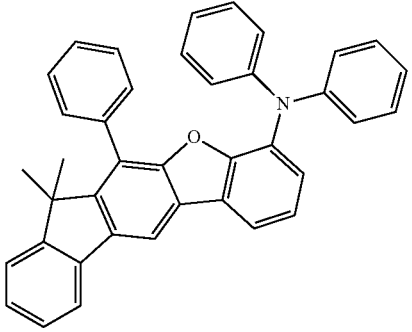
[Compound 62]
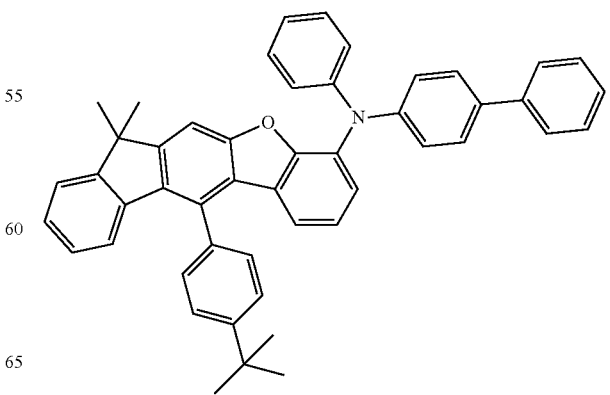

[Compound 63]
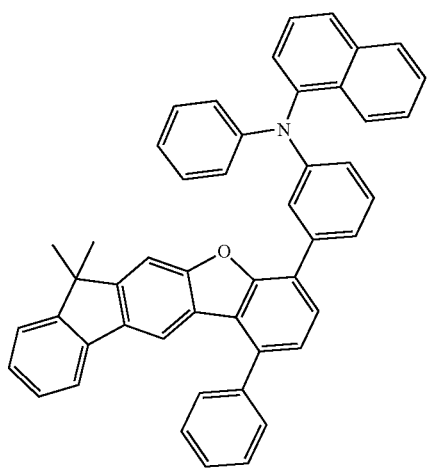
[Compound 64]
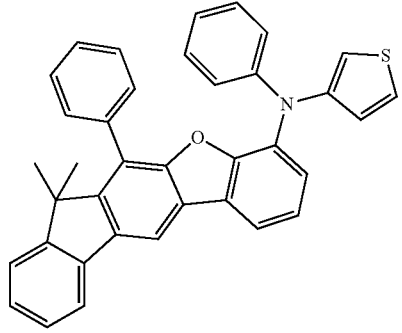
[Compound 65]
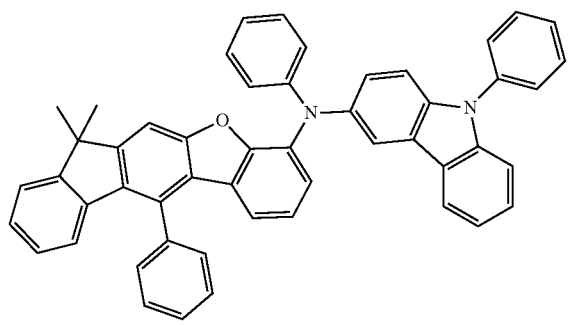
[Compound 66]
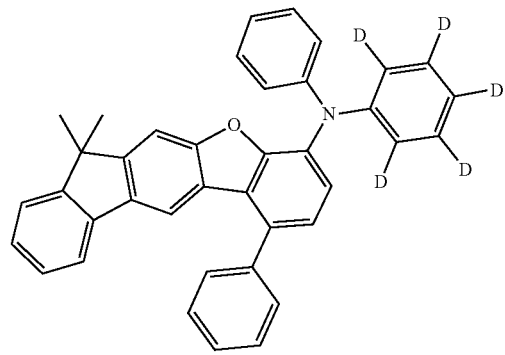
[Compound 67]
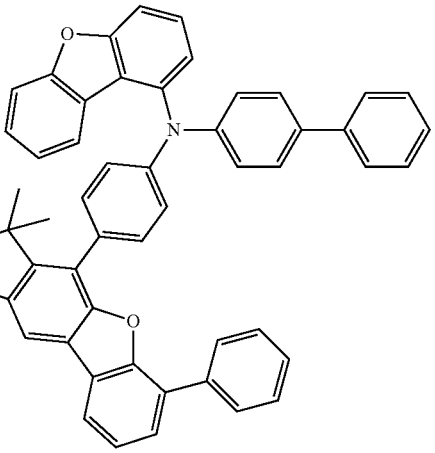
[Compound 68]
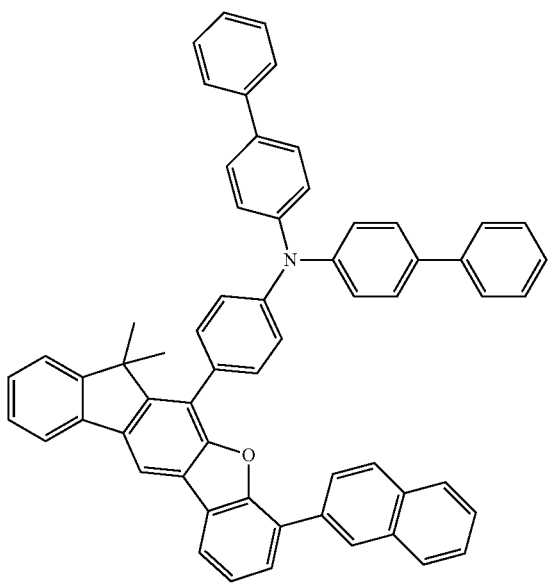
[Compound 69]
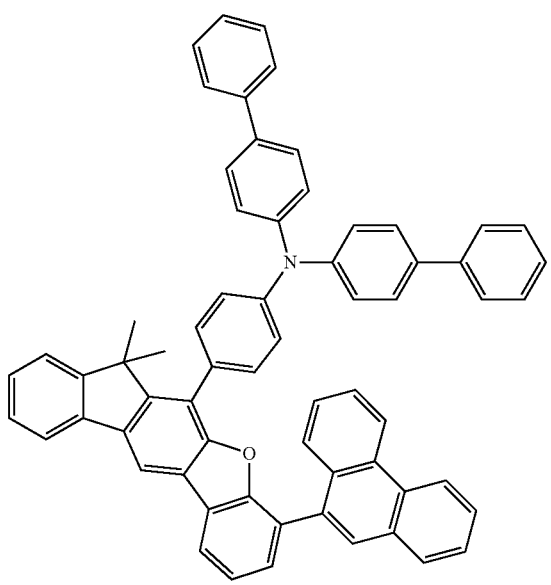

[Compound 70]

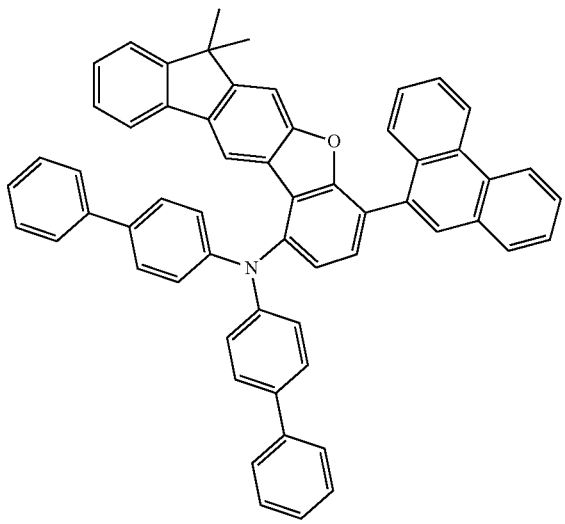

[Compound 71]

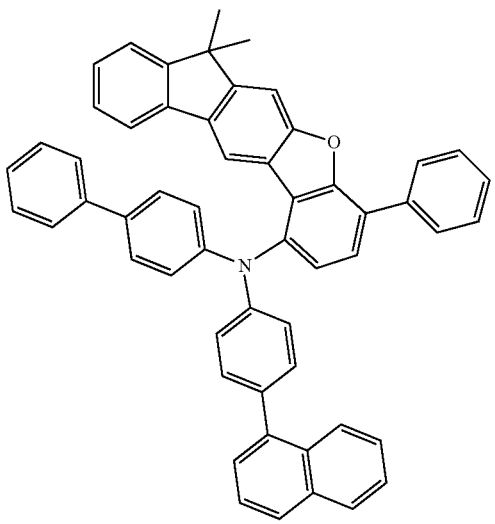

[Compound 72]

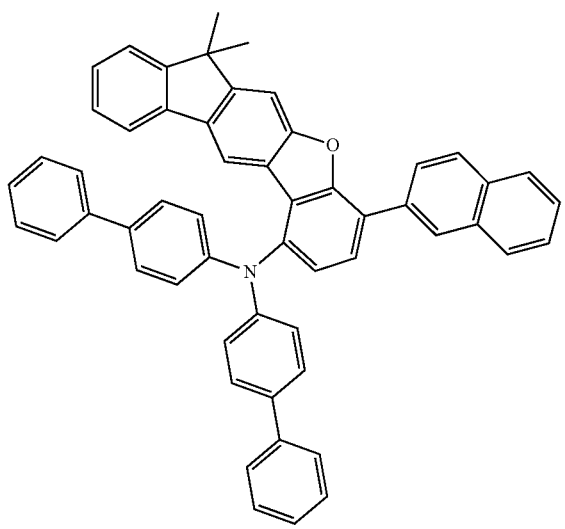

In a particular embodiment thereof, the present invention provides an organic light-emitting diode comprising: a first electrode; a second electrode facing the first electrode; and an organic layer interposed between the first electrode and the second electrode, wherein the organic layer comprises at least one of the amine compounds represented by Chemical Formulas A and B. Having such structural characteristics, the organic light-emitting diode according to the present disclosure can drive at high luminous efficiency.

In this regard, the organic light-emitting diode according to the present disclosure may include at least one of a hole injection layer, a hole transport layer, a functional layer capable of both hole injection and hole transport, an electron blocking layer, a light-emitting layer, an electron transport layer, an electron injection layer, and a capping layer.

Throughout the description of the present disclosure, the phrase "(an organic layer) includes at least one organic compound" may be construed to mean that "(an organic layer) may include a single organic compound species or two or more difference species of organic compounds falling within the scope of the present disclosure".

In a further particular embodiment of the present disclosure, the organic light-emitting diode may comprise: the first electrode as an anode; the second electrode as a cathode; and the organic layer interposed between the anode and the cathode, the organic layer including a hole transport layer or a hole injection layer, wherein the amine compound according to the present disclosure may be used in the hole transport layer. That is, at least one of the amine compounds represented by Chemical Formulas A and B may be used as a material for a hole transport layer in the organic light-emitting diode. According to a particular embodiment, the hole transport layer may be divided into two or more sub-hole transport layers employing respective different materials therein, wherein the amine compound may use at least one of the sub-layers.

In an exemplary embodiment thereof, the present disclosure provides an organic light-emitting comprising: a first electrode; a second electrode facing the first electrode; and an organic layer interposed between the first electrode and the second electrode and including at least one of the amine compounds represented by Chemical Formulas A and B, wherein the hole transport layer includes a first hole transport layer and a second hole transport layer different in material from the first hole transport layer and employing the amine compound. In addition, the present disclosure provides an organic light-emitting diode comprising: an anode as a first electrode; a cathode as a second electrode facing the first electrode; and a hole injection layer, a first hole transport layer, a second hole transport layer, a light-emitting layer, an electron transport layer, and an electron injection layer sequentially disposed in that order between the anode and the cathode, wherein the first hole transport layer and the second hole transport layer are different in terms of material and the second hole transport layer employs an amine compound represented by Chemical Formula A or B.

Here, the light-emitting layer in the organic light-emitting diode of the present disclosure includes a host and a dopant. As the host, an anthracene derivative represented by the following Chemical Formula C may be used, but without limitations thereto:

[Chemical Formula C]

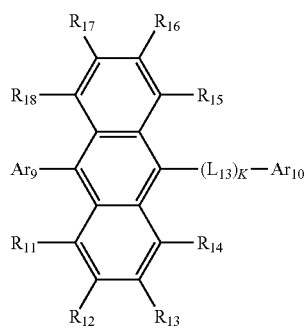

wherein.

$R_{11}$ to $R_{18}$, which may be the same or different, are each independently selected from a hydrogen, a deuterium, a substituted or unsubstituted alkyl of 1 to 30 carbon atoms, an alkenyl of 2 to 24 carbon atoms, an alkynyl of 2 to 24 carbon atoms, a substituted or unsubstituted aryl of 6 to 50 carbon atoms, a substituted or unsubstituted cycloalkyl of 3 to 30 carbon atoms, a substituted or unsubstituted heterocycloalkyl of 1 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a nitro, a cyano, and a halogen, $Ar_9$ and $Ar_{10}$, which may be the same or different, are each independently selected from a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, and a substituted or unsubstituted heteroaryl of 2 to carbon atoms;

$L_{13}$, which functions as a linker, is a single bond or is selected from a substituted or unsubstituted arylene of 6 to 20 carbon atoms, and a substituted or unsubstituted heteroarylene of 2 to 20 carbon atoms; and k is an integer of 1 to 3, wherein when k is 2 or greater, the corresponding $L_{13}$'s are each the same or different.

For a more exemplary host, $Ar_9$ in Chemical Formula C may be a substituent represented by the following Chemical Formula C-1:

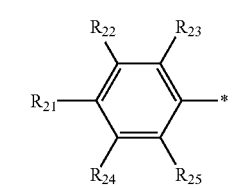

[Chemical Formula C-1]

wherein, $R_{21}$ to $R_{25}$, which may be the same or different, are as defined for $R_1$ to $R_{10}$, above; and may each be linked to an adjacent one to form a saturated or unsaturated cyclic ring. In this case, $L_{13}$ may be a single bond or a substituted or unsubstituted arylene of 6 to 20 carbon atoms, and k may be 1 or 2, with the proviso that when k is 2, corresponding $L_{13}$'s may be the same or different.

According to one embodiment, the anthracene derivative may be one selected from the compounds represented by the following <Chemical Formula 22> to <Chemical Formula 60>:

<Chemical Formula 22>

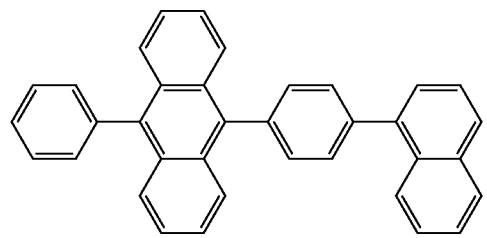

<Chemical Formula 23>

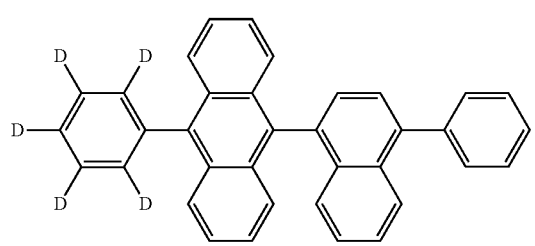

<Chemical Formula 24>

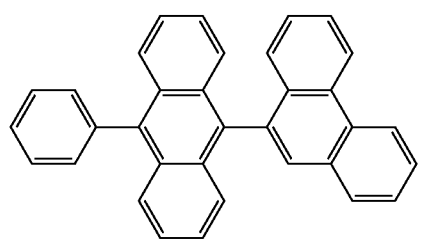

<Chemical Formula 25>

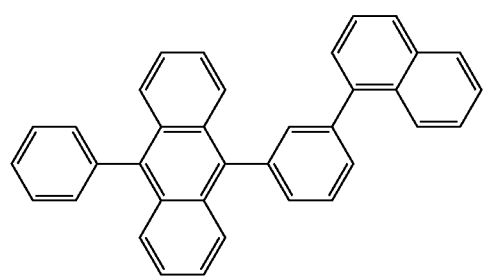

<Chemical Formula 26>

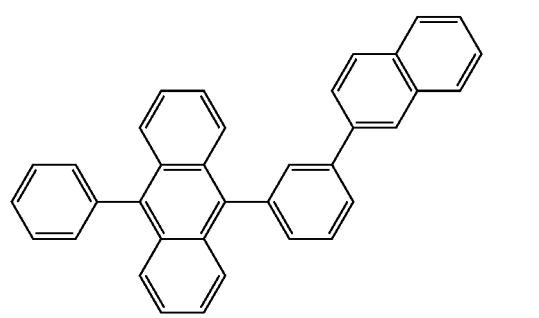

<Chemical Formula 27>
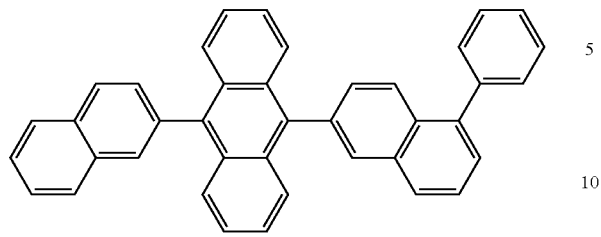
<Chemical Formula 28>
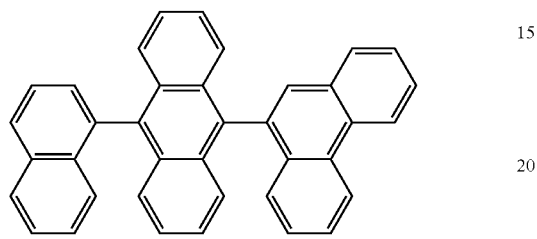
<Chemical Formula 29>
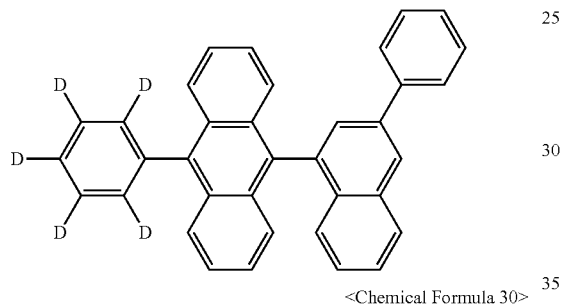
<Chemical Formula 30>
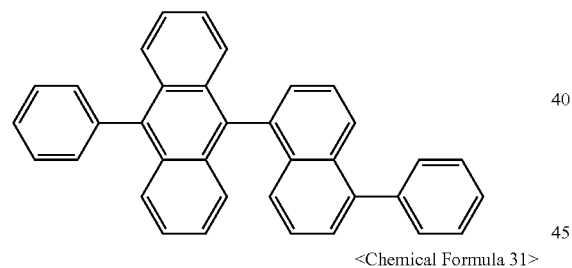
<Chemical Formula 31>
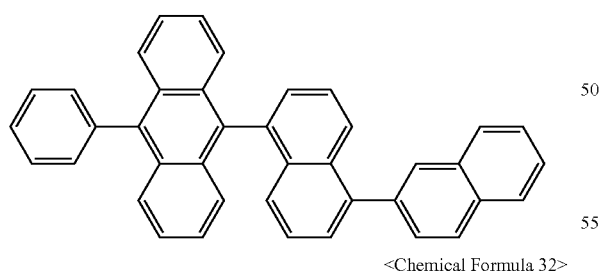
<Chemical Formula 32>
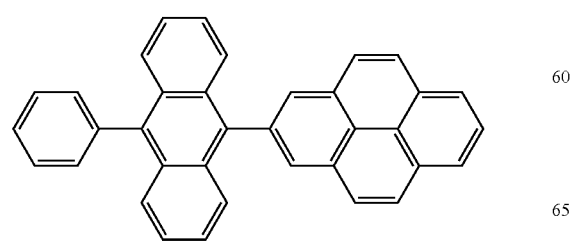
<Chemical Formula 33>
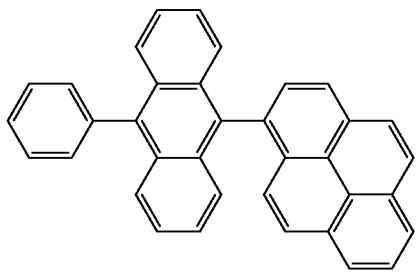
<Chemical Formula 34>
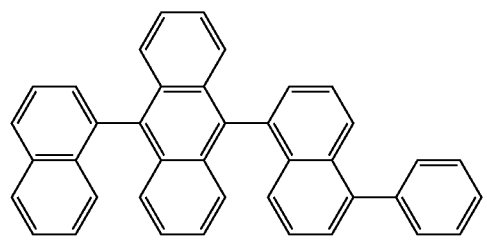
<Chemical Formula 35>
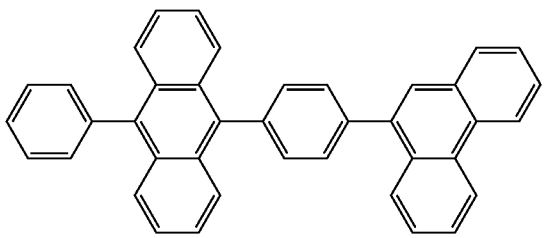
<Chemical Formula 36>
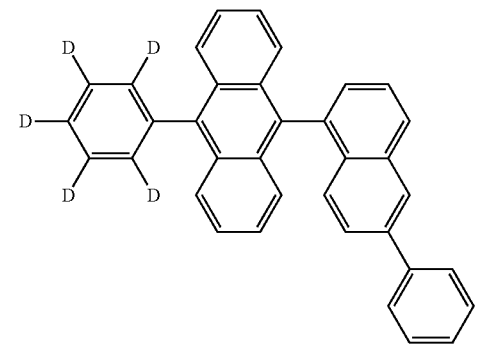
<Chemical Formula 37>
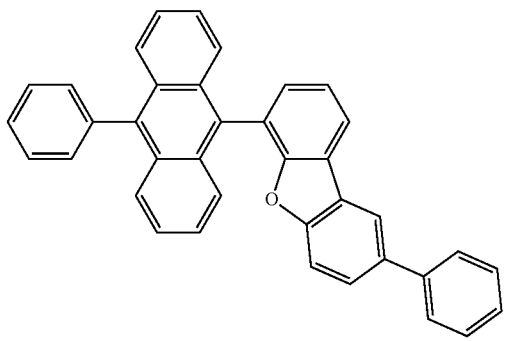

<Chemical Formula 38>
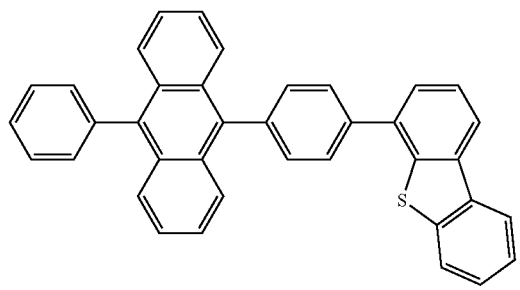
<Chemical Formula 39>
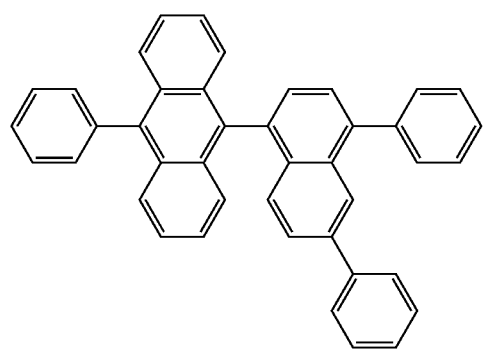
<Chemical Formula 40>
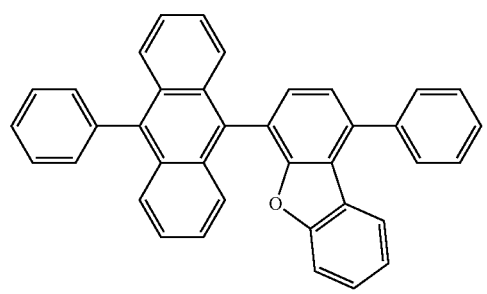
<Chemical Formula 41>
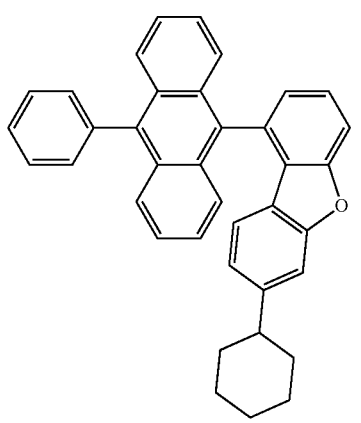
<Chemical Formula 42>
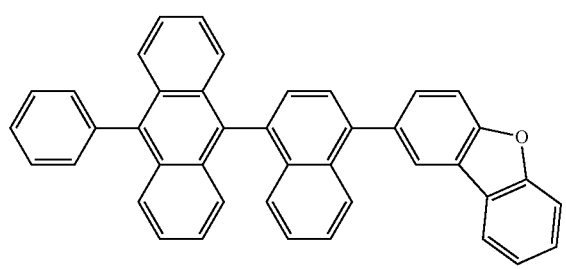
<Chemical Formula 43>
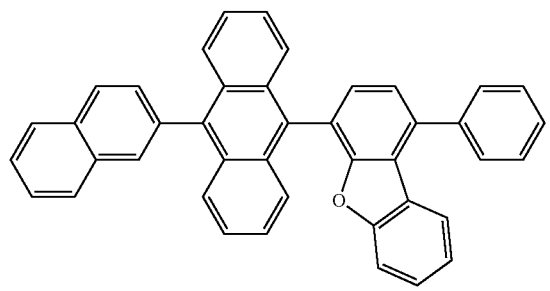
<Chemical Formula 44>
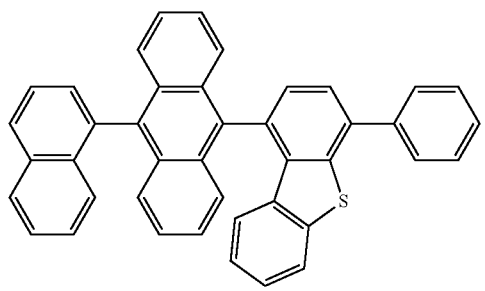
<Chemical Formula 45>
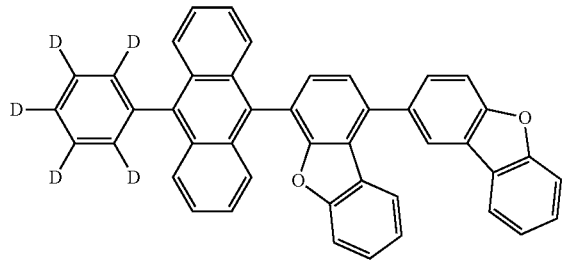
<Chemical Formula 46>
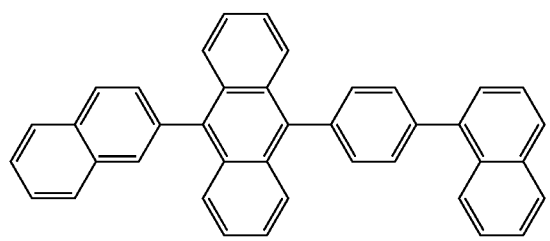

<Chemical Formula 47>
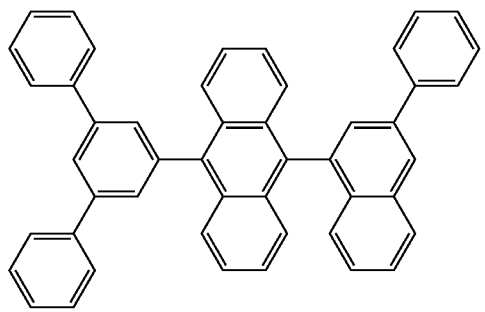
<Chemical Formula 48>
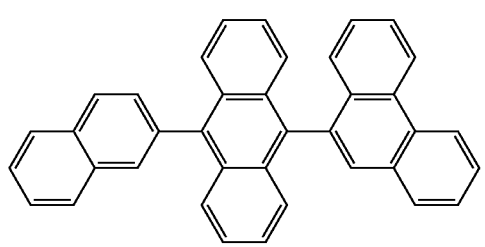
<Chemical Formula 49>
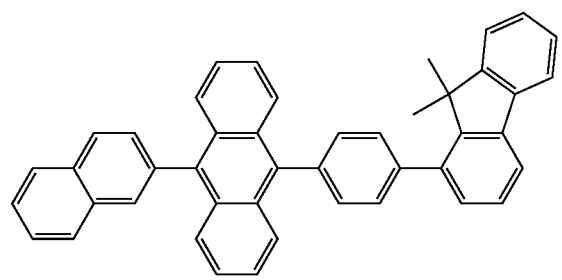
<Chemical Formula 50>
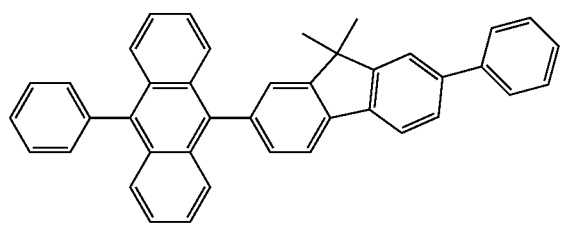
<Chemical Formula 51>
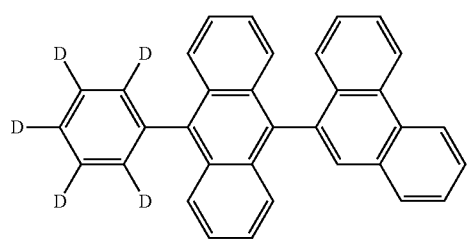
<Chemical Formula 52>
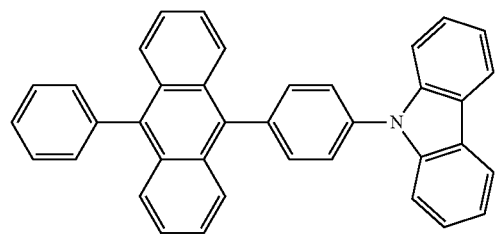
<Chemical Formula 53>
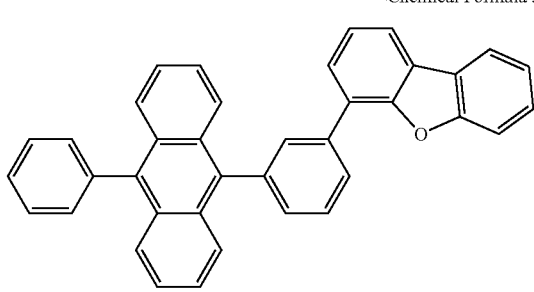
<Chemical Formula 54>
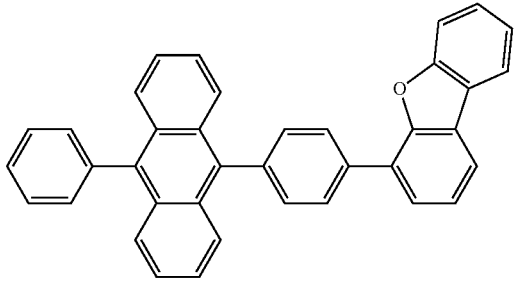
<Chemical Formula 55>
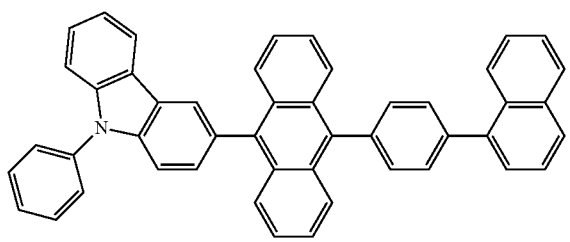
<Chemical Formula 56>
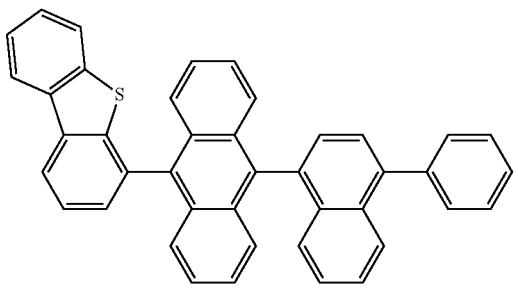

<Chemical Formula 57>
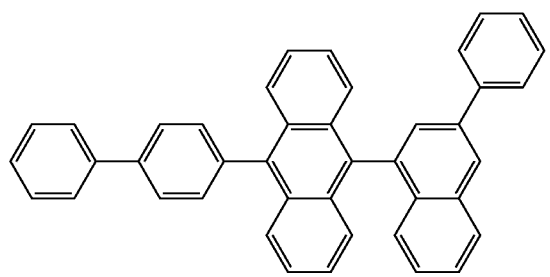
<Chemical Formula 58>
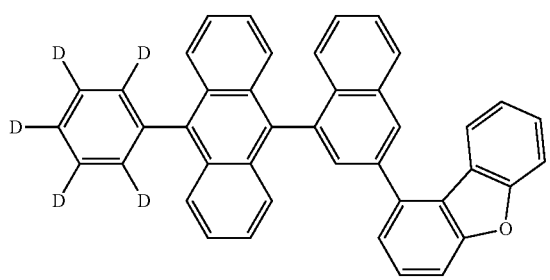
<Chemical Formula 59>
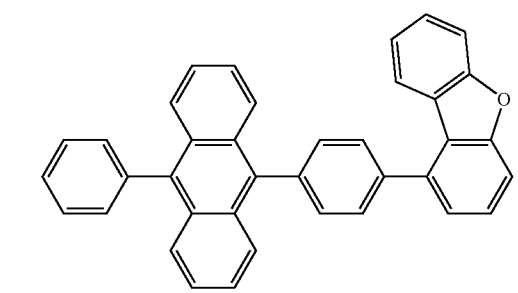
<Chemical Formula 60>
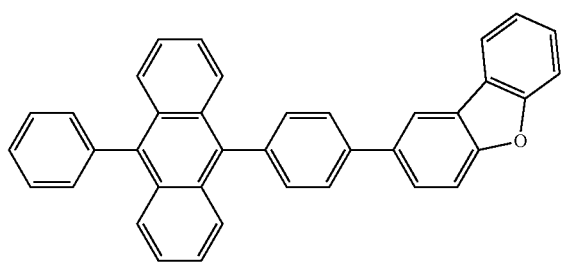
In addition, the light-emitting layer may employ as a dopant compound at least one selected from the compounds represented by the following Chemical Formulas D1 to D3:
[Chemical Formula D1]
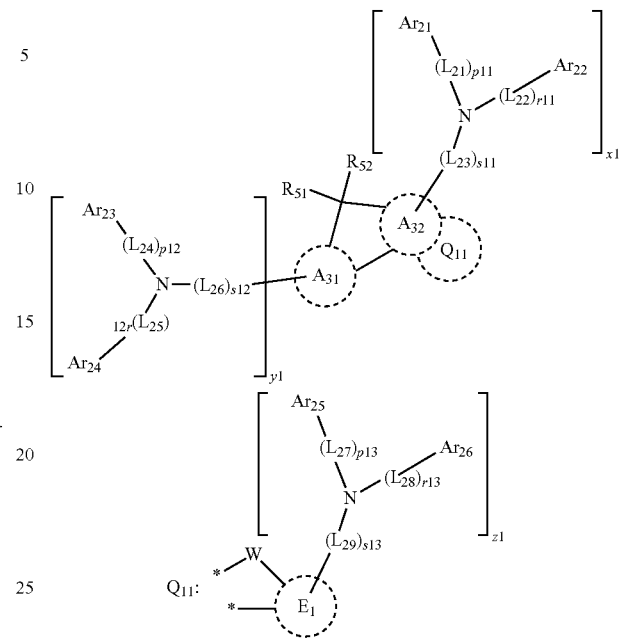
[Chemical Formula D2]
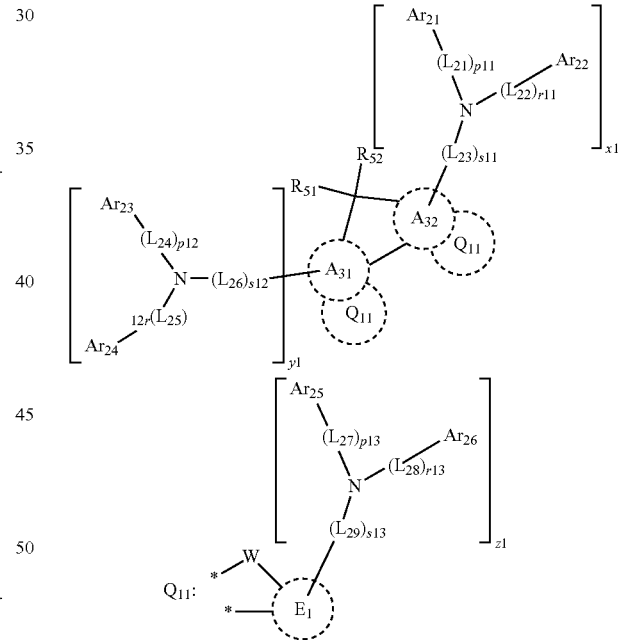
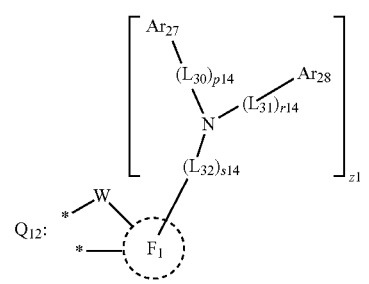

wherein, $A_{31}$, $A_{32}$, $E_1$, and $F_1$, which may be the same or different, are each independently a substituted or unsubstituted aromatic hydrocarbon ring of 6 to 50 carbon atoms, or a substituted or unsubstituted heteroaromatic ring of 2 to 40 carbon atoms;

wherein two adjacent carbon atoms within the aromatic ring of $A_{31}$ and two adjacent carbon atoms within the aromatic ring of $A_{32}$ form a 5-membered ring with a carbon atom connected to both substituents $R_{51}$ and $R_{52}$, thus establishing a fused ring structure;

linkers $L_{21}$ to $L_{32}$, which may be same or different, are each independently selected from a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

W is selected from N—$R_{53}$, $CR_{54}R_{55}$, $SiR_{56}R_{57}$, $GeR_{58}R_{59}$, O, S, and Se;

$R_{51}$ to $R_{59}$ and $Ar_{21}$ to $Ar_{28}$, which may be same or different, are each independently selected from a hydrogen atom, a deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkyl germanium of 1 to 30 carbon atoms, a substituted or unsubstituted aryl germanium of 1 to 30 carbon atoms a cyano, a nitro, and a halogen, wherein $R_{51}$ and $R_{52}$ may be connected to each other to form a mono- or polycyclic aliphatic or aromatic ring which may bear at least one heteroatom selected from N, O, P, Si, S, Ge, Se, and Te as a ring member;

p11 to p14, r11 to r14, and s11 to s14 are each independently an integer of 1 to 3, under which when any of them is 2 or greater, the corresponding linkers $L_{21}$ to $L_{32}$ may be the same or different, x1 is an integer of 1 or 2, and y1 and z1, which may be the same or different, are each independently an integer of 0 to 3, a bond may be made between at least one pair selected from $Ar_{21}$ and $Ar_{22}$, $Ar_{23}$ and $Ar_{24}$, $Ar_{25}$ and $Ar_{26}$, and $Ar_{27}$ and $Ar_{28}$ to form a ring;

two adjacent carbon atoms of the $A_{32}$ ring moiety of Chemical Formula D1 may occupy respective positions * of Structural Formula $Q_{11}$ to form a fused ring, two adjacent carbon atoms of the $A_{31}$ ring moiety of Chemical Formula D2 may occupy respective positions * of Structural Formula $Q_{12}$ to form a fused ring and two adjacent carbon atoms of the $A_{32}$ ring moiety of Chemical Formula D2 may occupy respective positions * of structural Formula $Q_{11}$ to form a fused ring

[Chemical Formula D3]

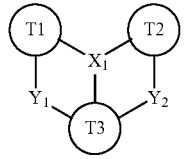

wherein, $X_1$ is selected from B, P, and P=O,

T1 to T3, which may be the same or different, are each independently a substituted or unsubstituted aromatic hydrocarbon ring of 6 to 50 carbon atoms, or a substituted or unsubstituted heteroaromatic ring of 2 to 40 carbon atoms;

$Y_1$ is selected from N—$R_{61}$, $CR_{62}R_{63}$, O, S, and $SiR_{64}R_{65}$;

$Y_2$ is selected from N—$R_{66}$, $CR_{66}R_{68}$, O, S, and $SiR_{69}R_{70}$;

wherein $R_{61}$ to $R_{70}$, which may be the same or different, are each independently selected from a hydrogen atom, a deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, and a halogen, wherein $R_{61}$ to $R_{70}$ may each be linked to at least one of T1 to T3 to further form a mono- or polycyclic aliphatic or aromatic ring.

Here, the term "substituted" in the expression "substituted or unsubstituted" used for Chemical Formulas D1 to D3 means having at least one substituent selected from the group consisting of a deuterium, a cyano, a halogen, a hydroxy, a nitro, an alkyl of 1 to carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

Among the dopant compounds according to the present disclosure, the boron compound represented by Chemical Formula D3 may have on the aromatic hydrocarbon rings or heteroaromatic rings of T1 to T3 a substituent selected from a deuterium, an alkyl of 1 to 24 carbon atoms, an aryl of 6 to 24 carbon atoms, an alkylamino of 1 to 24 carbon atoms, and an arylamino of 6 to 24 carbon atoms, wherein the alkyl radicals or the aryl radicals in the alkylamino of 1 to 24 carbon atoms and the arylamino of 6 to 24 carbon atoms on the rings may be linked to each other, and particularly selected from an alkyl of 1 to 12 carbon atoms, an aryl of 6 to 18 carbon atoms, an alkylamino of 1 to 12 carbon atoms, and an arylamino of 6 to 18 carbon atoms, wherein the alkyl radicals or aryl radicals in the alkylamino of 1 to 12 carbon atoms and the arylamino of 6 to 18 carbon atoms on the rings may be linked to each other.

In addition, concrete examples of the dopant compound used for the light-emitting layer, represented by one of Chemical Formulas D1 and D2, include compounds represented by the following Chemical Formulas d1 to D239:

<Chemical Formula d1>

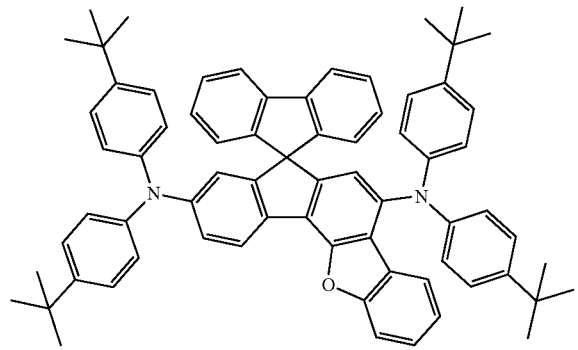

<Chemical Formula d2>

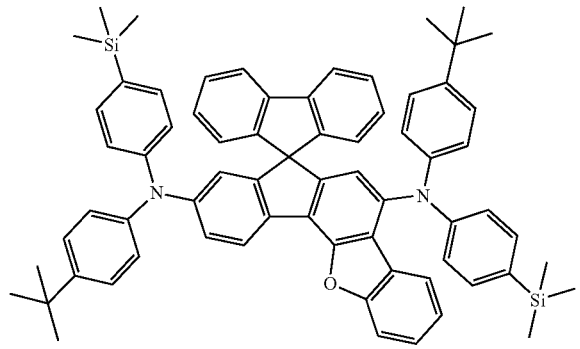

<ChemicaL Formula d3>

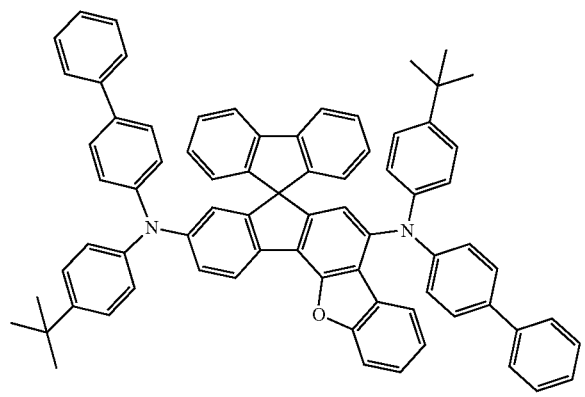

<Chemical Formula d4>

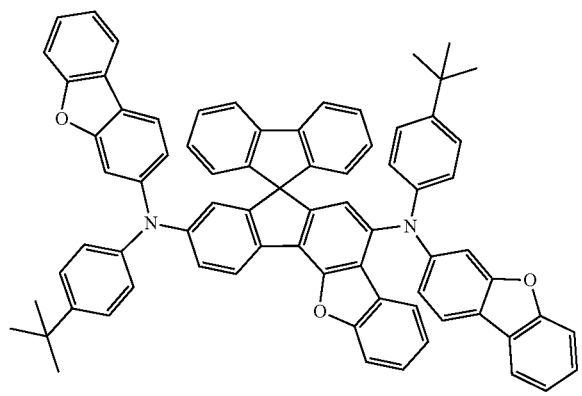

<Chemical Formula d5>

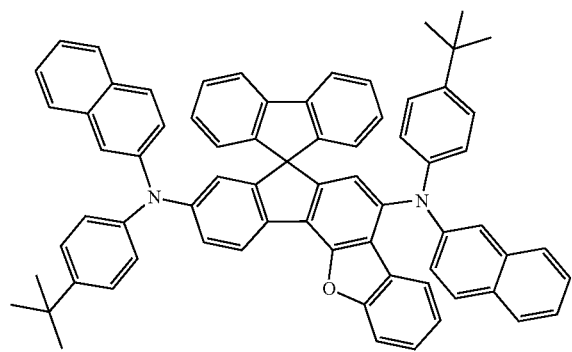

<Chemical Formula d6>

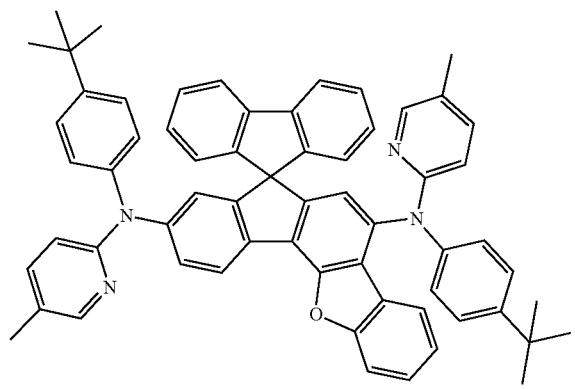

<Chemical Formula d7>
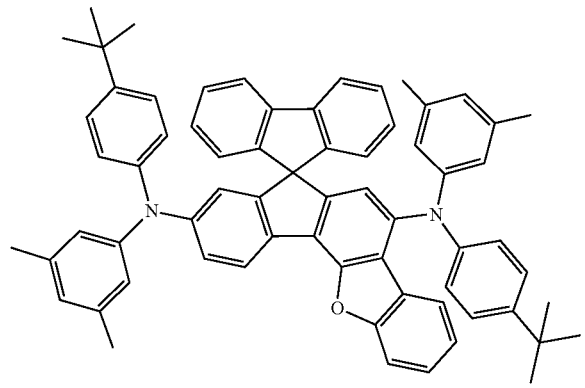
<Chemical Formula d8>
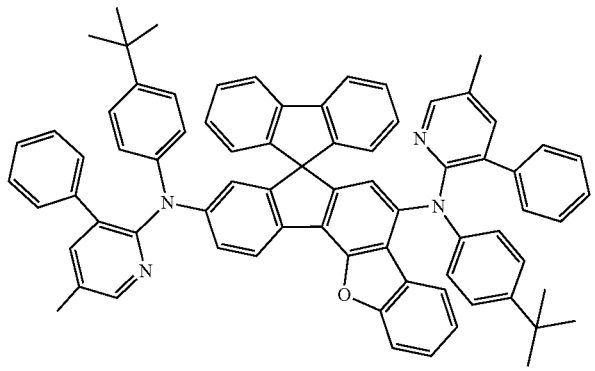
<Chemical Formula d9>
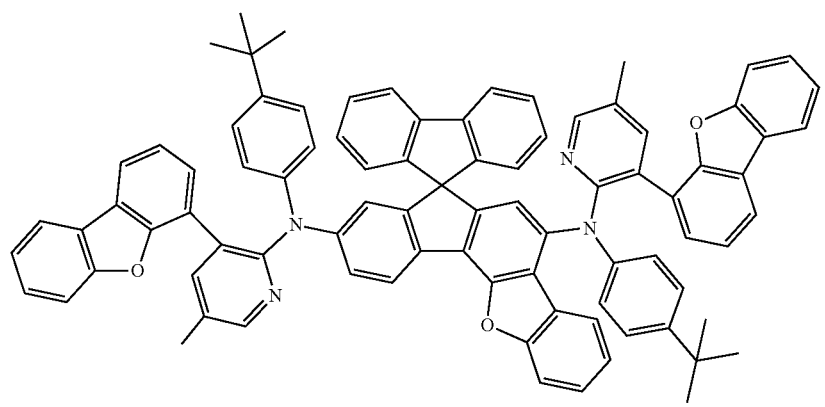
<Chemical Formula d10>
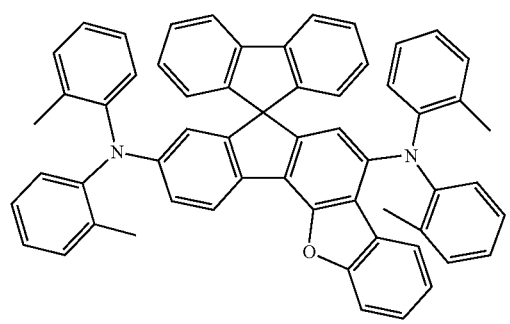
<Chemical Formula d11>
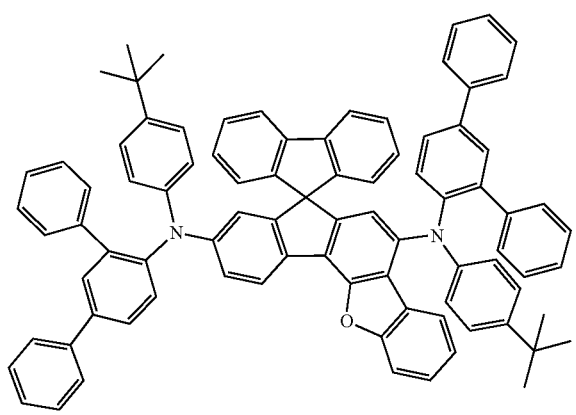

-continued
<Chemical Formula d12>
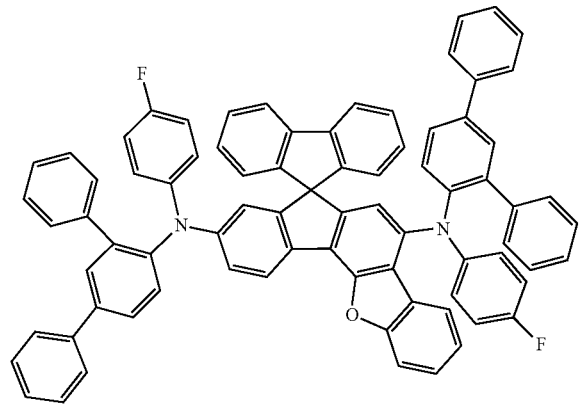
<Chemical Formula d13>
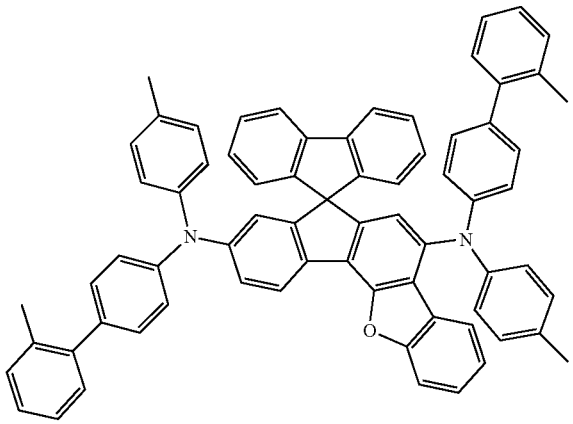
<Chemical Formula d14>
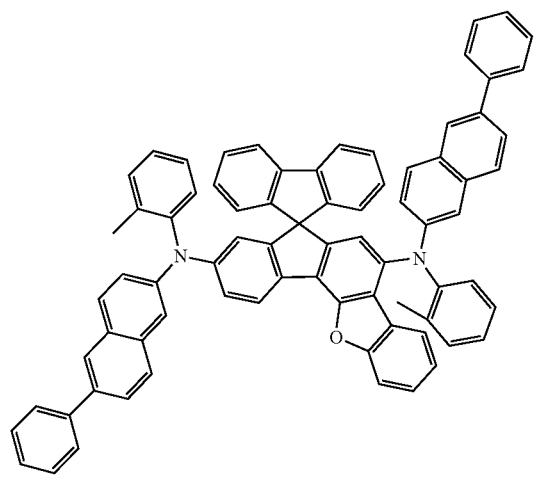
<Chemical Formula d15>
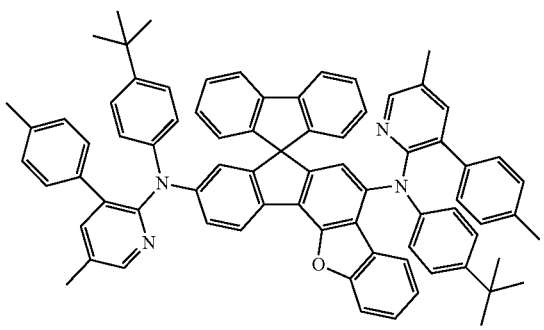
<Chemical Formula d16>
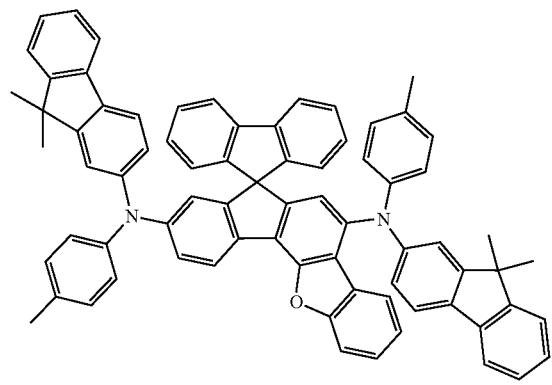
<Chemical Formula d17>
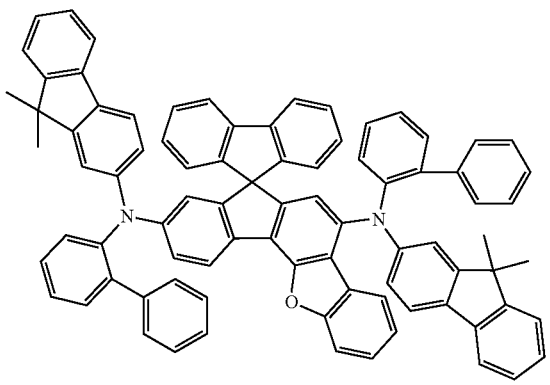

-continued
<Chemical Formula d18>
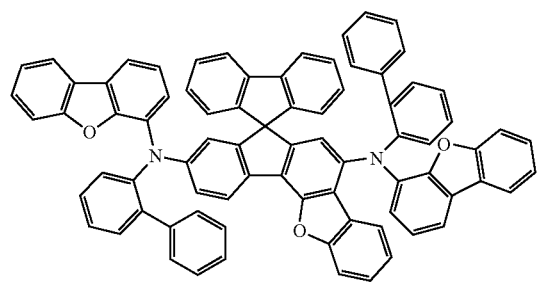
<Chemical Formula d19>
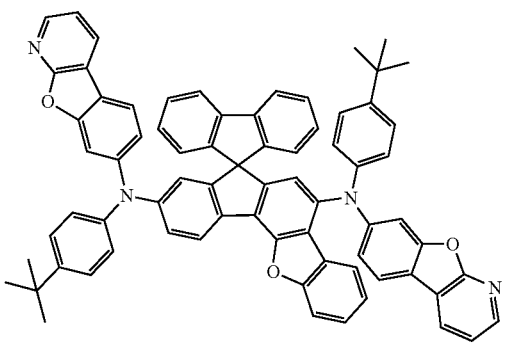
<Chemical Formula d20>
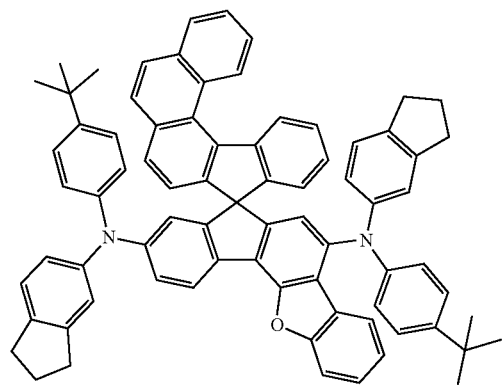
<Chemical Formula d21>
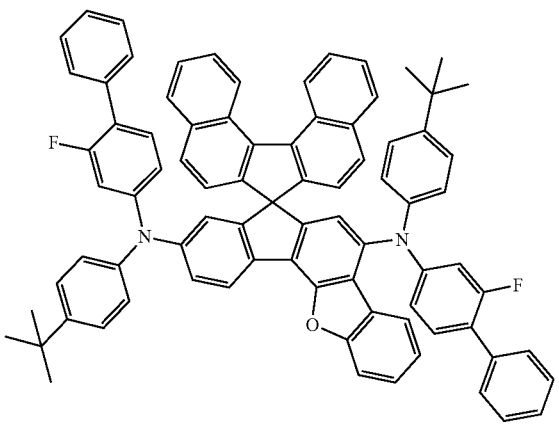
<Chemical Formula d22>
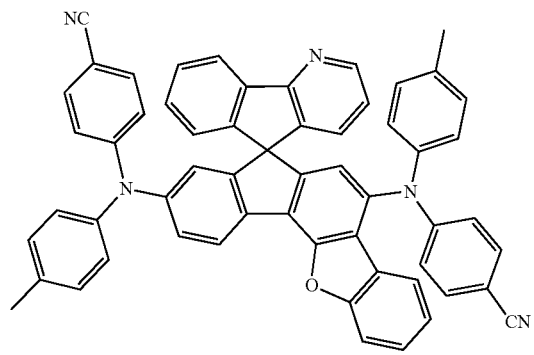
<Chemical Formula d23>
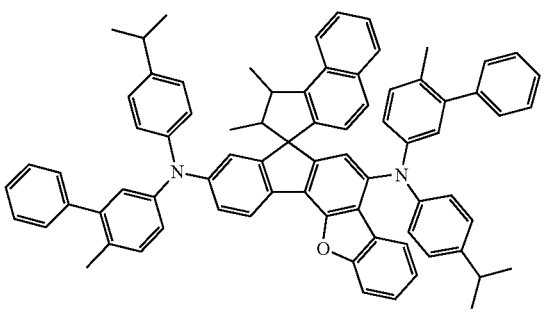
<Chemical Formula d24>
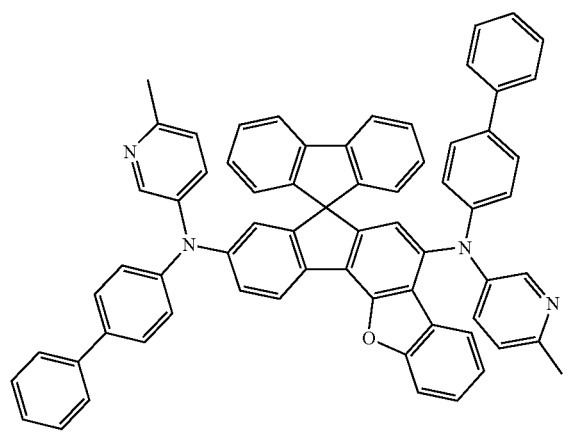
<Chemical Formula d25>
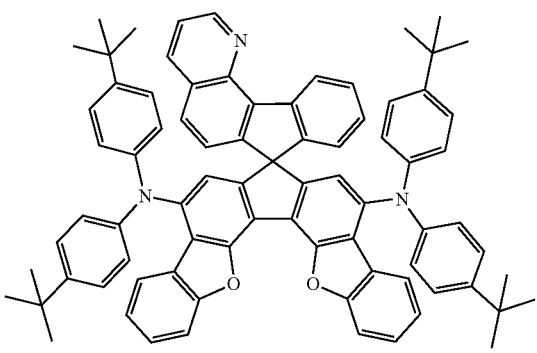

-continued
<Chemical Formula d26>
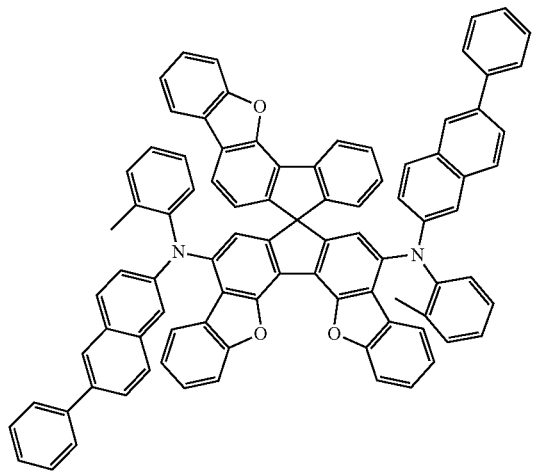
<Chemical Formula d27>
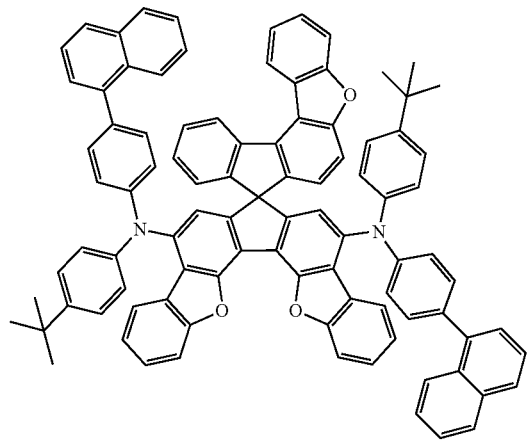
<Chemical Formula d28>
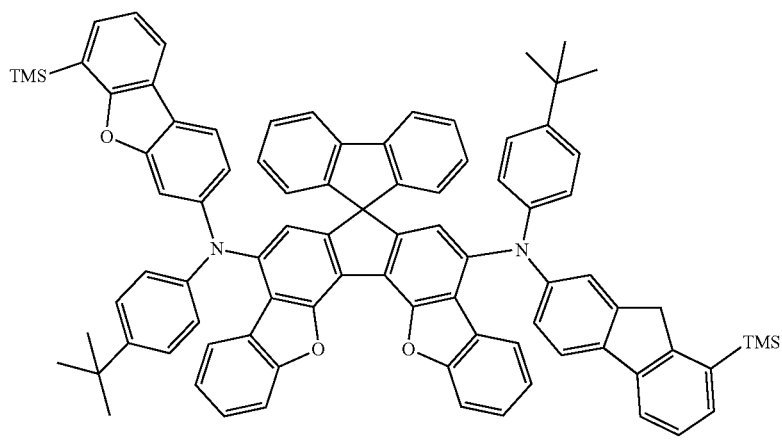
<Chemical Formula d29>
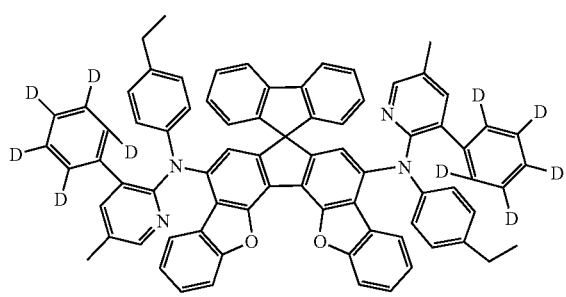
<Chemical Formula d30>
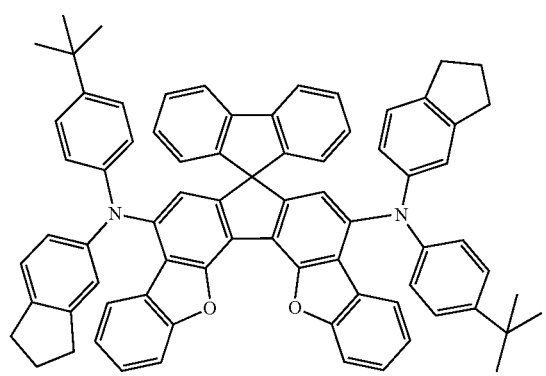

<Chemical Formula d31>
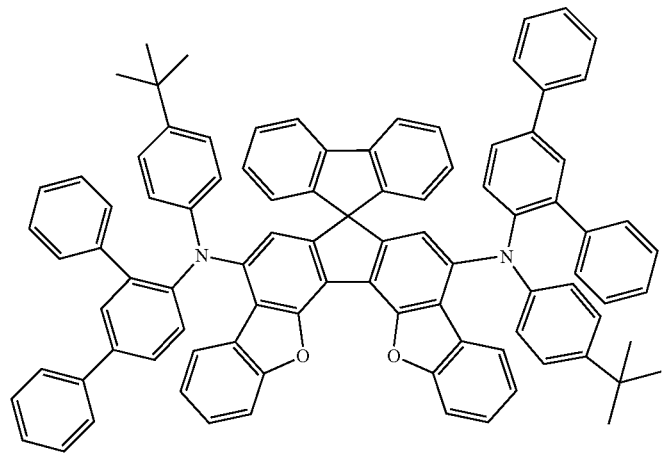
<Chemical Formula d32>
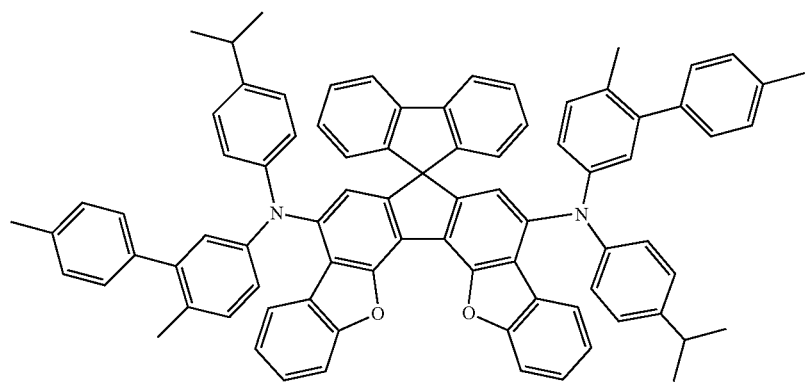
<Chemical Formula d33>
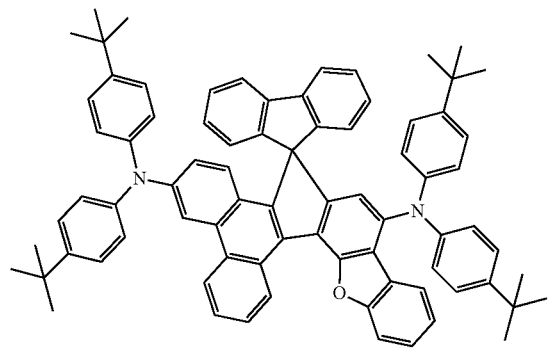
<Chemical Formula d34>
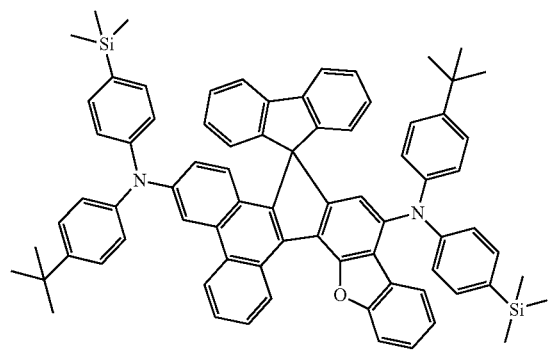

-continued
<Chemical Formula d35>
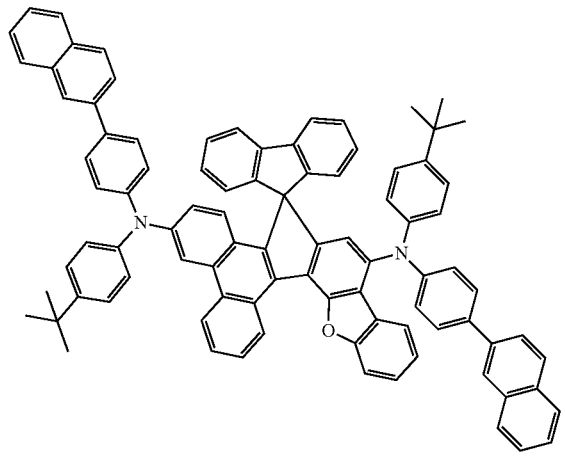
<Chemical Formula d36>
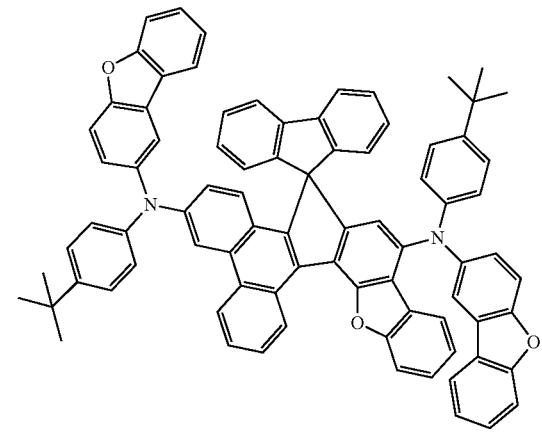
<Chemical Formula d37>
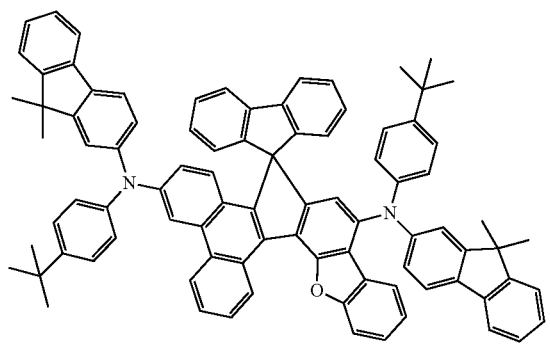
<Chemical Formula d38>
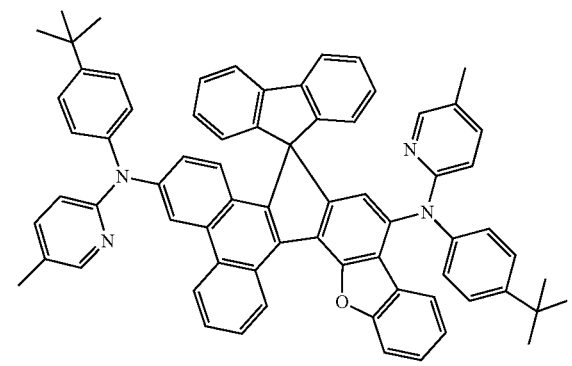
<Chemical Formula d39>
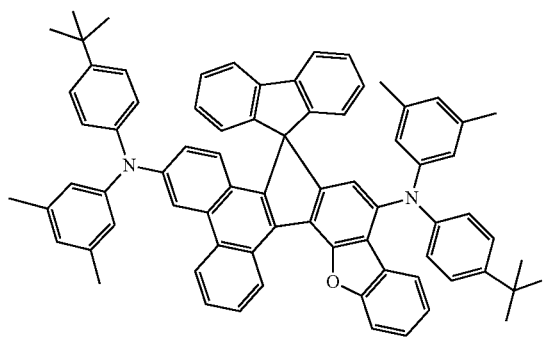
<Chemical Formula d40>
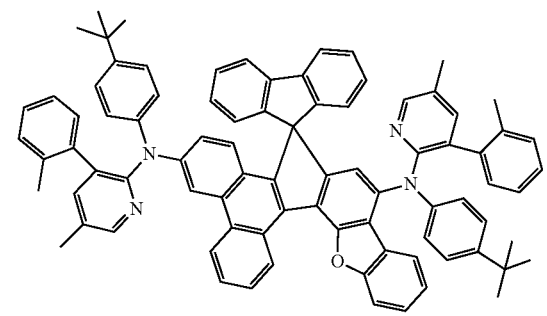
<Chemical Formula d41>
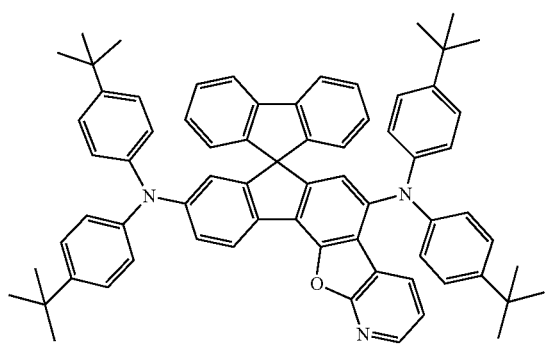
<Chemical Formula d42>
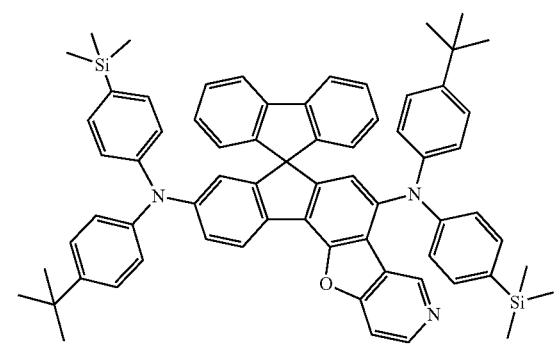

-continued
<Chemical Formula d43>
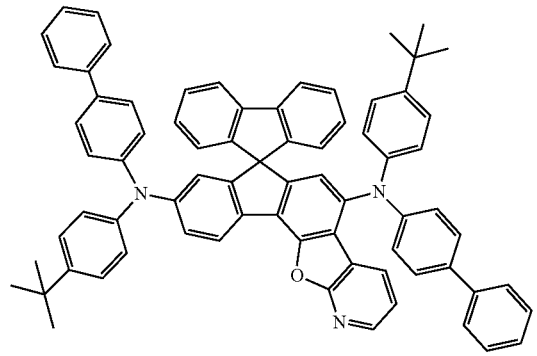
<Chemical Formula d44>
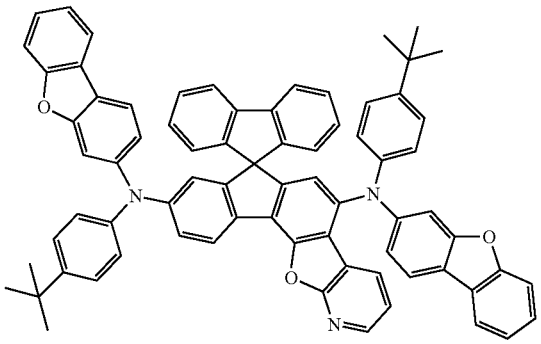
<Chemical Formula d45>
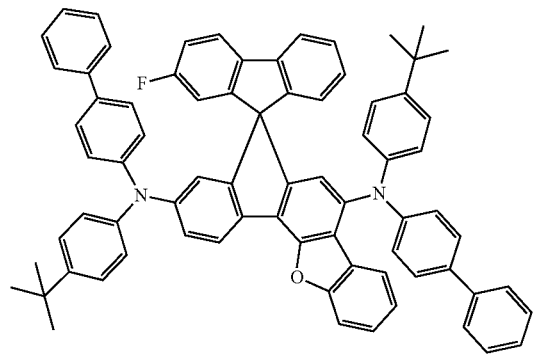
<Chemical Formula d46>
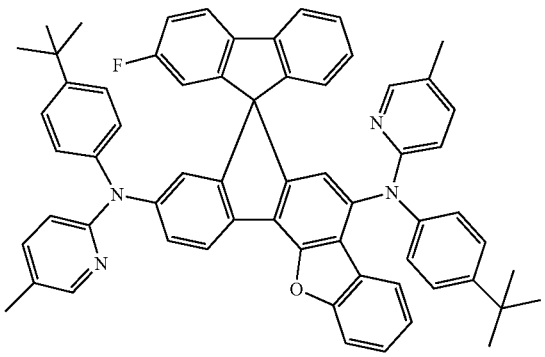
<Chemical Formula d47>
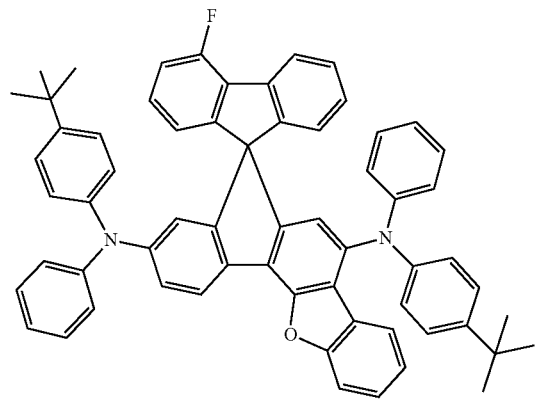
<Chemical Formula d48>
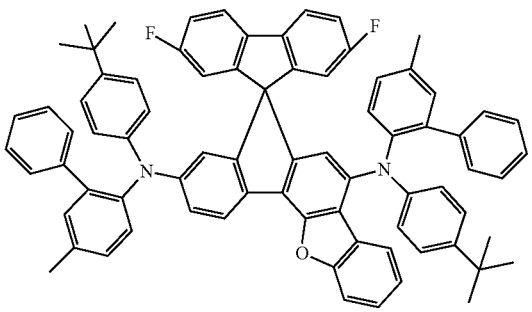
<Chemical Formula d49>
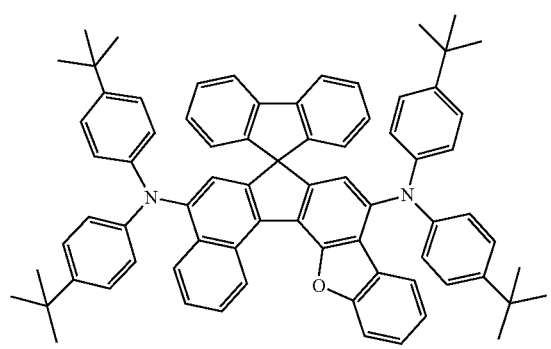
<Chemical Formula d50>
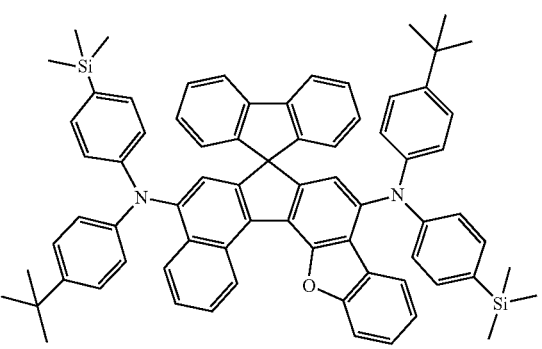

-continued
<Chemical Formula d51>
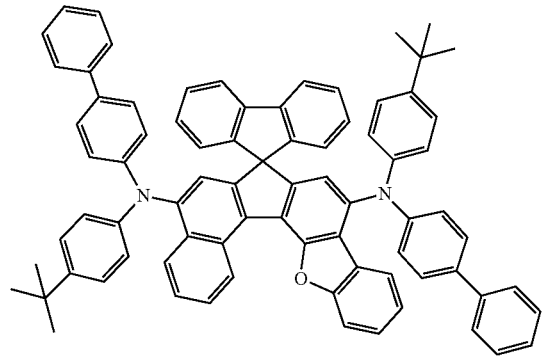
<Chemical Formula d52>
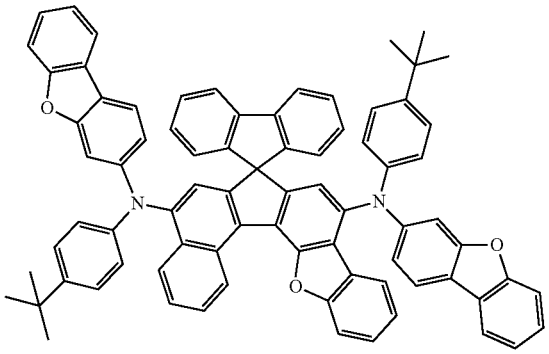
<Chemical Formula d53>
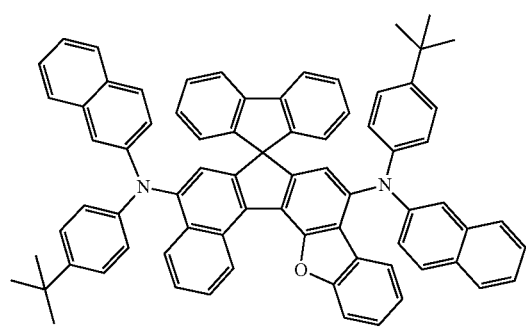
<Chemical Formula d54>
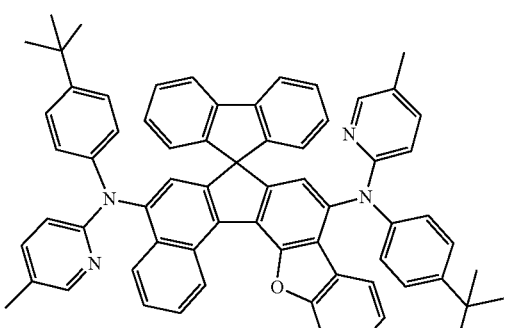
<Chemical Formula d55>
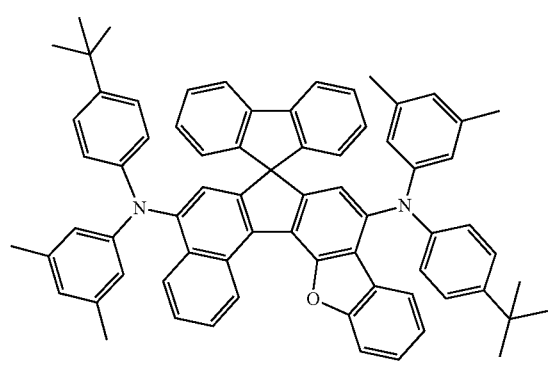
<Chemical Formula d56>
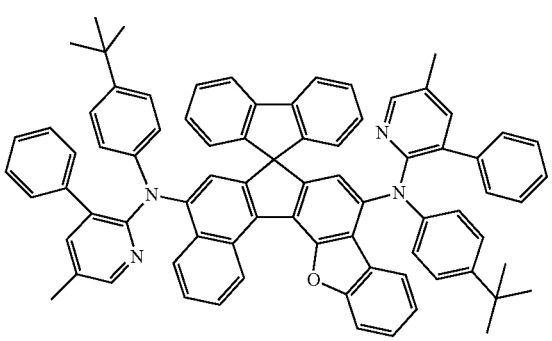
<Chemical Formula d57>
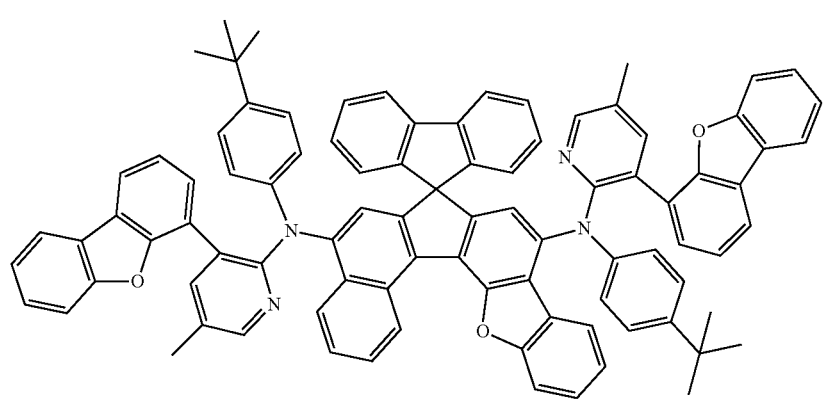

<Chemical Formula d58>
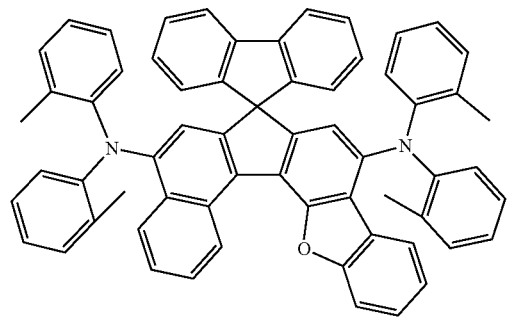
<Chemical Formula d59>
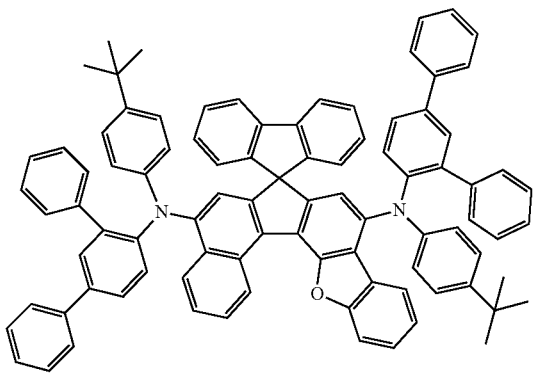
<Chemical Formula d60>
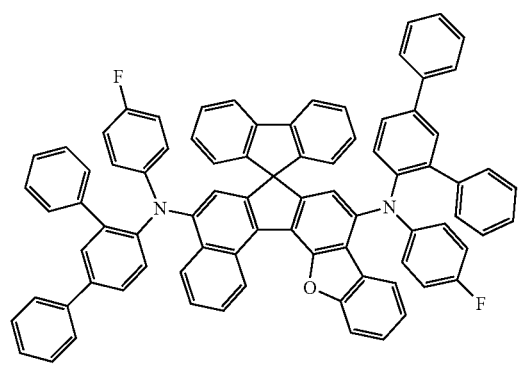
<Chemical Formula d61>
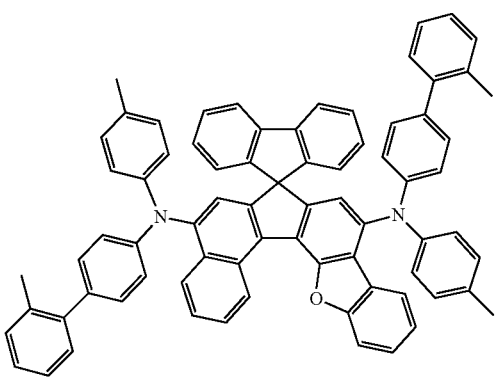
<Chemical Formula d62>
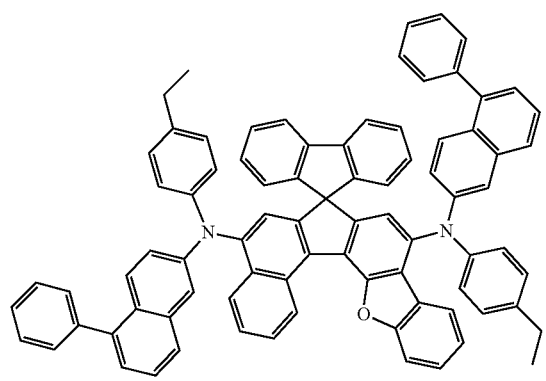
<Chemical Formula d63>
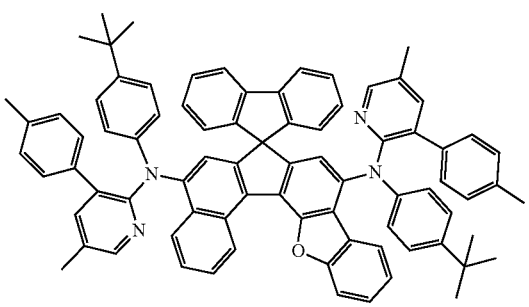
<Chemical Formula d64>
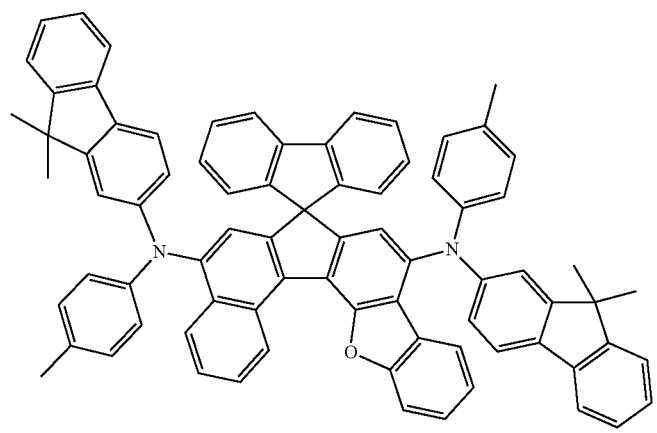

<Chemical Formula d65>
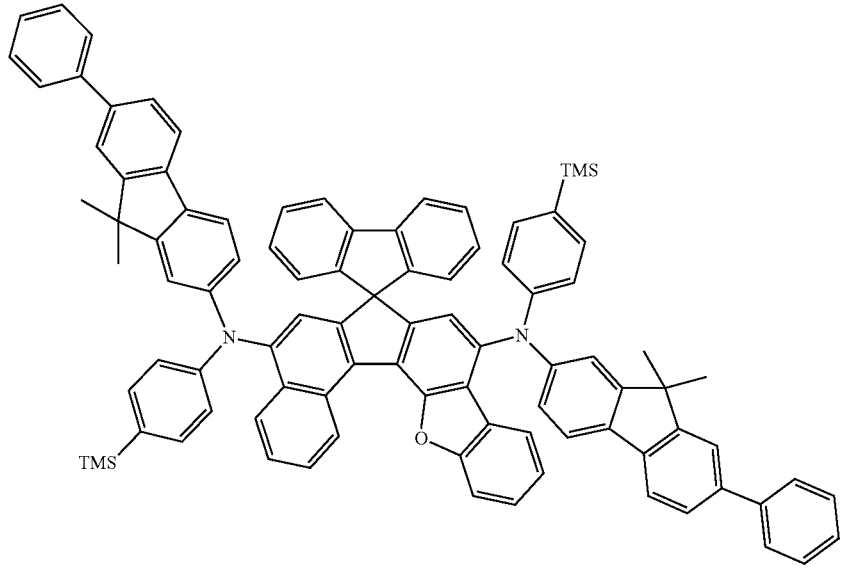
<Chemical Formula d66>
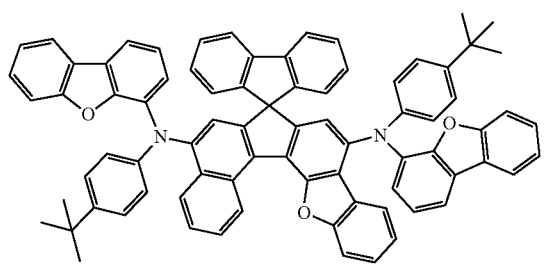
<Chemical Formula d67>
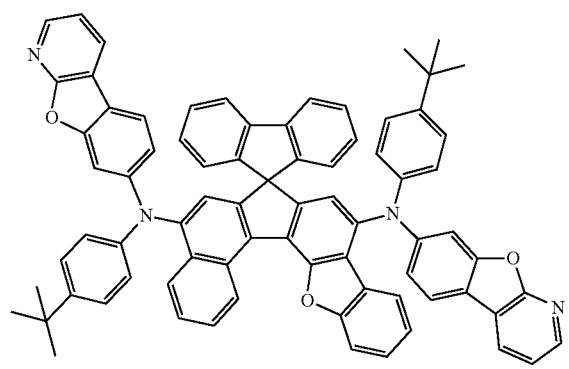
<Chemical Formula d68>
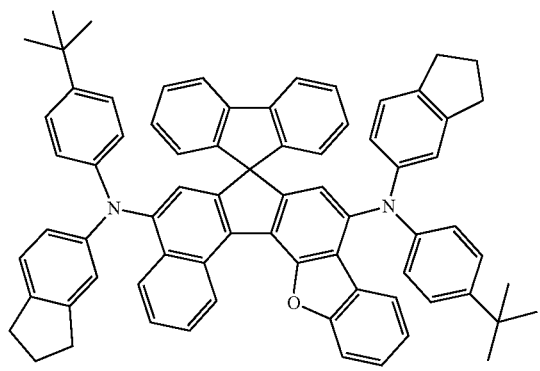
<Chemical Formula d69>
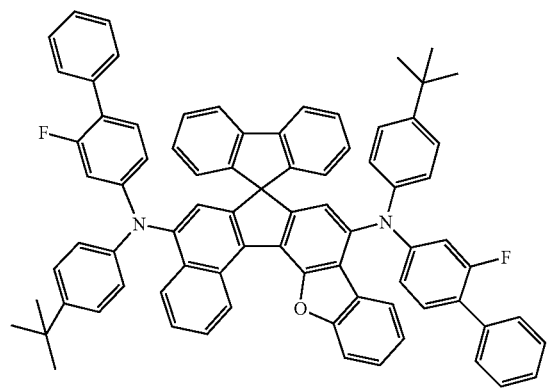

-continued
<Chemical Formula d70>
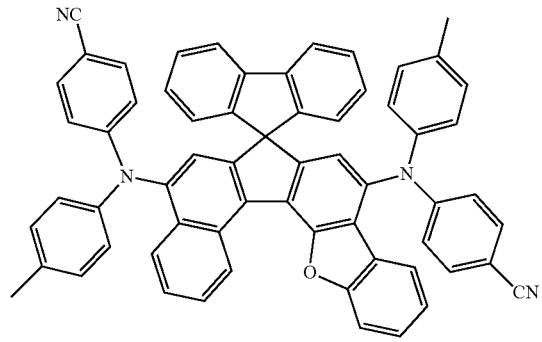
<Chemical Formula d71>
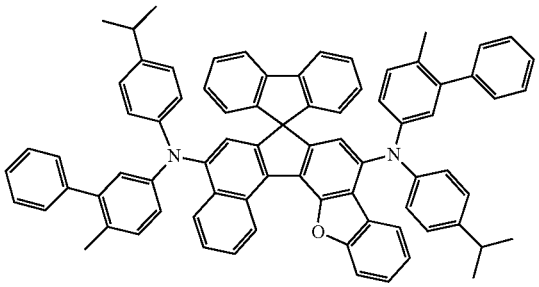
<Chemical Formula d72>
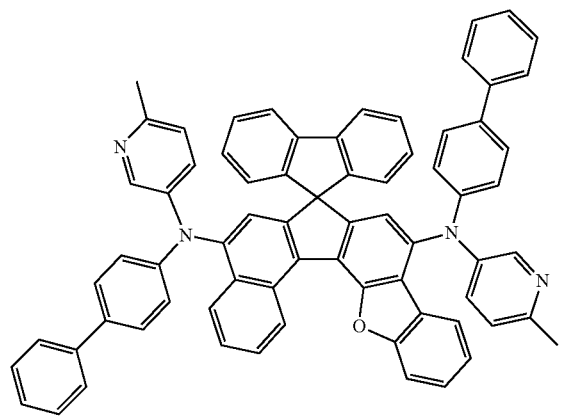
<Chemical Formula d73>
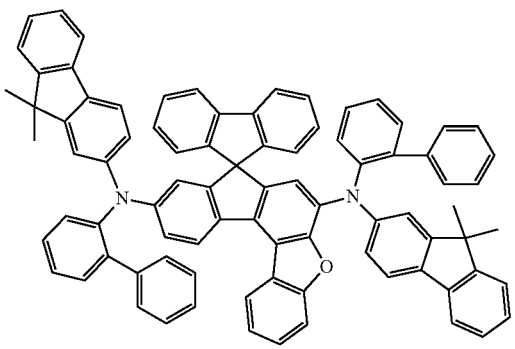
<Chemical Formula d74>
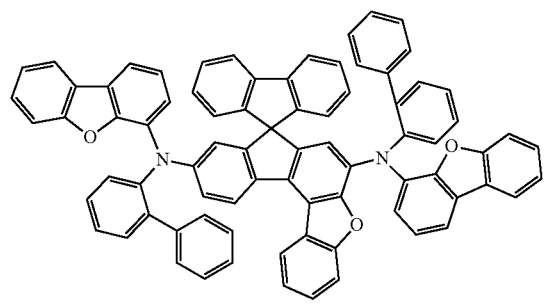
<Chemical Formula d75>
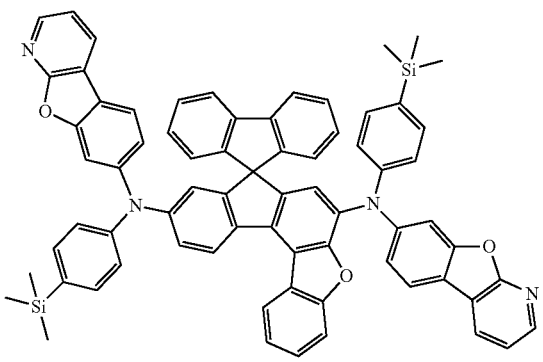
<Chemical Formula d76>
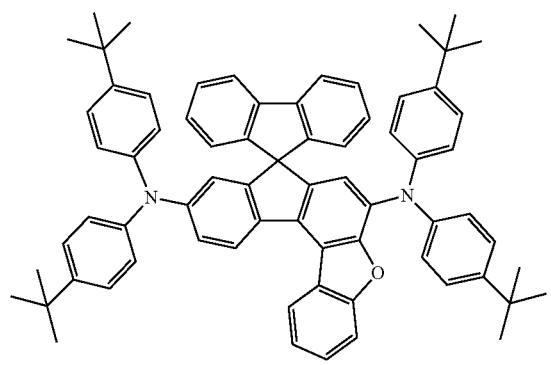
<Chemical Formula d77>
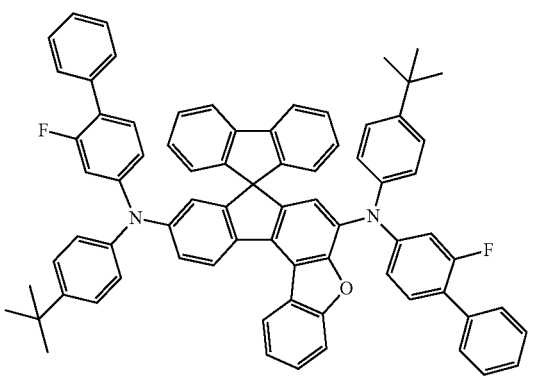

-continued
<Chemical Formula d78>
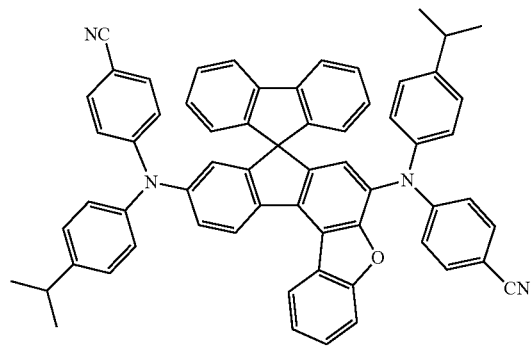
<Chemical Formula d79>
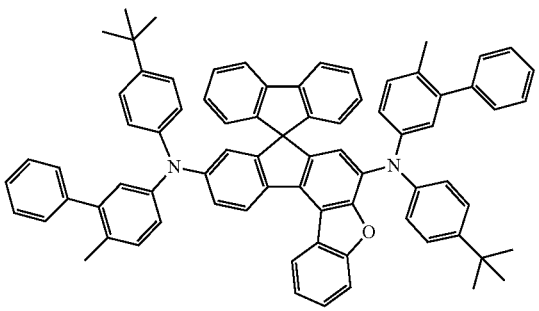
<Chemical Formula d80>
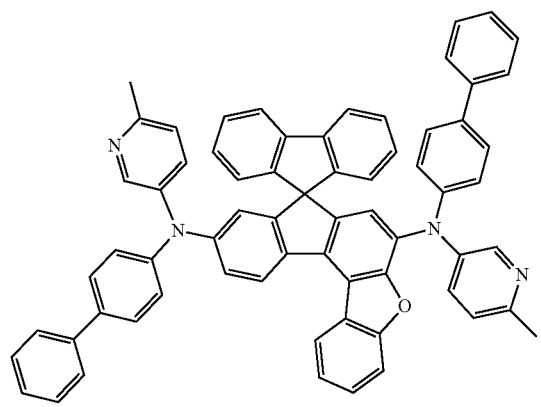
<Chemical Formula d81>
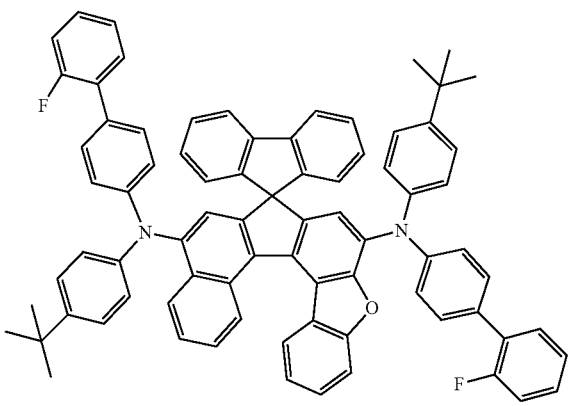
<Chemical Formula d82>
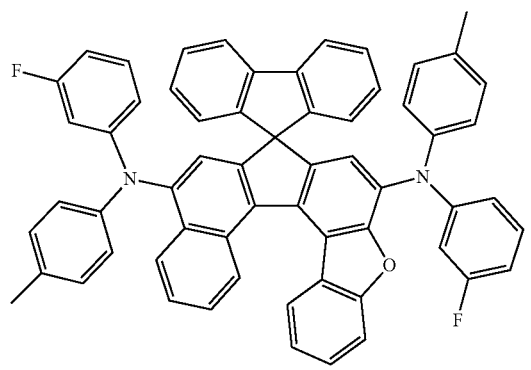
<Chemical Formula d83>
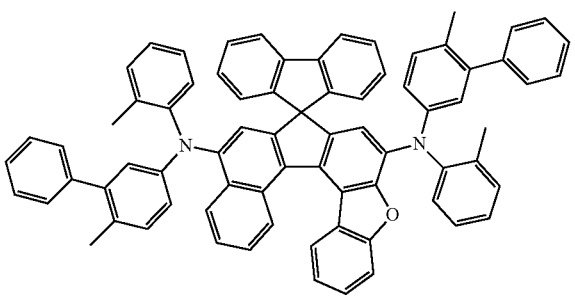
<Chemical Formula d84>
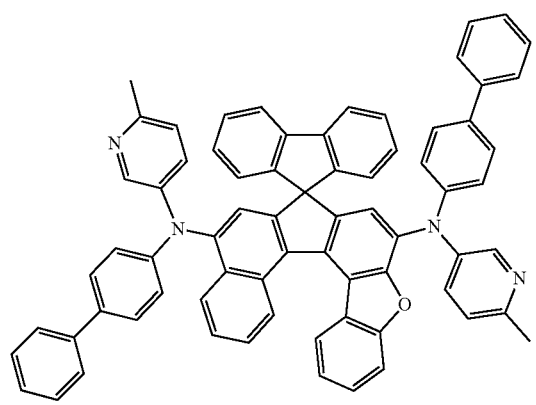
<Chemical Formula d85>
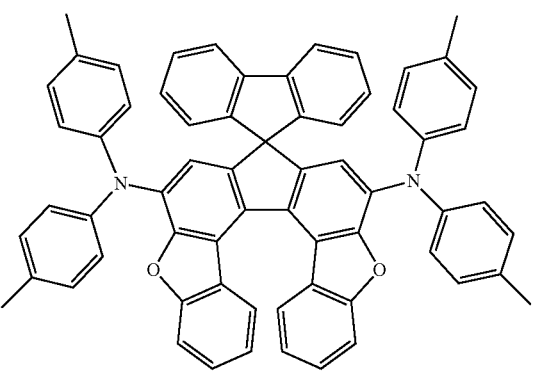

<Chemical Formula d86>
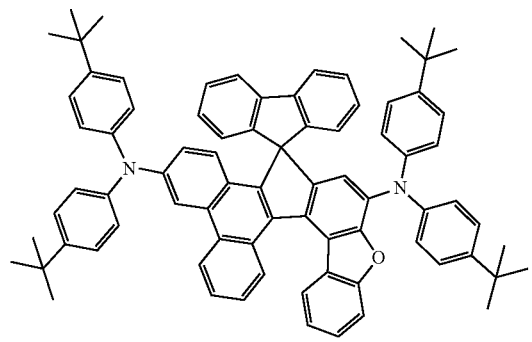
<Chemical Formula d87>
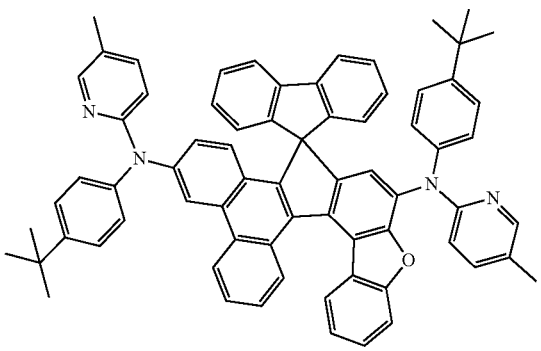
<Chemical Formula d88>
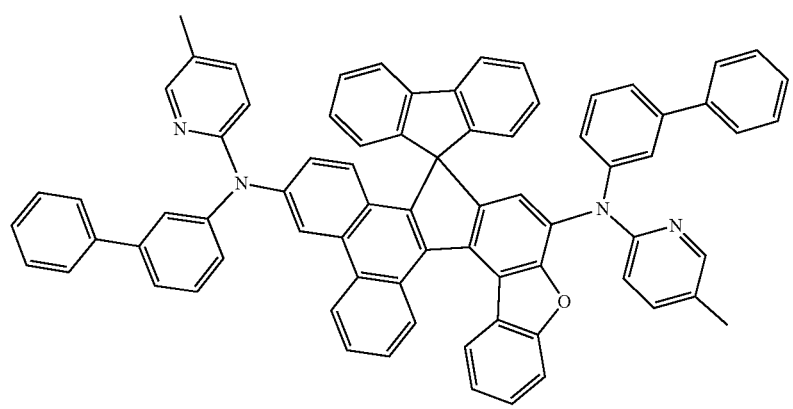
<Chemical Formula d89>
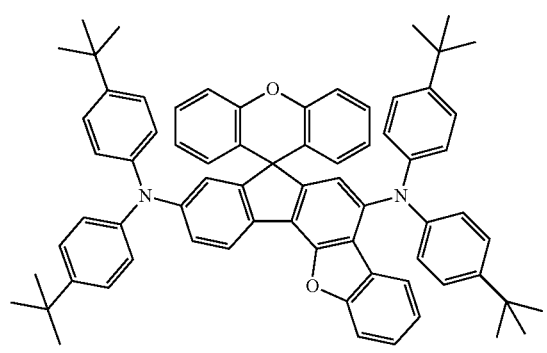
<Chemical Formula d90>
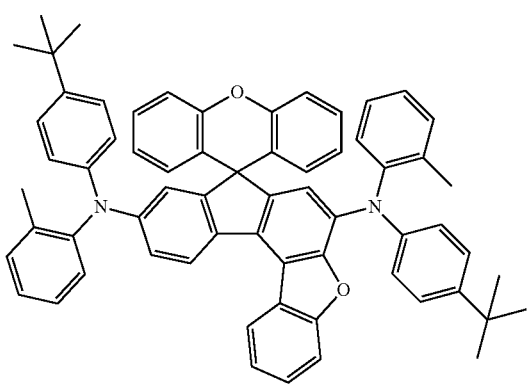

<Chemical Formula d91>
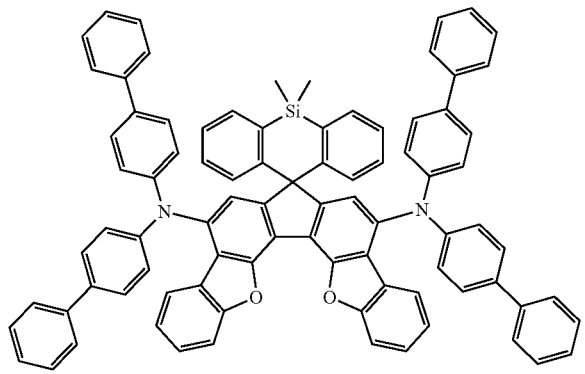
<Chemical Formula d92>
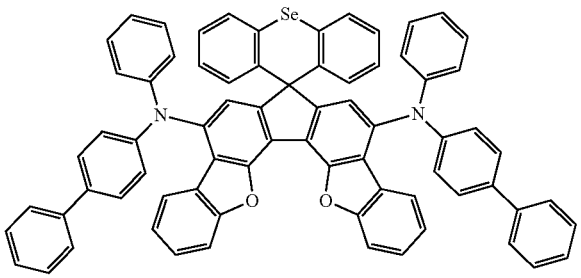
<Chemical Formula d93>
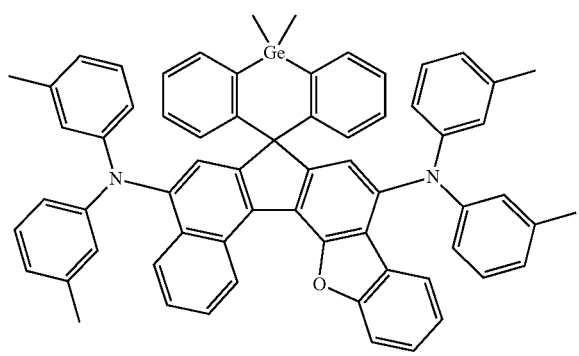
<Chemical Formula d94>
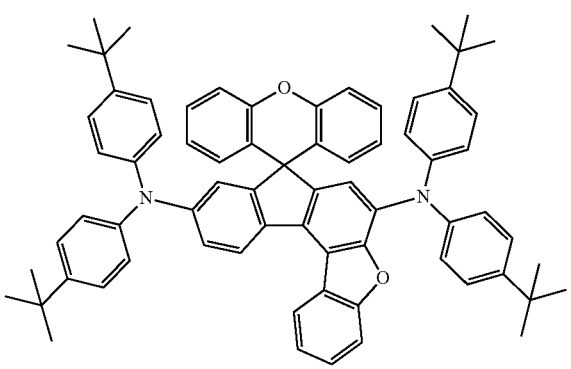
<Chemical Formula d95>
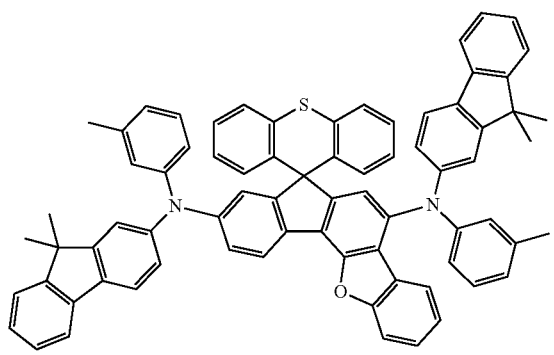
<Chemical Formula d96>
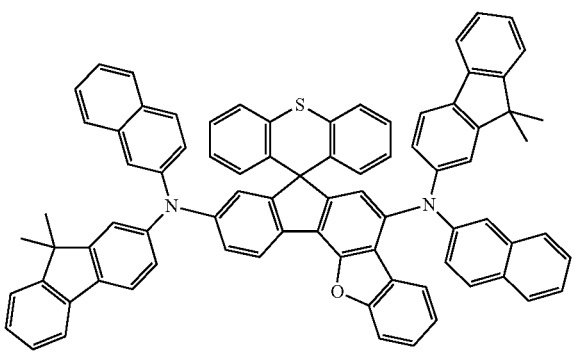
<Chemical Formula d97>
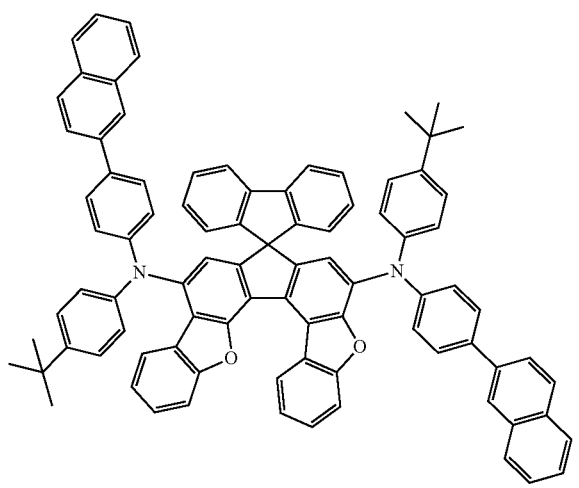
<Chemical Formula d98>
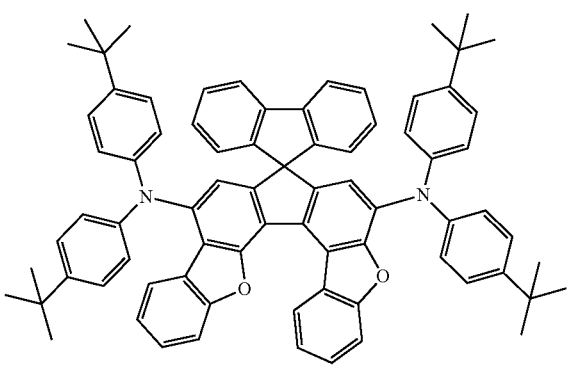

-continued
<Chemical Formula d99>
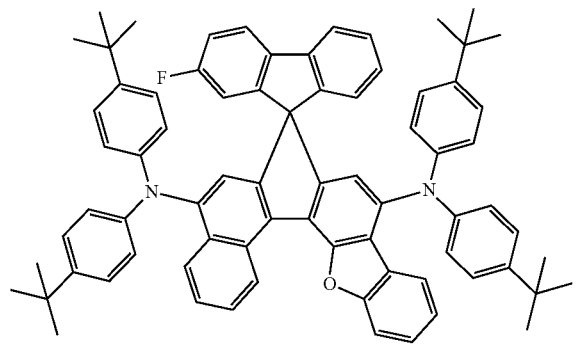
<Chemical Formula d100>
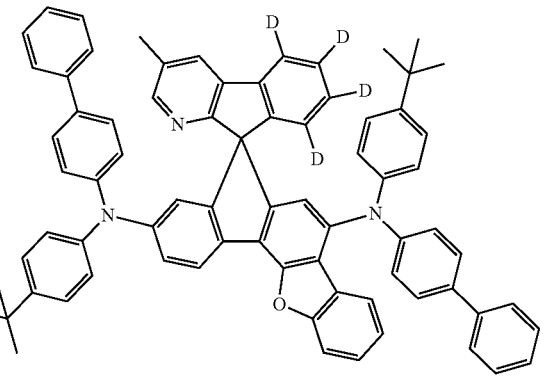
<Chemical Formula d101>
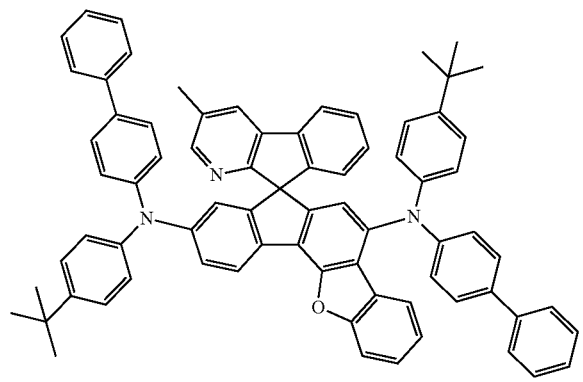
<Chemical Formula d102>
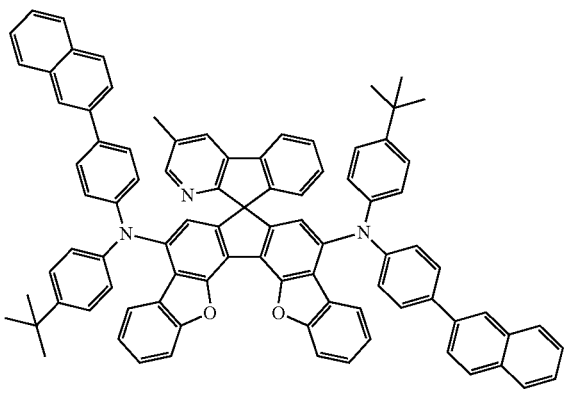
<Chemical Formula d103>
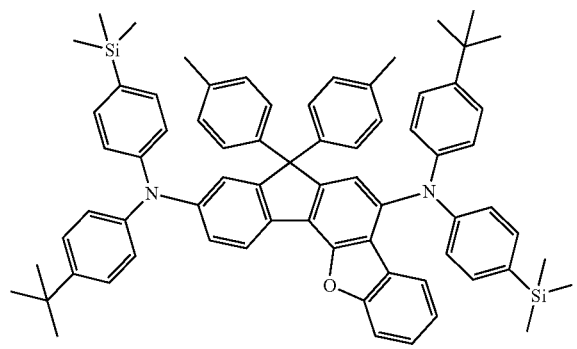
<Chemical Formula d104>
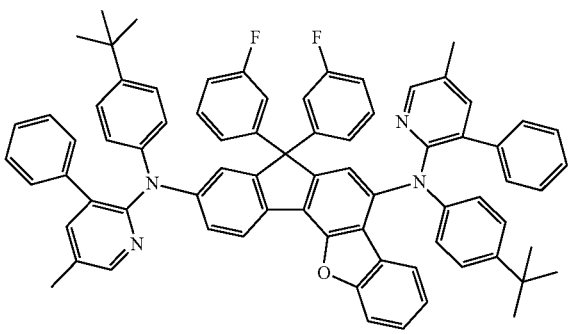
<Chemical Formula d105>
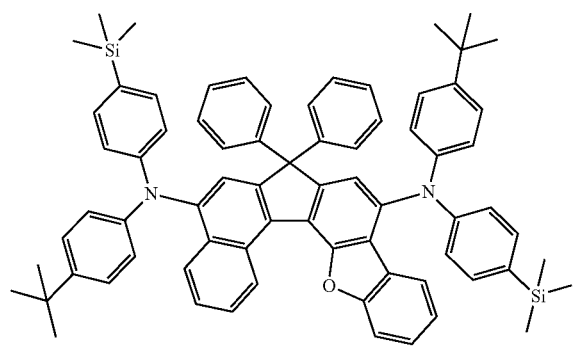
<Chemical Formula d106>
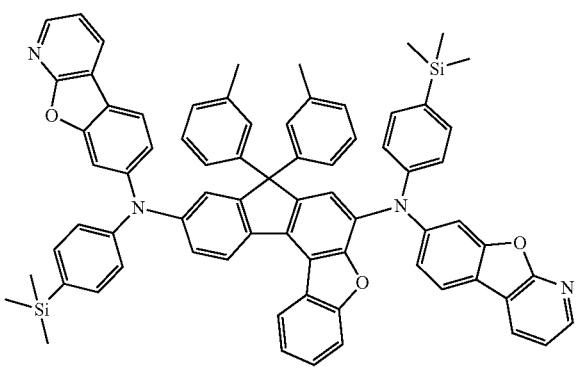

[Chemical Formula d107]
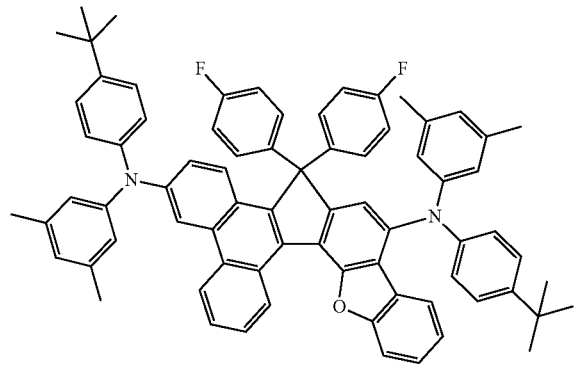
<Chemical Formula d108>
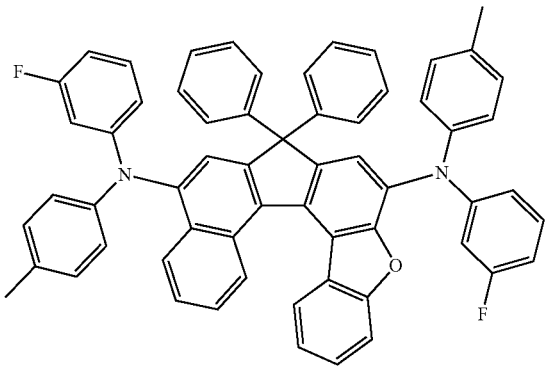
<Chemical Formula d109>
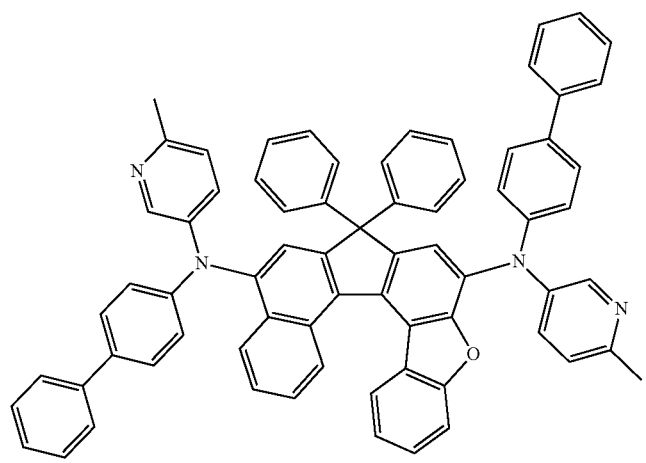
<Chemical Formula d110>
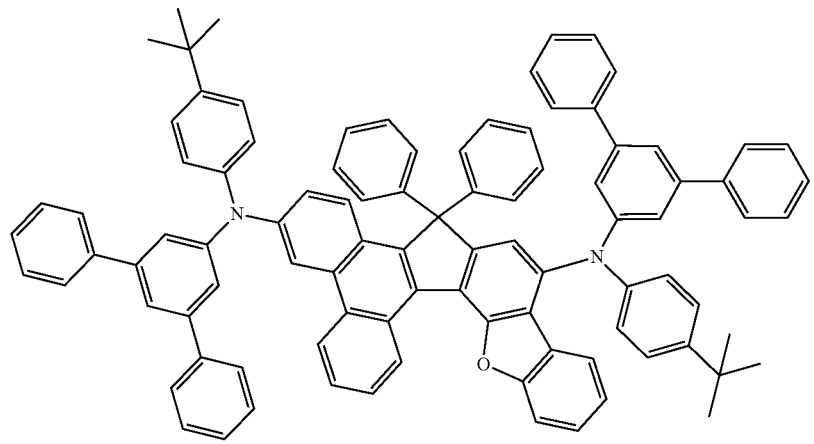

-continued
[Chemical Formula d111]
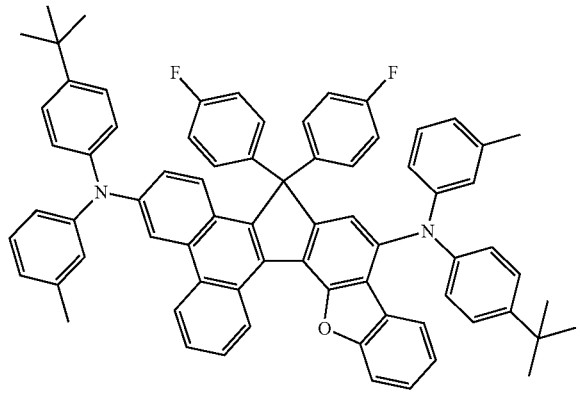
<Chemical Formula d112>
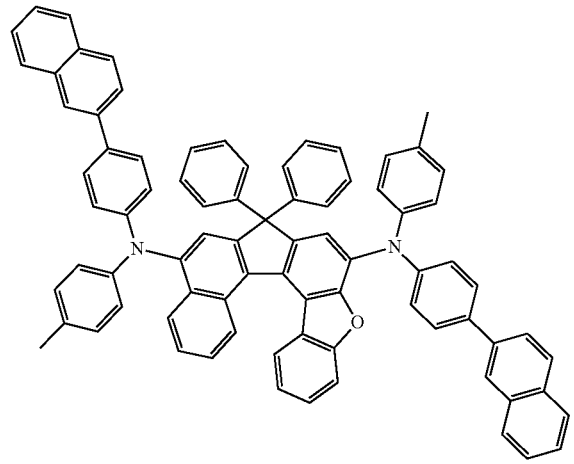
<Chemical Formula d113>
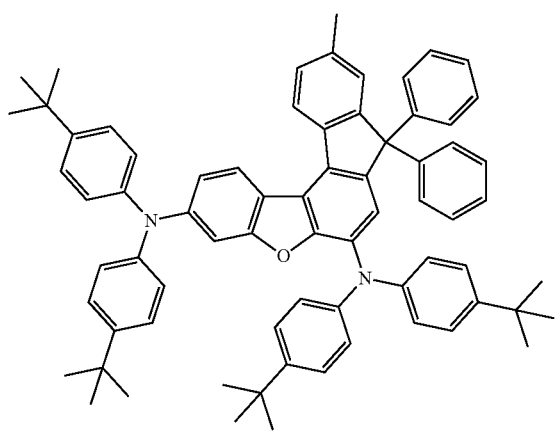
<Chemical Formula d114>
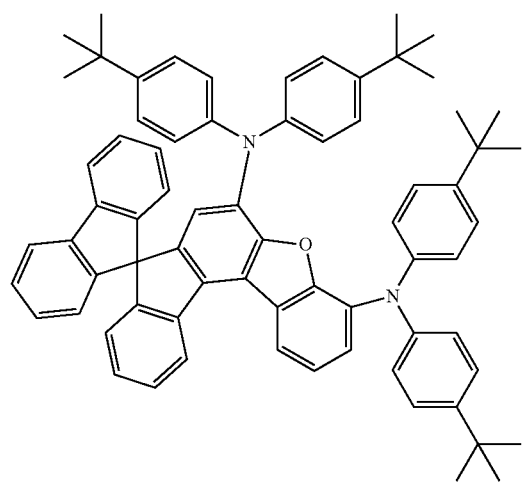
<Chemical Formula d115>
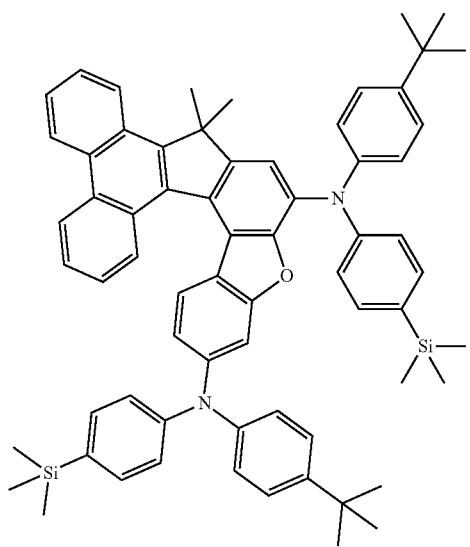
<Chemical Formula d116>
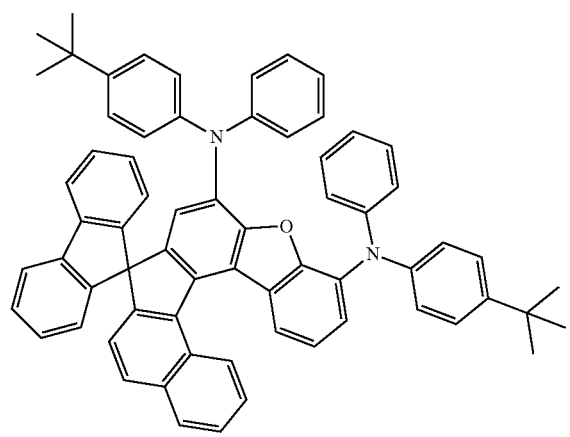

-continued
<Chemical Formula d117>
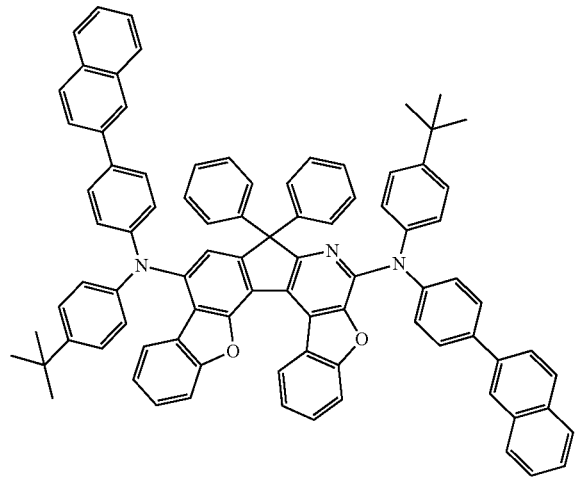
<Chemical Formula d118>
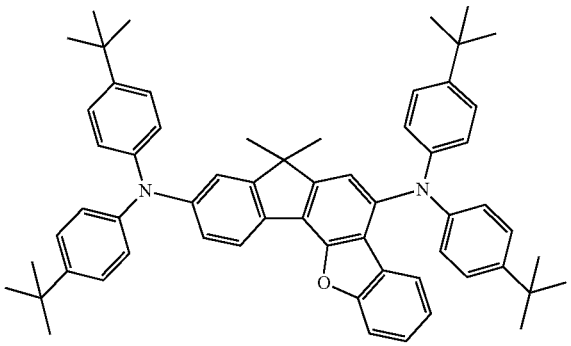
<Chemical Formula d119>
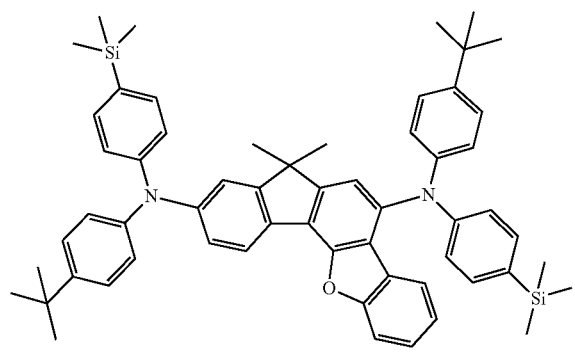
<Chemical Formula d120>
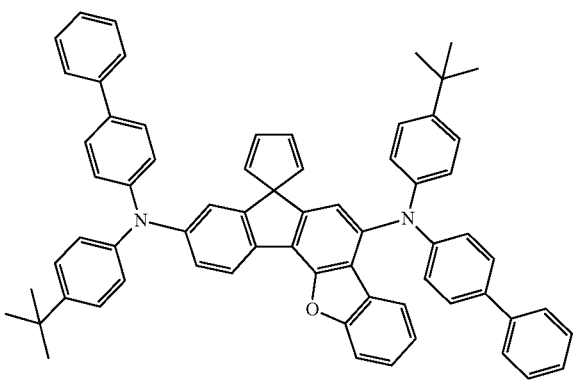
<Chemical Formula d121>
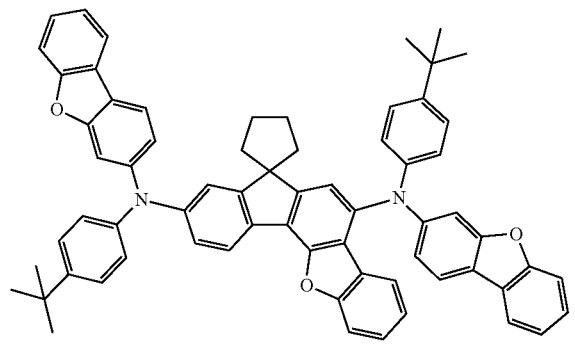
<Chemical Formula d122>
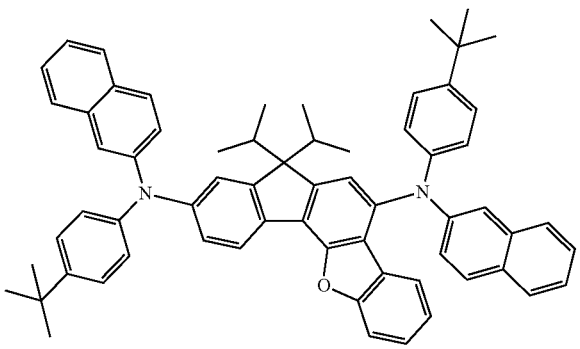
<Chemical Formula d123>
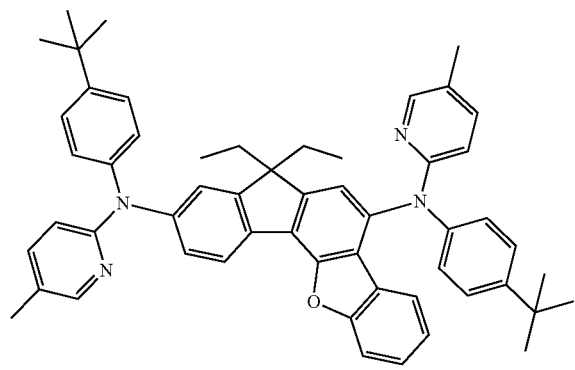
<Chemical Formula d124>
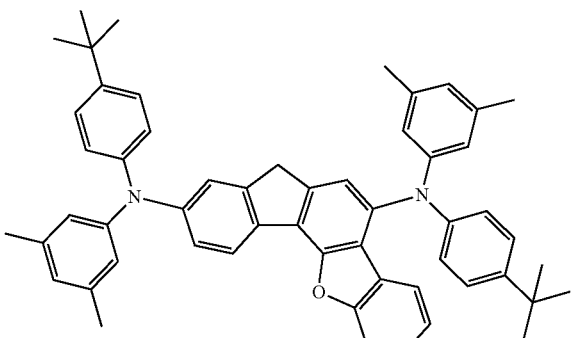

<Chemical Formula d125>
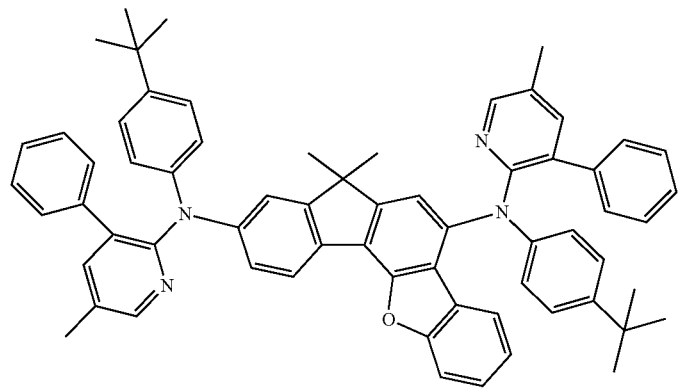
<Chemical Formula d126>
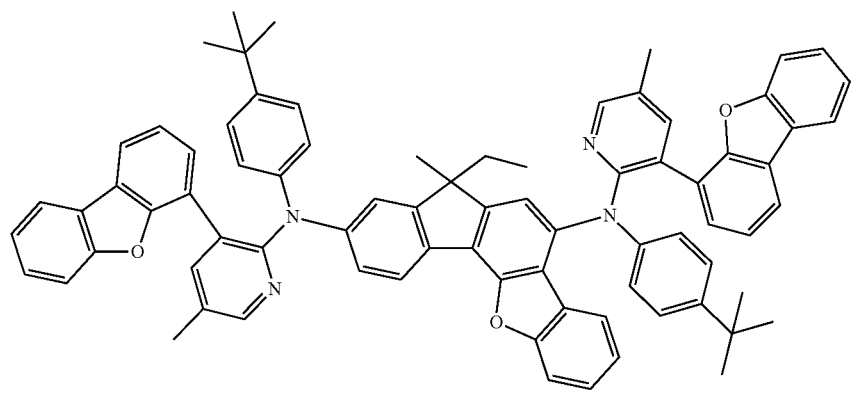
<Chemical Formula d127>
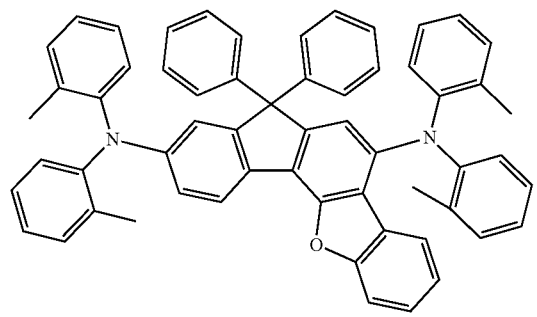
<Chemical Formula d128>
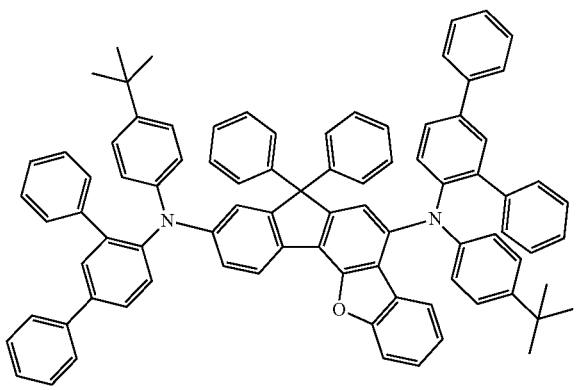
<Chemical Formula d129>
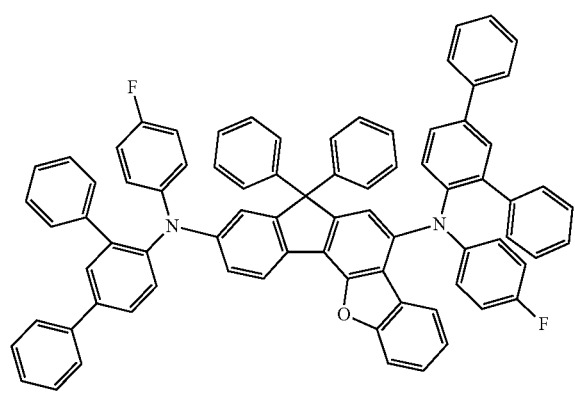
<Chemical Formula d130>
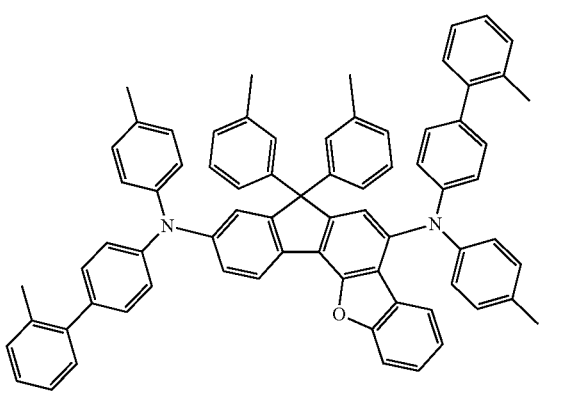

-continued
<Chemical Formula d131>
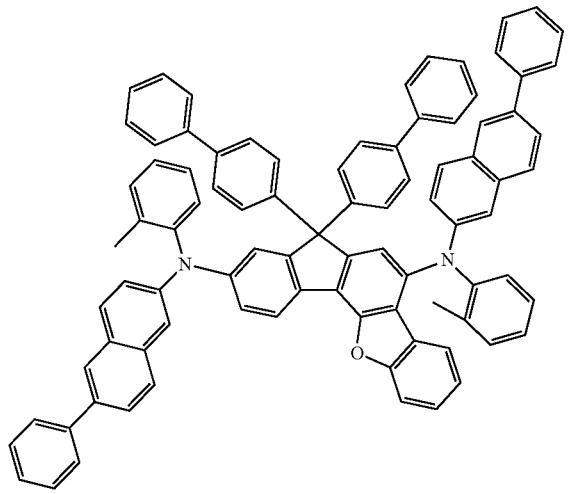
<Chemical Formula d132>
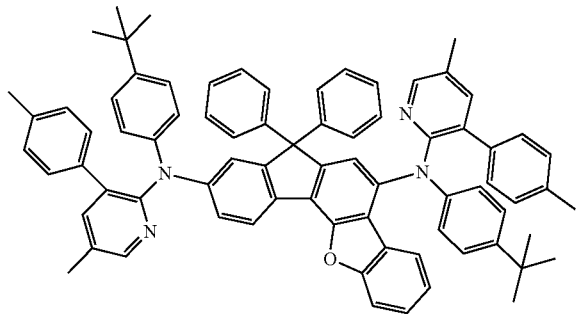
<Chemical Formula d133>
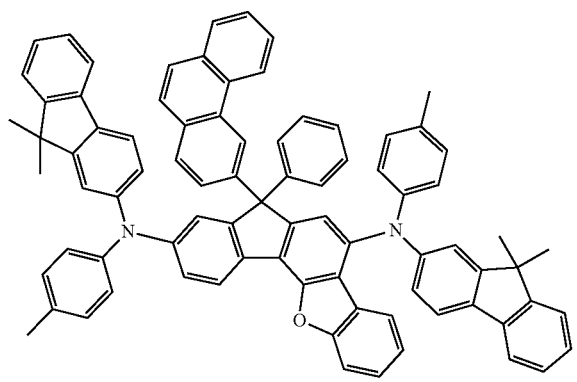
<Chemical Formula d134>
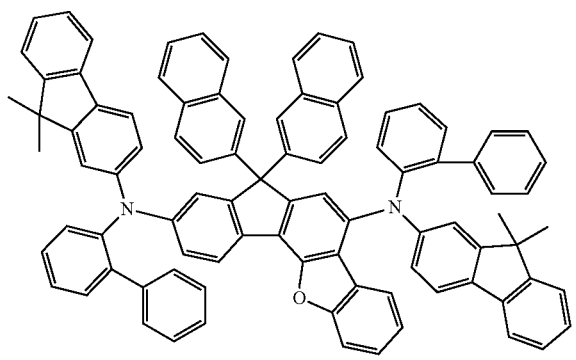
<Chemical Formula d135>
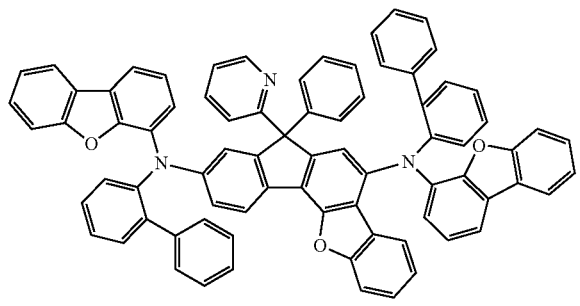
<Chemical Formula d136>
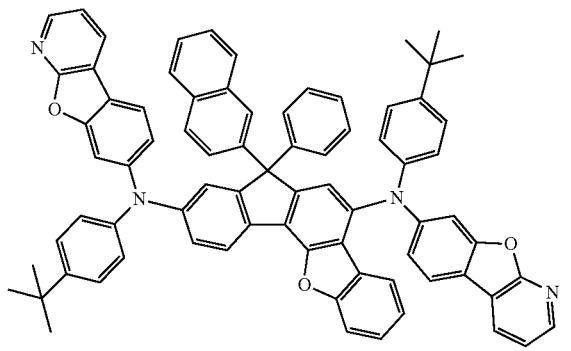

-continued
<Chemical Formula d137>
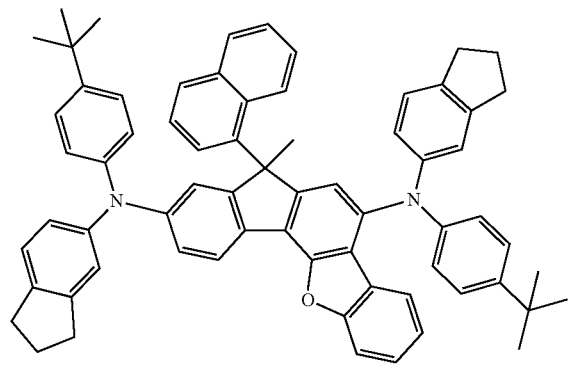
<Chemical Formula d138>
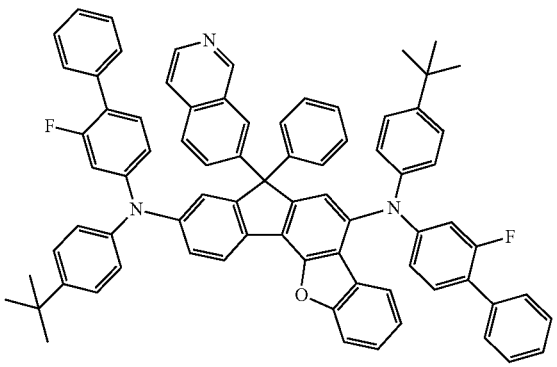
<Chemical Formula d139>
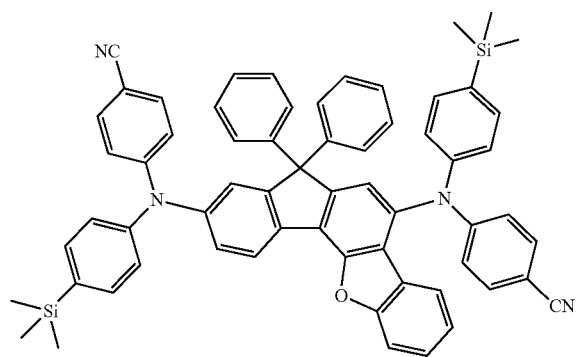
<Chemical Formula d140>
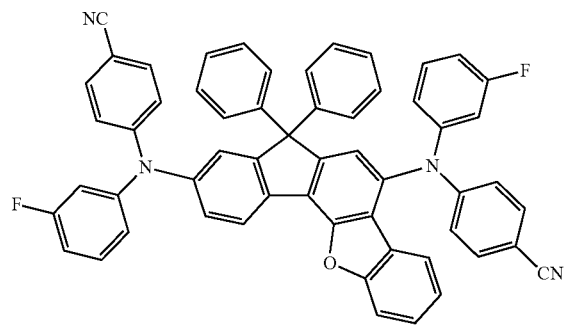
<Chemical Formula d141>
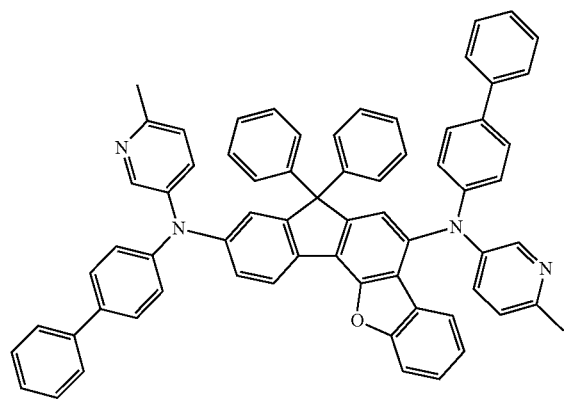
<Chemical Formula d142>
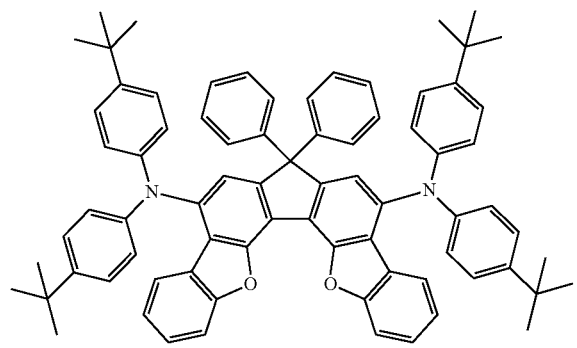

<Chemical Formula d143>
<Chemical Formula d144>
<Chemical Formula d145>
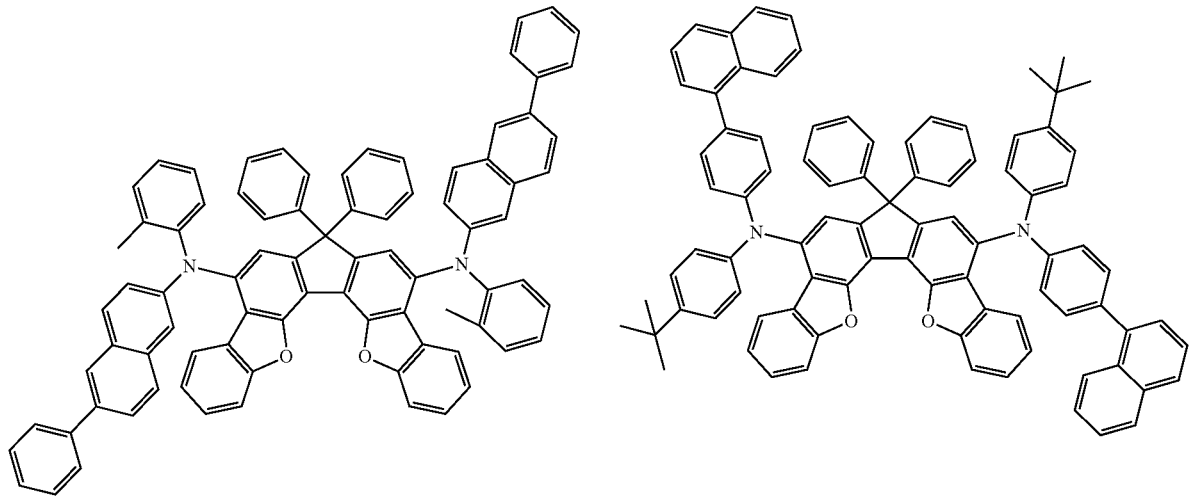
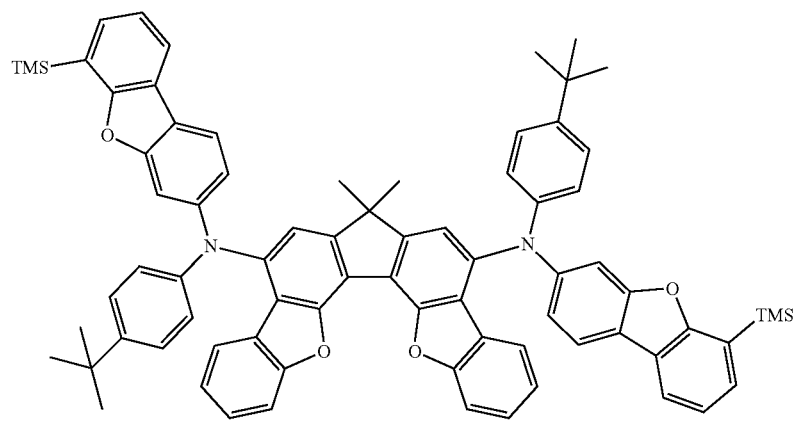
<Chemical Formula d146>
<Chemical Formula d147>
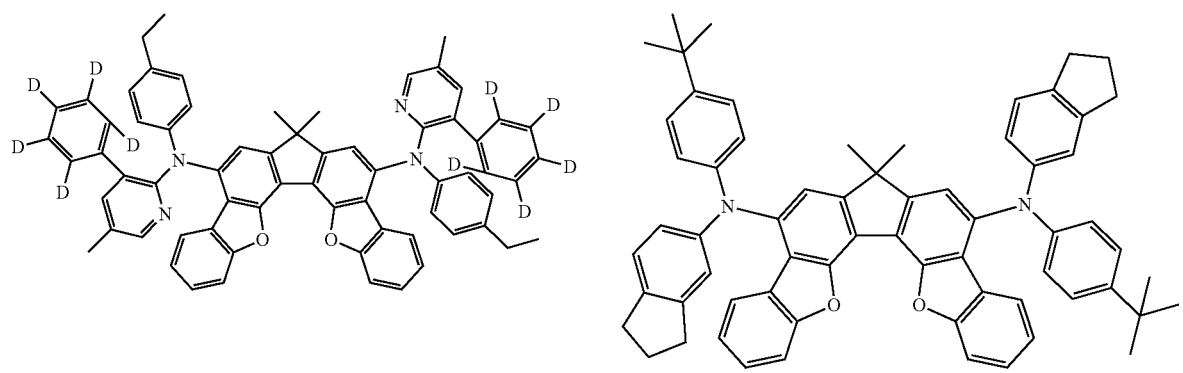

<Chemical Formula d148>
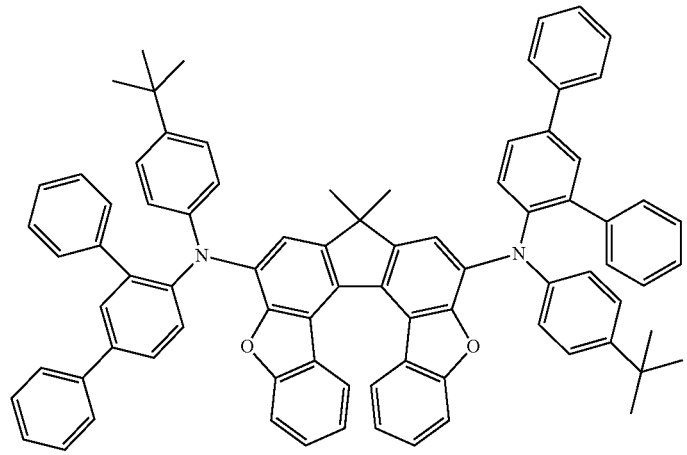
<Chemical Formula d149>
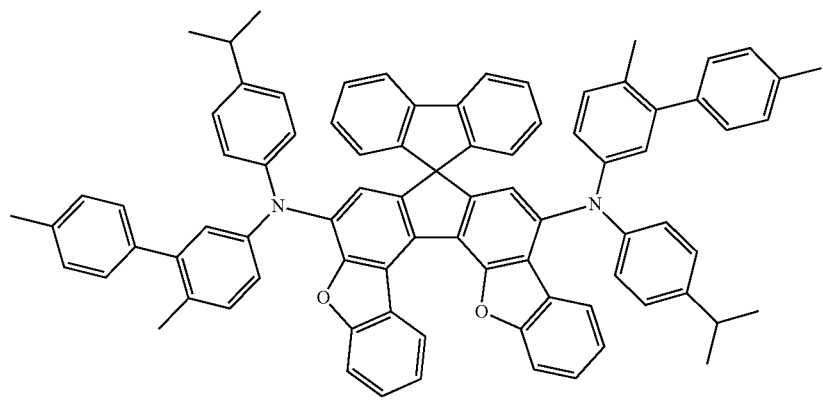
<Chemical Formula d150>
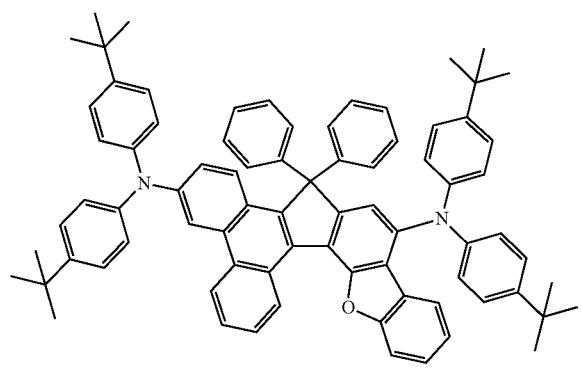
<Chemical Formula d151>
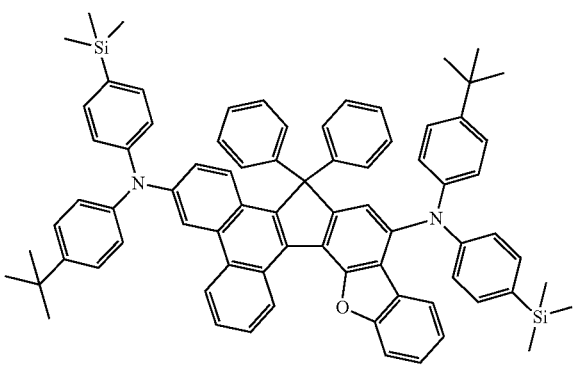

<Chemical Formula d152>
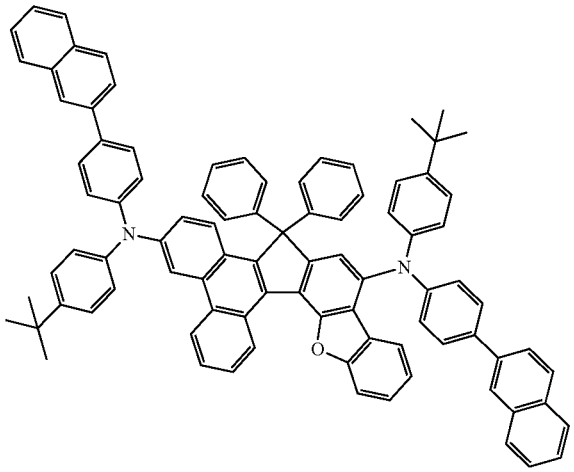
<Chemical Formula d153>
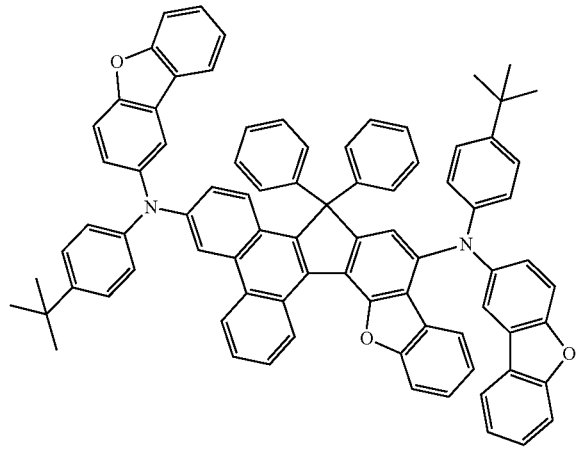
<Chemical Formula d154>
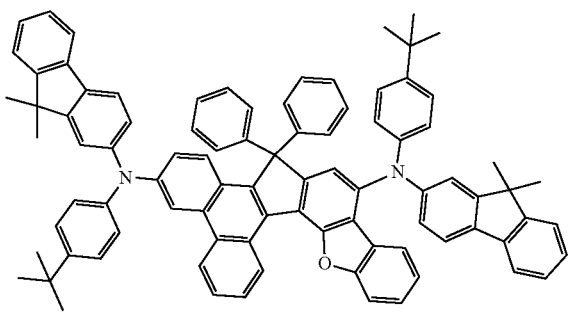
<Chemical Formula d155>
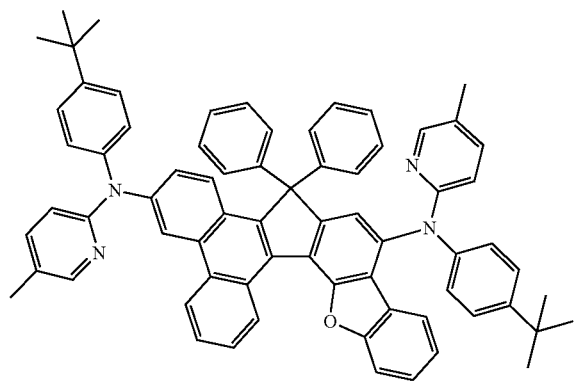
<Chemical Formula d156>
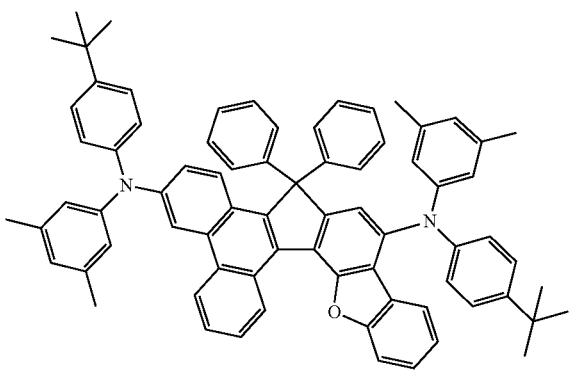
<Chemical Formula d157>
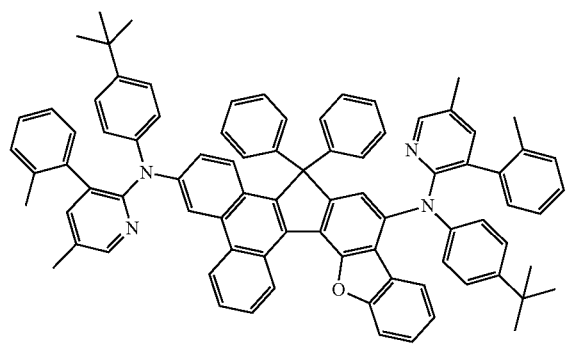

-continued
<Chemical Formula d158>
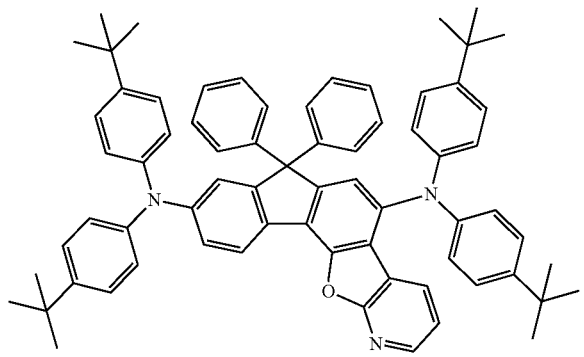
<Chemical Formula d159>
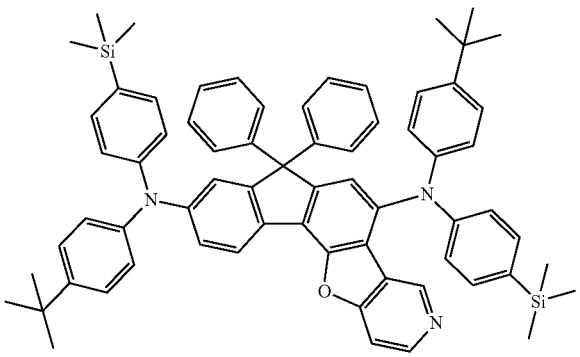
<Chemical Formula d160>
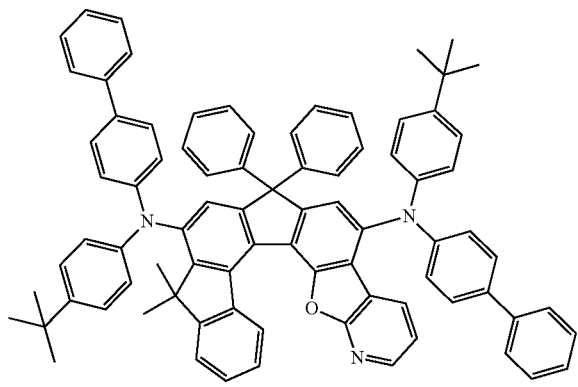
<Chemical Formula d161>
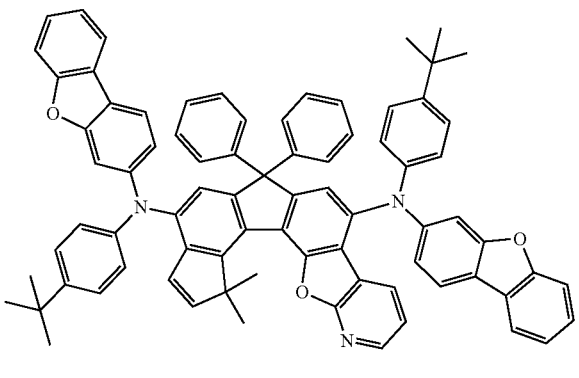
<Chemical Formula d162>
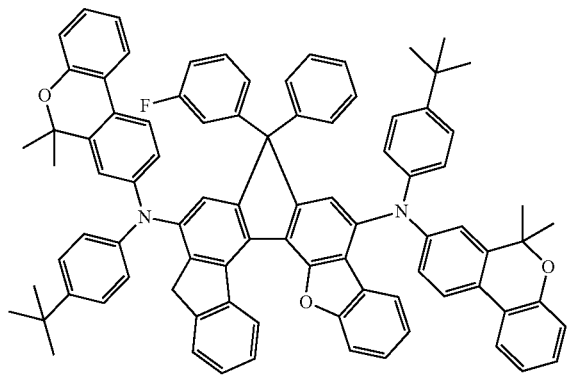
<Chemical Formula d163>
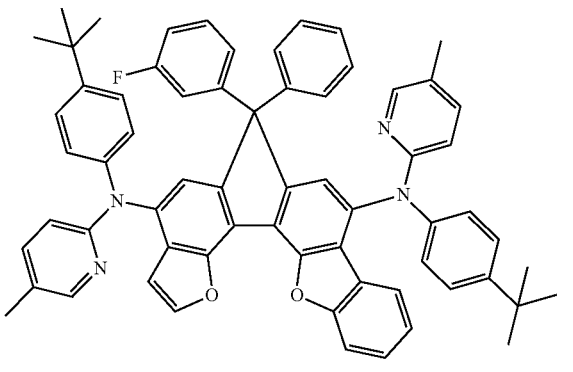
<Chemical Formula d164>
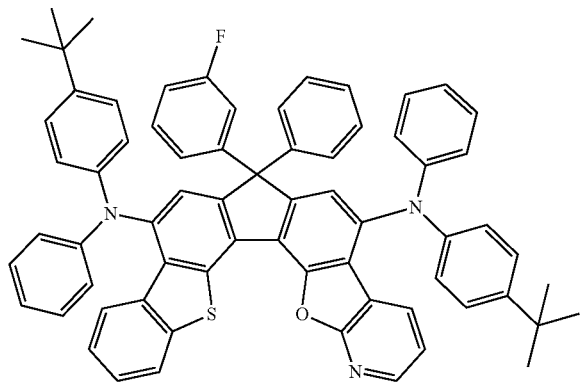
<Chemical Formula d165>
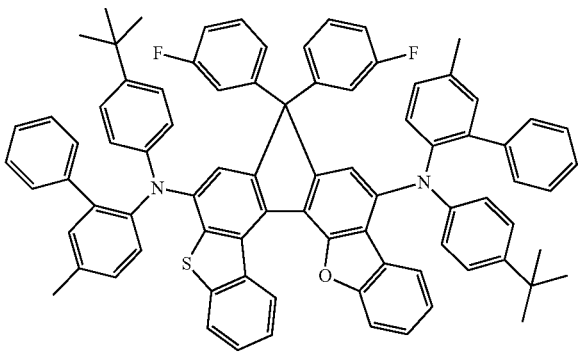

-continued
<Chemical Formula d166>
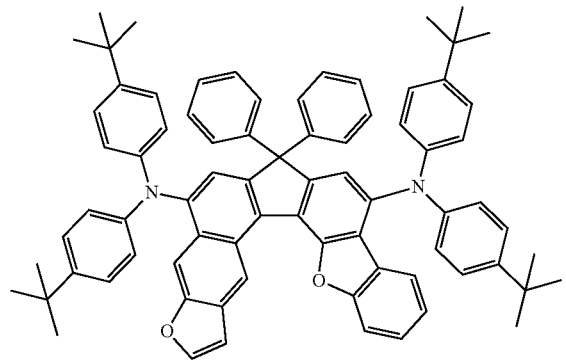
<Chemical Formula d167>
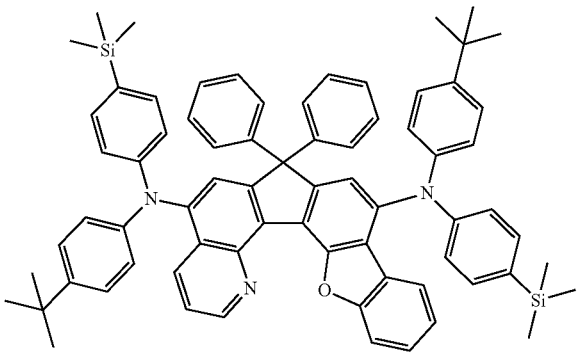
<Chemical Formula d168>
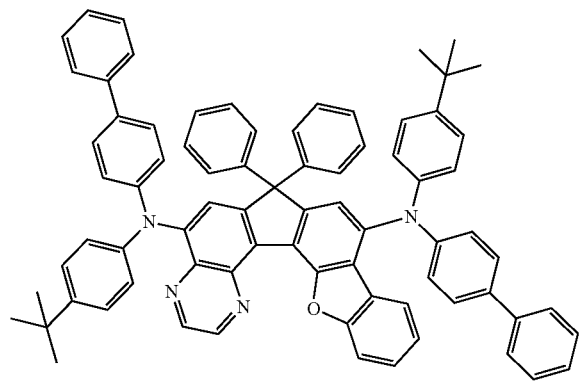
<Chemical Formula d169>
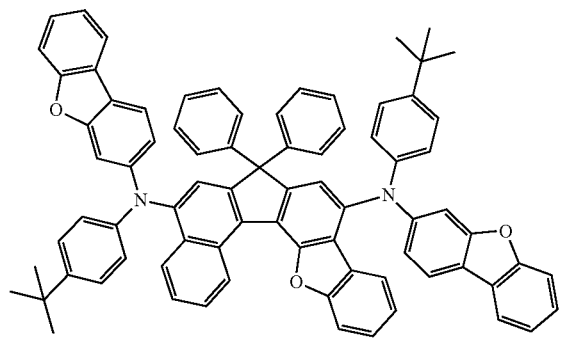
<Chemical Formula d170>
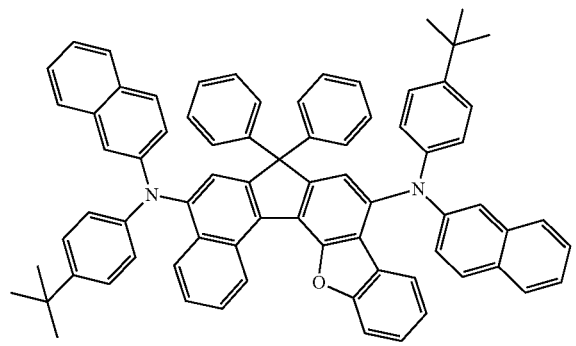
<Chemical Formula d171>
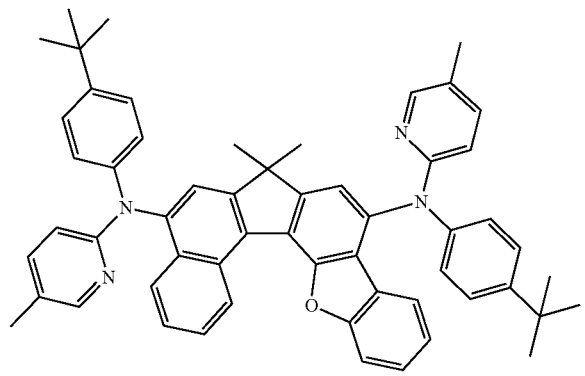
<Chemical Formula d172>
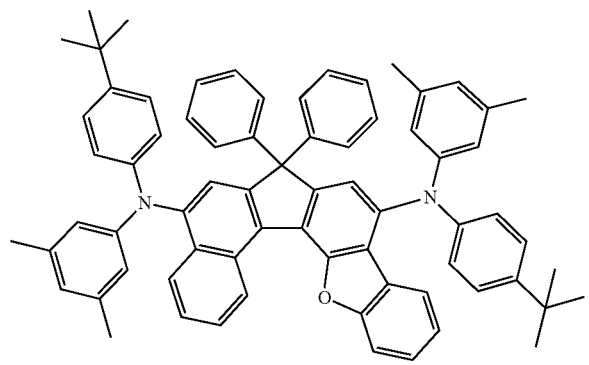
<Chemical Formula d173>
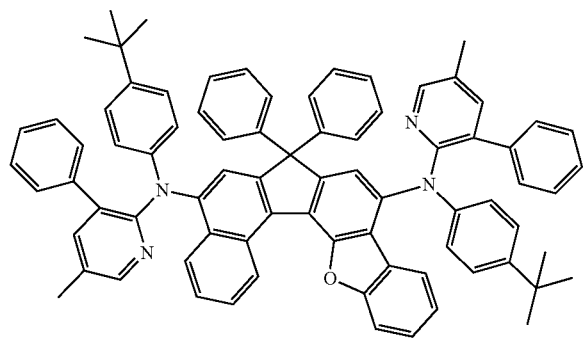

-continued
<Chemical Formula d174>
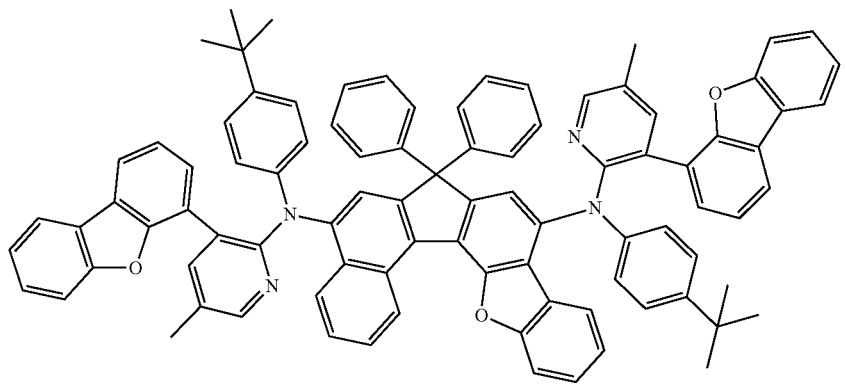
<Chemical Formula d175>
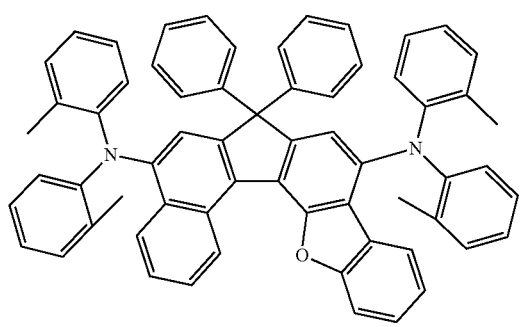
<Chemical Formula d176>
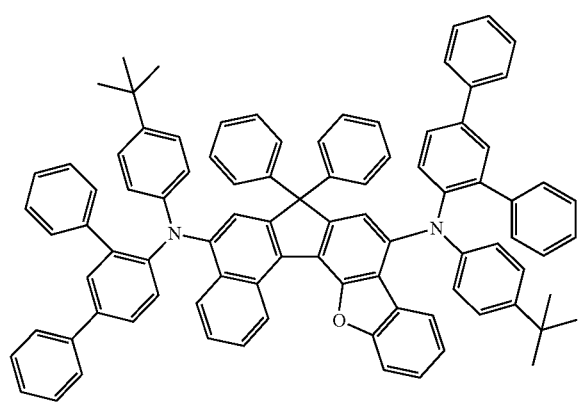
<Chemical Formula d177>
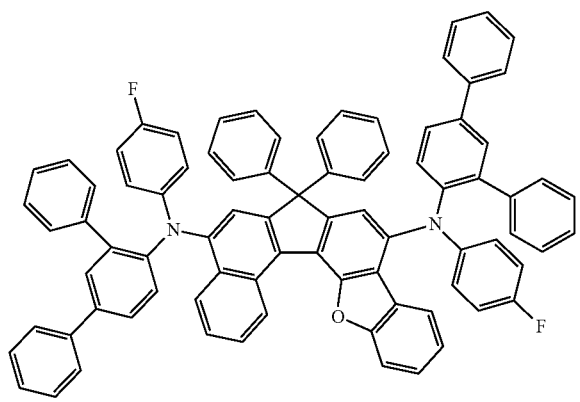
<Chemical Formula d178>
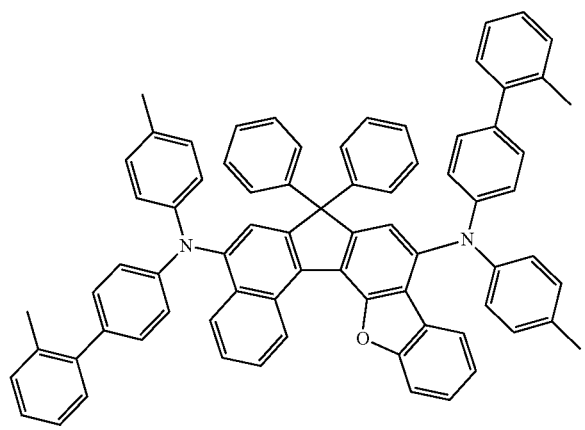
<Chemical Formula d179>
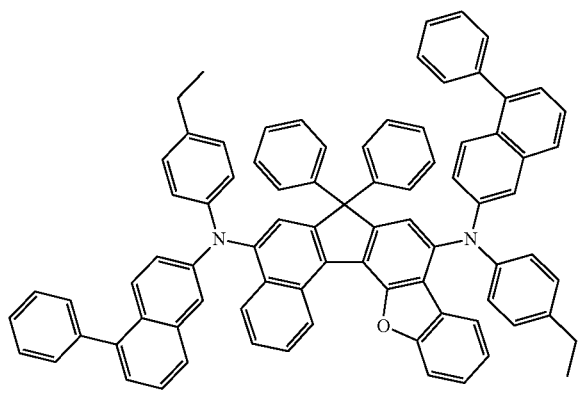
<Chemical Formula d180>
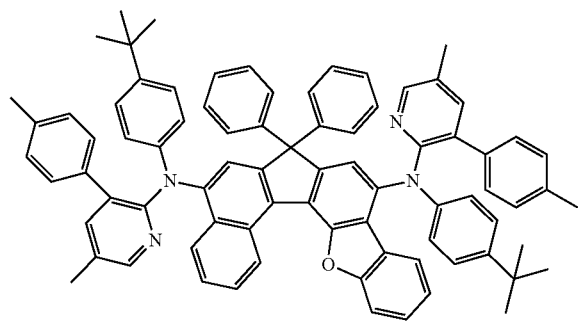

<Chemical Formula d181>
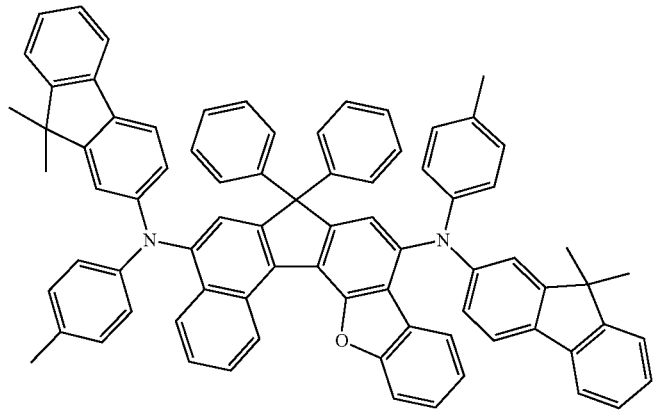
<Chemical Formula d182>
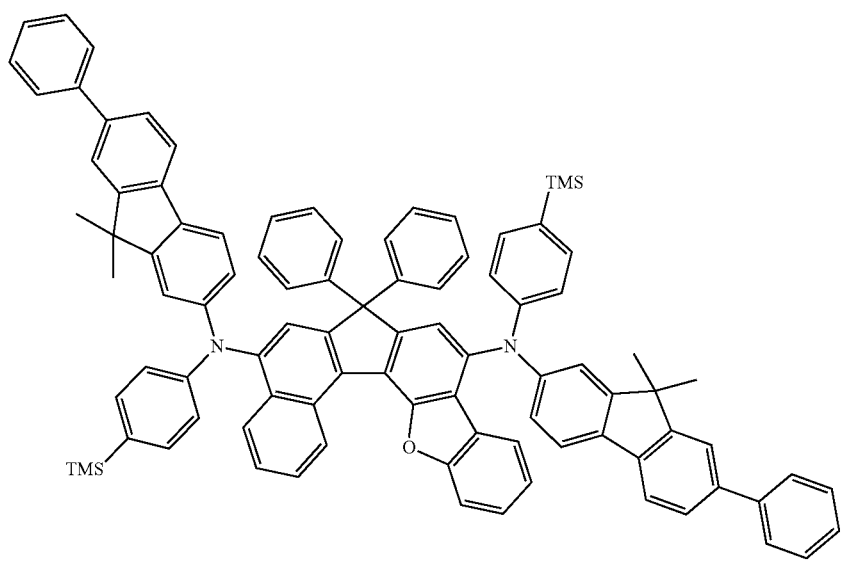
<Chemical Formula d183>
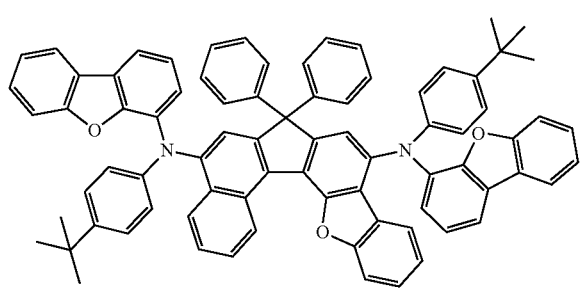
<Chemical Formula d184>
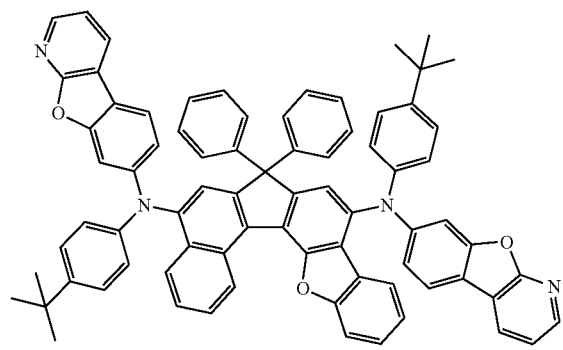

<Chemical Formula d185>
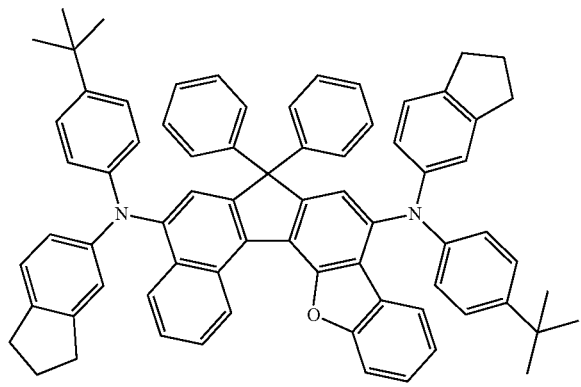
<Chemical Formula d186>
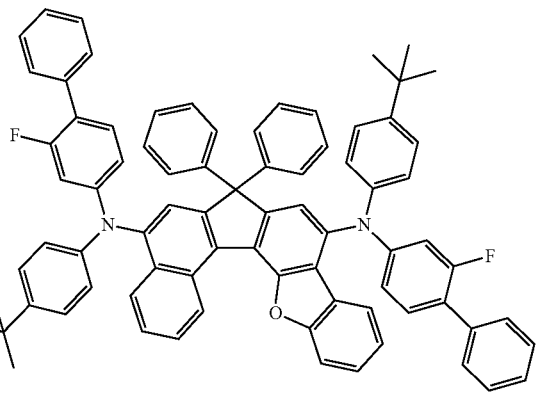
<Chemical Formula d187>
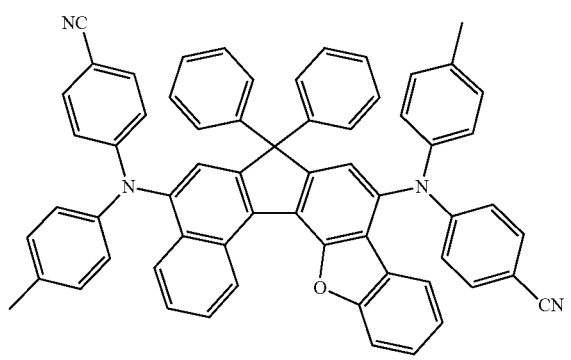
<Chemical Formula d188>
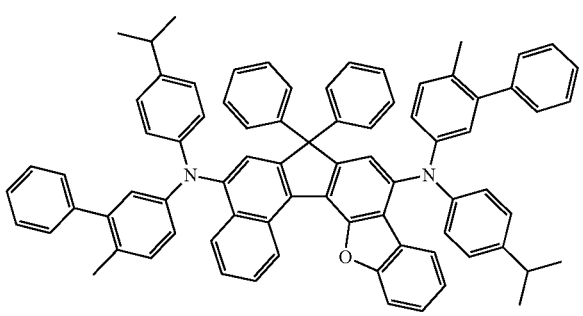
<Chemical Formula d189>
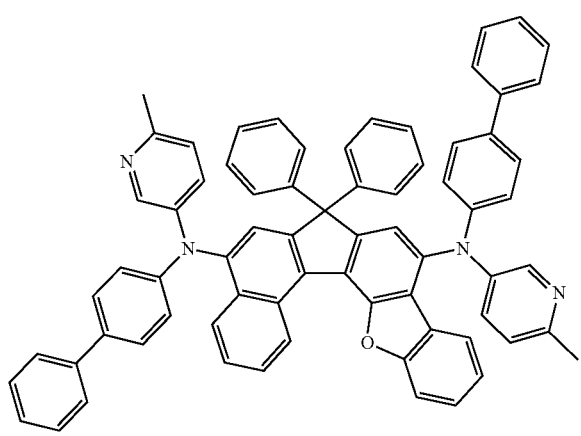
<Chemical Forula d190>
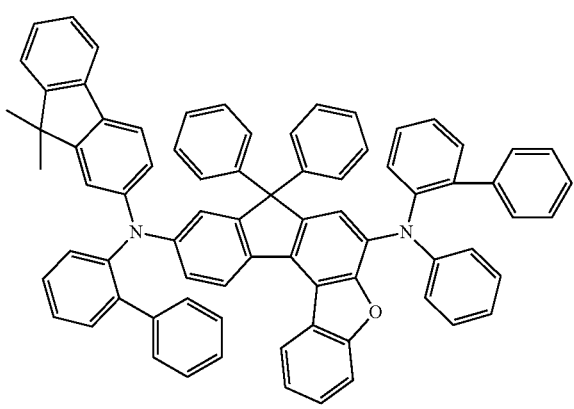

<Chemical Formula d191>
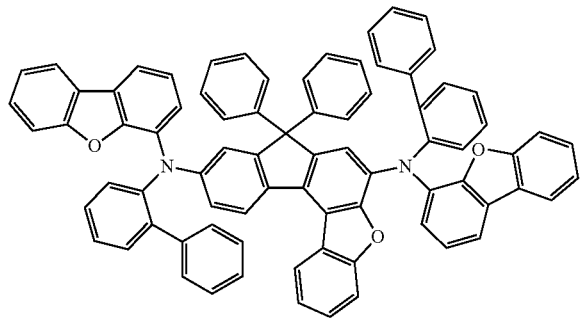
<Chemical Formula d192>
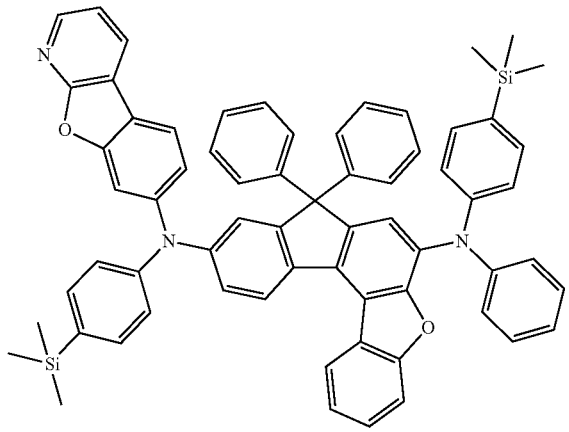
<Chemical Formula d193>
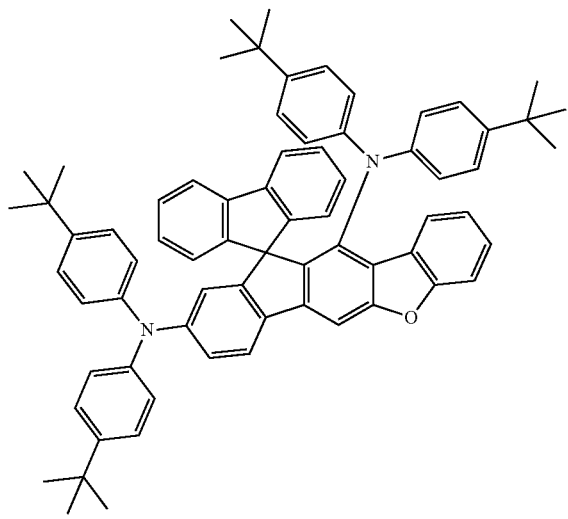
<Chemical Formula d194>
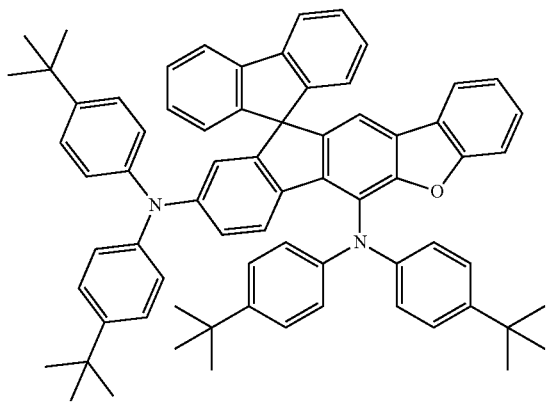
<Chemical Formula d195>
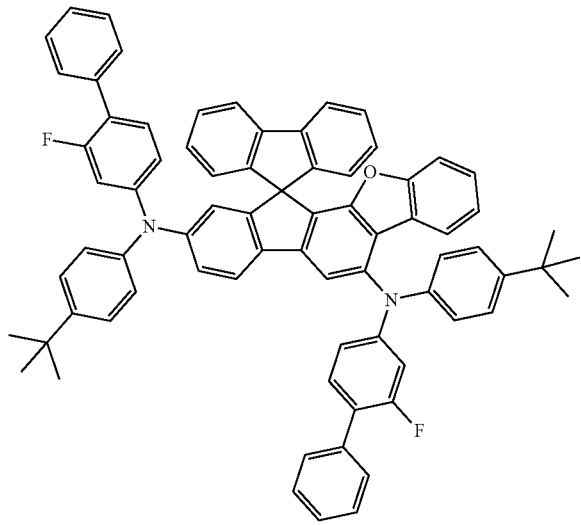
<Chemical Formula d196>
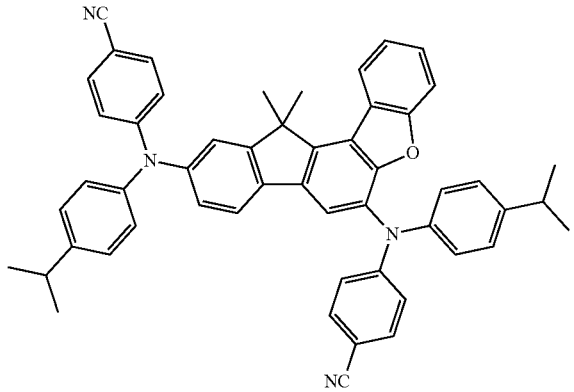

-continued
<Chemcial Formula d197>
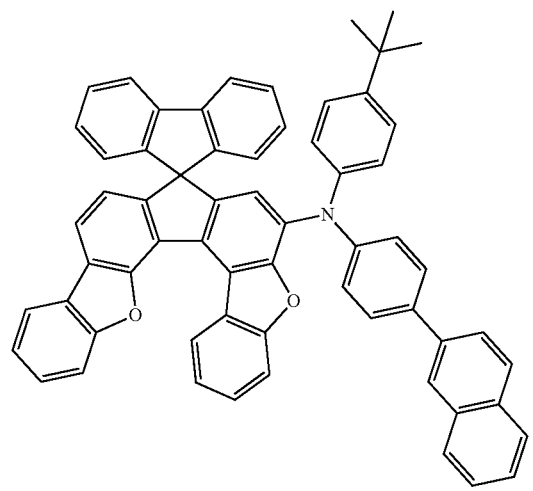
<Chemical Formula d198>
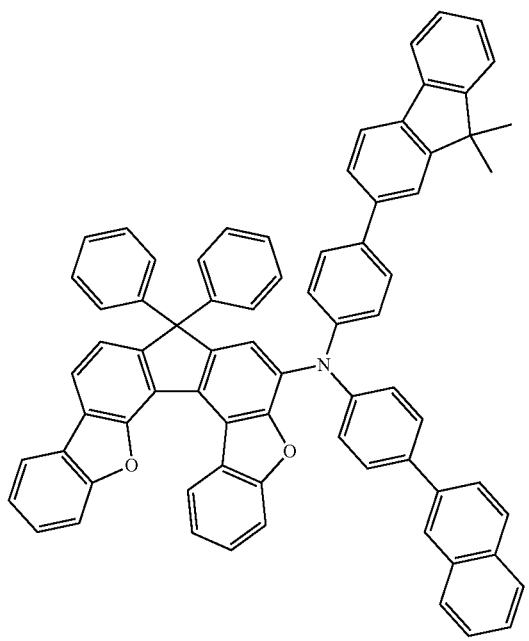
<Chemical Formula d199>
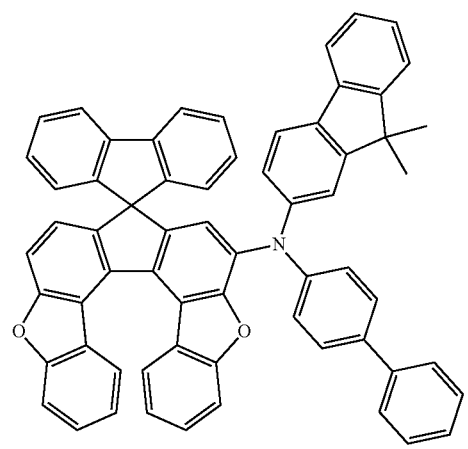
<Chemical Formula d200>
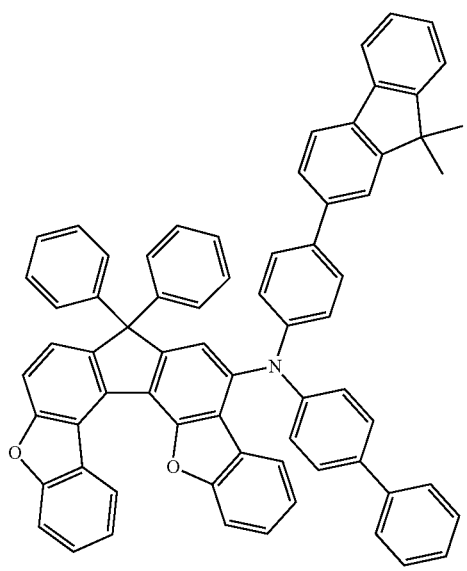

-continued
<Chemical Formula d201>
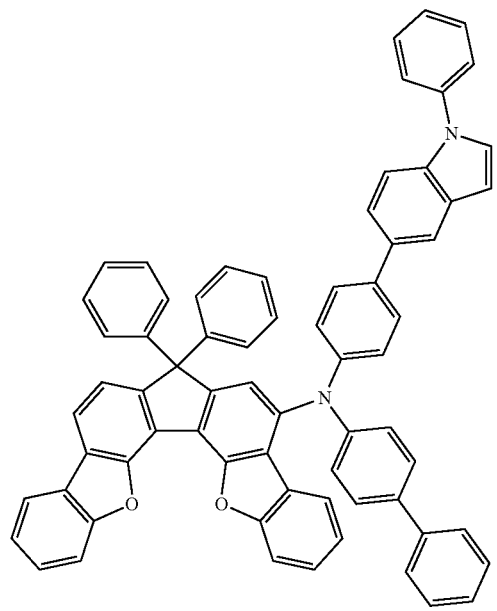
<Chemical Formula d202>
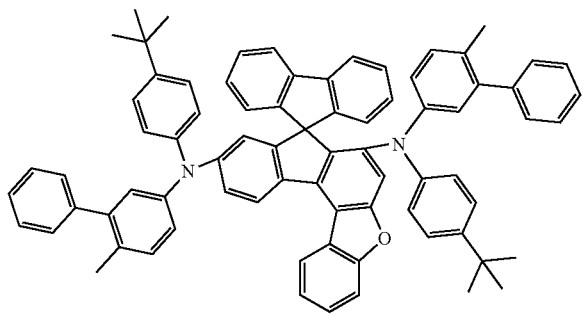
<Chemical Formula d203>
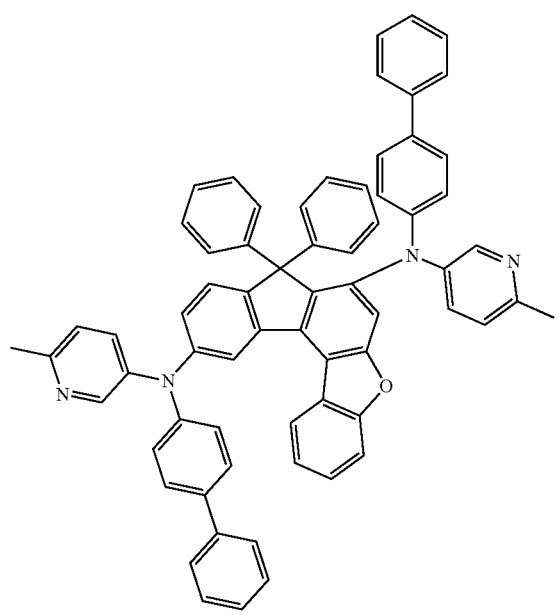
<Chemical Formula d204>
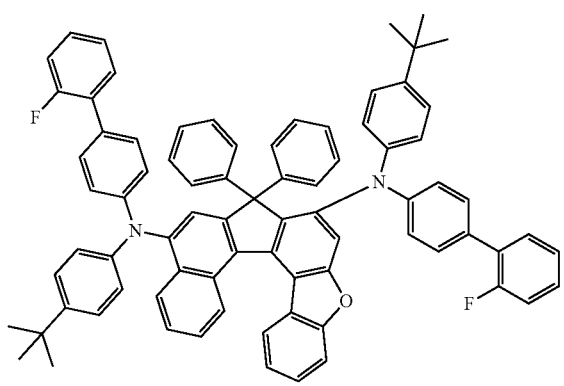
<Chemical Formula d205>
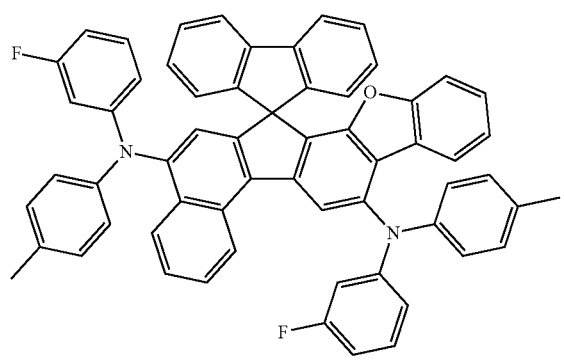
<Chemical Formula d206>
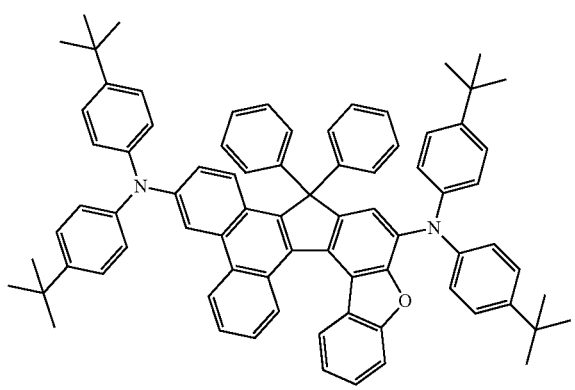

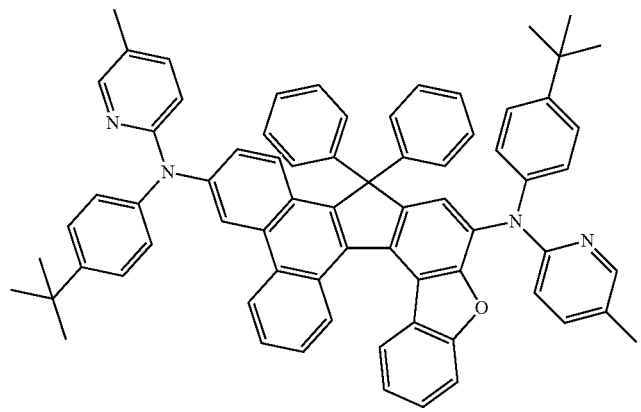
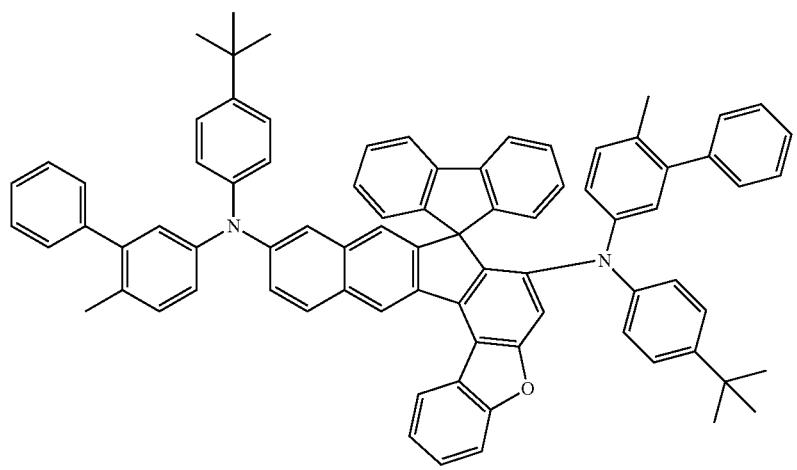
<Chemical Formula d207>
<Chemical Formula d208>
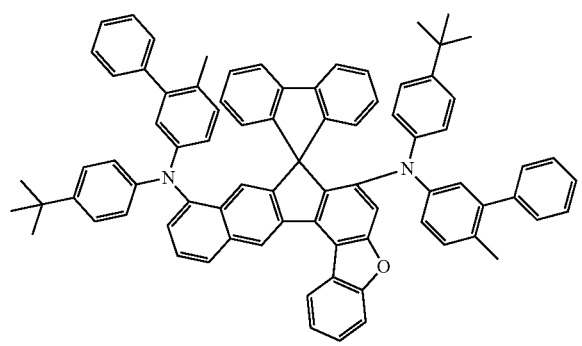
<Chemical Formula d 209>
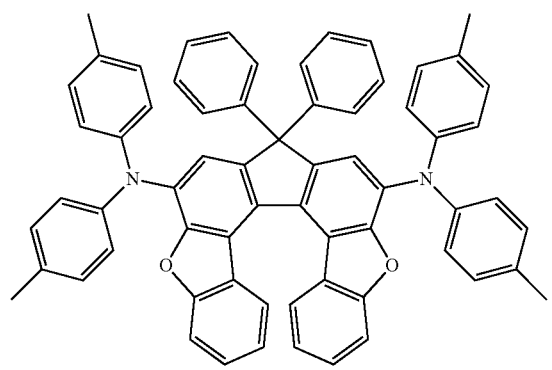
<Chemical Formula d210>

<Chemical Formula d211>
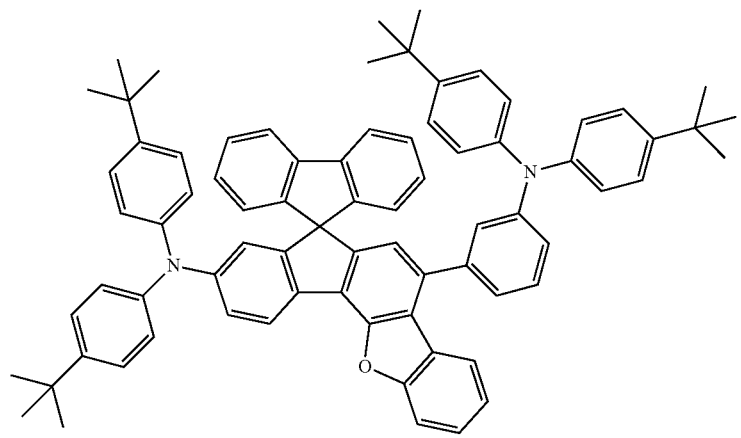
<Chemical Formula d212>
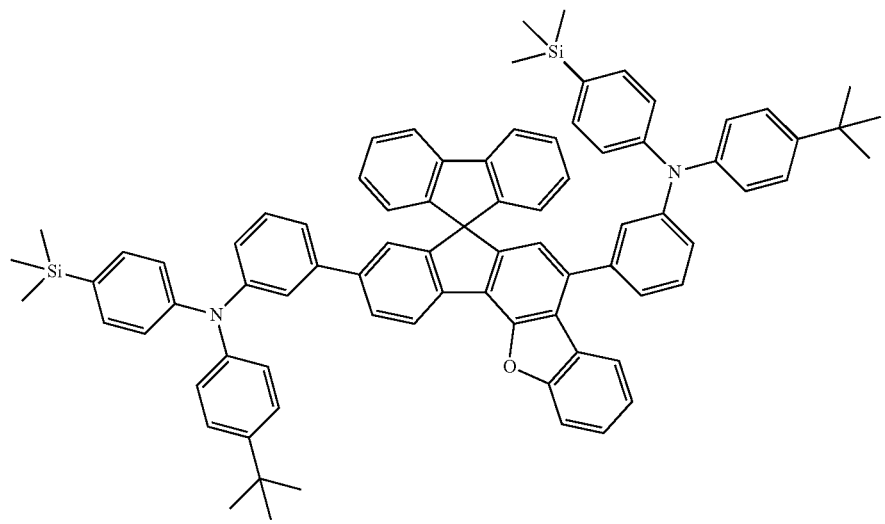
<Chemical Formula d213>
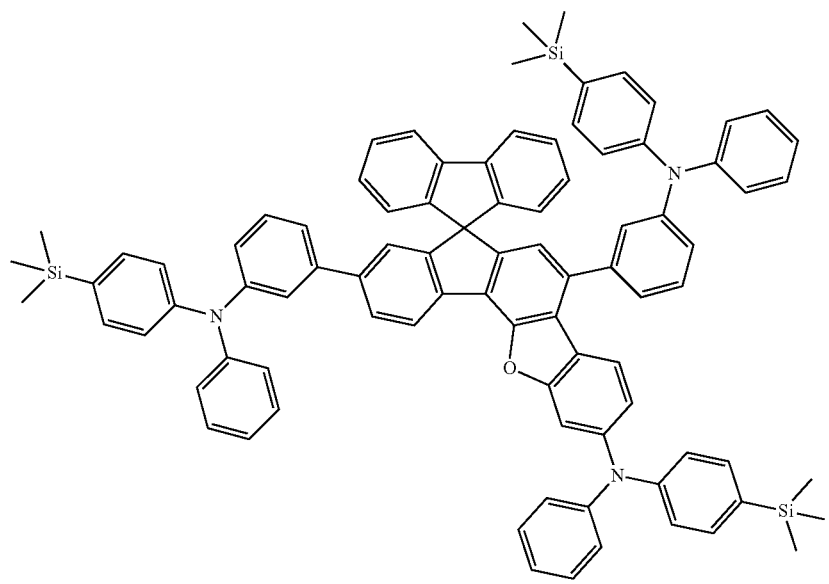

-continued
<Chemical Formula d214>
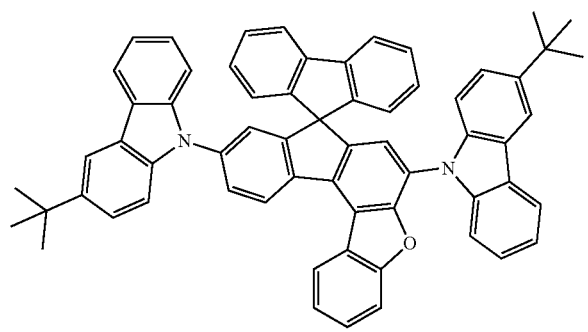
<Chemical Formula d215>
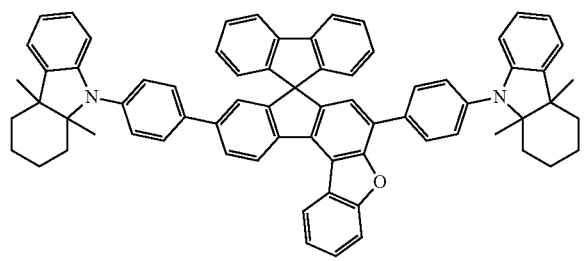
<Chemical Formula d216>
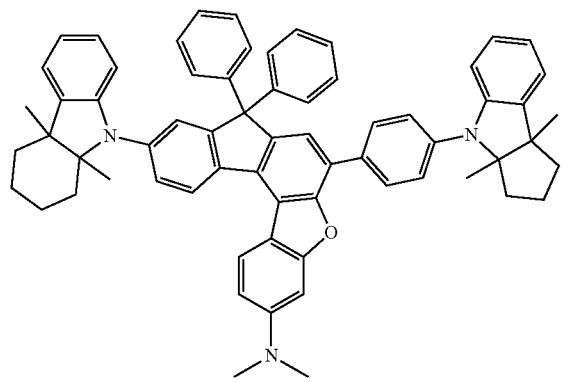
<Chemical Formula d217>
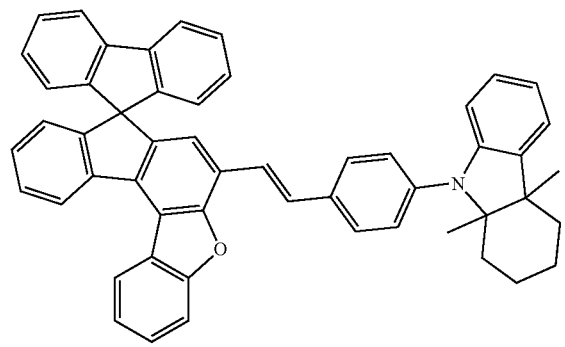
<Chemical Formula d218>
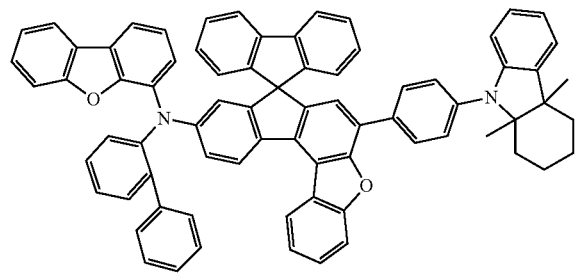
<Chemical Formula d219>
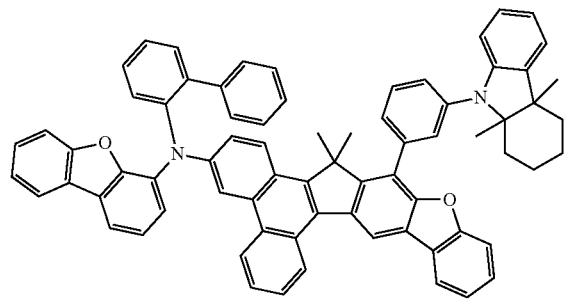
<Chemical Formula d220>
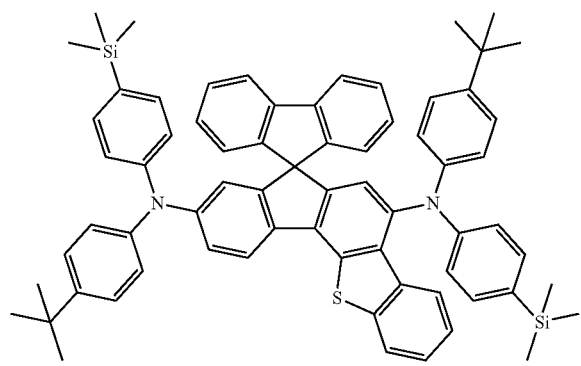
<Chemical Formula d221>
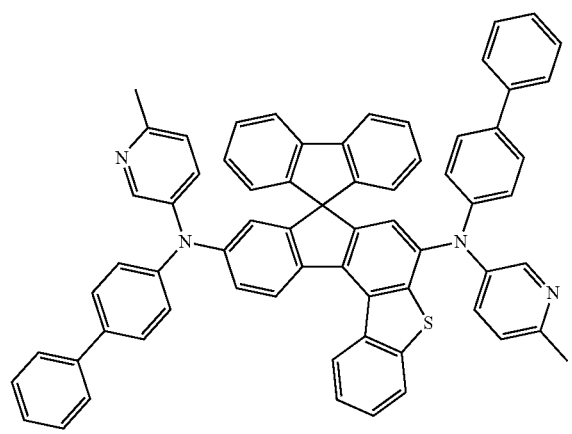

<Chemical Formula d222>
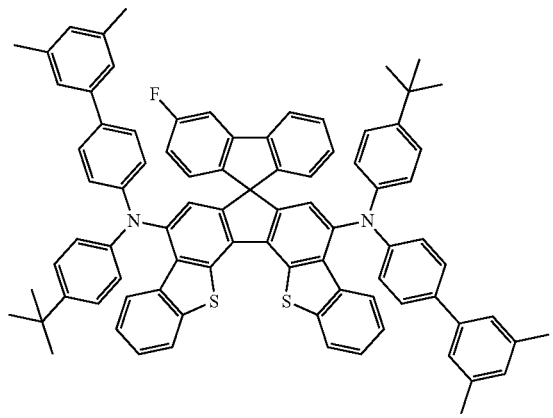
<Chemical Formula d223>
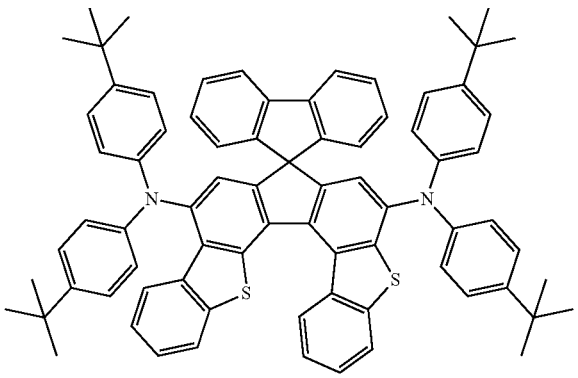
<Chemical Formula d224>
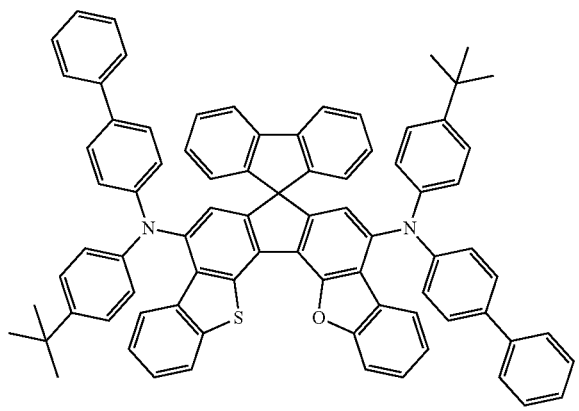
<Chemical Formula d225>
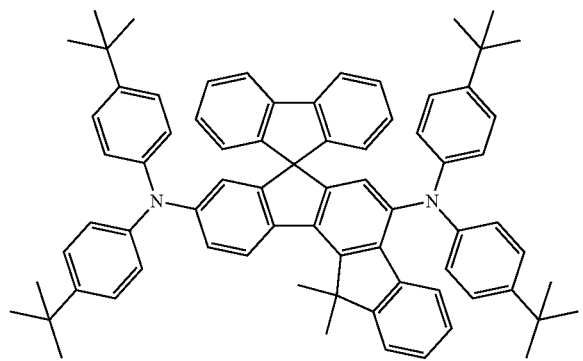
<Chemical Formula d226>
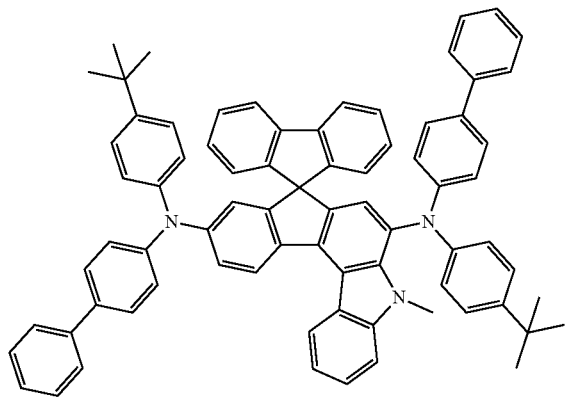
<Chemical Formula d227>
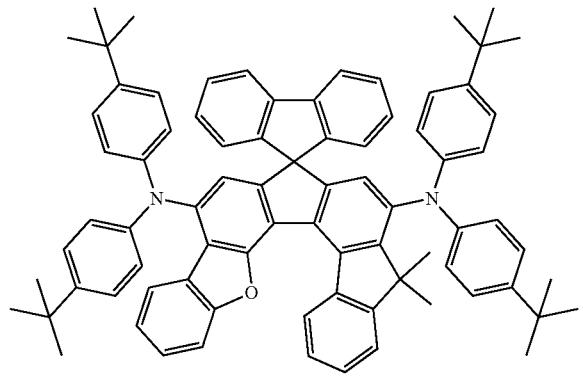

-continued
<Chemical Formula d228>
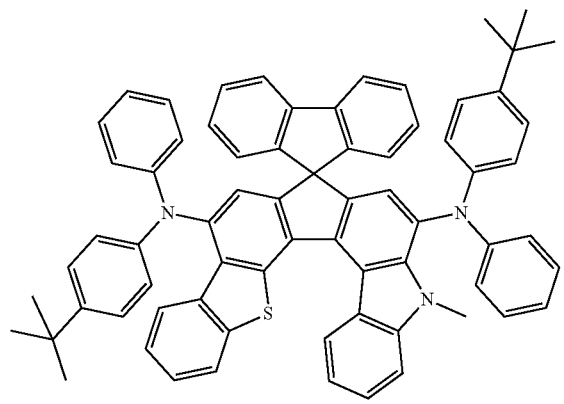
<Chemical Formula d229>
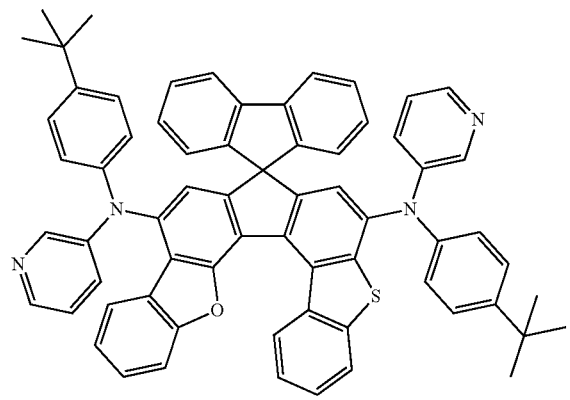
<Chemical Formula d230>
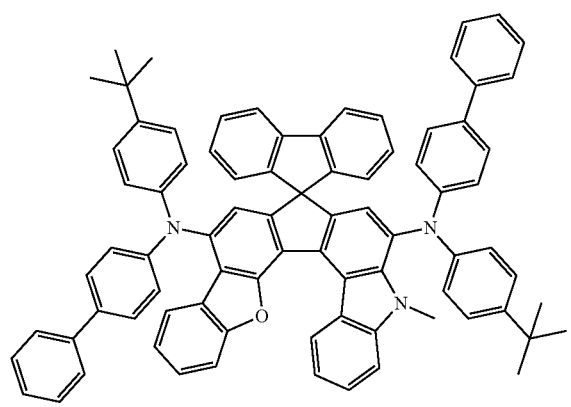
<Chemical Formula d231>
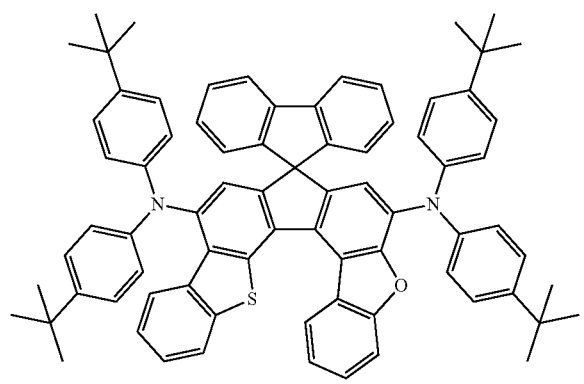
<Chemical Formula d232>
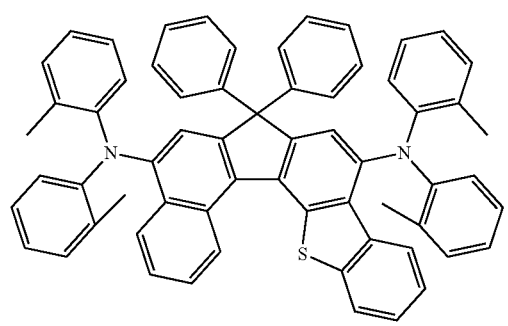
<Chemical Formula d233>
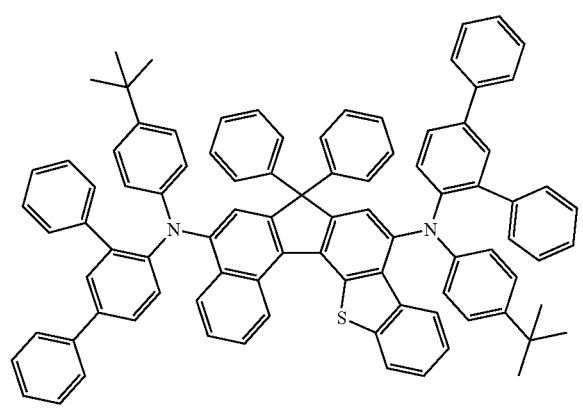

-continued
<Chemical Formula d234>
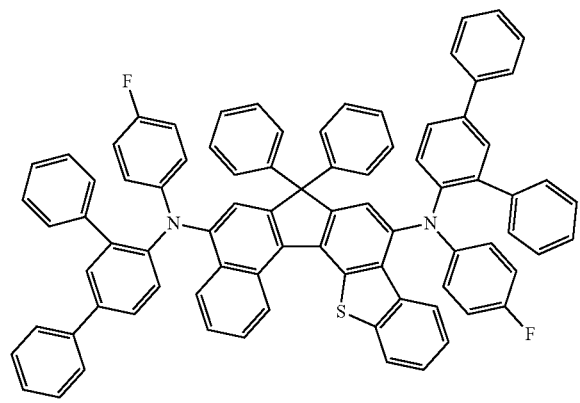
<Chemical Formula d235>
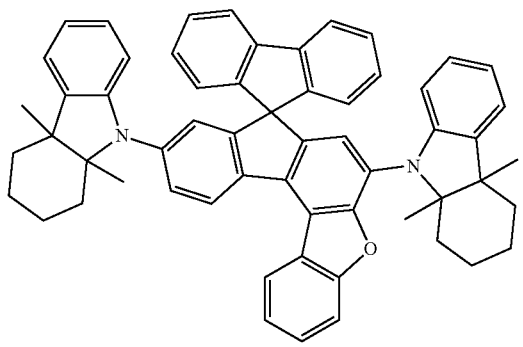
<Chemical Formula d236>
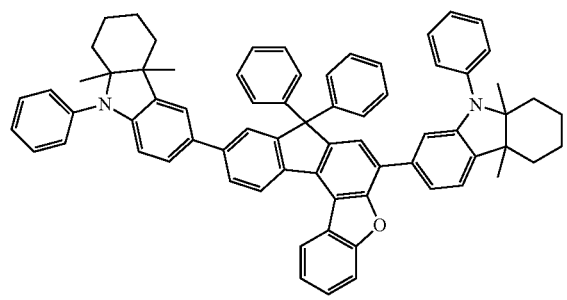
<Chemical Formula d237>
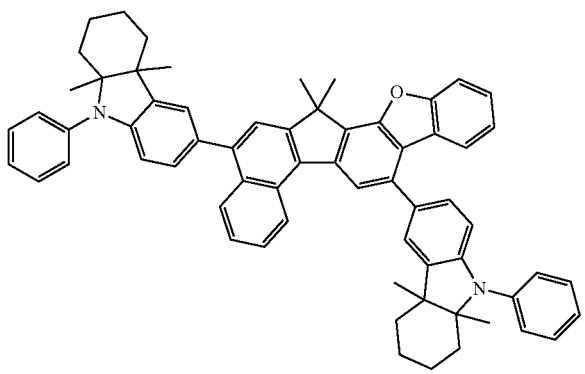
<Chemical Formula d238>
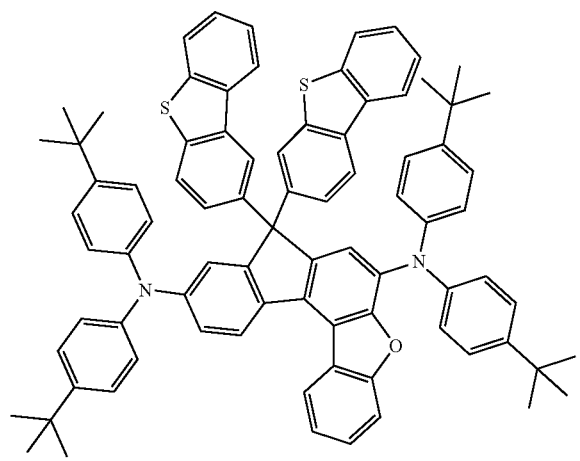
<Chemical Formula d239>
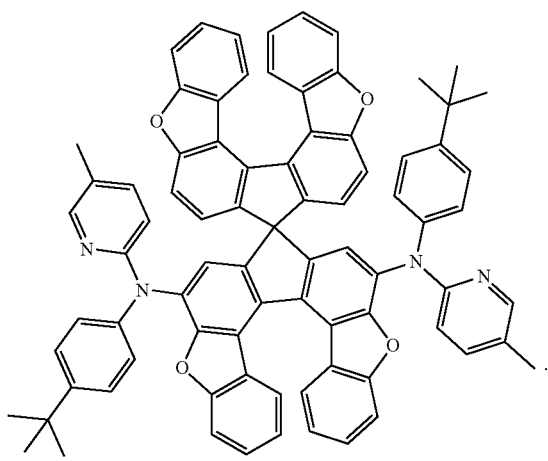

In addition, concrete examples of the compound represented by Chemical Formula D3 include the compounds represented by the following Chemical Formulas D101 to D130:
<Chemical Formula D 101>
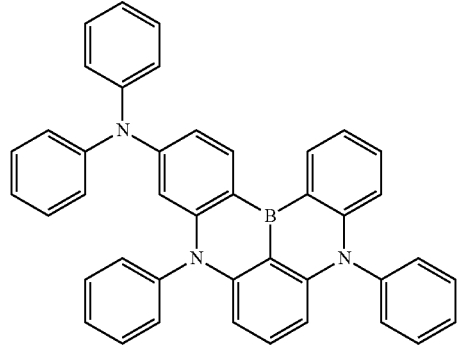
<Chemical Formula D 102>
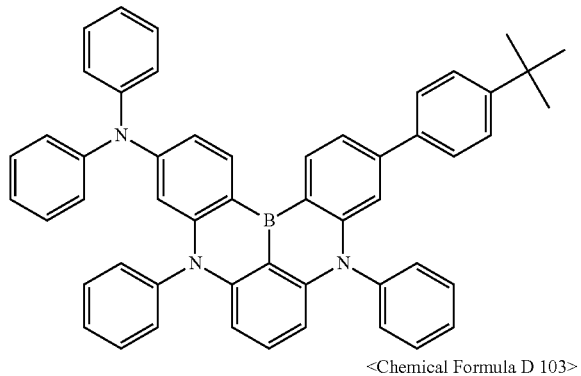
<Chemical Formula D 103>
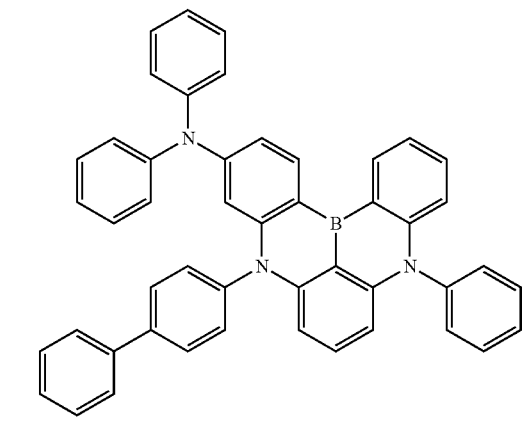
<Chemical Formula D 104>
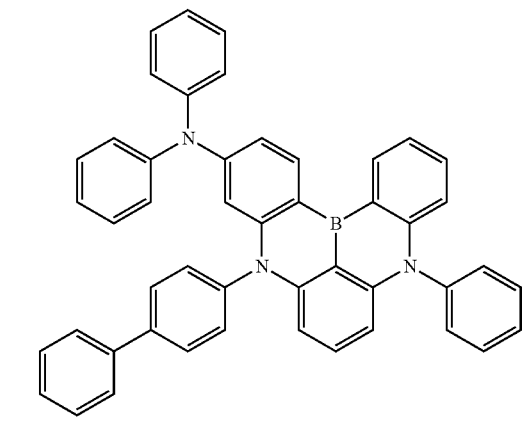
<Chemical Formula D 105>
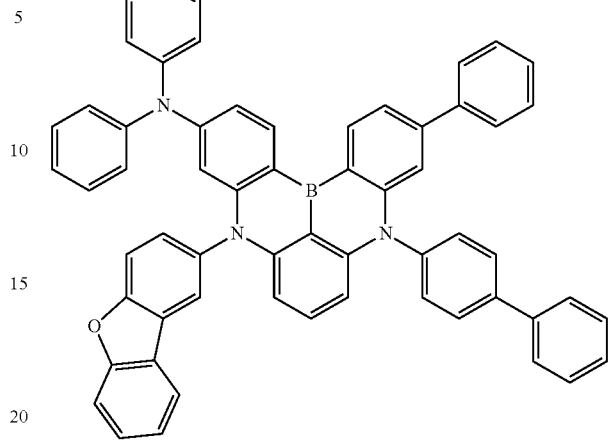
<Chemical Formula D 106>
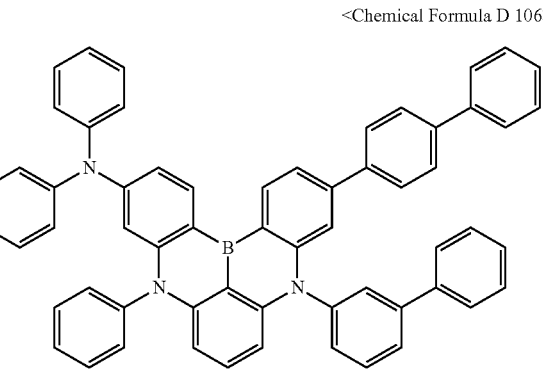
<Chemical Formula D 107>
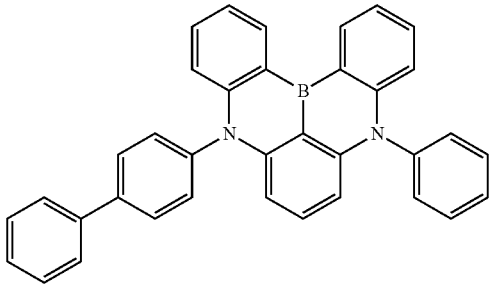
<Chemical Formula D 108>
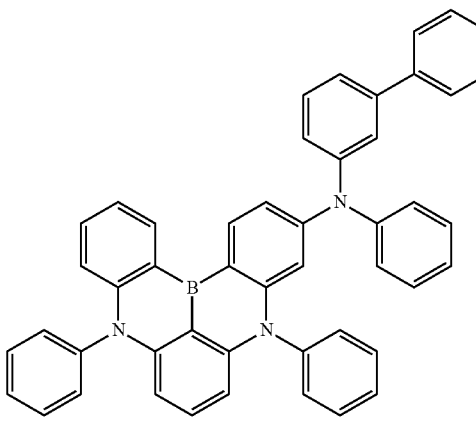

<Chemical Formula D 109>
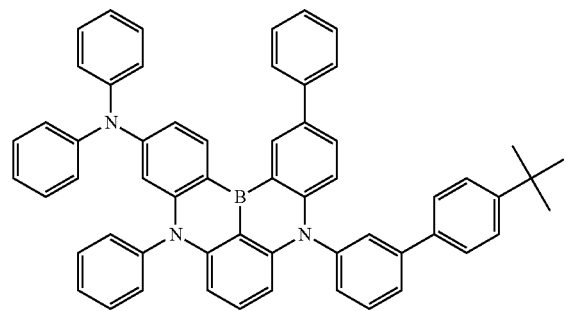
<Chemical Formula D 110>
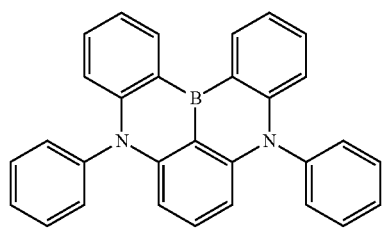
<Chemical Formula D 111>
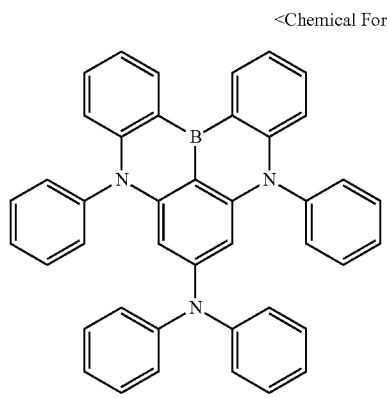
<Chemical Formula D 112>
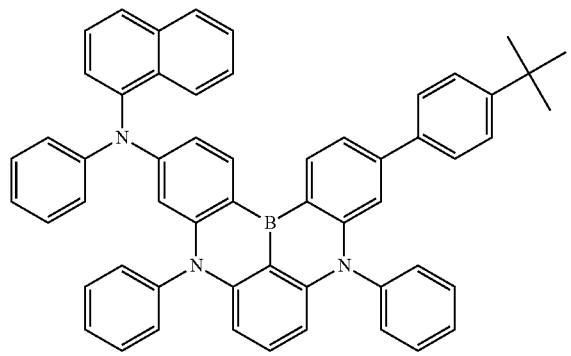
<Chemical Formula D 113>
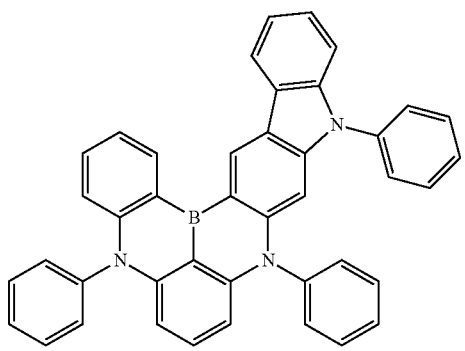
<Chemical Formula D 114>
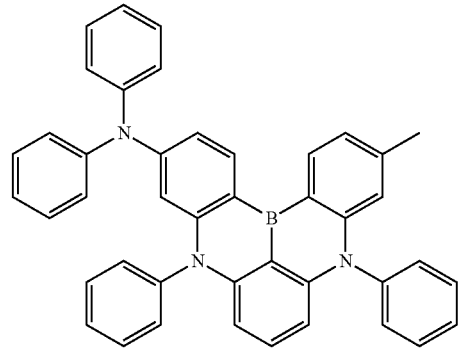
<Chemical Formula D 115>
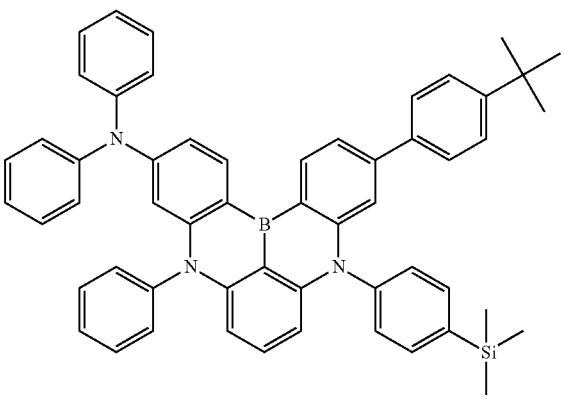

<Chemical Formula D 116>
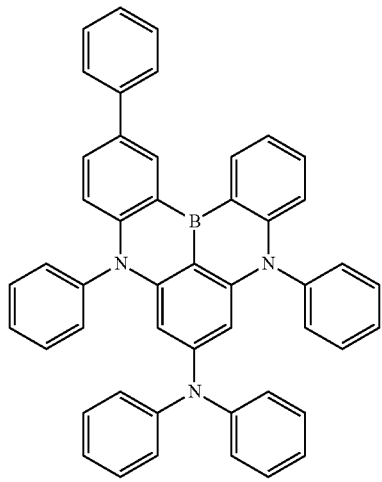
<Chemical Formula D 117>
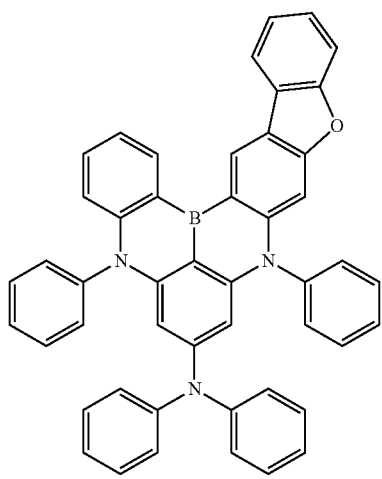
<Chemical Formula D 118>
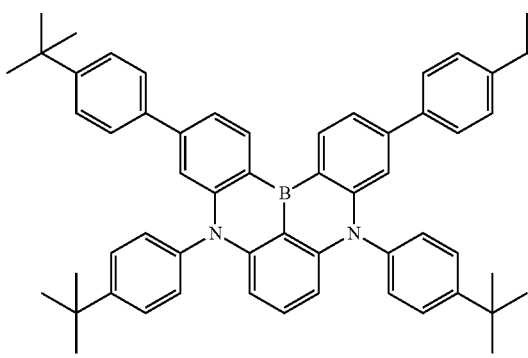
<Chemical Formula D 119>
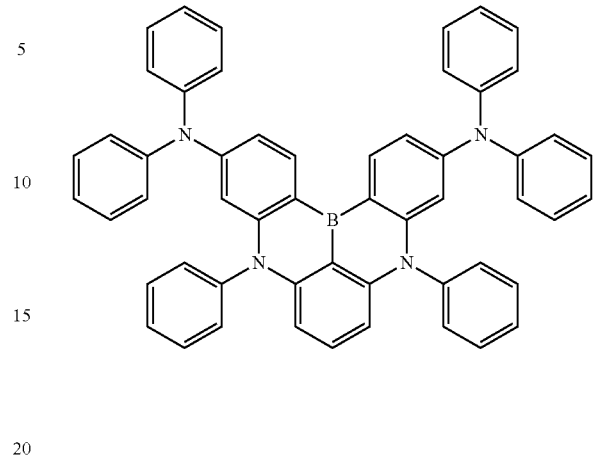
<Chemical Formula D 120>
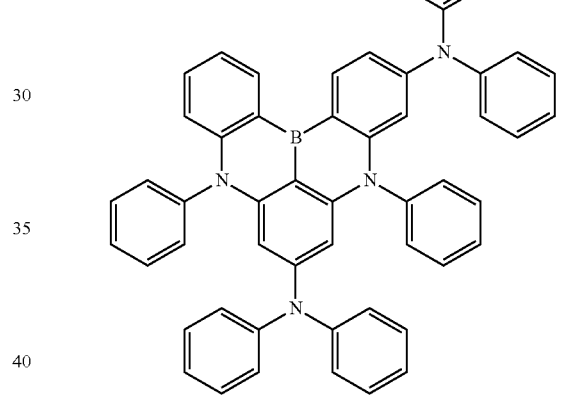
<Chemical Formula D 121>
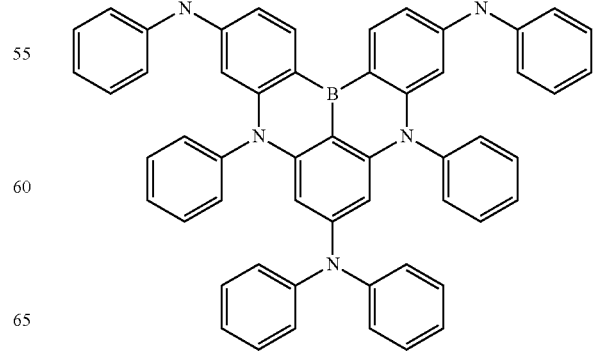

<Chemical Formula D 122>
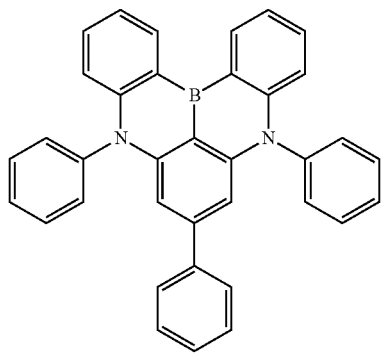
<Chemical Formula D 123>
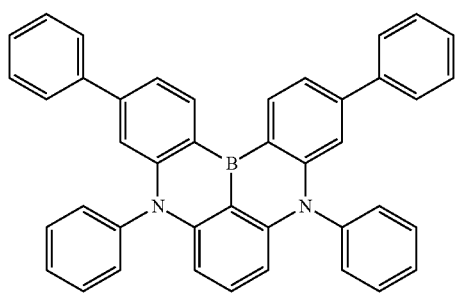
<Chemical Formula D 124>
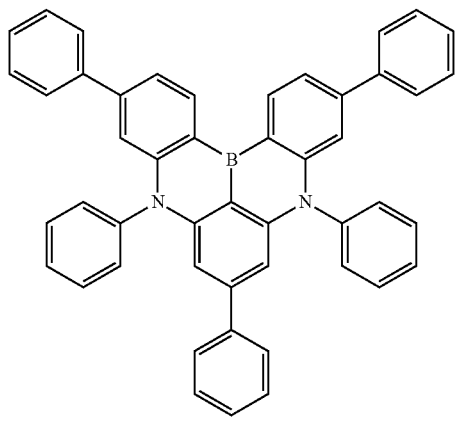
<Chemical Formula D 125>
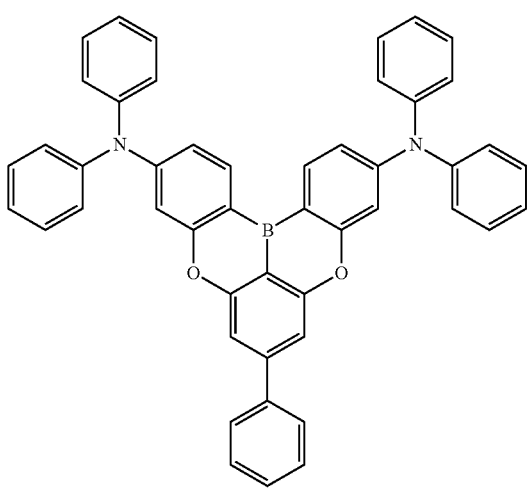
<Chemical Formula D 126>
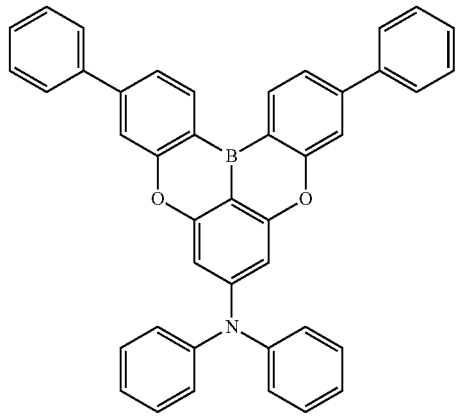
<Chemical Formula D 127>
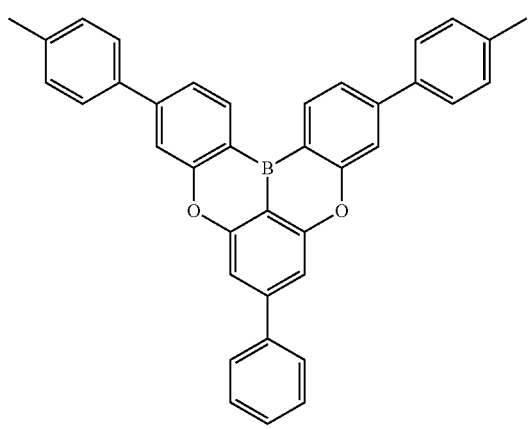
<Chemical Formula D 128>
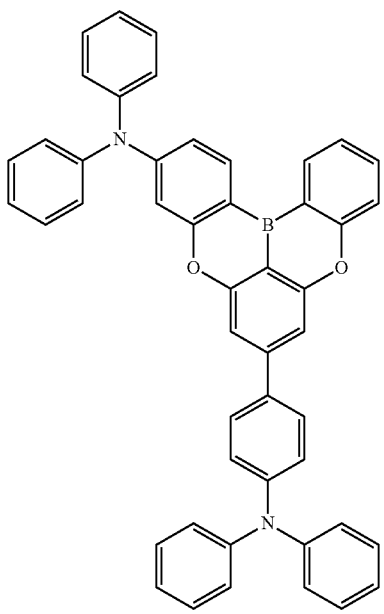

-continued

<Chemical Formula D 129>

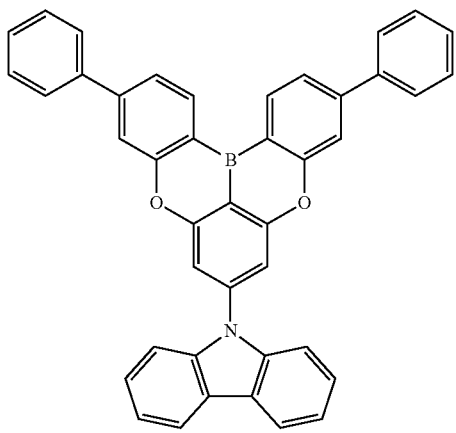

<Chemical Formula D 130>

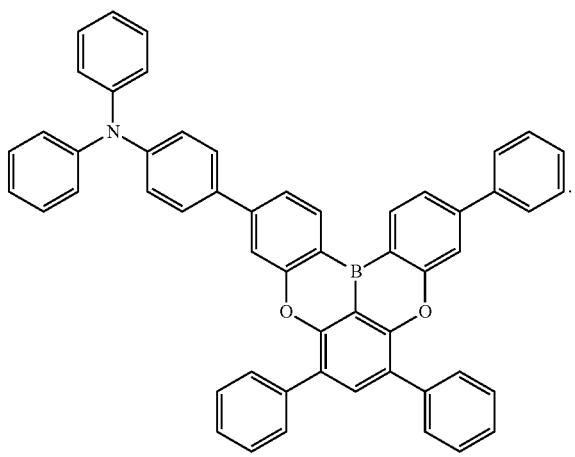

The content of the dopant in the light-emitting layer may range from about 0.01 to 20 parts by weight, based on 100 parts by weight of the host, but is not limited thereto.

In addition to the above-mentioned dopants and hosts, the light-emitting layer may further include various hosts and dopant materials.

Below, the organic light-emitting diode of the present disclosure is explained with reference to FIG. 1.

FIG. 1 is a schematic cross-sectional view of the structure of an organic light-emitting diode according to an embodiment of the present disclosure.

As shown in FIG. 1, the organic light-emitting diode according to an embodiment of the present disclosure comprises an anode 20, a hole transport layers 40 and 45, an organic light-emitting layer 50 containing a host and a dopant, an electron transport layer 60, and a cathode 80, wherein the anode and the cathode serve as a first electrode and a second electrode, respectively, with the interposition of the two hole transport layers 40 and 45 between the anode and the light-emitting layer, and the electron transport layer between the light-emitting layer and the cathode.

The hole transport layers 40 and 45 are composed of a first hole transport layer 40 and a second hole transport layer 45, wherein the second hole transport layer 45 is interposed between the first hole transport layer 40 and the light-emitting layer 50. In this regard, the amine compound represented by Chemical Formula A may be used as a material for the second hole transport layer 45 in the organic light-emitting diode of the present disclosure. Having such a structural characteristic, the organic light-emitting diode according to the present disclosure can be driven with high luminous efficiency.

Furthermore, the organic light-emitting diode according to an embodiment of the present disclosure may comprise a hole injection layer 30 between the anode 20 and the hole transport layers 40 and 45, and an electron injection layer 70 between the electron transport layer 60 and the cathode 80.

Reference is made to FIG. 1 with regard to the organic light emitting diode of the present disclosure and the fabrication thereof.

First, a substrate 10 is coated with an anode electrode material to form an anode 20. So long as it is used in a typical organic light emitting diode, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied on the anode 20 by thermal deposition in a vacuum or by spin coating to form a hole injection layer 30.

As a material for the hole injection layer 30, the amine compound represented by Chemical Formula A may be used. No particular limitations are imparted to the hole injection layer material, as long as it is one that is typically used in the art. For example, mention may be made of 2-TNATA [4,4',4"-tris(2-naphthylphenyl-phenylamino)-triphenylamine], NPD[N, N'-di(1-naphthyl)-N,N'-diphenyl-benzidine)], TPD[N,N'-diphenyl-N,N'-bis(3-methylphenyl)-1,1'-biphenyl-4,4'-diamine], DNTPD[N,N'-diphenyl-N,N'-bis-[4-(phenyl-m-tolyl-amino)-phenyl]-biphenyl-4,4'-diamine], but the present disclosure is not limited thereby.

Subsequently, thermal deposition in a vacuum or by spin coating may also be conducted to form a hole transport layer 40 with a hole transport layer material on the hole injection layer 30. When the hole transport layer is composed of two or more sub-layers, each of them may be separately formed by deposition or spin coating.

In addition, the amine compound represented by Chemical Formula A may be contained as a material for the hole transport layers 40 and 45. In a particular embodiment, the hole transport layer is composed of a first hole transport layer 40 and a second hole transport layer 45, wherein the amine compound represented by Chemical Formula A is used in the second hole transport layer 45. So long as it is typically used in the art, any material may be selected for the first hole transport layer without particular limitation. Examples include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

Then, an organic light-emitting layer 50 is deposited on the hole transport layers 40 and 45 by deposition in a vacuum or by spin coating.

Herein, the light-emitting layer 50 may contain a host and a dopant and the materials are as described above.

In some embodiments of the present disclosure, the light-emitting layer 50 particularly ranges in thickness from 50 to 2,000 Å.

Here, an electron transport layer 60 is deposited on the organic light emitting layer by deposition in a vacuum or by spin coating.

A material for use in the electron transport layer 60 functions to stably carry the electrons injected from the electron injection electrode (cathode), and may be an electron transport material known in the art. Examples of the electron transport material known in the art include quinoline derivatives, particularly, tris(8-quinolinorate)aluminum (Alq₃), Liq, TAZ, BAlq, beryllium bis(benzoquinolin-10-olate) (Bebq2), Compound 201, Compound 202, BCP, and oxadiazole derivatives such as PBD, BMD, and BND, but are not limited thereto:

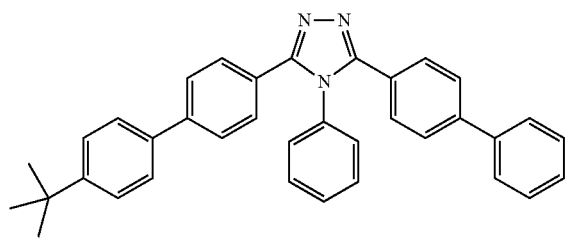

TAZ

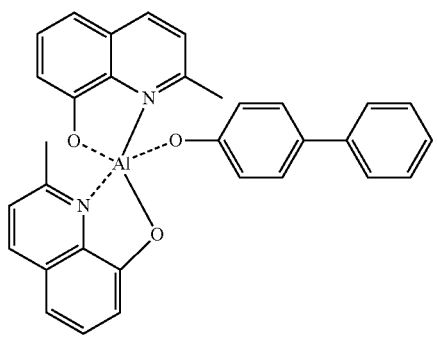

BAlq

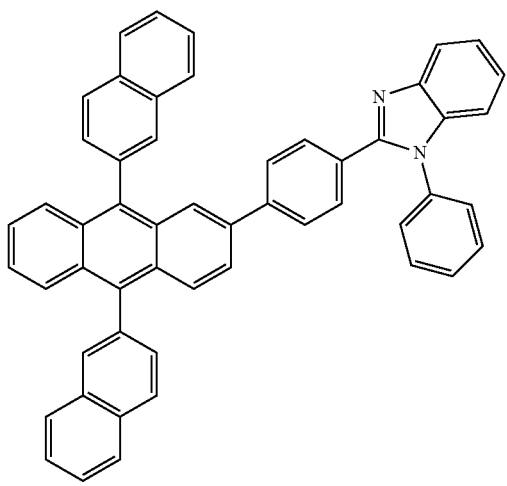

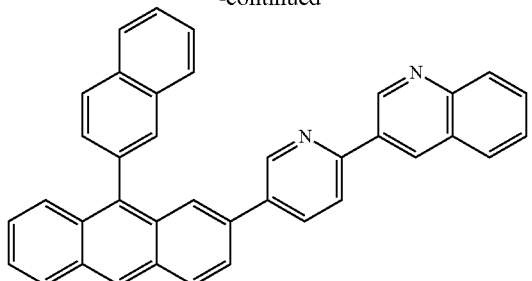

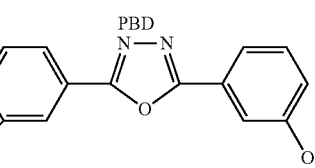

BCP

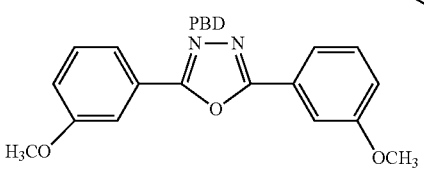

PBD

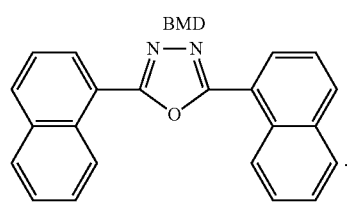

BMD

BND

In the organic light emitting diode of the present disclosure, an electron injection layer (EIL) that functions to facilitate electron injection from the cathode may be deposited on the electron transport layer. The material for the EIL is not particularly limited.

Any material that is conventionally used in the art can be available for the electron injection layer without particular limitations. Examples include CsF, NaF, LiF, Li₂O, and BaO. Deposition conditions for the electron injection layer may vary, depending on compounds used, but may be generally selected from condition scopes that are almost the same as for the formation of hole injection layers.

The electron injection layer may range in thickness from about 1 Å to about 100 Å, and particularly from about 3 Å to about 90 Å. Given the thickness range for the electron injection layer, the diode can exhibit satisfactory electron injection properties without actually elevating a driving voltage.

In order to facilitate electron injection, the cathode 80 may be made of a material having a small work function, such as metal or metal alloy such as lithium (Li), magnesium (Mg), calcium (Ca), aluminum (Al), aluminum-lithium (Al—Li), magnesium-indium (Mg—In), and magnesium-silver (Mg—Ag). Alternatively, ITO or IZO may be employed to form a transparent cathode for a top-emitting organic light-emitting diode.

Moreover, the organic light-emitting diode of the present disclosure may further comprise a light-emitting layer containing a blue, green, or red luminescent material that emits radiations in the wavelength range of 380 nm to 800 nm. That is, the light-emitting layer in the present disclosure has a multi-layer structure wherein the blue, green, or red luminescent material may be a fluorescent material or a phosphorescent material.

Furthermore, at least one selected from among the layers may be deposited using a single-molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the present disclosure may be obtained through the following examples which are set forth to illustrate, but are not to be construed as limiting the present invention.

Preparation Example 1: Synthesis of Compound 1

Synthesis of Intermediate 1-1

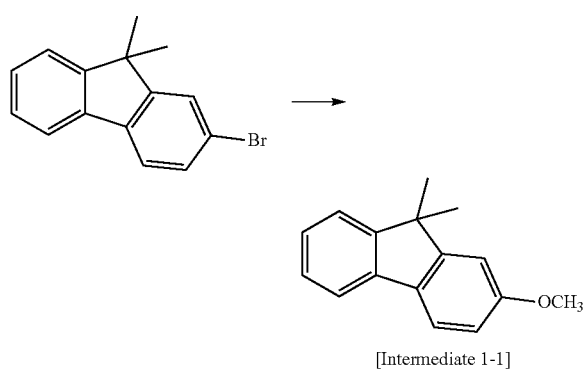

[Intermediate 1-1]

In a reactor, 2-bromo-dimethylfluorene (100 g, 0.366 mol) and methanol (1,000 mL) were stirred together and NaOMe (114 g, 2.196 mol) and CuI (20 g, 0.110 mol) were added dropwise before stirring overnight under reflux. After completion of the reaction, drops of distilled water (100 mL) were added. Subsequently, the reaction mixture was filtered. The filtrate was dissolved in methylene chloride (300 mL) and purified through a column. After enrichment, recrystallization in an excess of methanol afforded Intermediate 1-1 (69 g, yield 84%).

Synthesis of Intermediate 1-2

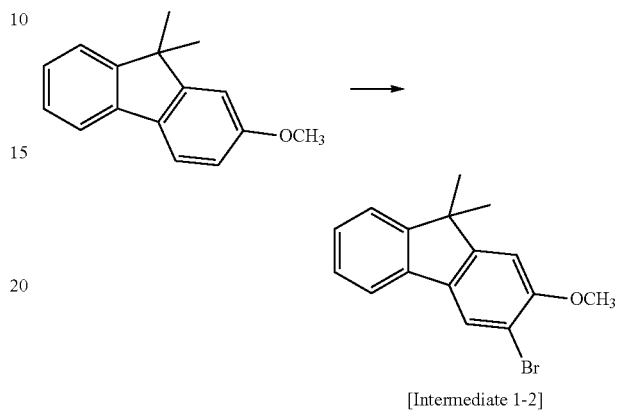

[Intermediate 1-2]

In a reactor, Intermediate 1-1 (69 g, 0.308 mol) was stirred together with IMF (897 mL). NBS (58.15 g, 0.327 mol) was dropwise added at room temperature and stirred overnight. After completion of the reaction, drops of distilled water (69 mL) were added. The reaction mixture was filtered, dissolved in methylene chloride (207 mL), and purified through a column. After enrichment, recrystallization in an excess of methanol afforded Intermediate 1-2 (60 g, yield 64%).

Synthesis of Intermediate 1-3

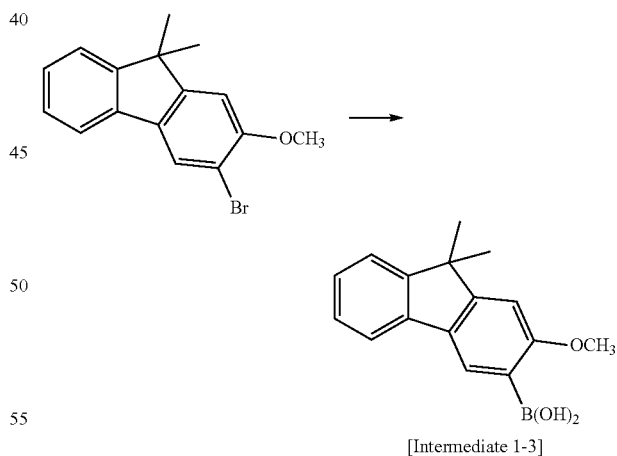

[Intermediate 1-3]

In a reactor, Intermediate 1-2 (46 g, 0.157 mol) was stirred together with THF (460 mL) and chilled to −78° C. at which drops of n-BuLi (113 mL, 0.182 mol) were slowly added. After 2 hours, trimethyl borate (15.85 g, 0.187 mol) was dropwise added. The reaction was terminated with an excess of 2M HCl. Extraction was made with ethyl acetate/distilled water, and the organic layer thus formed was pooled, concentrated, and added to methanol. Filtration and drying afforded Intermediate 1-3 (19 g, yield 50%).

Synthesis of Intermediate 1-4

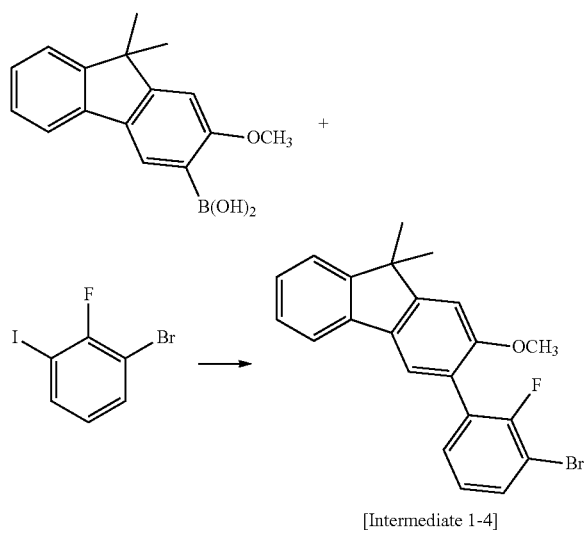

[Intermediate 1-4]

In a reactor, Intermediate 1-3 (20 g, 0.074 mol), 1-bromo-2-fluoro-3-iodobenzene (26.95 g, 0.089 mol), Pd(pph3)4 (1.638 g, 0.0014 mol), hydrazine (0.11 g, 0.0022 mol), and sodium tetraborate (19.5 g, 0.097 mol) were placed, added with 1,4-dioxane (140 mL) and distilled water (60 ml), and stirred together overnight at 90° C. Extraction was made with ethyl acetate/distilled water and the organic layer thus formed was concentrated and purified through a column to afford Intermediate 1-4 (20 g, yield 68%).

Synthesis of Intermediate 1-5

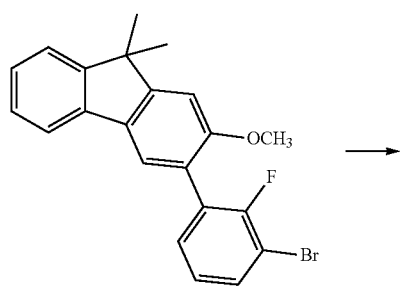

[Intermediate 1-5]

Intermediate 1-4 (20 g, 0.055 mol) and methylene chloride (200 mL) was placed in a reactor, cooled to 0° C., and added with drops of BBr3 (18.8 g, 0.076 mol). The mixture was warmed to room temperature, stirred for 5 hours, and added with drops of distilled water (600 mL). Extraction was made with ethyl acetate/distilled water. The organic layer thus formed was concentrated to afford Intermediate 1-5 (19 g, yield 94%).

Synthesis of Intermediate 1-6

[Intermediate 1-6]

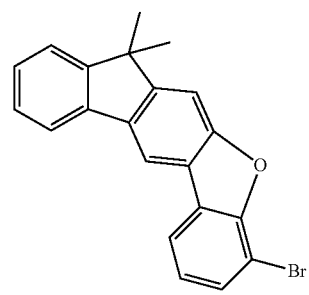

In a reactor, Intermediate 1-5 (19 g, 0.049 mol), potassium carbonate (13.7 g, 0.098 mol), and NMP (190 mL) were stirred together for 3 hours under reflux. The reaction mixture was cooled to room temperature and added with drops of 2M HCl (570 mL, 30 vol.) to form precipitates. The precipitates were filtered and then slurried in methanol to afford Intermediate 1-6 (17 g, yield 94%).

Synthesis of Intermediate 1-7

[Intermediate 1-7]

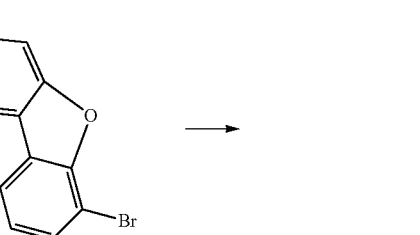

143

-continued

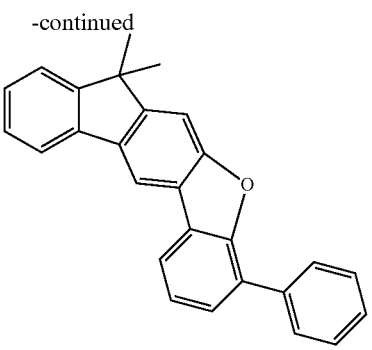

Intermediate 1-6 (17 g, 0.046 mol), phenyl boronic acid (6.2 g, 0.051 mol), potassium carbonate (12.9 g, 0.093 mol), pd(pph3)4 (1.6 g, 0.001 mol), toluene (119 mL), ethanol (51 mL), and distilled water (34 mL) were stirred together overnight under reflux. The reaction mixture was cooled to room temperature and subjected to extraction with ethyl acetate/distilled water. The organic layer thus formed was concentrated and purified through a column to afford Intermediate 1-7 (16 g, 95%).

Synthesis of Intermediate 1-8

[Intermediate 1-8]

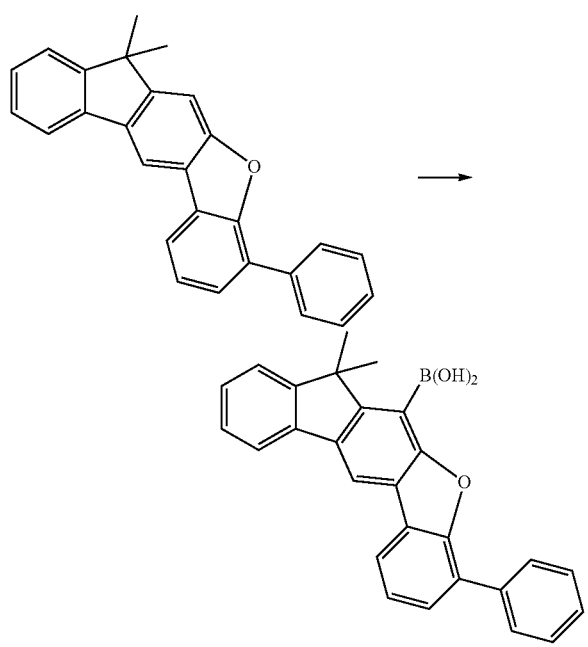

In a reactor, Intermediate 1-7 (16 g, 0.044 mol) and THF (160 mL) were chilled to −78° C. and slowly added with drops of n-BuLi (33.2 mL, 0.053 mol). Thereafter, the mixture was warmed to room temperature and stirred for 12 hours. Trimethyl borate (0.053 mol) was dropwise added, followed by terminating the reaction with an excess of 2M HCl. The reaction mixture was subjected to extraction with ethyl acetate/distilled water and the organic layer thus formed was pooled and concentrated. The concentrate was slurried in methanol, filtered, and dried to afford Intermediate 1-8 (8 g, yield 37%).

144

Synthesis of Compound 1

[Compound 1]

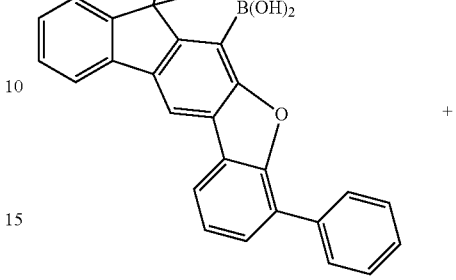

+

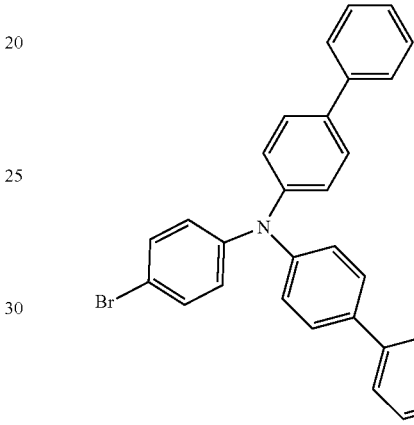

→

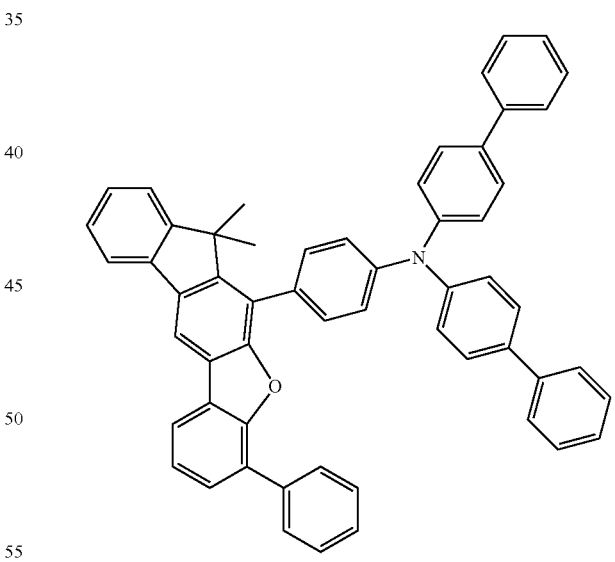

In a reactor, Intermediate 1-8 (8 g, 0.019 mol) and N,N-bis(4-biphenylyl)-N-(4-bromophenyl)amine (10.3 g, 0.021 mol), Pd (pph3) 4 (0.45 g, 0.0004 mol), and potassium carbonate (5.25 g, 0.038 mol) were stirred together with toluene (56 mL), ethanol (24 ml), and distilled water (16 ml), overnight under reflux. Extraction was made with ethyl acetate/distilled water and the organic layer thus formed was concentrated and hot filtered with toluene. The filtrate was concentrated and recrystallized in acetone to afford Compound 1 (3 g, yield 20%).

Preparation Example 2. Synthesis of Compound 20

Synthesis of Intermediate 2-1

Synthesis of Intermediate 2-2

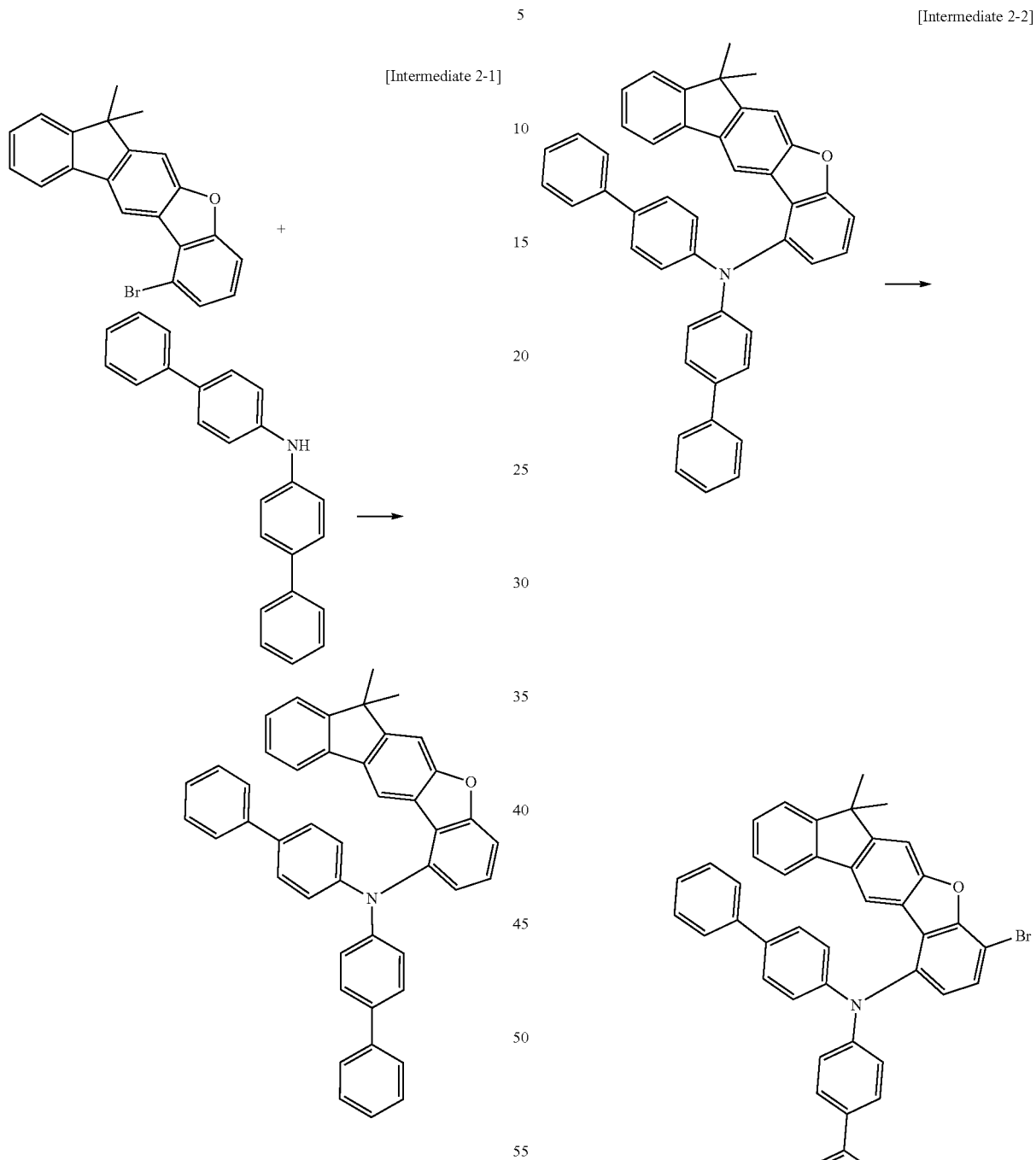

In a reactor, SM (15 g, 0.041 mol) synthesized with reference to Korean Patent Number KR 2018-0037889 Å, bis(4-biphenylyl)amine (14.6 g, 0.045 mol), Pd2dba3 (0.76 g, 0.003 mol), tributyl phosphine (0.25 g, 0.001 mol), sodium tert-butoxide (4.37 g, 0.045 mol), and toluene (150 mL) were stirred together for 3 hour under reflux. The reaction mixture was hot filtered with toluene and subjected to extraction with ethyl acetate/distilled water. The organic layer thus formed was concentrated and purified through a column to afford Intermediate 2-1 (16 g, yield 64%).

In a reactor, Intermediate 2-1 (16 g, 0.026 mol) and IMF (160 mL) were chilled to 0° C., added with drops of NBS (4.71 g, 0.026 mol), and stirred for 6 hours. After completion of the reaction, the reaction mixture was added with drops of distilled water (480 mL), filtered, and slurried in an excess of methanol to afford Intermediate 2-2 (11 g, yield 61%).

147
Synthesis of Compound 20

[Compound 20]

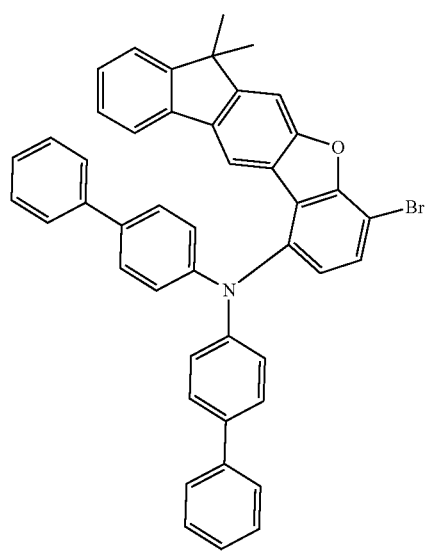

In a reactor, Intermediate 2-2 (11 g, 0.016 mol), phenyl boronic acid (2.1 g, 0.017 mol), potassium carbonate (4.4 g, 0.032 mol), pd(pph3)4 (0.37 g, 0.0003 mol), toluene (77 mL), ethanol (33 mL), and distilled water (22 mL) were stirred overnight under reflux. The reaction mixture was added with drops of methanol (330 mL), filtered, hot filtered with toluene, and recrystallized in acetone to afford Compound 20 (3 g, yield 30%).

148
Preparation Example 3: Synthesis of Compound 55

Synthesis of Intermediate 3-1

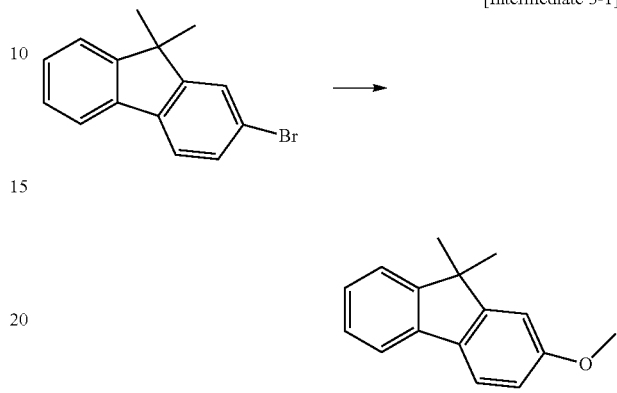

[Intermediate 3-1]

In a reactor, the starting material (100 g, 0.366 mol) and methanol (1000 mL) were stirred together. NaOMe (114 g, 2.196 mol) and CuI (20 g, 0.110 mol) were added dropwise, followed by stirring overnight under reflux. After completion of the reaction, distilled water (100 mL) was added. The reaction mixture was filtered and the filtrate was dissolved in dichloromethane (300 mL) and allowed to pass through a column. After concentration, recrystallization in an excess of methanol afforded Intermediate 3-1 (69 g, yield 84%).

Synthesis of Intermediate 3-2

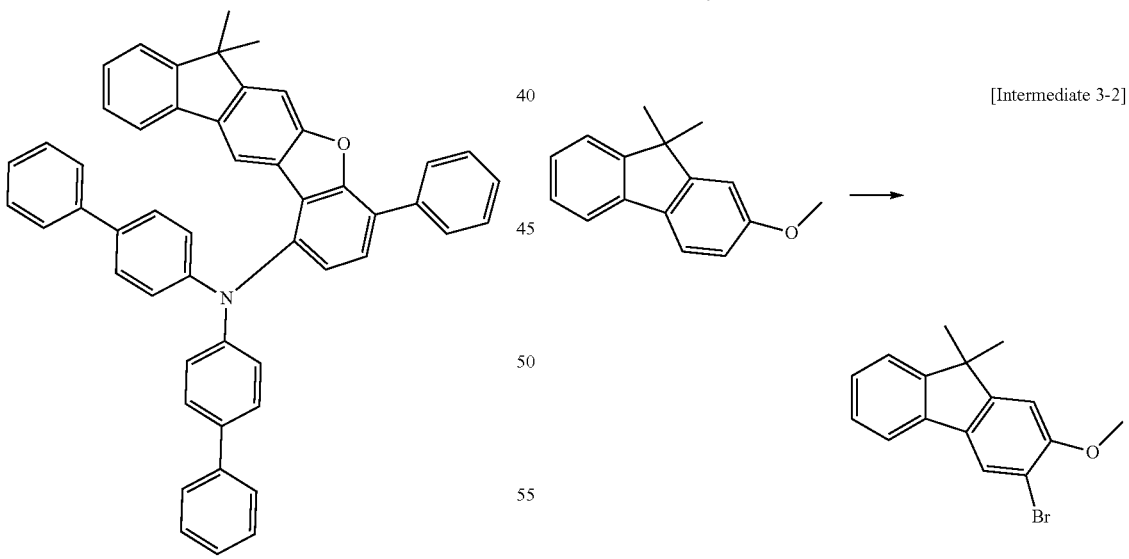

[Intermediate 3-2]

In a reactor, Intermediate 3-1 (69 g, 0.308 mol) and DMF (897 mL) were stirred together. Then, NBS (58.15 g, 0.327 mol) was dropwise added for 1 hour and stirred overnight at room temperature. After completion of the reaction, distilled water (69 mL) was dropwise added. The reaction mixture was filtered and the filtrate was dissolved and allowed to pass through a column. After concentration, recrystallization in an excess of methanol afforded Intermediate 3-2 (60 g, yield 64%).

Synthesis of Intermediate 3-3

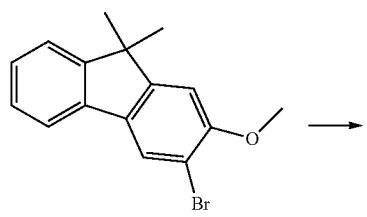
[Intermediate 3-3]

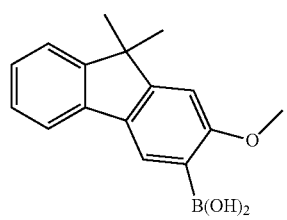
[Intermediate 3-4]

In a reactor, Intermediate 3-2 (46 g, 0.157 mol) and THF (460 mL) were stirred together and chilled to −78° C. before slowly adding drops of n-BuLi (113 mL, 0.182 mol). After 2 hours, trimethyl borate (15.85 g, 0.187 mol) was dropwise added. At room temperature, the reaction was terminated with an excess of 2 M HCl. The reaction mixture was subjected to extraction with ethyl acetate/distilled water and the organic layer thus formed was pooled and concentrated. The concentrate was added with methanol, filtered, and dried to afford Intermediate 3-3 (20 g, yield 50%).

Synthesis of Intermediate 3-4

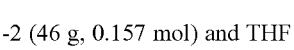
[Intermediate 3-4]

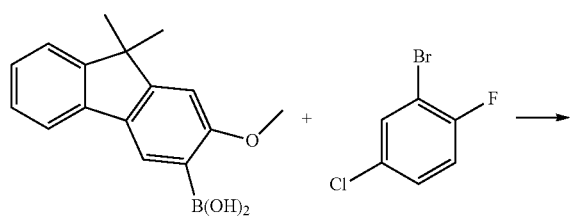

In a reactor, Intermediate 3-3 (20 g, 0.074 mol), 1-bromo-4-chloro-2-fluorobenzene (18.74 g, 0.089 mol), Pd(pph3)4 (1.638 g, 0.0014 mol), hydrazine (0.11 g, 0.022 mol), and sodium tetraborate (19.5 g, 0.097 mol) were placed and stirred, together with 1,4-dioxane (140 mL) and distilled water (60 ml), overnight at 90° C. Extraction was made with ethyl acetate/distilled water and the organic layer thus formed was purified through a column to afford Intermediate 3-4 (20 g, yield 68%).

Synthesis of Intermediate 3-5

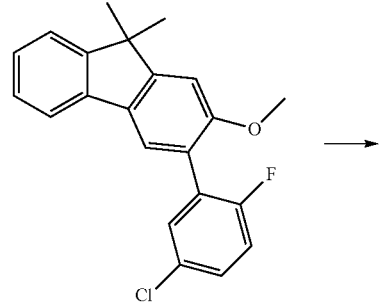
[Intermediate 3-5]

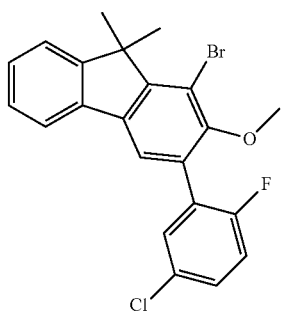

In a reactor, Intermediate 3-4 (20 g, 0.056 mol) and dichloromethane (200 mL) was stirred together. Br2 (10.87 g, 0.061 mol) was dropwise added and then stirred for 1 hour. After completion of the reaction, recrystallization in an excess of methanol afforded Intermediate 3-5 (21 g, yield 86%).

Synthesis of Intermediate 3-6

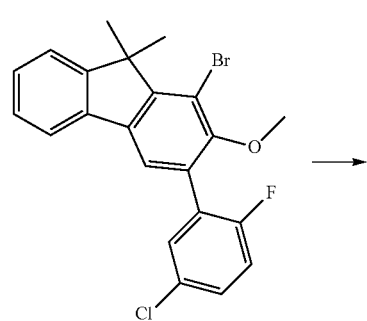
[Intermediate 3-6]

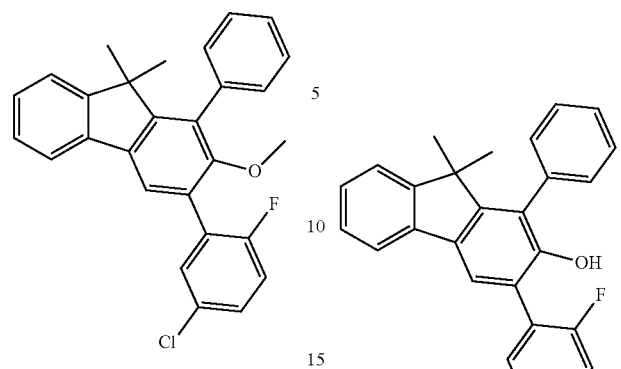

In a reactor, Intermediate 3-5 (21 g, 0.048 mol), phenyl boronic acid (7.1 g 0.058 mol), Pd(pph3)4 (1.12 g, 0.00096 mol), and potassium carbonate (13.3 g, 0.097 mol) were stirred, together with toluene (147 mL), ethanol (63 ml), and distilled water (42 ml), overnight at 90° C. Extraction was made with ethyl acetate/distilled water and the organic layer thus formed was concentrated and purified through a column to afford Intermediate 3-6 (18 g, yield 86%).

Synthesis of Intermediate 3-7

[Intermediate 3-7]

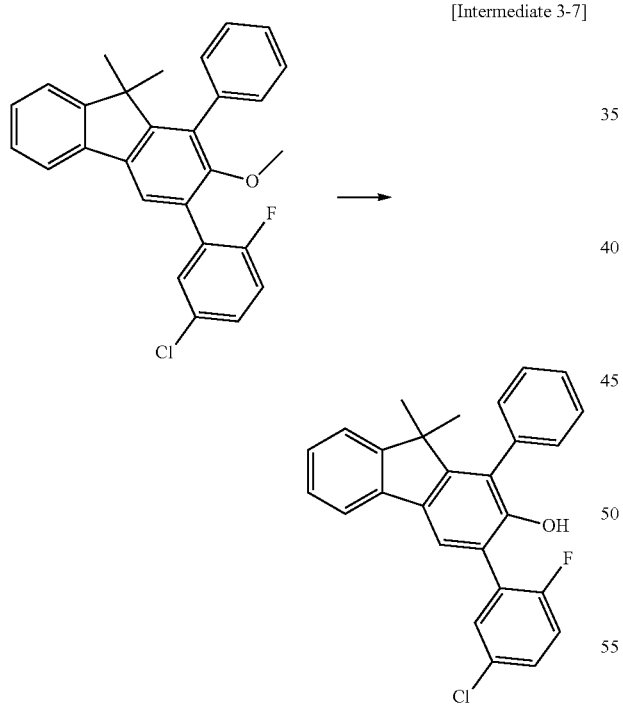

In a reactor, a mixture of Intermediate 3-6 (18 g, 0.041 mol) and dichloromethane (180 mL) was chilled to 0° C., followed by adding drops of BBr3 (12.6 g, 0.051 mol). At room temperature, the mixture was stirred for 5 hours and added with drops of distilled water (540 mL). Extraction was made with ethyl acetate/distilled water and the organic layer thus formed was concentrated to afford Intermediate 3-7 (15 g, yield 86%).

Synthesis of Intermediate 3-8

[Intermediate 3-8]

In a reactor, Intermediate 3-7 (15 g, 0.036 mol), potassium carbonate (9.99 g, 0.0723 mol), and NMP (150 mL) were stirred together at 150° C. for 3 hours. The reaction mixture was cooled to room temperature and added with drops of 2M HCl (450 mL). The solid thus formed was filtered and slurried in methanol to afford Intermediate 3-8 (12 g, yield 84%).

Synthesis of Compound 55

[Compound 55]

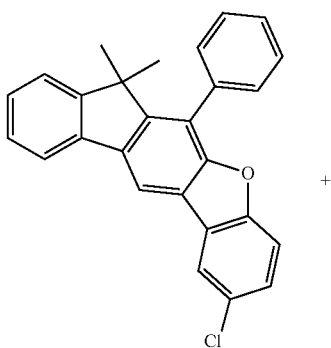

+

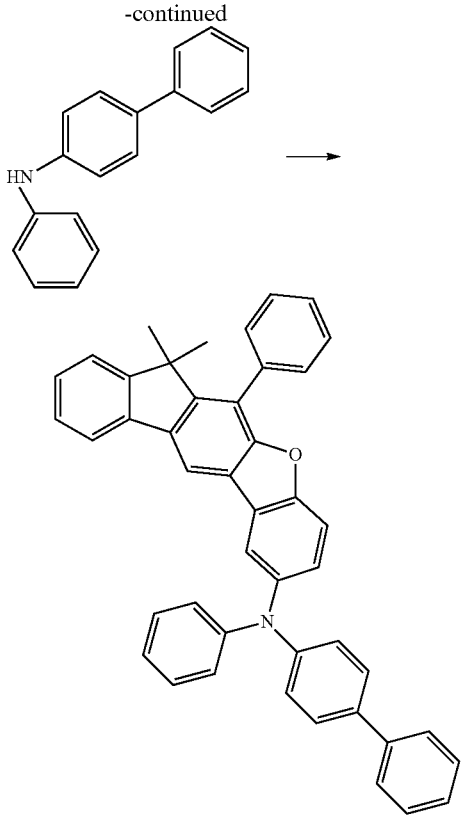

In a reactor, Intermediate 3-8 (12 g, 0.031 mol), N-phenyl [1,1'-biphenyl]-4-amine (8.2 g, 0.0033 mol), bis(tri-tert-butlyphosphine)palldium (0.31 g, 0.0004 mol), sodium tert-butoxide (5.84 g, 0.061 mol), and toluene (144 ml) were stirred overnight at 100° C. Extraction was made with ethyl acetate/distilled water and the organic layer thus formed was concentrated and hot filtered in toluene. The filtrate was concentrated and recrystallized in dichloromethane and acetone to afford Compound 55 (5 g, yield 37%).

Preparation Example 4: Synthesis of Compound 67

The same procedure as in Preparation Example 1 was carried out, with the exception of using N-[1,1'-biphenyl]-4-yl-N-(4-bromophenyl)-1-dibenzofuranamine instead of N,N-bis(4-biphenylyl)-N-(4-bromophenyl)amine, to afford Compound 67 (4.5 g, yield 27%).

Preparation Example 5: Synthesis of Compound 68

The same procedure as in Preparation Example 1 was carried out, with the exception of using 2-naphthyl boronic acid instead of phenyl boronic acid for the synthesis of Intermediate 1-7 to afford Compound (5 g, yield 25%).

Preparation Example 6: Synthesis of Compound 69

The same procedure as in Preparation Example 1 was carried out, with the exception of using 9-phenanthrene boronic acid instead of phenyl boronic acid for the synthesis of Intermediate 1-7 to afford Compound 69 (4.2 g, yield 21%).

Preparation Example 7: Synthesis of Compound 70

The same procedure as in Preparation Example 2 was carried out, with the exception of using 9-phenanthrene boronic acid instead of phenyl boronic acid for the synthesis of Compound 20 to afford Compound 70 (4.5 g, yield 28%).

Preparation Example 8: Synthesis of Compound 71

The same procedure as in Preparation Example 2 was carried out, with the exception of using N-[4-(1-naphthale-nyl)phenyl][1,1'-biphenyl]-4-amine instead of bis(4-biphe-nylyl)amine for the synthesis of Intermediate 2-1 to afford Compound 71 (4 g, yield 29%).

Preparation Example 9: Synthesis of Compound 72

The same procedure as in Preparation Example 2 was carried out, with the exception of using 2-naphthyl boronic acid instead of phenyl boronic acid for the synthesis of Compound 20 to afford Compound 72 (3.7 g, yield 32%).

Examples 1 to 9: Fabrication of Organic Light-Emitting Diodes

An ITO glass substrate was patterned to have a translucent area of 2 mm×2 mm and cleansed. The ITO glass was mounted in a vacuum chamber that was then set to have a base pressure of $1\times10^{-7}$ torr. On the ITO glass substrate, films were sequentially formed of DNTPD (450 Å), [Chemical Formula G] (200 Å), and the compound listed in Table 1, below, as a material for the second hole transport layer (50 Å).

Subsequently, a light-emitting layer (250 Å) was formed of a combination of [Chemical Formula BH] and [Chemical Formula BD] (97:3). Then, [Chemical Formula E-2] was deposited to form an electron transport layer (300 Å) on which an electron injecting layer of [Chemical Formula E-1] (10 Å) was formed and then covered with an Al layer (1000 Å) to fabricate an organic light-emitting diode. The organic light-emitting diodes thus obtained were measured at 0.4 mA for luminescence properties:

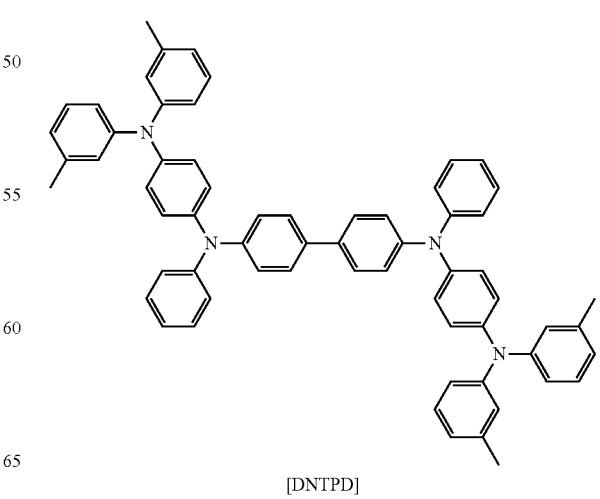

[DNTPD]

[Chemical Formula G]

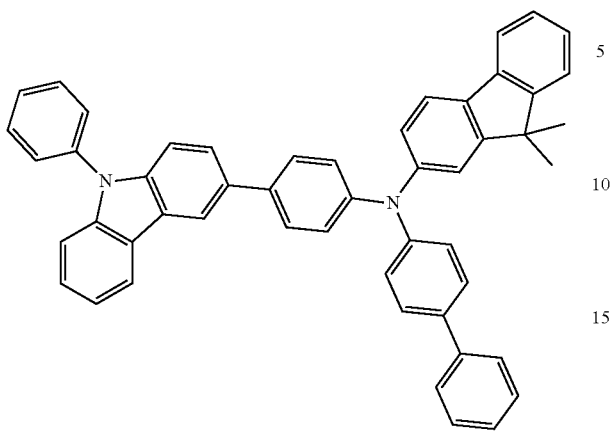

[Chemical Formula E-1]

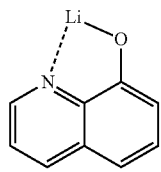

[Chemical Formula E-2]

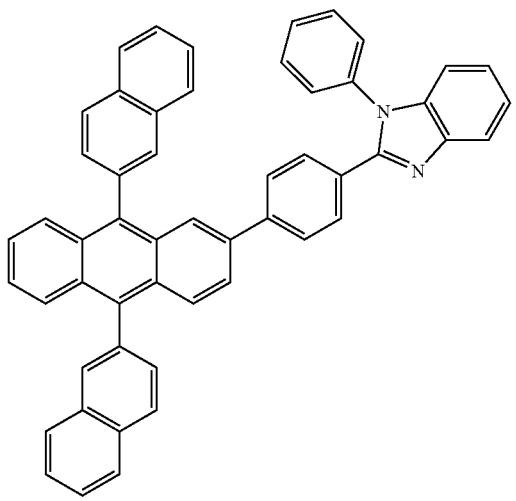

[Chemical Formula BH]

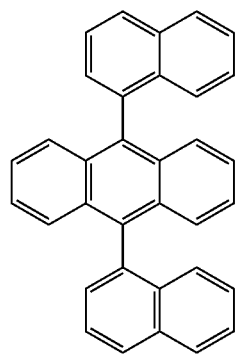

[Chemical Formula BD]

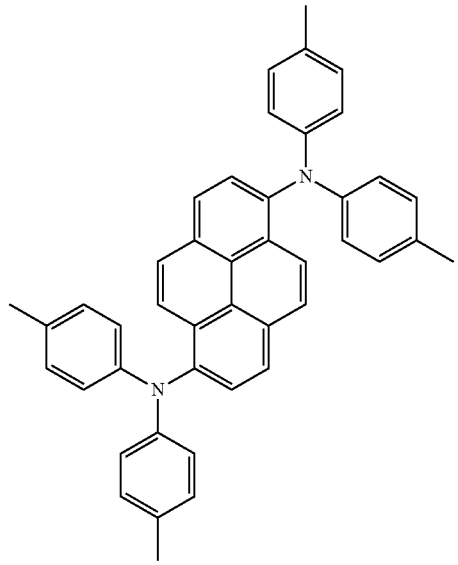

Comparative Examples 1 to 3

Organic light emitting diodes were fabricated in the same manner as in the Examples, with the exception of using the following Chemical Formula B, C, or D instead of the compounds according to the present disclosure. The luminescence of the organic light-emitting diodes thus obtained was measured at 0.4 mA.

[Chemical Formula B]

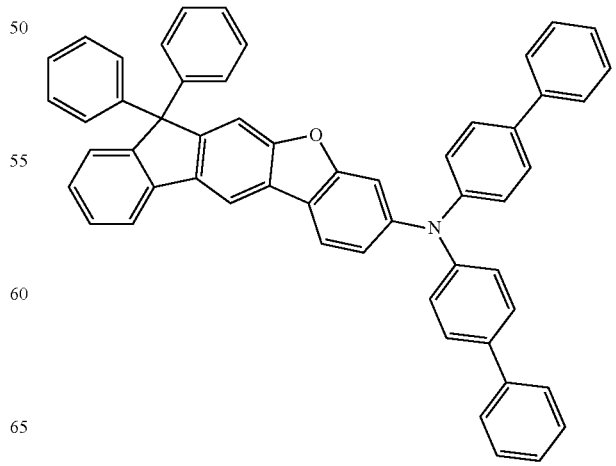

-continued

[Chemical Formula C]

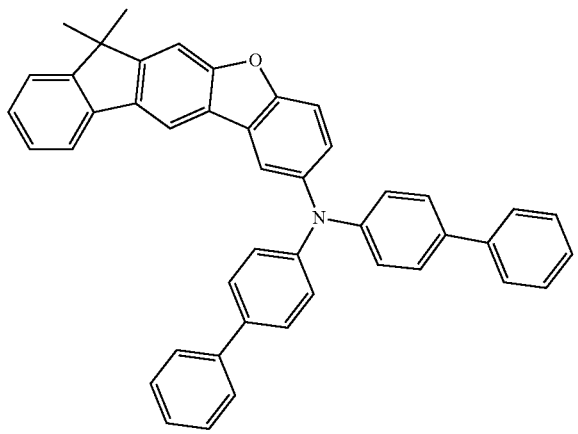

[Chemical Formula D]

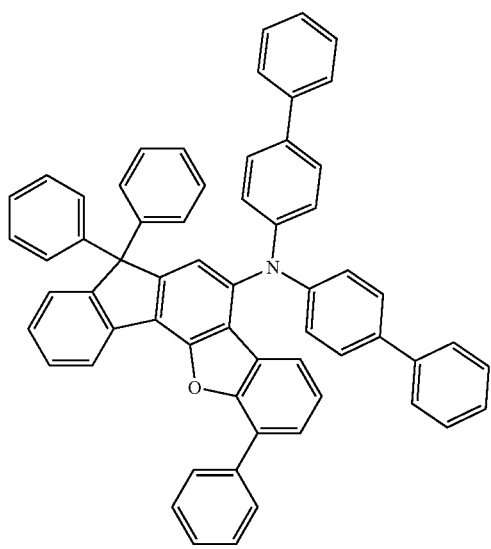

The organic light emitting diodes fabricated in Examples 1 to 9 and Comparative Examples 1 to 3 were measured for driving voltage and efficiency, and the results are summarized in Table, below.

TABLE 1

| No. | | Driving Volt. (V) | Efficiency (Cd/A) |
|---|---|---|---|
| Ex. 1 | Compound 1 | 3.96 | 8.51 |
| Ex. 2 | Compound 20 | 4.01 | 8.42 |
| Ex. 3 | Compound 55 | 3.93 | 8.15 |
| Ex. 4 | Compound 67 | 3.82 | 8.48 |
| Ex. 5 | Compound 68 | 3.95 | 8.54 |
| Ex. 6 | Compound 69 | 3.98 | 8.67 |
| Ex. 7 | Compound 70 | 3.96 | 8.62 |
| Ex. 8 | Compound 71 | 3.94 | 8.50 |
| Ex. 9 | Compound 72 | 3.95 | 8.57 |
| C. Ex. 1 | Chemical Formula B | 4.04 | 7.60 |
| C. Ex. 2 | Chemical Formula C | 3.95 | 7.85 |
| C. Ex. 3 | Chemical Formula D | 3.96 | 7.36 |

As is understood from data of Table 1, the organic light-emitting diodes according to the present disclosure exhibited excellent luminous efficiency, compared to those of the Comparative Examples 1 to 3.

What is claimed is:

1. An amine compound represented by the following Chemical Formula A or Chemical Formula B:

[Chemical Formula A]

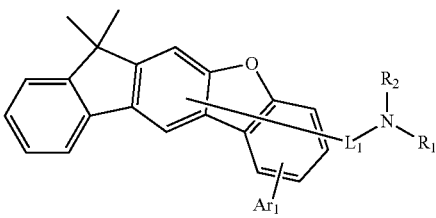

[Chemical Formula B]

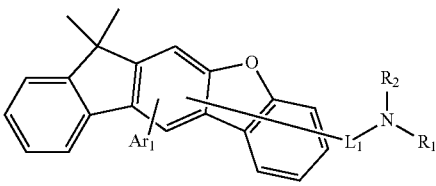

wherein, $Ar_1$ is one selected from a substituted or unsubstituted alkyl of 1 to 30 carbon atoms, a substituted or unsubstituted haloalkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, and a substituted or unsubstituted arylsilyl of 5 to 30 carbon atoms, $L_1$ is one selected from a single bond, a substituted or unsubstituted arylene of 6 to 30 carbon atoms, and a substituted or unsubstituted heteroarylene of 1 to 30 carbon atoms, $R_1$ and $R_2$, which are same or different, are each independently one selected from a substituted or unsubstituted alkyl of 1 to 30 carbon atoms, a substituted or unsubstituted haloalkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, a nitro, and a halogen, $R_1$ and $R_2$ can be connected to each other to form a ring, and each of the carbon atoms on the aromatic rings of the indenodibenzofuran fuse ring moiety

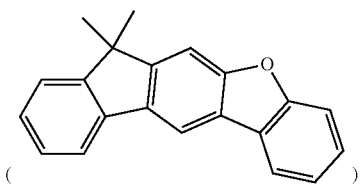 [SMILES: CC1(C)c2ccccc2-c2cc3c(cc21)oc1ccccc13]

in Chemical Formulas A and B can be bound with a hydrogen or deuterium, except for the carbon atoms bound with $Ar_1$ or $L_1$, wherein the term "substituted" in the expression "substituted or unsubstituted" means having at least one substituent selected from the group consisting of a deuterium, a cyano, a halogen, a hydroxy, a nitro, an alkyl of 1 to 24 carbon atoms, a cycloalkyl of 3 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, an alkylaryl of 7 to 24 carbon atoms, a heteroaryl of 2 to 24 carbon atoms, a heteroarylalkyl of 2 to 24 carbon atoms, an alkoxy of 1 to 24 carbon atoms, an alkylamino of 1 to 24 carbon atoms, a diarylamino of 12 to 24 carbon atoms, a diheteroarylamino of 2 to 24 carbon atoms, an aryl (heteroaryl)amino of 7 to 24 carbon atoms, an alkylsilyl of 1 to carbon atoms, an arylsilyl of 6 to 24 carbon atoms, an aryloxy of 6 to 24 carbon atoms, and an arylthionyl of 6 to 24 carbon atoms.

2. The amine compound of claim 1, wherein the amine radical

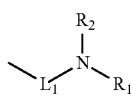

in Chemical Formulas A and B is connected to the aromatic ring which has the substituent $Ar_1$ bonded thereto.

3. The amine compound of claim 1, wherein the amine radical

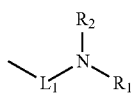

in Chemical Formulas A and B is connected to the aromatic ring which does not have the substituent Ar1 bonded thereto.

4. The amine compound of claim 1, wherein the substituent $Ar_1$ is a substituted or unsubstituted an aryl of 6 to 18 carbon atoms or a substituted or unsubstituted a heteroaryl of 2 to 18 carbon atoms.

5. The amine compound of claim 1, wherein at least one of the substituents $R_1$ and $R_2$ is a substituted or unsubstituted an aryl of 6 to 18 carbon atoms, or a substituted or unsubstituted a heteroaryl of 2 to 18 carbon atoms.

6. The amine compound of claim 1, wherein the linker $L_1$ is selected from a single bond and a substituted or unsubstituted arylene of 6 to 18 carbon atoms.

7. The amine compound of claim 4, wherein the substituent $Ar_1$ on Chemical Formulas A and B is represented by the following Structural Formula A:

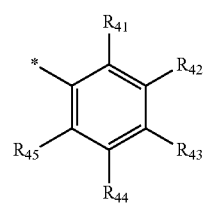

[Structural Formula A]

wherein "-*" denotes a bonding site at which the substituent $Ar_1$ is bonded to a carbon atom within the terminal aromatic ring or middle aromatic ring of the dibenzofuran moiety in Chemical Formulas A and B and, $R_{41}$ to $R_{45}$, which are same or different, are each independently selected from a hydrogen, a deuterium, a cyano, a halogen, a hydroxy, a nitro, an alkyl of 1 to 24 carbon atoms, a cycloalkyl of 3 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, an alkylaryl of 7 to 24 carbon atoms, a heteroaryl of 2 to 50 carbon atoms, a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

8. The amine compound of claim 1, wherein the substituents $R_1$ and $R_2$, which are same or different, are each independently a substituted or unsubstituted an aryl of 6 to 18 carbon atoms, or a substituted or unsubstituted a heteroaryl of 2 to 18 carbon atoms.

9. The amine compound of claim 1, wherein at least one of the substituents $Ar_1$, $R_1$, and $R_2$ is a deuterium-substituted aryl of 6 to carbon atoms.

10. The amine compound of claim 1, wherein the substituent $Ar_1$ in Chemical Formulas A and B is bonded to the dibenzofuran moiety at position 1 or 2.

11. The amine compound of claim 1, wherein the substituent $Ar_1$ in Chemical Formulas A and B is bonded to the dibenzofuran moiety at position 3 or 4.

12. The amine compound of claim 1, wherein the amine compound is selected from the following Compounds 1 to 72:

[Compound 1]
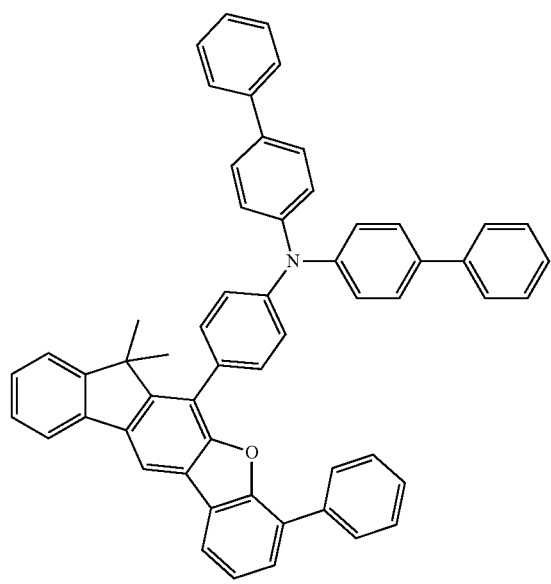
[Compound 2]
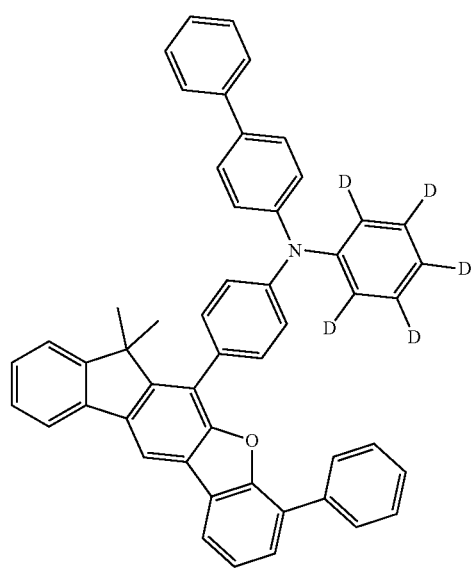
[Compound 3]
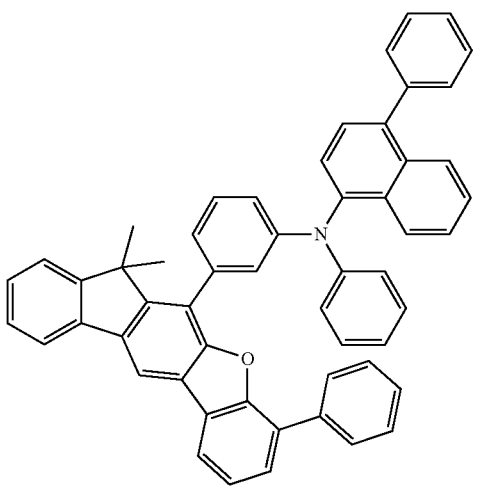
[Compound 4]
[Compound 5]
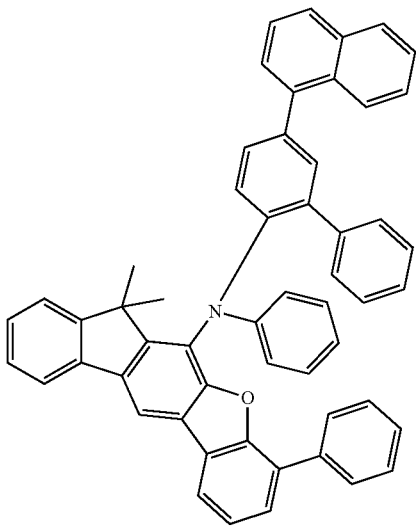

[Compound 6]
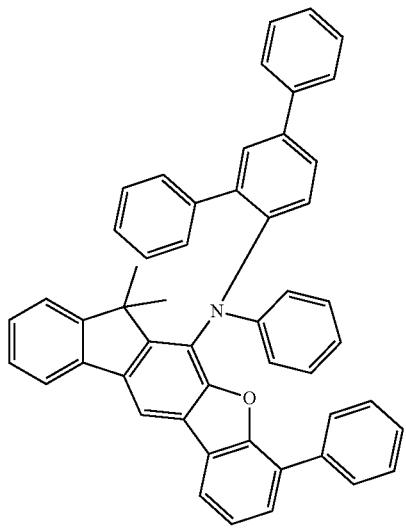
[Compound 7]
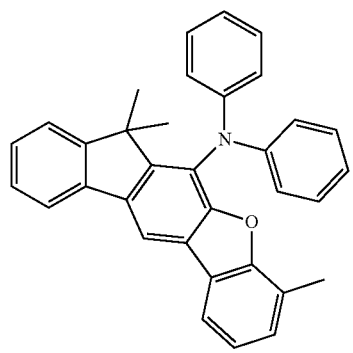
[Compound 8]
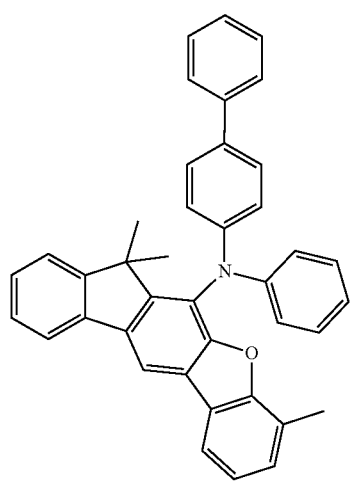
[Compound 9]
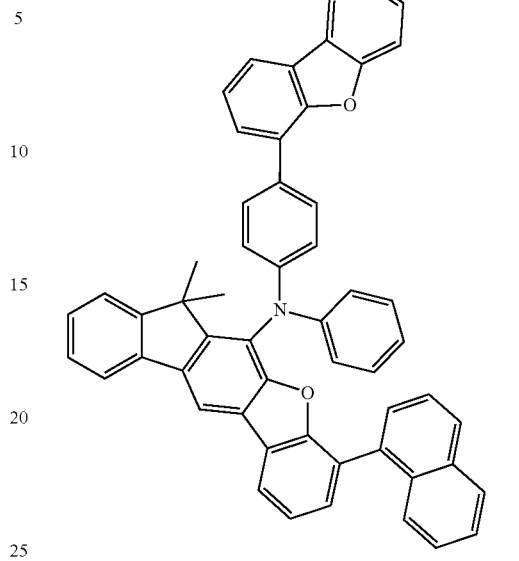
[Compound 10]
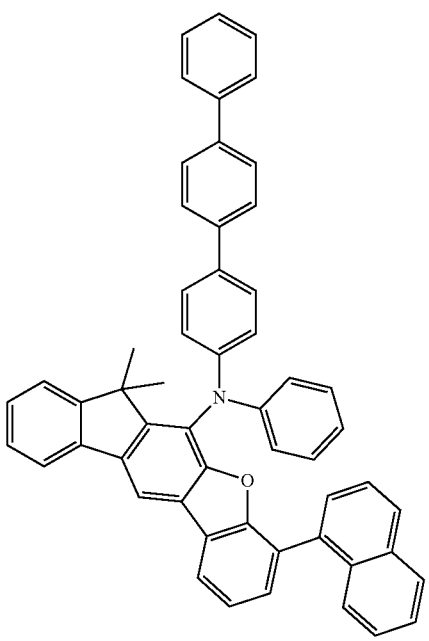

[Compound 11]
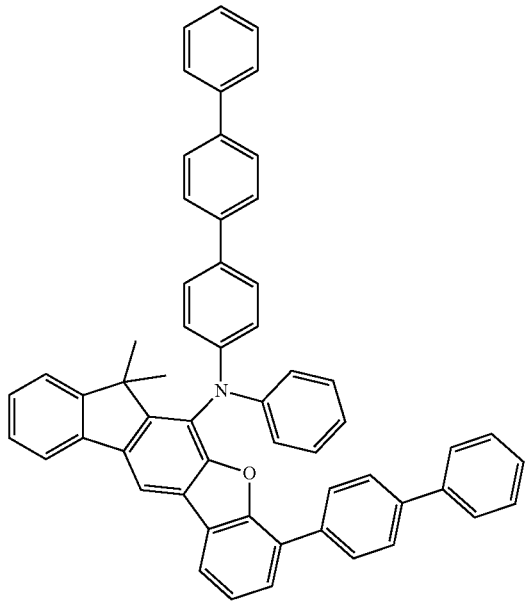
[Compound 13]
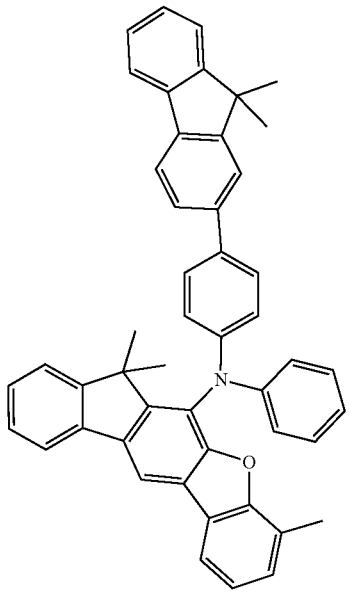
[Compound 12]
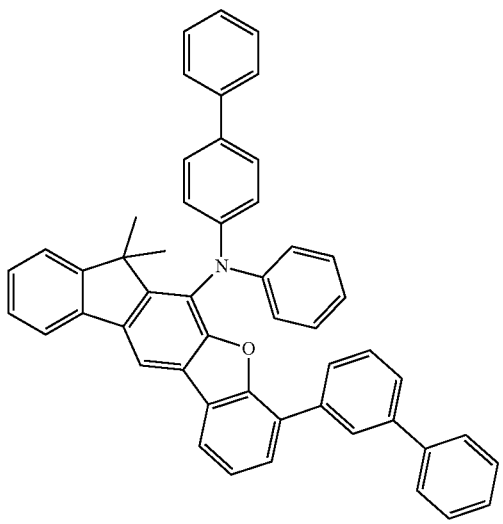
[Compound 14]
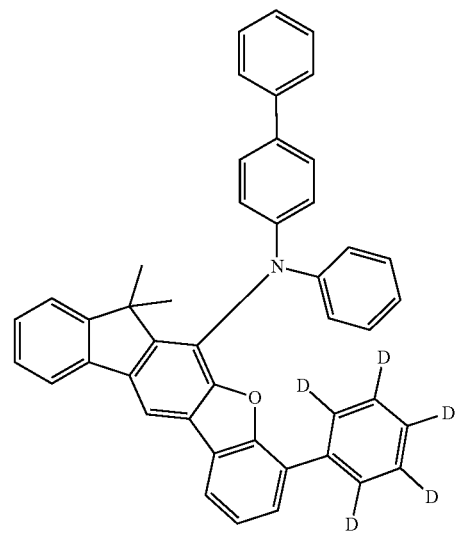

[Compound 15]
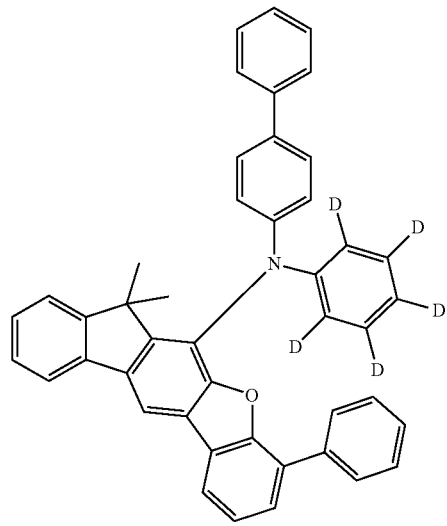
[Compound 16]
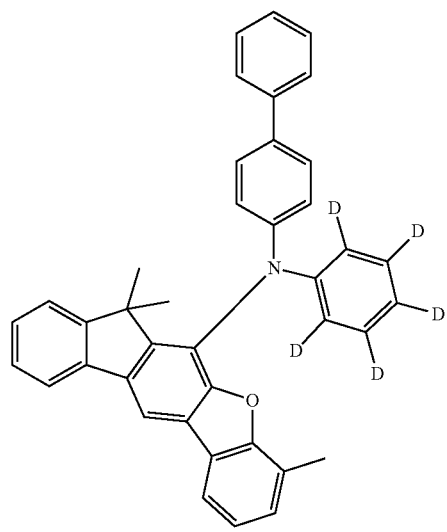
[Compound 17]
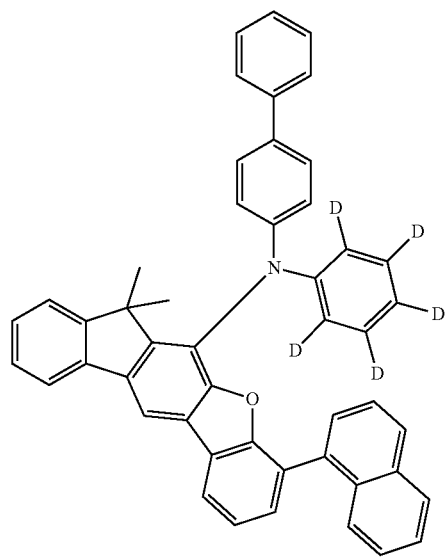
[Compound 18]
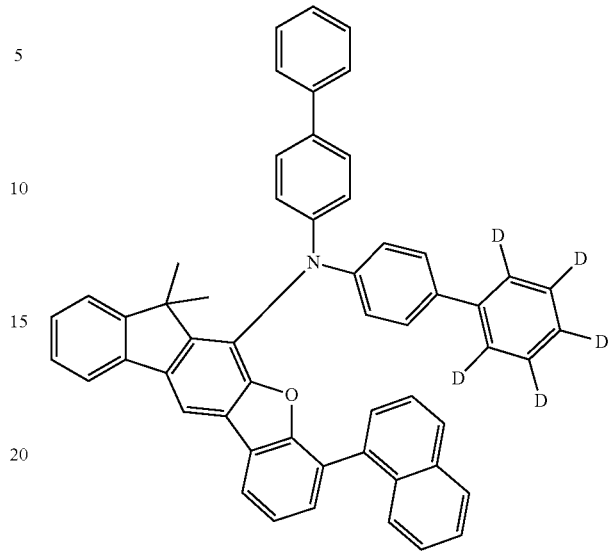
[Compound 19]
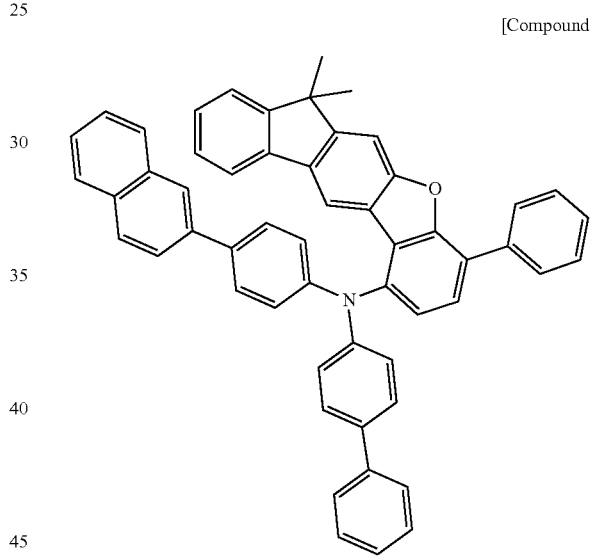
[Compound 20]

[Compound 21]
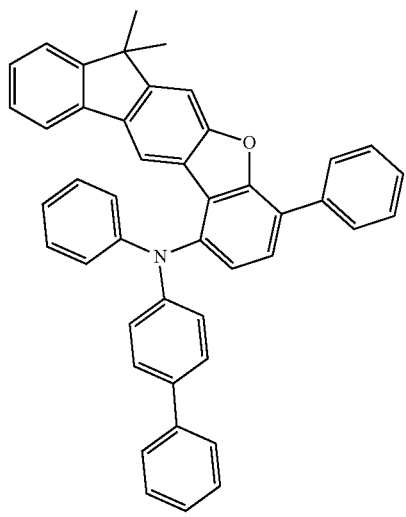
[Compound 22]
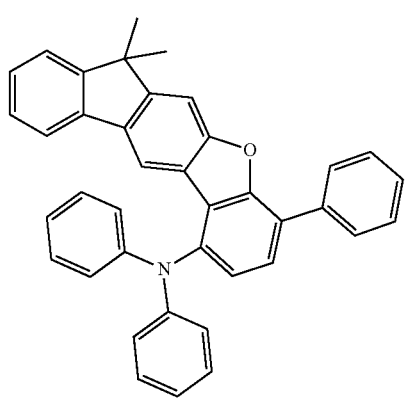
[Compound 23]
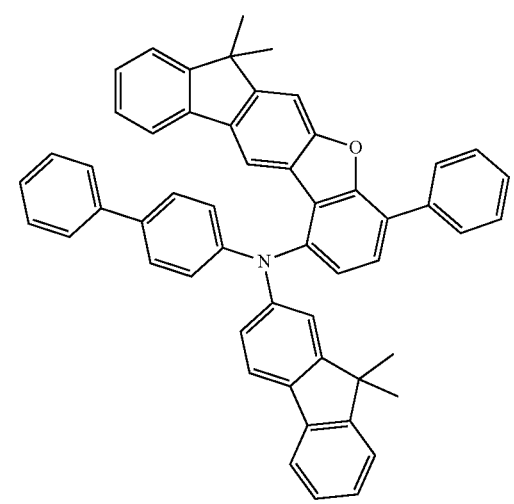
[Compound 24]
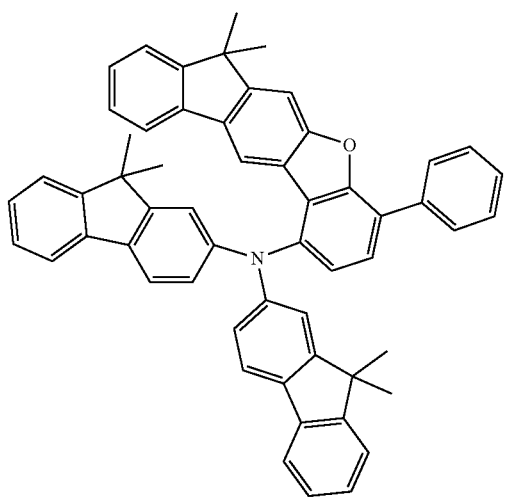
[Compound 25]
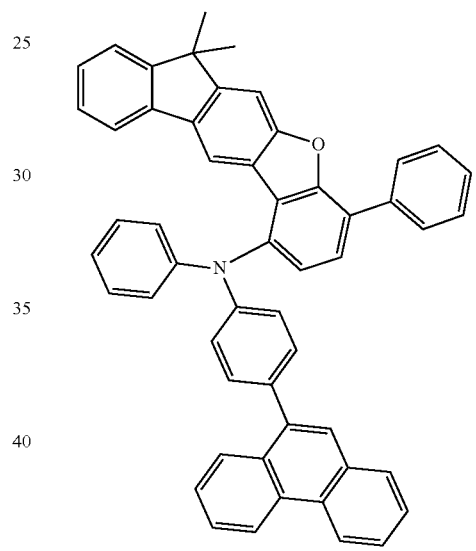
[Compound 26]
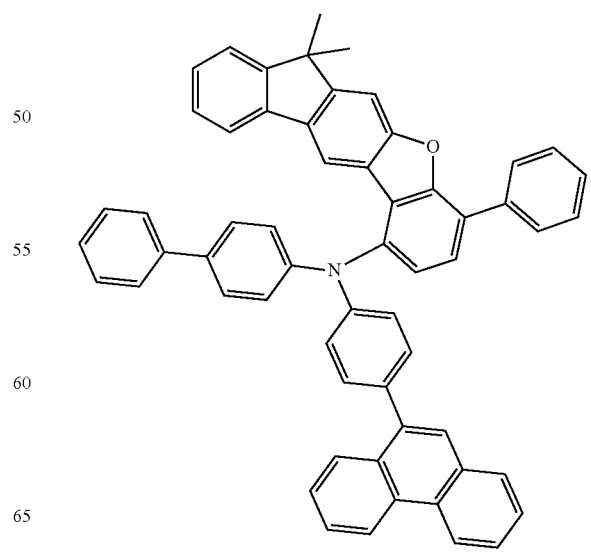

[Compound 27]
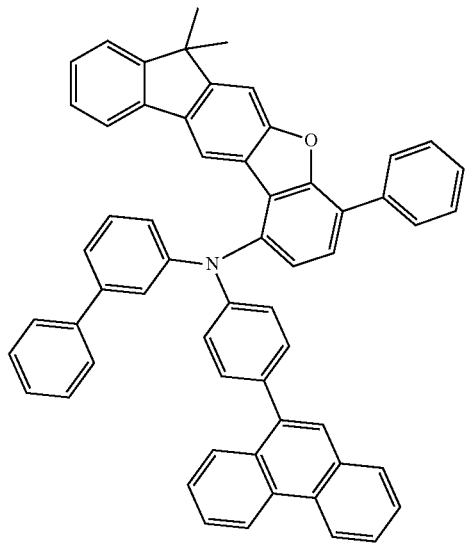
[Compound 28]
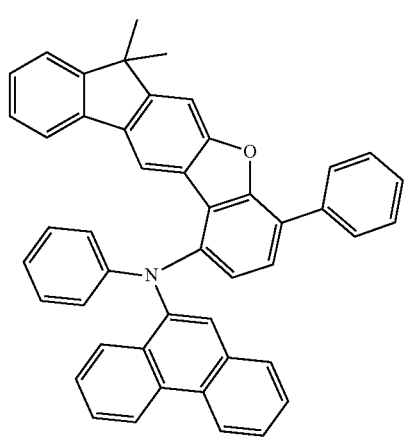
[Compound 29]
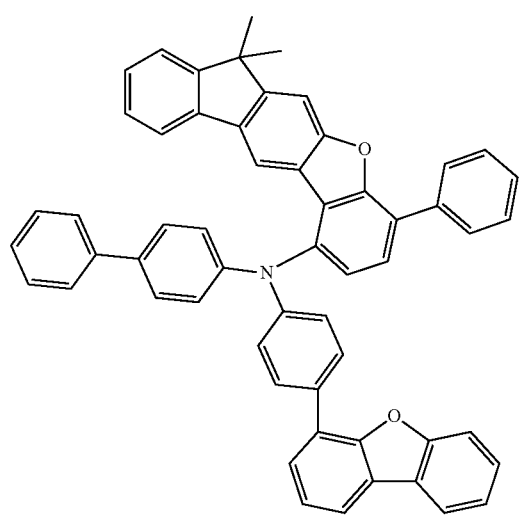
[Compound 30]
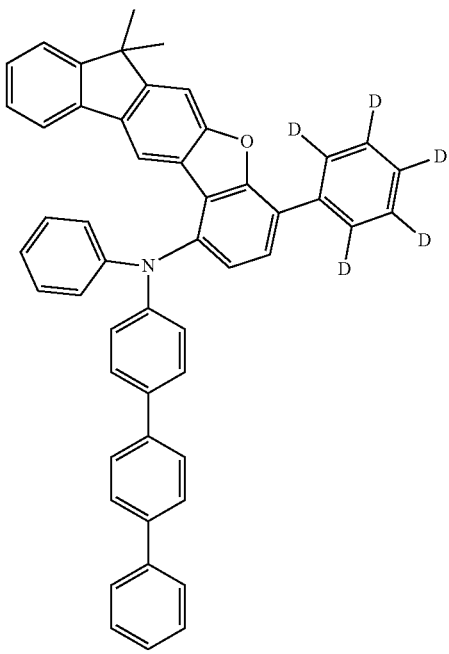
[Compound 31]
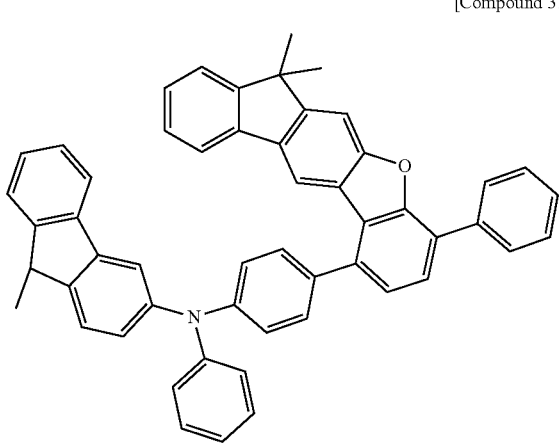

[Compound 32]
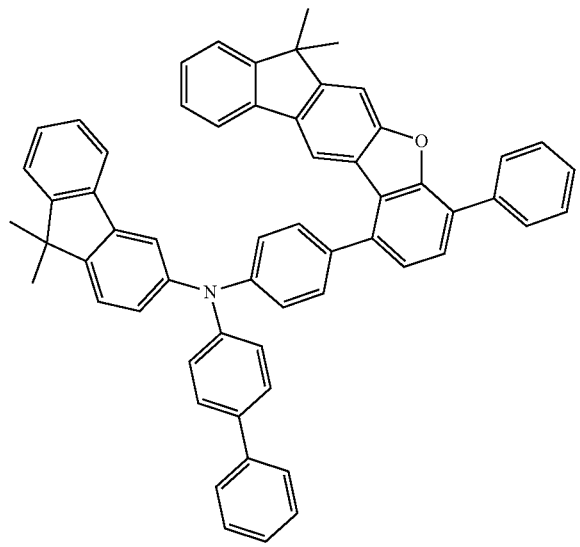
[Compound 33]
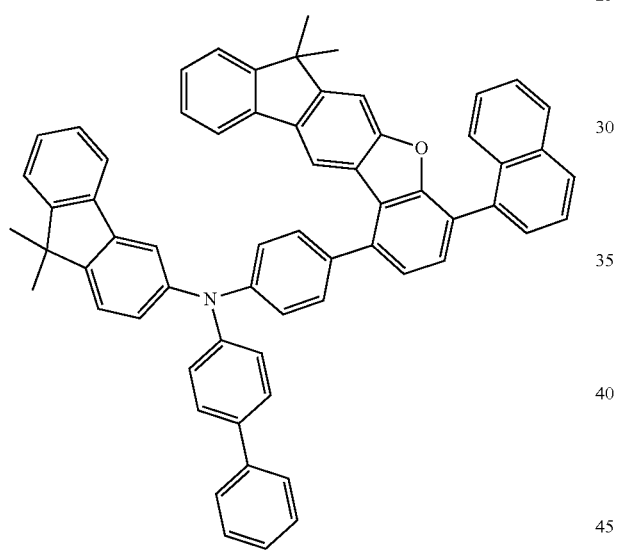
[Compound 34]
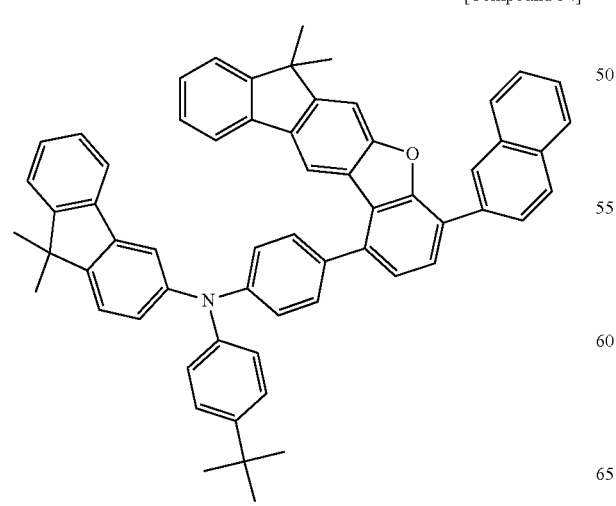
[Compound 35]
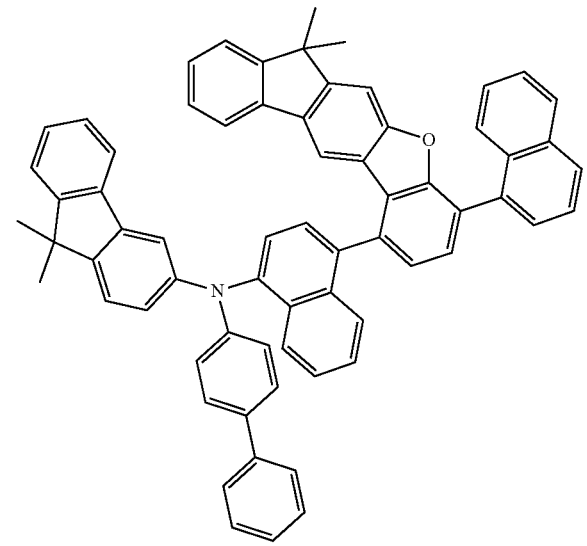
[Compound 36]
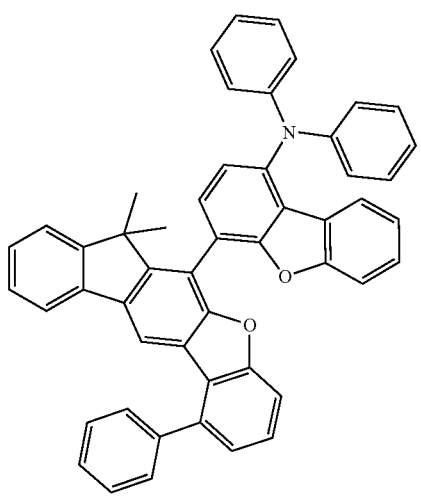

[Compound 37]
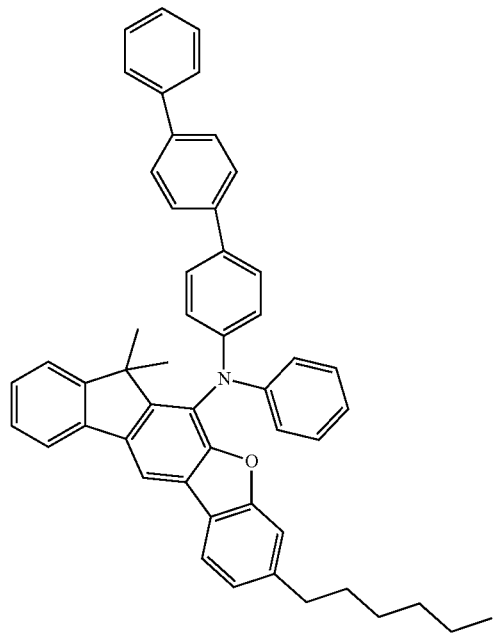
[Compound 38]
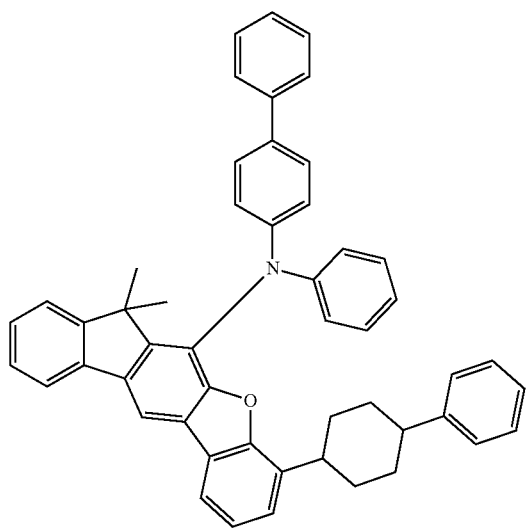
[Compound 39]
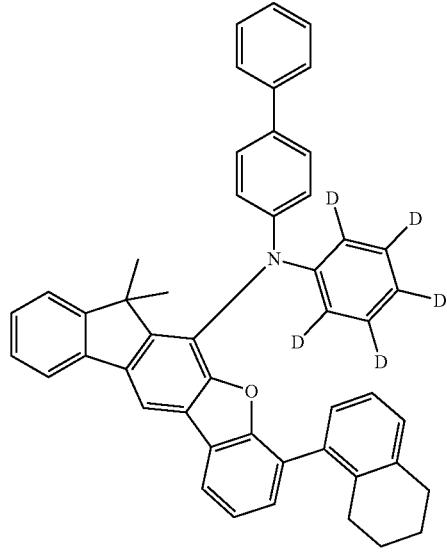
[Compound 40]
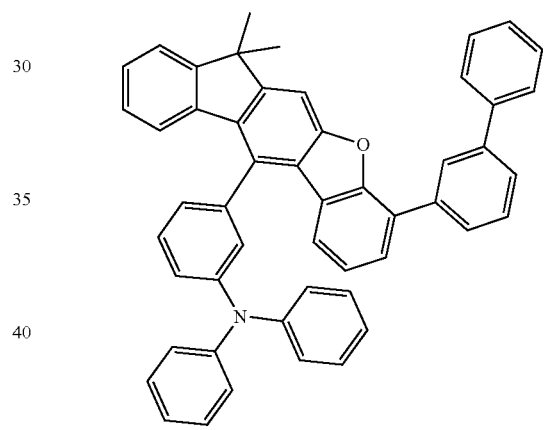
[Compound 41]
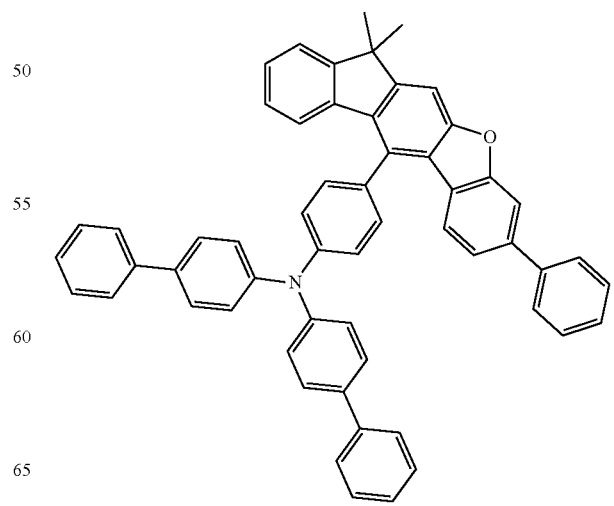

[Compound 42]
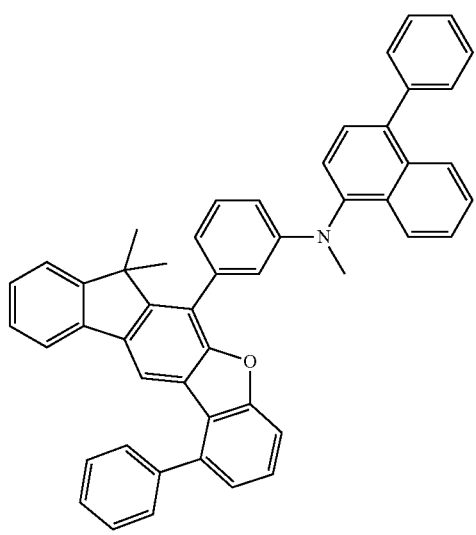
[Compound 43]
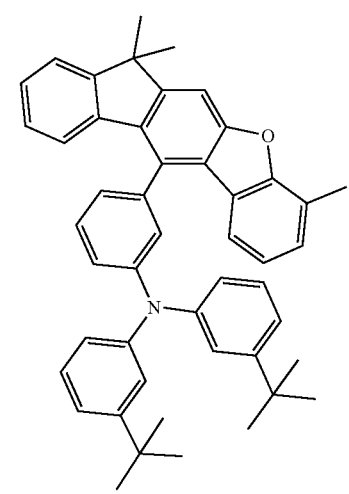
[Compound 44]
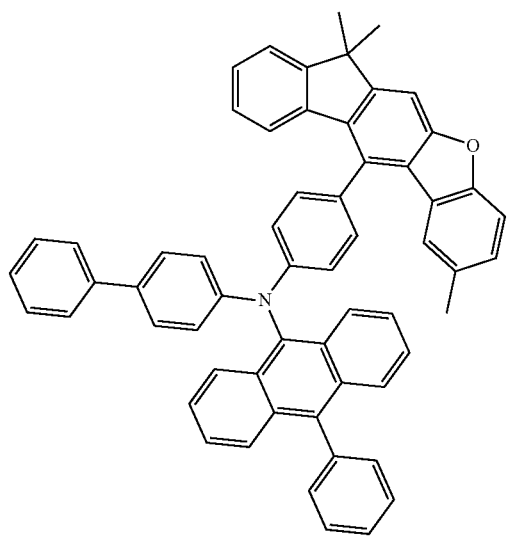
[Compound 45]
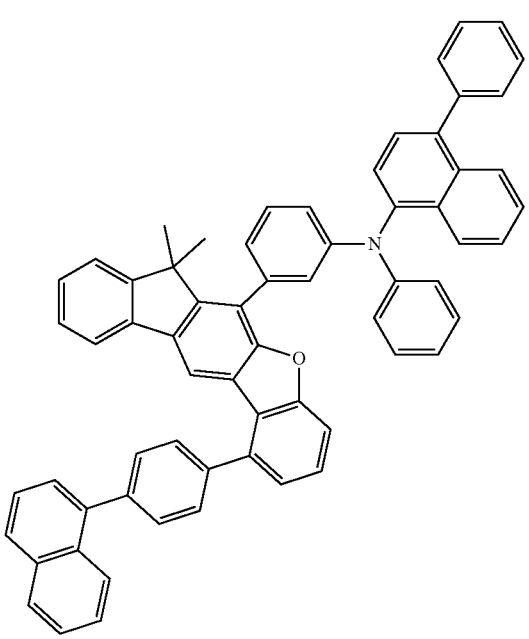
[Compound 46]
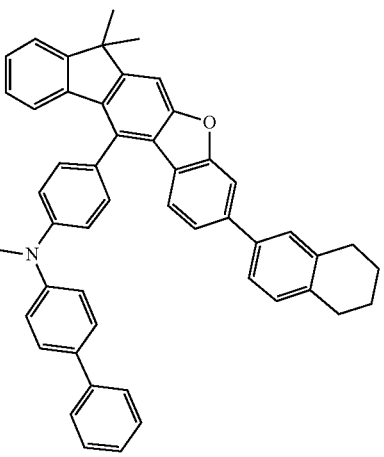
[Compound 47]
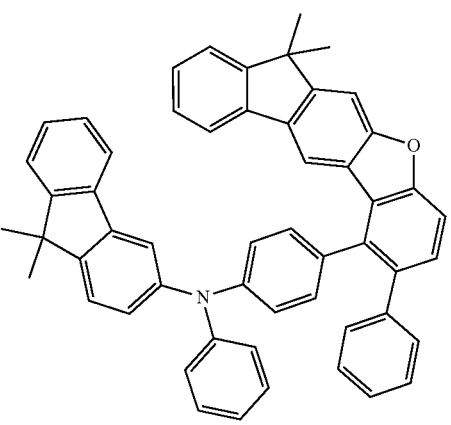

[Compound 48]
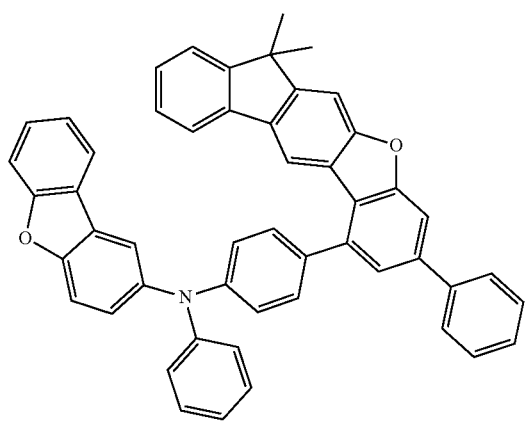
[Compound 49]
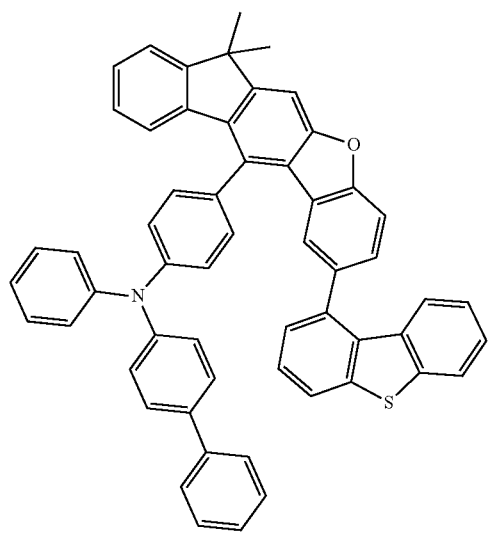
[Compound 50]
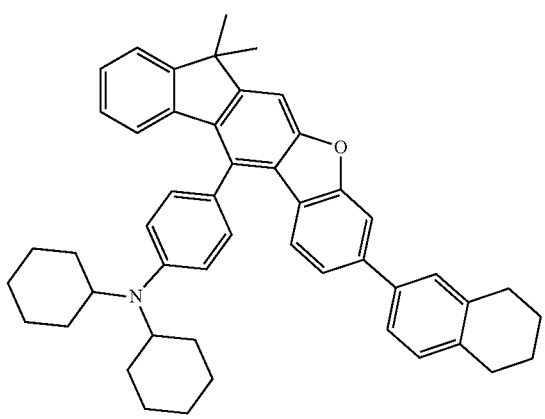
[Compound 51]
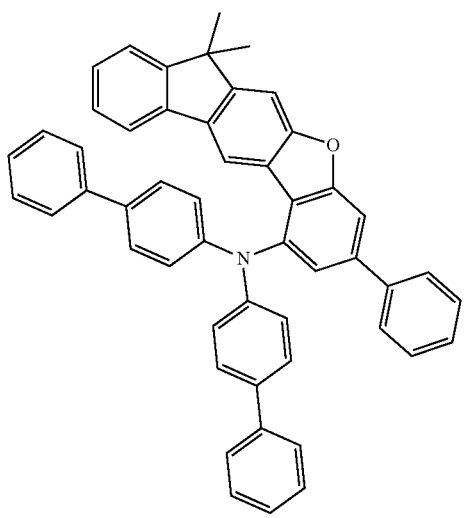
[Compound 52]
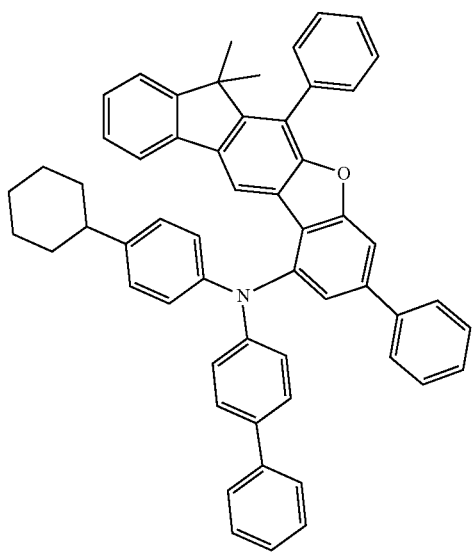
[Compound 53]

[Compound 54]
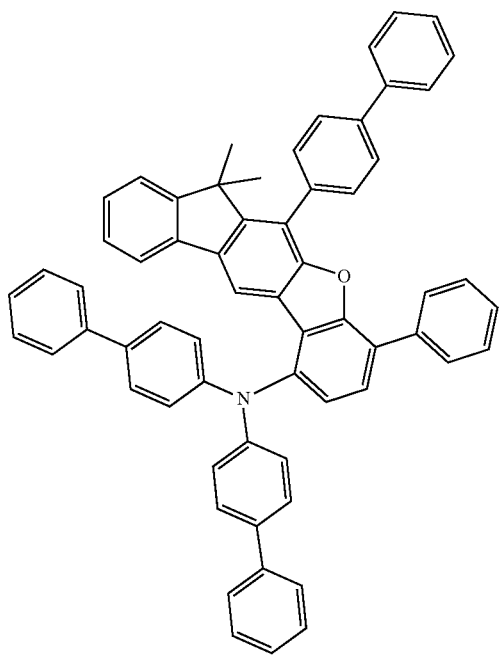
[Compound 55]
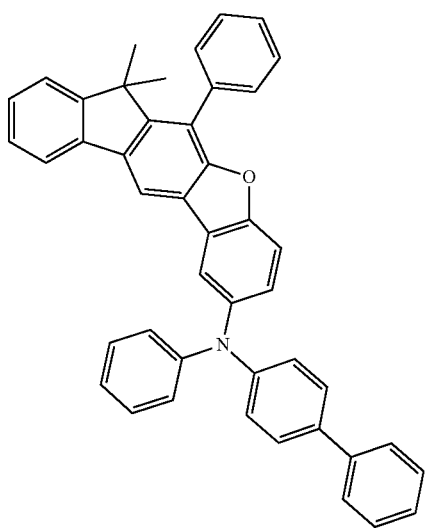
[Compound 56]
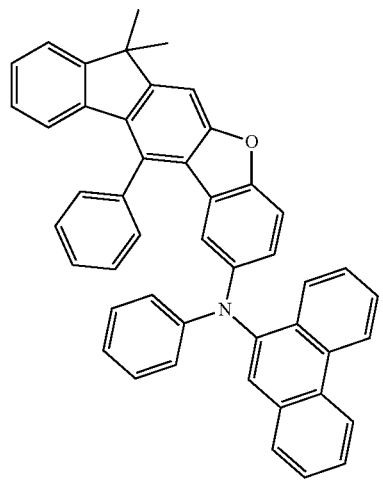
[Compound 57]
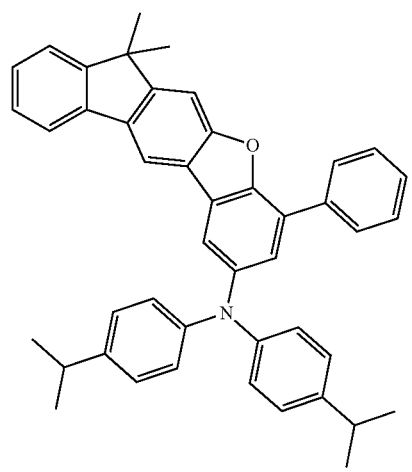
[Compound 58]
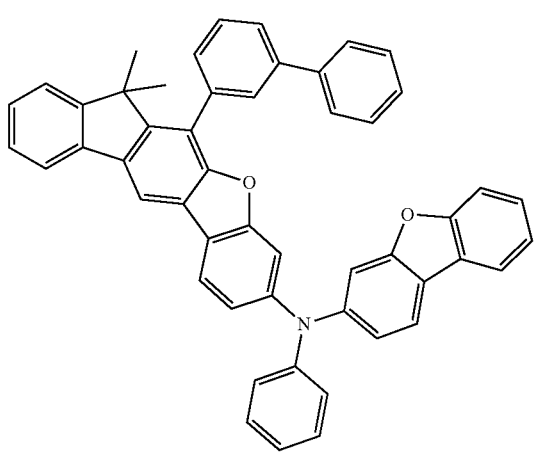

[Compound 59]
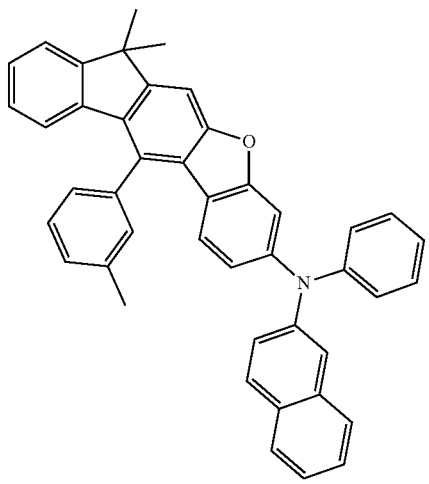
[Compound 60]
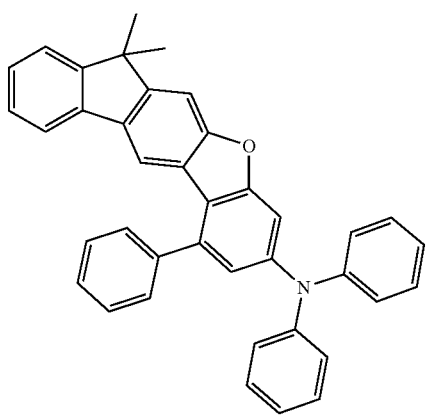
[Compound 61]
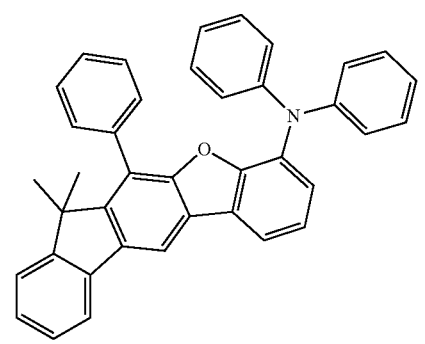
[Compound 62]
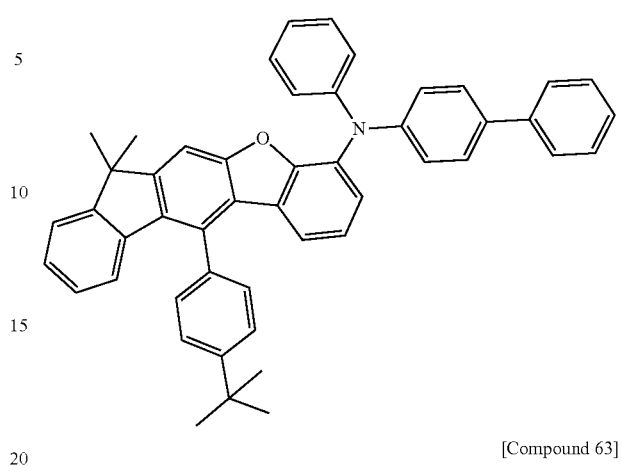
[Compound 63]
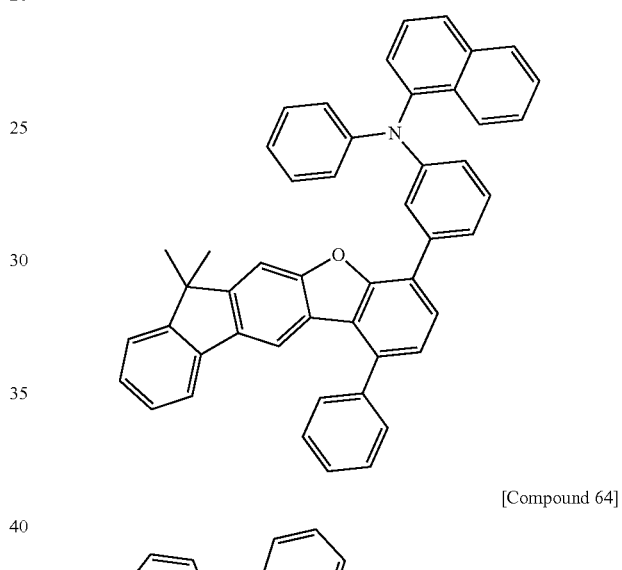
[Compound 64]
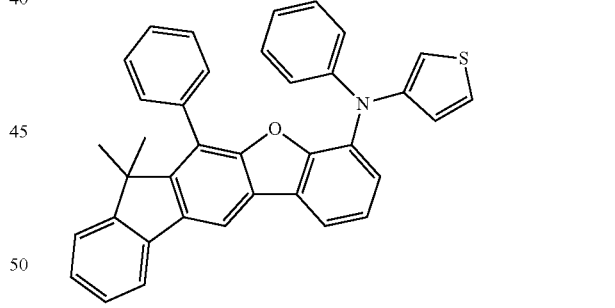
[Compound 65]
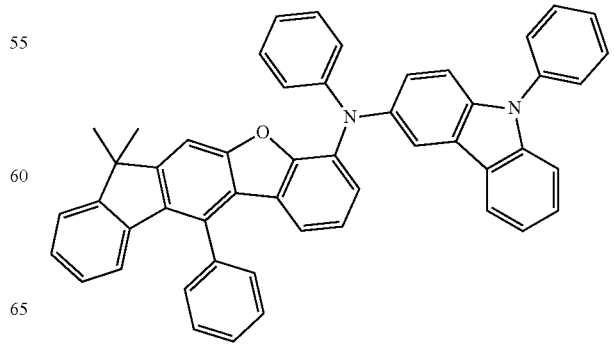

[Compound 66]
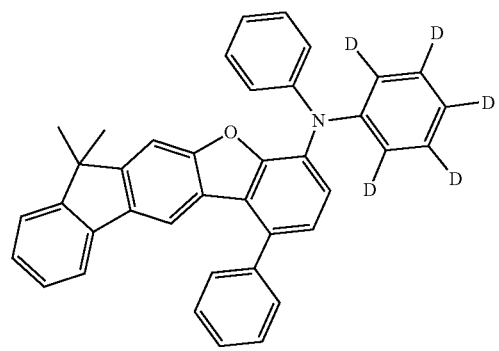
[Compound 67]
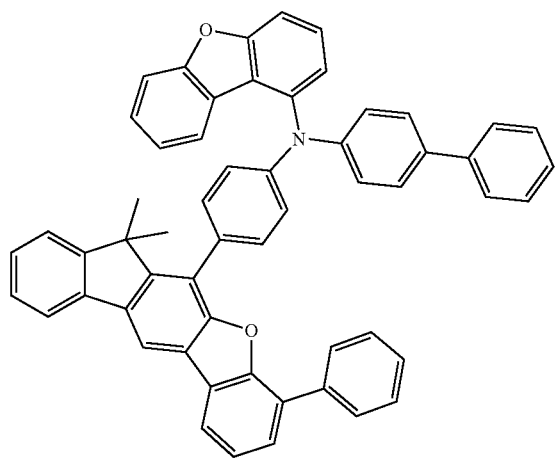
[Compound 68]
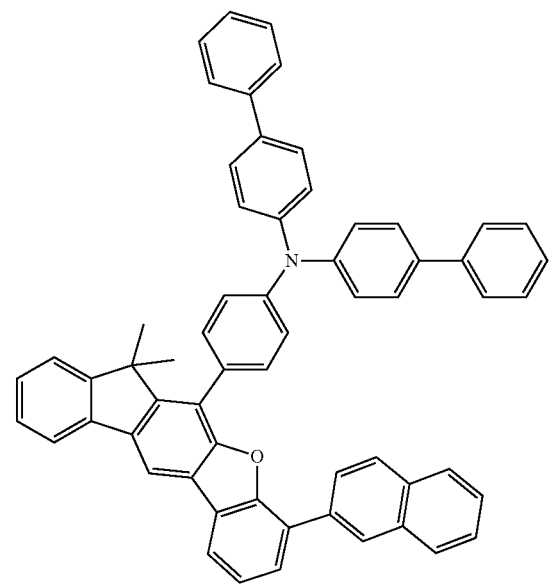
[Compound 69]
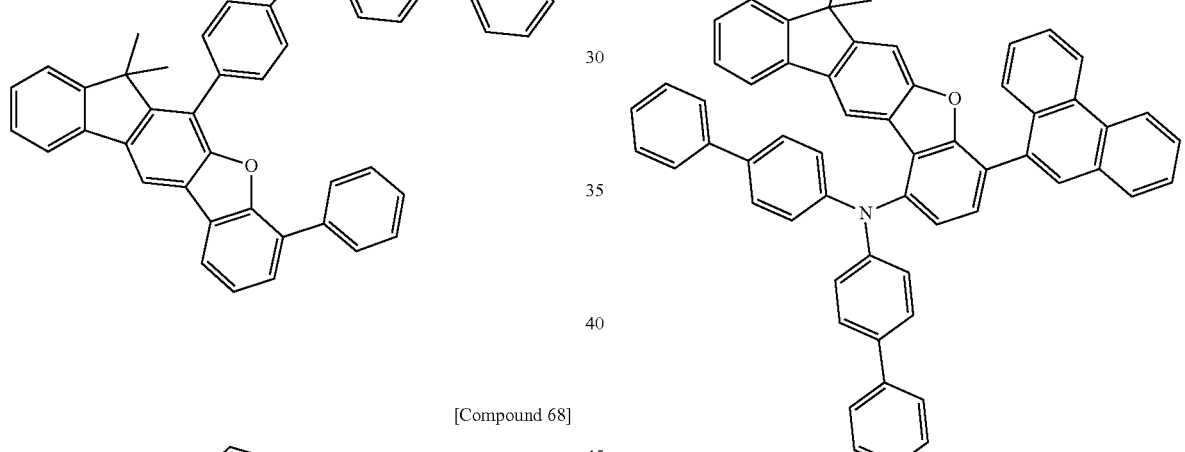
[Compound 70]
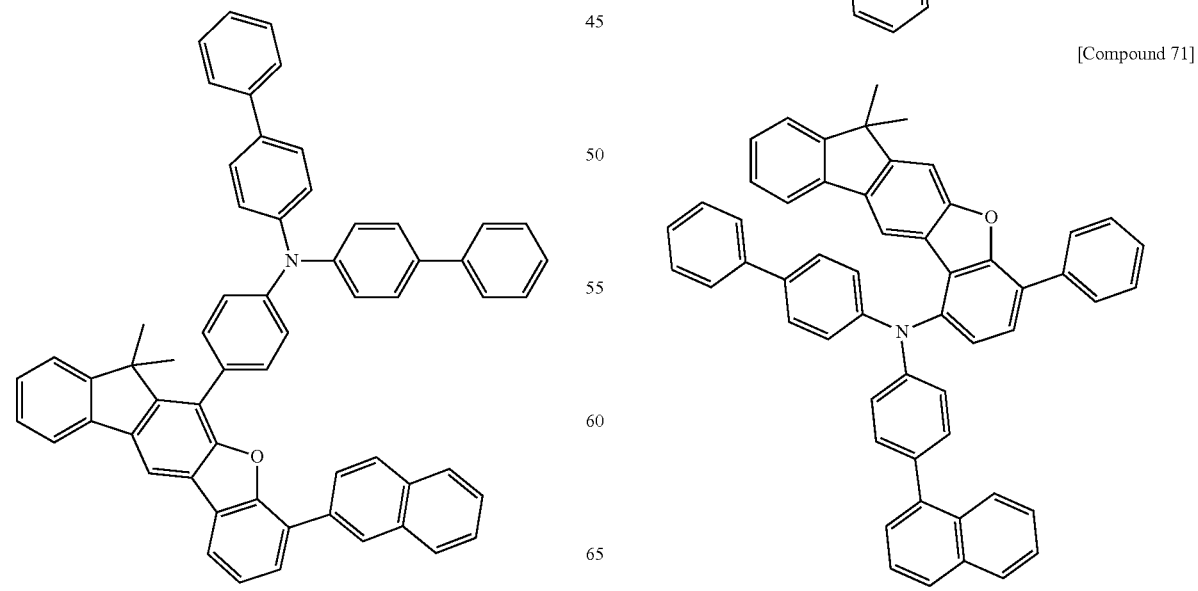
[Compound 71]

[Compound 72]

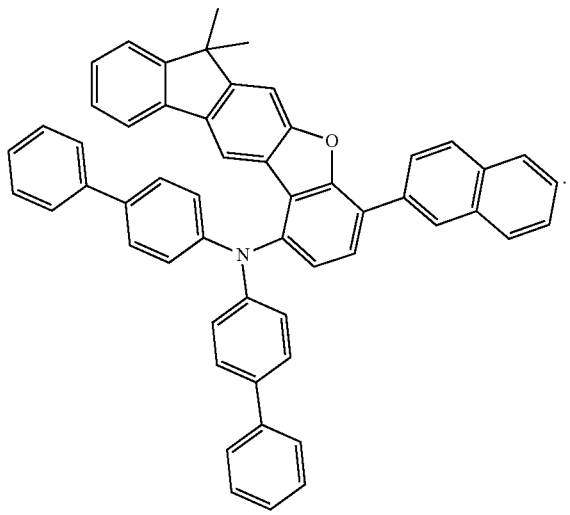

13. An organic light-emitting diode, comprising:
a first electrode;
a second electrode facing the first electrode; and
an organic layer interposed between the first electrode and the second electrode,
wherein the organic layer comprises the amine compound of claim 1.

14. The organic light-emitting diode of claim 13, wherein the organic layer comprises at least one of a hole injection layer, a hole transport layer, a functional layer capable of both hole injection and hole transport, an electron blocking layer, a light-emitting layer, an electron transport layer, an electron injection layer, and a capping layer.

15. The organic light-emitting diode of claim 14, wherein the hole transport layer includes a first hole transport layer and a second hole transport layer which is different from the first hole transport layer in terms of material and employs the amine compound represented by Chemical Formula A or B.

16. The organic light-emitting diode of claim 14, wherein at least one selected from among the layers is deposited using a single-molecule deposition process or a solution process.

17. The organic light-emitting diode of claim 13, wherein the organic light-emitting diode is used for a device selected from among a flat display device; a flexible display device; a monochrome or grayscale flat illumination; and a monochrome or grayscale flexible illumination device.

18. An organic light-emitting diode, comprising: an anode, a hole injection layer, a first hole transport layer, a second hole transport layer, a light-emitting layer, an electron transport layer, an electron injection layer, and a cathode sequentially,
wherein the second hole transport layer contains the amine compound of claim 1.

* * * * *